United States Patent [19]

Yoshioka et al.

[11] Patent Number: 4,897,489
[45] Date of Patent: * Jan. 30, 1990

[54] ANTIBIOTIC DERIVATIVES, THEIR PRODUCTION AND USE

[75] Inventors: Kouichi Yoshioka, Kyoto; Setsuo Harada, Kawanishi; Michihiko Ochiai, Suita; Hirotomo Masuya, Kawabe, all of Japan

[73] Assignee: Takeda Chemical Industries, Ltd., Osaka, Japan

[*] Notice: The portion of the term of this patent subsequent to Apr. 7, 2004 has been disclaimed.

[21] Appl. No.: 58,265

[22] Filed: May 21, 1987

Related U.S. Application Data

[63] Continuation-in-part of Ser. No. 810,696, Dec. 18, 1985, abandoned.

[30] Foreign Application Priority Data

Dec. 18, 1984 [WO] PCT Int'l Appl. ... PCT/JP84/00602
Jun. 25, 1985 [WO] PCT Int'l Appl. ... PCT/JP85/00358
Sep. 4, 1985 [JP] Japan ................ 60-195075
Nov. 11, 1985 [JP] Japan ................ 60-253188
May 21, 1986 [JP] Japan ................ 61-116674
Jun. 12, 1986 [JP] Japan ................ 61-137741

[51] Int. Cl.⁴ ............... C07D 413/04; C07D 417/14
[52] U.S. Cl. ................... 548/128; 548/194; 548/243; 548/244
[58] Field of Search ............... 548/243, 244, 194, 178

[56] References Cited

U.S. PATENT DOCUMENTS 4,656,288  4/1987  Ono ......................... 548/244

FOREIGN PATENT DOCUMENTS 8603752  7/1986  World Int. Prop. O. ......... 548/244

OTHER PUBLICATIONS

Tetrahedron Letters, 27 (51), 6229–6232, (Dec. 1986).
Nature, 325 (No. 7000), 179–180, (Jan. 8, 1987).

*Primary Examiner*—Robert Gerstl
*Attorney, Agent, or Firm*—Wenderoth, Lind & Ponack

[57] ABSTRACT

The compounds of the formula:

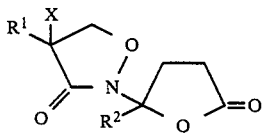

wherein $R^1$ is hydrogen, amino, isonitrile or an organic residue bonded through nitrogen; $R^2$ is carboxy or a group derivable therefrom; X is hydrogen, methoxy, formylamino, alkyl which may be substituted, alkylthio in which the sulfur atom may be oxidized or azido, or forms a double bond together with the adjacent carbon atom; provided that when $R^1$ is acetylamino or amino and X is hydrogen, $R^2$ is not para-nitrobenzyloxycarbonyl or benzhydryloxycarbonyl, or a pharmaceutically acceptable salt thereof, exhibit excellent antimicrobial activity, and are utilized as antimicrobial agents.

24 Claims, No Drawings

ANTIBIOTIC DERIVATIVES, THEIR PRODUCTION AND USE

This is a Continuation-in-part of Ser. No. 810,696, filed Dec. 18, 1985 (now abandoned).

This invention relates to novel 2-(4-substituted-amino-3-oxo-2-isoxazolidinyl)-5-oxo-2-tetrahydrofurancarboxylic acid derivatives exhibiting excellent antimicrobial and β-lactamase inhibitory activities, to processes for production thereof and to uses thereof.

Recently, a novel antibiotic TAN-588 (hereinafter referred to in some instances briefly as "TAN-588") exhibiting antimicrobial activity against gram-positive and gram-negative bacteria has been harvested from new species of microorganisms belonging to the genera Empedobacter and Lysobacter as isolated from soil. The present inventors conducted research to elucidate the chemical structure of the said antibiotic TAN-588, and as a result, it has been found that the antibiotic TAN-588 has a peculiar skeleton consisting of a 3-oxoisoxazolidine ring having 5-oxo-2-tetrahydrofurancarboxylic acid bonded at its nitrogen atom.

Heretofore, there has been reported a synthesis of a compound consisting of a 3-oxoisoxazolidine ring having a 1-methylacetic acid group introduced at its nitrogen atom [Tsuji and Yamana; Heterocycles, 8, 153 (1977)]. However, it has been reported that the compound having the said 1-methylacetic acid group was not observed to exhibit antimicrobial activity.

The present inventors synthesized derivatives of the antibiotic TAN-588 exhibiting antimicrobial activity, and as a result, it was found that the said derivatives possess excellent antimicrobial activity. The finding was followed by further research, leading to the completion of this invention.

This invention is concerned with:

(1) a compound of the formula:

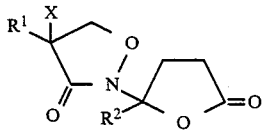
(I)

wherein $R^1$ is hydrogen, amino, isonitrile or an organic residue bonded through nitrogen; $R^2$ is carboxy or a group derivable therefrom; X is hydrogen, methoxy, formylamino, alkyl which may be substituted, alkylthio in which the sulfur atom may be oxidized or azido, or forms a double bond together with the adjacent carbon atom; provided that when $R^1$ is acetylamino or amino and X is hydrogen, $R^2$ is not para-nitrobenzyloxycarbonyl or benzhydryloxycarbonyl, or a pharmaceutically acceptable salt thereof, (2) a process for producing a compound (I), which comprises deprotecting a compound of the formula:

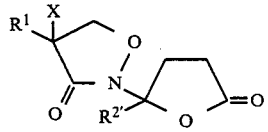
(II)

wherein $R^{2'}$ is a protected carboxy; $R^1$ and X are as defined hereinbefore, and if desired, esterifying the resulting compound, (3) a process for producing a compound of the formula:

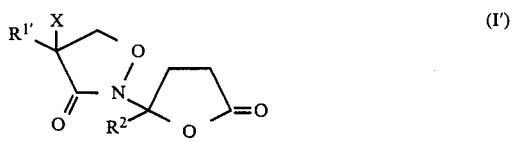
(I')

wherein $R^{1'}$ is an organic residue bonded through nitrogen; $R^2$ and X are as defined hereinbefore, which comprises reacting a compound of the formula

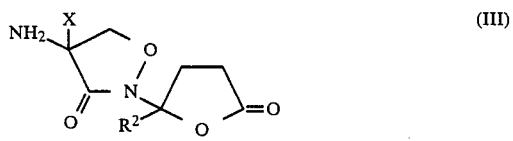
(III)

wherein $R^2$ and X are as defined hereinbefore, with a compound capable of introducing a group forming an organic residue bonded through nitrogen, (4) a process for producing a compound (I), which comprises reacting a compound of the formula:

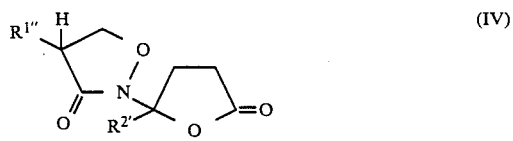
(IV)

wherein $R^{1''}$ is isonitrile or an organic residue bonded through nitrogen; $R^{2'}$ is as defined hereinbefore, with a nucleophilic reagent, and if desired, subjecting the resulting compound to hydrolysis, elimination reaction, substitution reaction and/or converting reaction.

In the formulae indicated in the present specification, examples of the organic residue bonded through nitrogen as represented by $R^1$, $R^{1'}$ or $R^{1''}$ include, for example, acylamino, amino substituted through carbon, alkenylamino, thioamino, silylamino, phosphoamino and a group represented by the formula —CO—CO—NH—.

The acyl in the above acylamino includes, for example, the conventionally known acyl groups, such as acyl groups which are substituted in the 6-amino group of penicillin derivatives and acyl groups which are substituted in the 7-amino group of cephalosporin derivatives.

Examples of the said acylamino group include, for example, groups of the formula:

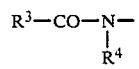

wherein $R^3$ is hydrogen, alkyl*, alkenyl*, cycloalkyl*, aryl*, heterocyclic ring*, alkoxy* or aryloxy*; $R^4$ is hydrogen or alkyl*, and $R^4$ also cooperates with $R^3$ to form a ring*; groups of the formula:

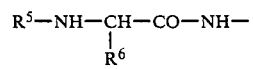

wherein $R^5$ is hydrogen, amino acid residue*, amino-protecting group or a group represented by the formula $R^7-(CH_2)_n-C(=Z)-$ {wherein $R^7$ is a heterocyclic ring*, alkoxy* or amino*; n is 0, 1 or 2; Z is O or S}; $R^6$ is alkyl*, aryl*, cycloalkenyl* or heterocyclic ring*; groups of the formula:

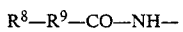

wherein $R^8$ is a group represented by the formula

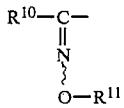

}wherein $R^{10}$ is alkyl*, heterocyclic ring* or aryl*; $R^{11}$ is hydrogen, alkyl*, alkenyl*, cycloalkyl*, heterocyclic ring*, or a group represented by the formula $-R^{12}-R^{13}$ (wherein $R^{12}$ is alkylene*, cycloalkylene or alkenylene; $R^{13}$ is aryl*, carboxy* or its ester or mono- or dialkylamide)}; $R^9$ is a chemical bond or a group represented by the formula

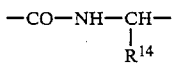

(wherein $R^{14}$ is alkyl*, aryl* or heterocyclic ring*); groups of the formula:

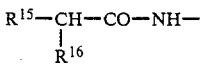

wherein $R^{15}$ is aryl*, heterocyclic ring* or cycloalkenyl*; $R^{16}$ is hydroxy, sulfamoyl, sulfo, sulfoxy or acyloxy*; groups of the formula:

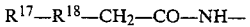

wherein $R^{17}$ is alkyl*, cyano, aryl*, aryloxy*, alkenylene*, heterocyclic ring*, amino* or a group represented by the formula $R^{17'}-C(=S)-$ (wherein $R^{17'}$ is alkoxy); $R^{18}$ is chemical bond or $-S-$; and groups of the formula:

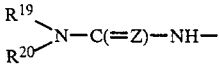

wherein $R^{19}$ and $R^{20}$ are the same or different, and represent independently hydrogen, alkyl*, aryl*, heterocyclic ring*, or cycloalkyl; Z is O or S.

In the descriptions for each of the groups as used herein, the groups bearing the mark "*" designate that they may have a substituent or substituents.

The formula

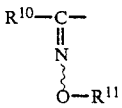

in the group $R^8$ represents the syn isomer represented by the formula

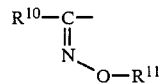

and the anti isomer represented by the formula

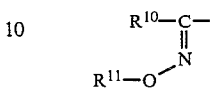

or a mixture thereof.

Examples of the amino which are substituted through carbon which exemplifies the organic residue bonded through nitrogen as represented by the above $R^1$ include, for example, groups of the formula:

$$R^{21}-NH-$$

wherein $R^{21}$ is alkyl*, aryl*, alkenyl* or heterocyclic ring*; groups of the formula:

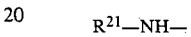

wherein $R^{22}$ and $R^{23}$ are the same or different and represent independently alkyl*, aryl* or alkenyl*, and also cooperate with the adjacent nitrogen atom to form a heterocyclic ring, and groups of the formula:

wherein $R^{24}$, $R^{25}$ and $R^{26}$ are the same or different and represent independently alkyl*, aryl* or alkenyl*, and also $R^{24}$ and $R^{25}$ or $R^{26}$ cooperate with the adjacent nitrogen atom to form a heterocyclic ring*.

Examples of the alkenylamino which exemplifies the group represented by the above $R^1$ include, for example, groups of the formula:

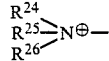

wherein $R^{27}$ and $R^{28}$ are the same or different, and represent independently hydrogen, alkyl*, aryl*, cycloalkyl, amino* or heterocyclic ring*, and also $R^{27}$ and $R^{28}$ cooperate with the adjacent nitrogen atom to form cycloalkyl* or heterocyclic ring*.

Examples of the thioamino which exemplifies the group represented by the above $R^1$ include, for example, groups of the formula:

$$R^{29}-SO_n-NH-$$

wherein $R^{29}$ is alkyl* or aryl*; n is 0, 1 or 2.

Examples of the silylamino which exemplifies the group represented by the above $R^1$ include, for example, groups of the formula:

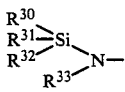

wherein $R^{30}$, $R^{31}$ and $R^{32}$ are the same or different, and represent independently alkyl* or aryl*, and also they form a cyclic group; $R^{33}$ is hydrogen or silyl*.

Examples of the phosphoamino which exemplifies the group represented by the above $R^1$ includes, for example, groups of the formula:

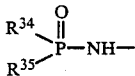

wherein $R^{34}$ and $R^{35}$ are the same or different, and represent independently alkyl*, aryl*, alkoxy* or aryloxy*, and also $R^{34}$ and $R^{35}$ form a heterocyclic ring*.

Examples of the group represented by the above $R^1$ include, for example, groups of the formula:

$$R^{36}-CO-CO-NH-$$

wherein $R^{36}$ is hydrogen, alkyl*, alkoxy*, aryl*, aryloxy*, heterocyclic ring* or amino*.

In the above formulae, the organic residue bonded through nitrogen as represented by $R^1$ or $R^{1'}$ preferably shows a molecular weight of up to 500.

In the formulae indicated in the present specification, the group derivable from carboxy or the protected carboxyl group as represented by $R^2$ or $R^{2'}$ include, for example, groups of the formulae:

$$-COOR^{37}$$

wherein $R^{37}$ is alkyl*, alkenyl*, aryl*, cycloalkyl*, heterocyclic ring* or silyl*, and groups of the formula:

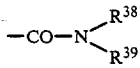

wherein $R^{38}$ and $R^{39}$ are the same or different and represent independently hydrogen, alkyl*, aryl*, cycloalkyl*, alkenyl* or heterocyclic ring*, and also $R^{38}$ and $R^{39}$ cooperate with the adjacent nitrogen atom to form a heterocyclic ring*.

The carboxyl group or the group derivable therefrom represented by $R^2$ is preferably in the form of a salt or ester. In the case of a salt, the salt with an alkali metal (especially sodium) is preferable, and, in the case of an ester, the ester whose residual group is carbonyloxy-substituted-methylene (when further substituted, methylene becomes methine) [e.g. pivaloyloxymethylester, 1-(ethoxycarbonyloxy)ethylester, 1-(cyclohexyloxycarbonyloxy)ethylester, 1,3-dihydro-3-oxo-1-isobenzofuranylester, etc.] is preferable.

In the above formulae, the group derivable from carboxy or the protected carboxyl group as represented by $R^2$ and $R^{2'}$ preferably shows a molecular weight of, for example, up to 500.

In the above formulae, the alkyl in $R^3$, $R^4$, $R^6$, $R^{10}$, $R^{11}$, $R^{14}$, $R^{17}$ and $R^{19\text{-}39}$ is preferably those of 1 to 6 carbon atoms, and their examples include, for example, methyl, ethyl, n-propyl, isopropyl, n-butyl, isobutyl, secbutyl, t-butyl, 1,1-dimethylpropyl, n-pentyl, isopentyl, n-hexyl and isohexyl.

The substituent group which the said alkyls may have includes, for example, halogen, oxo, thioxo, nitro, amino (which may have as a substituent alkyl, alkenyl, cycloalkyl, aryl, acyl, carbamoyl or N-sulfocarbamoyl), sulfo, cyano, hydroxy, carboxy (which may be esterified with alkyl), cycloalkyl, cycloalkenyl, alkoxy (which may have as a substituent amino, hydroxy, carboxy, halogen, aryl, cycloalkyl or alkoxy), aryl (which may have as a substituent halogen, alkyl, alkoxy, alkylamino, amino, carbamoyl, sulfo, alkylsulfonyl, cyano, hydroxy, carboxy, nitro, acyloxy, aralkyloxy, or sulfoxy), arylcarbonyl which may have substituents similar to those mentioned above for aryl, aryloxy which may have substituents similar to those mentioned above for aryl, heterocyclic ring (which may have as a substituent nitro, oxo, aryl, alkenyl, halogenoalkyl, alkylsulfonyl, alkyl, alkoxy, alkylamino, amino, halogen, carbamoyl, hydroxy, cyano, carboxy or sulfo), acyl (which may have as a substituent arylcarbonylhydrazino which may have as a substituent hydroxy, halogen, amino or nitro), acyloxy, alkoxycarbonyl, alkoxycarbonyloxy (which may have as a substituent halogen), acyloxy-ethoxy, aralkyl (which may have as a substituent alkyl, alkoxy, halogen, amino, hydroxy, nitro, cyano, carbamoyl or sulfamoyl), aralkyloxy (which may have as a substituent acyloxy, alkyl, alkoxy, halogen, amino, hydroxy, nitro, cyano, carbamoyl or sulfamoyl), hydroxysulfonyloxy, alkylsulfonyloxy, arylsulfonyloxy, alkylsulfonyl, aminosulfonyl, alkylsulfinyl, arylsulfonyl, alkylsulfinyl, alkylthio (which may have as a substituent cyano, halogen, carboxyl, alkylamino, imino, carbamoyl or acylamino), arylthio, heterocyclic ring-thio (which may have as a substituent cyano, hydroxy, amino, alkylamino, alkyl, halogen or oxo), heterocyclic ring (which may have as a substituent cyano, hydroxy, amino, alkylamino, alkyl, halogen or oxo)-alkyl-thio, iminomethylamino, iminoethylamino, silyl (which may have alkyl or aryl as a substituent), alkyloxycarbonyl, arylcarbonyl (which may have as a substituent acyloxy, halogen, amino, hydroxy, alkoxy, or sulfamoyl), phthalimido, succinimido, dialkylamino, dialkylaminocarbonyl, arylcarbonylamino, carbamoyl, carbamoyloxy, N-sulfocarbamoyloxy, alkylcarbonylcarbamoyloxy (which may have as a substituent halogen), alkoxyimino, and groups of the formula:

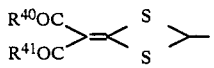

wherein $R^{40}$ and $R^{41}$ are the same of different and represent independently a hydroxyl or amino group.

In the above formulae, the alkylene as represented by $R^{12}$ is preferably, for example, those of 1 to 6 carbon atoms, and their examples include, for example, methylene, ethylene, trimethylene, tetramethylene, pentamethylene and hexamethylene.

The substituent which the said alkylene group may have includes, for example, halogen, amino, hydroxy, alkoxy, carboxy, carbamoyl, cyano and nitro.

In the above formulae, the cycloalkyl in, or the cycloalkyl formed by, $R^3$, $R^{11}$, $R^{19}$, $R^{20}$, $R^{27}$, $R^{28}$, $R^{37}$, $R^{38}$ and $R^{39}$ is desirably those of 3 to 8 carbon atoms, and their examples include, for example, cyclopropyl, cyclobutyl, cyclopentyl, cyclohexyl, cycloheptyl and cyclooctyl.

The substituent group which the said cycloalkyl groups may have includes, for example, halogen, nitro, amino, hydroxy, sulfo, cyano, carboxy, oxo and thioxo.

The cycloalkylene as represented by $R^{12}$ includes, for example, those consisting of the above cycloalkyl which is provided with an additional bond.

In the above formulae, the aryl in the aryl, arylcarbonyl, aryloxycarbonyl or aryloxy as represented by $R^3$, $R^6$, $R^{10}$, $R^{13-17}$, $R^{19-32}$ and $R^{34-39}$ includes, for example, phenyl, naphthyl, biphenyl, anthryl and indenyl.

The substituent which the said aryl group may have includes, for example, halogen, nitro, cyano, amino (which may have as a substituent alkyl, alkenyl, cycloalkyl or aryl), sulfo, mercapto, hydroxy, carboxy, acyl, sulfoxy, sulfamoyl, carbamoyl, alkyl (which may have as a substituent amino, halogen, hydroxy, cyano or carboxy), alkoxy, aralkyloxy, alkylsulfonamido, methylenedioxy, alkylsulfonyl and alkylsulfonylamino. Also, they, together with cycloalkyl, may form a fused ring (e.g., tetrahydronaphthyl, indanyl, acenaphthyl, etc.).

In the above formulae, the alkoxy as represented by $R^3$, $R^7$, $R^{17'}$ and $R^{34-36}$ is desirably those of 1 to 6 carbon atoms, and their examples include, for example, methoxy, ethoxy, n-propoxy, i-propoxy, n-butoxy, i-butoxy, t-butoxy, n-pentyloxy and n-hexyloxy.

The substituent, which the said alkoxy group may have, includes, for example, halogen, nitro, amino, hydroxy, sulfo, cyano, carboxy, aryl (which may have as a substituent nitro, amino, hydroxy, alkyl or alkoxy) and silyl (which may have as a substituent alkyl, aryl or aralkyl).

In the above formulae, the alkenyl as represented by $R^3$, $R^{11}$, $R^{21-26}$ and $R^{37-39}$ is preferably, for example, those of 1 to 6 carbon atoms, and their examples include, for example, methylene, vinyl, allyl, isopropenyl, 1-propenyl, 2-butenyl, 3-methyl-3-butenyl, 1,3-butadienyl, 1,3-pentadienyl, 4-pentaenyl, 1,3-hexadienyl, ethylidene, propylidene, isopropylidene and butylidene.

The substituent which the said alkylene group may have includes, for example, halogen, nitro, amino (which may have acyl as a substituent), sulfo, cyano, hydroxy, carboxy, carbamoyl, sulfamoyl, aryl and acyl.

In the above formulae, the alkenylene as represented by $R^{12}$ and $R^{17}$ is preferably, for example, those of 2 to 6 carbon atoms, and their examples include, for example, vinylene, 1-propenylene, 2-butenylene, 2-pentenylene and 1,3-hexadienylene.

The substituent which the said alkenylene group may have includes, for example, halogen, cyano and carbamoyl.

In the above formulae, the cycloalkenyl represented by $R^6$ and $R^{15}$ is preferably those of 3 to 8 carbon atoms, and their examples include, for example, 1-cyclopropenyl, 1-cyclobutenyl, 1-cyclopentenyl, 2-cyclopentenyl, 3-cyclopentenyl, 1-cyclohexenyl, 2-cyclohexenyl, 3-cyclohexenyl, 1-cycloheptenyl and 1,4-cyclohexadienyl. The substituent which the said cycloalkenyl groups may have includes, for example, halogen, nitro, amino, sulfo, cyano, hydroxy, carboxy, carbamoyl and sulfamoyl.

In the above formulae, the heterocyclic ring represented by, or the heterocyclic ring formed by, $R^3$, $R^6$, $R^7$, $R^{10}$, $R^{14}$, $R^{15}$, $R^{17}$, $R^{19-28}$ and $R^{34-39}$ includes, for example, 5-membered to 7-membered heterocyclic groups containing a sulfur, nitrogen or oxygen atom, 5-membered to 6-membered heterocyclic groups containing 2 to 4 nitrogen atoms, and 5-membered to 6-membered heterocyclic groups containing 1 to 2 nitrogen atoms and a sulfur or oxygen atom, whereby these heterocyclic groups may be fused to a six-membered cyclic group containing not more than 2 nitrogen atoms, benzene ring or five-membered cyclic group containing a sulfur atom.

Specific examples of the above heterocyclic groups include, for example, 2-pyridyl, 3-pyridyl, 4-pyridyl, pyrimidinyl, pyradinyl, pyridazinyl, piperazinyl, piperidyl, pyrazolyl, pyranyl, thiopyranyl, pyrimidyl, imidazolyl, thiazolyl, isothiazolyl, oxazolyl, isoxazolyl, pyrido[2,3-d]pyrimidyl, benzopyranyl, 1,8-naphthylidyl, 1,5-naphthylidyl, 1,6-naphthylidyl, 1,7-naphthylidyl, 2,7-naphthylidyl, 2,6-naphthylidyl, quinolyl, thieno[2,3-b]pyridyl, tetrazolyl, thiadiazolyl, oxadiazolyl, triazinyl, triazolyl, thienyl, pyrrolyl, furyl, pyrrolidinyl, imidazolidinyl, dithiethane, tetrahydropyranyl, tetrahydrofuranyl, benzothienyl, pyranyl, hexahydro-1H-azepinyl, indolyl, isoindolyl and chromanyl.

The substituent which the said heterocyclic groups may have includes, for example, amino (which may as a substituent acyl, halogen-substituted alkylacyl, phenyl or alkyl), halogen, nitro, sulfo, cyano, hydroxy, carboxy, oxo, thioxo, $C_{1-10}$-alkyl [which may have as a substituent aryl, halogen, amino, hydroxy, carboxy, alkoxy, alkylsulfonyl, dialkylamino or phosphono (which may have alkyl as a substituent)], cycloalkyl, alkoxy (which may have as a substituent halogen or hydroxy), acyl of 1 to 4 carbon atoms, aryl (which may have as a substituent halogen, nitro, alkyl, alkoxy, amino, sulfo, hydroxy or cyano), oxo, thioxo, amino acid residue-thio (examples of the amino acid residue include residues similar to those to be mentioned below), $C_{1-10}$-alkyl-thio [which may have as a substituent aryl, halogen, amino hydroxy, carboxy, alkoxy, alkylsulfonyl, dialkylamino, or phosphono (which may have alkyl as a substituent)], heterocyclic rings (which may have as a substituent alkyl, alkoxy, halogen, nitro, cyano, carboxy, formyl or alkylsulfonyl) and groups of the formula $R^{42}$—CH=N— [wherein $R^{42}$ include heterocyclic ring (which may have alkyl, alkoxy, halogen, nitro, cyano, hydroxy, carboxy, formyl or alkylsulfonyl as a substituent)].

In the above formulae, the cyclic group represented by $R^4$ which are formed with $R^3$, includes cyclic groups which have, for example, phthaloyl, succinyl, maleoyl, citraconoyl, glutaryl, and adipoyl, and furthermore, 2,2-dimethyl-5-oxo-4-phenylimidazolidine. The substituent which the said cyclic groups may have includes, for example, halogen, nitro, amino, hydroxy, sulfo, cyano, and carboxy.

In the above formulae, the acyl in the acyloxy as represented by $R^{16}$ is preferably those of 1 to 4 carbon atoms, and their examples include, for example, formyl, acetyl, propionyl, butyryl and isobutyryl, and substituent groups for them include, for example, alkyl (which may have as a substituent amino, halogen, cyano, alkoxy, carboxy or hydroxy).

In the above formulae, the amino acid residue as represented by $R^5$ includes, for example, glycyl, alanyl, valyl, leucyl, isoleucyl, seryl, threonyl, cysteinyl, cystyl, methionyl, α- or β-aspargyl, α- or γ-glutamyl, lysyl, arginyl, phenylalanyl, phenylglycyl, thyrosyl, histidyl, triptophanyl, and prolyl.

The substituent group which the said amino acid residue may have includes, for example, halogen, hydroxy, sulfo, carboxy, cyano, alkylamino, aralkyloxycarbonyl, aralkyloxy and guanidino.

In the above formulae, as a protective group for the amino group as represented by $R^5$, there are suitably used those to be used for this purpose in the fields of for example β-lactam and peptide synthesis. Their examples include, for example, aromatic acyl groups, such as phthaloyl, 4-nitrobenzoyl, 4-tert-butylbenzoyl, 4-tert-butylbenzenesulfonyl, benzenesulfonyl and toluenesulfonyl; aliphatic acyl groups, such as formyl, acetyl, propionyl, monochloroacetyl, dichloroacetyl, trichloroacetyl, methanesulfonyl, ethanesulfonyl, trifluoroacetyl, malonyl and succinyl; esterified carboxyl groups, such as methoxycarbonyl, ethoxycarbonyl, t-butoxycarbonyl, isopropoxycarbonyl, 2-cyanoethoxycarbonyl, 2,2,2-trichloroethoxycarbonyl, benzyloxycarbonyl, 4-nitrobenzoyloxycarbonyl, 4-methoxybenzyloxycarbonyl, diphenylmethyloxycarbonyl, methoxymethyloxycarbonyl, acethylmethyloxycarbonyl, isobornyloxycarbonyl and phenyloxycarbonyl; methylene groups, such as (hexahydro-1H-azepin-1-yl)methylene; sulfonyl groups, such as 2-amino-2-carboxyethylsulfonyl; and amino-protecting groups other than acyl groups, such as trityl, 2-nitrophenylthio, benzylidene, 4-nitrobenzylidene, di- or trialkylsilyl, benzyl and nitrobenzyl. Selection of the said protective groups is not limited in this invention, but among others, monochloroacetyl, benzyloxycarbonyl, 4-methoxybenzyloxycarbonyl and 4-nitrobenzyloxycarbonyl are preferable.

In the above formulae, the substituent group in the carboxy group which may have a substituent as represented by $R^{13}$ includes, for example, alkyl (which may have as a substituent halogen, cyano or hydroxy), aryl (which may have as a substituent alkyl, alkoxy, halogen, hydroxy, acyloxy, sulfo, cyano or sulfamoyl), silyl (which may have as a substituent alkyl, aryl or aralkyl), heterocyclic rings (which may have as a substituent amino, alkylamino, sulfamoyl, carbamoyl, halogen, cyano or nitro), etc.

In the above formulae, the ester group in the ester of carboxyl represented by $R^{13}$ is preferably those of 1 to 6 carbon atoms, and their examples includes, for example, methyl ester, ethyl ester, propyl ester, n-butyl ester, isobutyl ester and tert-butyl ester.

In the above formulae, the substituent group in the amino which may have a substituent as represented by $R^7$, $R^{17}$, $R^{27}$, $R^{28}$, and $R^{36}$ includes, for example, amidine, iminomethyl, imino-(aryl-substituted)-methyl, guanidylcarbonyl, heterocyclic ring (which may have substituents similar to those mentioned above for the heterocyclic rings), imino-(heterocyclic-substituted)-methyl, arylcarbonyl, hydroxyalkyl and alkyl.

In the above formulae, the substituent group in the silyl which may have a substituent as represented by $R^{33}$ and $R^{37}$ includes, for example, alkyl, aryl and aralkyl.

The above $R^{30}$, $R^{31}$ and $R^{32}$, together with $R^{33}$, may form a cyclic group, and its examples include, for example, 2,5-disilylazacyclopentyl and may have substituent groups such as alkyl and aryl.

The halogen as the above substituent group includes, for example, chlorine, bromine, fluorine and iodine.

The alkyl in the description of the above substituent groups is preferably those of 1 to 10, more preferably those of 1 to 6 or still more preferably those of 1 to 4 carbon atoms, and their examples include, for example, methyl, ethyl, n-propyl, i-propyl, n-butyl, i-butyl, t-butyl, sec-butyl, n-pentyl, isopentyl, n-hexyl, isohexyl, heptyl, octyl, nonyl and decyl.

The cycloalkyl is preferably those of 3 to 6 carbon atoms, and their examples include, for example, cyclopropyl, cyclobutyl, cyclopentyl and cyclohexyl.

The alkoxy is preferably those of 1 to 4 carbon atoms, and their examples include, for example, methoxy, ethoxy, n-propoxy, i-propoxy, n-butoxy, i-butoxy and t-butoxy.

The aryl includes, for example, phenyl and naphthyl.

The heterocyclic ring includes those similar to the heterocyclic rings mentioned above for $R^3$, etc.

The acyl is preferably those of 1 to 6 carbon atoms, more preferably those of 1 to 4 carbon atoms, and includes, for example, formyl, acetyl, propionyl, butyryl, isobutyryl, valeryl, isovaleryl, pivaloyl and hexanoyl.

The aralkyl includes, for example, benzyl, phenethyl, and phenyl-propyl.

The alkenyl includes, for example, those similar to the alkenyl mentioned above for $R^3$, etc.

The amino acid residue includes, for example, those similar to the amino acid residues mentioned above for $R^5$.

The substituent groups in each of the above groups exist preferably in number of 1 to 3.

Especially, a group of the formula:

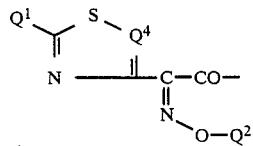

wherein $Q^1$ is amino or a protected amino group, and $Q^2$ is H, alkyl, alkenyl, a group $-CH_2COOQ^3$ or a group

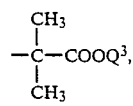

wherein $Q^3$ is H or alkyl*, and $Q^4$ is $-CH=$ or $N=$, is more preferable as the acyl moiety of the acylamino for $R^1$. The said alkyl, alkyl* and alkenyl are those mentioned above. The protective group in the said protected amino group includes those mentioned above.

Or a group of the formula;

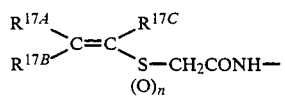

wherein $R^{17A}$, $R^{17B}$ and $R^{17C}$ independently stand for hydrogen, halogen, cyano or carbamoyl, and n denotes an integer of 0, 1 or 2, included in the group of the formula: $R^{17}-R^{18}-CH_2-CO-NH$ mentioned above.

The halogen shown by $R^{17A}$, $R^{17B}$ and $R^{17C}$ is exemplified by fluorine, chlorine, bromine or iodine.

The carbamoyl shown by $R^{17A}$, $R^{17B}$ and $R^{17C}$ may have one or two substituents as exemplified by a lower ($C_{1-6}$)alkyl, optionally substituted phenyl or aralkyl (benzyl, phenethyl, etc.) or may form an N-containing 5- to 7-membered ring (pyrrolidine, piperidine, morpholine, N-methylpiperazine, hexamethyleneimine, etc.) together with the nitrogen atom of carbamoyl.

The sulphur atom may be in the form of sulfide (n=0), sulfoxide (n=1) or sulfone (n=2).

The substituted ethylene may take the form of a geometrical isomer depending on the state of substitution and substituents, and, in that case, the isomer may be E- or Z-isomer.

Among the groups mentioned above, those having substituents at one or two of $R^{17A}$, $R^{17B}$ and $R^{17C}$ are preferable. Preferable substitueents are a combination of one or two halogens (especially chlorine), one halogen (especially fluorine) and one carbamoyl (especially unsubstituted carbamoyl), one cyano, etc.

Also, those wherein either one of $R^{17A}$ and $R^{17B}$ is carbamoyl and the other is fluorine, and when $R^{17C}$ is H, $R^{17A}$ is carbamoyl and $R^{17B}$ is fluorine (Z-isomer) are preferable.

As the sulphur atom, sulfide (n=0) is especially preferable.

Referring to X mentioned above, as the optionally substituted alkyl as represented by X are mentioned straight-chain or branched lower alkyl groups, preferably those of 1 to 6 carbon atoms, which are exemplified by methyl, ethyl, propyl, i-propyl, butyl, i-butyl, sec-butyl, t-butyl, pentyl and hexyl. These alkyl groups may be substituted, and the substituent is examplified by hydroxy (primary, secondary, tertiary), substituted hydroxy-carbonyl (benzhydryloxycarbonyl, benzyloxycarbonyl, etc.), substituted carbonyloxy (lower alkanoyloxy, aminocarbonyloxy, acylaminocarbonyloxy, etc.), lower($C_{1-4}$)alkyl sulfonyloxy, azido, etc.

Examples of the alkylthio in which sulfur atom is oxidized, as represented by X, include a lower($C_{1-4}$)alkylthio. The sulfur atom may have 1 or 2 oxygen atoms. These alkylthio groups are exemplified by methylthio, ethylthio, methylsulfinyl, methylsulfonyl, etc.

When X cooperates with the adjacent carbon atom to form a double bond, formation of the double bond with the adjacent carbon atom on the isoxazole ring (endo double bond) and formation of the double bond with the adjacent carbon atom on $R^1$ (exo double bond) are mentioned.

In the above acyl groups, specific examples of the acylamino group as represented by the formula

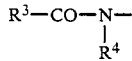

include for example, 3-(2,6-dichlorophenyl)-5-methylisoxazol-4-yl-carbonylamino, 4-ethyl-2,3-dioxo-1-piperazino-carbonylamino, 3-phenyl-5-methylisoxazole-4-yl-carbonylamino, 3-(2-chloro-phenyl)-5-methylisoxazole-4-yl-carbonylamino, 3-(2-chloro-6-fluorophenyl)-5-methylisoxazole-4-yl-carbonylamino, nicotinylamino, benzoylamino, 4-bromobenzoylamino, 2,6-dimethoxybenzoylamino, formylamino, acetylamino, propionylamino, butyrylamino, isobutyrylamino, pivaloylamino, methoxycarbonylamino, benzyloxycarbonylamino, 1-aminocyclohexylcarbonylamino, 2-amino-cyclohexylcarbonylamino, 3-ethoxynaphthoylamino, 2-(2-amino-4-thiazolyl)-2-ethylideneacetylamino, 2-(2-amino-4-thiazolyl)-2-chloromethyleneacetylamino, phthalimido, succinimido, 1,2-cyclohexanedicarboximide, 2-(trimethylsilyl)ethoxycarbonylamino, 2,2-dimethyl-5-oxo-4-phenylimidazolidine and 4-(carbamoylcarboxymethylene)-1,3-dithiethane-2-yl-carbonylamino.

Specific examples of the acylamino group represented by the formula

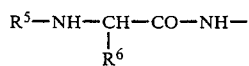

include, for examples, D-alanylamino, benzyl-N-carbobenzoxy-γ-D-glutamyl-D-alanylamino, D-phenylglycyl-D-alanylamino, N-carbobenzoxy-D-alanylamino, N-carbobenzoxy-D-phenylglycylamino, D-alanyl-D-phenylglycylamino, γ-D-glutamyl-D-alanylamino, 2-(4-ethyl-2,3-dioxo-1-piperazinocarboxamido)-2-phenylacetylamino, 2-(4-cyclohexyl-2,3-dioxo-1-piperazinocarboxamido)-2-phenylacetylamino, 2-(4-ethyl-2,3-dioxo-1-piperazinocarboxamido)-2-(4-sulfoxyphenyl)acetylamino, N-(4-ethyl-2,3-dioxo-1-piperazinocarbonyl)-D-alanylamino, N-(4-ethyl-2,3-dioxo-1-piperazinocarbonyl)-D-phenylglycylamino, 2-[(2-amino-4-thiazolyl)-2-(4-ethyl-2,3-dioxo-1-piperazinocarboxamido)acetylamino, 2-(4-hydroxy-6-methylnicotinamido)-2-phenylacetylamino, 2-(4-hydroxy-6-methylnicotinamido)-2-(4-hydroxyphenyl)acetylamino, 2-{5,8-dihydro-2-(4-formyl-1-piperazinyl)-5-oxopyrido[2,3-d]pyrimidine-6-carboxamido}-2-phenylacetylamino, 2-(3,5-dioxo-1,2,4-triazine-6-carboxamido)-2-(4-hydroxyphenyl)acetylamino, 2-(3-furfurylideneamino-2-oxoimidazolidine-1-carboxamido)-2-phenylacetylamino, 2-(coumarin-3-carboxamido)-2-phenylacetylamino, 2-(4-hydroxy-7-methyl-1,8-naphthylidene-3-carboxamido)-2-phenylacetylamino, 2-(4-hydroxy-7-trifluoromethylquinoline-3-carboxamido)-2-phenylacetylamino, N-[2-(2-amino-4-thiazolyl)acetyl]-D-phenylglycylamino, 2-(6-bromo-1-ethyl-1,4-dihydro-4-oxothieno[2,3-b]pyridine-3-carboxamido)-2-phenylacetylamino, 2-(4-ethyl-2,3-dioxo-1-piperazinocarboxamido)-2-thienylacetylamino, 2-(4-n-pentyl-2,3-dioxo-1-piperazinocarboxamido)-2-thienylacetylamino, 2-(4-n-octyl-2,3-dioxo-1-piperazinocarboxamido)-2-thienylacetylamino, 2-(4-cyclohexyl-2,3-dioxo-1-piperazinocarboxamido)-2-thienylacetylamino, 2-[4-(2-phenylethyl)-2,3-dioxo-1-piperazinocarboxamido]-2-thienylacetylamino, 2-(3-methylsulfonyl-2-oxoimidazolidine-1-carboxamido)-2-phenylacetylamino, 2-(3-furfurylideneamino-2-oxoimidazolidine-1-carboxamido)-2-(4-hydroxyphenyl)acetylamino, 2-(4-ethyl-2,3-dioxo-1-piperazinocarboxamido)-2-(4-benzyloxyphenyl)acetylamino, 2-(4-ethyl-2,3-dioxo-1-piperazinocarboxamido)-2-(4-methoxyphenyl)acetylamino, 2-(8-hydroxy-1,5-naphthylidine-7-carboxamido)-2-phenylacetylamino, 2-(2-amino-4-thiazolyl)-2-formamidoacetylamino, 2-(2-amino-4-thiazolyl)-2-acetoamidoacetylamino, 2-phenyl-ureidoacetylamino, 2-phenyl-2-sulfoureidoamino, 2-theinyl-2-ureidoacetylamino, 2-amino-3-sulfamoylpropionylamino, 2-amino-2-(1H-indole-3-yl)acetylamino, 2-amino-2-(3-benzo[b]thienyl)acetylamino, 2-amino-2-(2-naphthyl)acetylamino, D-phenylglycyl, D-2-amino-(4-hydroxyphenyl)acetylamino, D-2-amino-2-(1,4-cyclohexadienyl)acetylamino, D-2-amino-2-(1-cyclohexenyl)acetylamino, D-2-amino-2-(3-chloro-4-hydroxyphenyl)acetylamino, 2-hydroxymethylamino-2-phenylacetylamino, 2-(1-cyclohexenyl)-2-(4-ethyl-2,3-dioxo-1-piperazinocarboxamido)acetylamino, N-[2-(4-ethyl-2,3-dioxo-1-piperazinocarbonyl)]-D-threonylamino, 2-guanylcarboxamido-2-phenylacetylamino, 2-(4-ethyl-2,3-dioxo-1- piperazinocarboxamido-2-(3,4-dihydroxyphenyl-)acetylamino, 2-(4-carboxy-5-imidazolylcarboxamido)-2-phenylacetylamino and 2-amino-2-(3-methylsulfonamidophenyl)acetylamino.

Specific examples of the acylamino group represented by the formula R⁸—R⁹—CO—NH— include, for example, N-[2-(2-amino-4-thiazolyl)-2-methoxyiminoacetyl]-D-alanylamino, N-[2-(2-amino-4-thiazolyl)-2-methoxyiminoacetyl]-D-phenylglycylamino, 2-(2-amino-4-thiazolyl)-2-[2-(2-amino-4-thiazolyl)-2-methoxyiminoacetamido]acetylamino, 2-(2-chloroacetamido-4-thiazolyl)-2-methoxyiminoacetylamino, 2-(2-amino-4-thiazolyl)-2-methoxyiminoacetylamino, 2-(2-amino-4-thiazolyl)-2-ethoxyiminoacetylamino, 2-(2-amino-4-thiazolyl)-2-isopropoxyiminoacetylamino, 2-(2-amino-4-thiazolyl)-2-butoxyiminoacetylamino, 2-(2-amino-4-thiazolyl)-2-cyclopropylmethyloxyiminoacetylamino, 2-(2-amino-4-thiazoly)-2-benzyloxyiminoacetylamino, 2-(2-amino-4-thiazolyl)-2-allyloxyiminoacetylamino, 2-(2-amino-4-thiazolyl)-2-[(1-methyl-1-carboxyethyl)oxyimino]acetylamino, 2-(2-amino-4-thiazolyl)-2-[(1-methyl-1-methoxycarbonylethyl)oxyimino]acetylamino, 2-(2-amino-4-thiazolyl)-2-carboxymethyloxyiminoacetylamino, 2-(2-amino-4-thiazolyl)-2-carboxyvinyloxyiminoacetylamino, 2-(2-amino-4-thiazolyl)-2-carboxyethyloxyiminoacetylamino, 2-(2-amino-4-thiazolyl)-2-methoxycarbonylethyloxyiminoacetylamino, 2-(2-amino-5-chloro-4-thiazolyl)-2-methoxyiminoacetylamino, 2-(2-amino-5-bromo-4-thiazolyl)-2-methoxyiminoacetylamino, 2-(2-amino-4-thiazolyl)-2-oxyiminoacetylamino, 2-thienyl-2-methoxyiminoacetylamino, 2-furfuryl-2-methoxyiminoacetylamino, 2-(1,2,4-thiadiazole-3-yl)-2-methoxyiminoacetylamino, 2-(1,2,4-thiadiazole-5-yl)-2-methoxyiminoacetylamino, 2-(1,3,4-thiadiazolyl)-2-methoxyiminoacetylamino, 2-(4-hydroxyphenyl)-2-methoxyiminoacetylamino, 2-phenyl-2-methoxyiminoacetylamino, 2-phenyl-2-oxyiminoacetylamino, 2-[4-(γ-D-glutamyloxy)phenyl]-2-oxyiminoacetylamino, 2-[4-(3-amino-3-carboxypropoxy)phenyl]-2-oxyiminoacetylamino, 2-thienyl-2-oxyiminoacetylamino, 2-(5-amino-1,2,4-thiadiazole-3-yl)-2-methoxyiminoacetylamino, 2-(5-amino-1,2,4-thiadiazole-3-yl)-2-ethoxyiminoacetylamino, 2-(5-amino-1,2,4-thiadiazole-3-yl)-2-carboxymethyloxyiminoacetylamino, 2-(5-amino-1,2,4-thiadiazole-3-yl)-2-[(1-methyl-1-carboxyethyl)oxyimino]acetylamino, 2-(2-amino-4-thiazolyl)-2-(2-amino-2-carboxy)ethyloxyiminoacetylamino, 2-(2-amino-4-thiazolyl)-2-(dimethylamidomethyloxyimino)acetylamino, 2-(2-amino-4-thiazolyl)-2-(3,4-diacetoxy-benzoyloxyimino)acetylamino, 2-(2-amino-4-thiazolyl)-2-(1-carboxycyclopropyloxyimino)acetylamino, 2-(2-amino-4-thiazolyl)-2-(1-carboxycyclobutyloxyimino)acetylamino, 2-(2-amino-4-thiazolyl)-2-(2-imidazolylmethyloxyimino)acetylamino, 2-(2-amino-4-thiazolyl)-2-(2-methyl-4-nitro-1-imidazolylethyloxyimino)acetylamino, 2-(2-amino-4-thiazolyl)-2-(3-pyrazolylmethyloxyimino)acetylamino, 2-(2-amino-4-thiazolyl)-2-(1H-tetrazole-5-yl-methyloxyimino)acetylamino, 2-(2-amino-4-thiazolyl)-2-(2-oxo-3-pyrrolidinyloxyimino)acetylamino, 2-[2-(2-amino-2-carboxyethylthio)]-4-thiazolyl-2-methoxyiminoacetylamino, and 2-(2-thioxo-4-thiazolidinyl)-2-methoxyiminoacetylamino.

Specific examples of the acylamino group represented by the formula

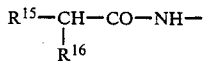

include, for example, 2-phenyl-2-sulfoacetylamino, 2-hydroxy-2-phenylacetylamino, 2-phenyl-2-sulfamoylacetylamino, 2-carboxy-2-phenylacetylamino, 2-(4-hydroxyphenyl)-2-carboxyacetylamino, 2-phenoxycarbonyl-2-phenylacetylamino, 2-phenyl-2-tolyloxycarbonylacetylamino, 2-(5-indanyloxycarbonyl)-2-phenylacetylamino, 2-formyloxy-2-phenylacetylamino, 2-alanyloxy-2-phenylacetylamino, 2-carboxy-2-thienylacetylamino, 2-(2-methylphenoxycarbonyl)-2-thienylacetylamino, 2-(2-amino-4-thiazolyl)-2-hydroxyacetylamino and 2-[4-(2-amino-2-carboxyethoxycarboxamido)phenyl]-2-hydroxyacetylamino.

Specific examples of the acylamino group represented by the formula R¹⁷—R¹⁸—CH₂—CO—NH— include, for example, cyanoacetylamino, phenylacetylamino, phenoxyacetylamino, trifluoromethylthioacetylamino, cyanomethylthioacetylamino, difluoromethylthioacetylamino, 1H-tetrazolyl-1-acetylamino, thienylacetylamino, 2-(2-amino-4-thiazolyl)acetylamino, 4-pyridylthioacetylamino, 2-thienylthioacetylamino, 3,5-dichloro-1,4-dihydro-4-oxopyridine-1-acetylamino, 2-carboxyvinylthioacetylamino, 2-(2-aminomethylphenyl)acetylamino, 2-chloroacetylamino, 3-aminopropionylamino, (2-amino-2-carboxy)ethylthioacetylamino, 4-amino-3-hydroxybutyrylamino, 2-carboxyethylthioacetylamino, 2-benzyloxycarbonylaminoacetylamino, 2-carbamoyl-2-fluorovinylthioacetylamino, 2-chlorovinylthioacetylamino, 2,2-dichlorovinylthioacetylamino, 1,2-dichlorovinylacetylamino, 2-cyanovinylthioacetylamino, 2,2-dichlorovinylsulfonylacetylamino, 2-(1-isopropylamino-1-isopropyliminomethylthio)acetylamino, 2-[1-(2-dimethylaminoethyl)-1H-tetrazole-5-yl-thio]acetylamino, 2-(1-methyl-1,3,5-triazole-2-yl)acetylamino, and 2-(4-cyano-3-hydroxy-5-isothiazolylthio)acetylamino.

Specific examples of the group represented by the formula

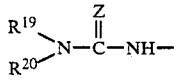

include, for example, carbamoylamino, methylaminocarbonylamino, ethylaminocarbonylamino, t-butylaminocarbonylamino, isobutylaminocarbonylamino, dimethylaminocarbonylamino, 2-methylphenylaminocarbonylamino, phenylaminocarbonylamino, 3-chlorophenylaminocarbonylamino, 4-nitrophenylaminocarbonylamino, 4-bromophenylaminocarbonylamino, thiocarbamoylamino, methylaminothiocarbonylamino, ethylaminothiocarbonylamino, phenylaminothiocarbonylamino, dimethylaminocarbonylamino and 3-fluorophenylaminocarbonylamino.

Specific examples of the group represented by the formula R²¹—NH— include, for example, methylamino, ethylamino, allylamino, cyclohexylamino, cylcohexylmethylamino, benzylamino, 4-chlorobenzylamino, phenylamino, 2-imidazolylamino, 1-methyl-2-imidazolylamino, 2-(2-amino-4-thiazolyl)-2-methoxyiminothioacetylamino, 1-benzyl-4-pyridiniumamino, and 2-acetyl-1-methlvinylamino.

Specific examples of the alkylamino group represented by the formula

include, for example, dimethylamino, diethylamino, dipropylamino, dibenzylamino, dicyclohexylamino, N-benzyl-N-methylamino, diallylamino, N-phenyl-N-methylamino, pyrrolidinyl, piperidinyl, piperazinyl and morpholinyl.

Specific examples of the alkylamino group represented by the formula

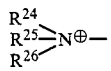

include, for example, trimethylammonium, triethylammonium, tribenzylammonium, benzyldimethylammonium, methylpyrrolidinium and methylpiperidinium.

Specific examples of the alkenylamino group represented by the formula

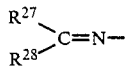

include, for example, dimethylaminomethyleneamino, 1-dimethylaminoethylideneamino, hexahydro-1H-azepine-1-yl-methyleneamino, 1-(N-benzyl-N-methylamino)ethylideneamino, 4-dimethylaminobenzylideneamino, (p-nitro)benzylideneamino and benzylideneamino.

Specific examples of the thioamino group represented by the formula $R^{29}$—$SO_n$—NH— include, for example, benzenesulfonylamino, 4-methylbenzenesulfonylamino, 4-methoxybenzenesulfonylamino, 2,4,6-trimethylbenzenesulfonylamino, benzylsulfonylamino, 4-methylbenzylsulfonylamino, trifluoromethylsulfonylamino, phenacylsulfonylamino, methylsulfonylamino, ethylsulfonylamino, 4-fluorobenzenesulfonylamino, benzenesulfinylamino, 2-nitrobenzenesulfinylamino, 2,4-dimethylbenzenesulfinylamino, 4-chlorobenzenesulfinylamino, 4-methoxybenzenesulfinylamino, phenylthioamino, 2,4-dinitrophenylthioamino, triphenylmethylthioamino and 2-nitro-4-methoxyphenylthioamino.

Specific examples of the silylamino group represented by the formula

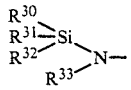

include, for example, trimethylsilylamino, triethylsilylamino, t-butyldimethylsilylamino, t-butyldiphenylsilylamino, isopropyldimethylsilylamino, triphenylsilylamino, triisopropylsilylamino, tribenzylsilylamino, (triphenylmethyl)dimethylsilylamino, and 2,2,5,5-tetramethyl-2,5-disilylazacyclopentane.

Specific examples of the group represented by the formula

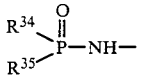

include, for example, dimethylphosphoamino, diethylphosphoamino, diphenylphosphoamino, dibenzylphosphoamino, and di-4-chlorophenylphosphoamino.

Specific examples of the group represented by the formula $R^{36}$—CO—CO—NH— include, for example, methoxalylamino, ethoxalylamino, phenoxalylamino, benzyloxalylamino, pyruvoylamino, ethyloxalylamino, oxamoylamino, benzylaminooxalylamino, thienyloxalylamino, 2-amino-4-thiazolyloxalylamino and ethylaminooxalylamino.

Specific examples of the group represented by the formula —$COOR^{37}$ include, for example, methyl ester, ethyl ester, n-propyl ester, isopropyl ester, t-butyl ester, t-amyl ester, benzyl ester, 4-bromobenzyl ester, 4-nitrobenzyl ester, 2-nitrobenzyl ester, 3,5-dinitrobenzyl ester, 4-methoxybenzyl ester, benzhydryl ester, phenacyl ester, 4-bromophenacyl ester, phenyl ester, 4-nitrophenyl ester, methoxymethyl ester, methoxyethoxymethyl ester, ethoxymethyl ester, benzyloxymethyl ester, acetoxymethyl ester, pivaloyloxymethyl ester, 2-methylsulfonylethyl ester, 2-trimethylsilylethyl ester, methylthiomethyl ester, trityl ester, 2,2,2-trichloroethyl ester, 2-iodoethyl ester, cyclohexyl ester, cyclopentyl ester, allyl ester, cinnamyl ester, 4-picolinyl ester, 2-tetrahydropyranyl ester, 2-tetrahydrofuranyl ester, trimethylsilyl ester, t-butyldimethyl silyl ester, t-butyldiphenylsilyl ester, acetylmethyl ester, 4-nitrobenzoylmethyl ester, 4-mesylbenzoylmethyl ester, phthalimidomethyl ester, propionyloxymethyl ester, 1,1-dimethylpropyl ester, 3-methyl-3-butenyl ester, succinimidomethyl ester, 3,5-di-t-butyl-4-hydroxybenzyl ester, mesylmethyl ester, benzenesulfonylmethyl ester, phenylthiomethyl ester, iminomethylaminoethyl ester, 1-iminoethylaminoethyl ester, dimethylaminoethyl ester, pyridine-1-oxido-2-methyl ester, methylsulfinylmethyl ester, bis-(4-methoxyphenyl)methyl ester, 2-cyano-1,1-dimethylethyl ester, t-butyloxycarbonylmethyl ester, benzoylaminomethyl ester, 1-acetoxyethyl ester, 1-isobutyryloxyethyl ester, 1-ethoxycarbonyloxyethyl ester, phthalide ester, 4-t-butylbenzyl ester, 5-indanyl ester, 5-methyl-2-oxo-1,3-dioxolene-4-yl-methyl ester, and 5-t-butyl-2-oxo-1,3-dioxolene-4-yl-methyl ester.

Specific examples of the group represented by the formula

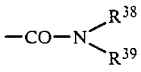

include, for example, dimethylamide diethylamide, dipropylamide, dibenzylamide, dicyclohexylamide, N-benzyl-N-methylamide, diallylamide, N-phenyl-N-methylamide, pyrrolidineamide, piperidineamide, piperazineamide, morpholineamide, carboxymethylamide and 1-carboxyethylamide.

The reaction, which involves reacting the compound (III) with a compound capable of introducing the organic residue bonded through nitrogen, includes, for example, acylation, ureidization (thioureidization), alkylation, alkenylation, thionation, silylation and phosphorylation reactions.

Acylation

Acylation of the amino group can be carried out by reacting a starting compound with an acylating agent containing the acyl group in the group $R^1$, such as a reactive derivative of carboxylic acid, in a solvent. As the reactive derivative of carboxylic acid, there are used, for example, acid halides, acid anhydrides, amide compounds, active esters or active thioesters, and specific examples of such a reactive derivative are to be mentioned in the following.

(1) Acid halides:

As the acid halide as employed herein, there are used, for example, acid chlorides, or acid bromides.

(2) Acid anhydrides:

As the acid anhydride as employed herein, there are used, for example, mono alkyl carbonic acid mixed acid anhydrides, mixed acid anhydrides comprising aliphatic carboxylic acids (e.g., acetic acid, pivalic acid, valeric acid, isovaleric acid, trichloroacetic acid, etc.), mixed acid anhydrides comprising aromatic carboxylic acids (e.g., benzoic acid, etc.) or symmetric type acid anhydrides.

(3) Amide compounds:

As the amide compound as employed herein, there are used, for example, compounds having an acyl group attached to the nitrogen in the ring, such as pyrazole, imidazole, 4-substituted imidazoles, dimethylpyrazole and benzotriazole.

(4) Active esters:

As the active ester, there are used, for example, esters such as methyl esters, ethyl esters, methoxymethyl esters, propargyl esters, 4-nitrophenyl esters, 2,4-dinitrophenyl esters, trichlorophenyl esters, pentachlorophenyl esters and mesylphenyl esters as well as esters formed with 1-hydroxy-1H-2-pyrrolidone, N-hydroxysuccinimide or N-hydroxyphthalimide, etc.

(5) Active thioesters:

As the active thioester, there are used, for example, thioesters formed with heterocyclic thiols, such as 2-pyridylthiol or 2-benzothiazolylthiol.

Various kinds of reactive derivatives as described above are selected depending upon the type of carboxylic acids.

This reaction is in some instances carried out in the presence of a base, whereupon as the suitable base, there are used, for example, aliphatic tertiary amines (e.g., trimethylamine, triethylamine, tripropylamine, tri-n-butylamine, etc.), tertiary amines such as N-methylpiperidine, N-methylpyrrolidine, cyclohexyldimethylamine and N-methylmorpholine, alkylamines such as di-n-butylamine, diisobutylamine and dicyclohexylamine, aromatic amines such as pyridine, lutidine and γ-collidine, hydroxides or carbonates of alkali metals such as lithium, sodium and potassium, or hydroxides or carbonates of alkaline earth metals such as calcium and magnesium, etc.

In this procedure, the reactive derivative of carboxylic acid is normally used at a ratio of about 1 mole per mole of the compound (III), but can also be employed in excess, unless it affects adversely the reaction. In the case of a base being used, the amount of such base to be used is normally about 1 to 30 moles per mole of the compound (III), preferably about 1 to 10 moles, varying with the types of the starting compound (III) used and reactive derivative of carboxylic acid employed and other reaction conditions. This reaction is carried out normally in a solvent. As the said solvent, there are used conventional solvents, either alone or as a mixture, for example, ethers such as dioxane, tetrahydrofurane, diethyl ether, diisopropyl ether, propylene oxide and butylene oxide, esters such as ethyl acetate and ethyl formate, halogenated hydrocarbons such as chloroform, dichloromethane 1,2-dichloroethane and 1,1,1-trichloroethane, hydrocarbons such as benzene, toluene and n-hexane, amides such as N,N-dimethylformamide and N,N-dimethylacetamide, or nitriles such as acetonitrile. In the above mentioned bases, the liquid ones can also be used to allow them to serve dual purposes of the base and solvent. The reaction temperature is not specifically limited, as far as the reaction proceeds, but the reaction is conducted normally at about −50° C. to 150° C., preferably about −30° C. to 80° C.. The reaction goes to termination normally within several ten minutes to several ten hours, varying with the types of used starting compounds and base, the reaction temperature and the kind of solvent but it in some instances requires several ten days.

Ureido formation (thioureido formation)

The reaction of converting the amino group into the ureido or thioureido group is carried out by reacting the starting compound with a substituted isocyanate or isothiocyanate containing a group represented by the above-described formula

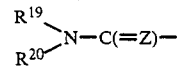

(wherein $R^{19}$, $R^{20}$ and Z are as defined hereinbefore) in the presence of a solvent. As the said substituted isocyanate, there are used, for example, methyl isocyanate, ethyl isocyanate, phenyl isocyanate or p-bromophenyl isocyanate, while as the substituted isothiocyanate, there are employed, for example, methyl isothiocyanate or phenyl isothiocyanate. In this reaction, the substituted isocyanate or substituted isothiocyanate is normally used at a ratio of about 1 mole per mole of the compound (III), but can also be employed in excess, unless it affects adversely the reaction. As the suitable solvent, there are used, for example, tetrahydrofurane, diethyl ether, ethyl acetate, chloroform, dichloromethane or toluene. The reaction temperature is in the range of about −20° C. to 50° C., and the reaction time ranges normally from about 10 minutes to 5 hours.

Alkylation

The reaction of combining the amino group of the compound (III) with a group bonded through carbon is to be described below as alkylation.

The alkylated derivative of the compound (III) can be prepared by reacting the compound (III) with an alkylating agent containing a group bonded to the relevant nitrogen of the group $R^1$ through carbon. As the alkylating agent, there are used, for example, halogenated alkyl compounds such as propyl chloride, butyl chloride, benzyl chloride, butyl bromide benzyl bromide, allyl bromide, methyl iodide, ethyl iodide and propyl iodide, dialkyl sulfate compounds such as dimethyl sulfate and diethyl sulfate, substituted sulfonate compounds such as methyl mesylate, ethyl mesylate, methyl tosylate and ethyl tosylate, or dihalogenated alkyl compounds (e.g., 1,5-dichloropentane, 1,4-dichlorobutane, etc.). This reaction is normally carried out in a solvent, whereupon examples of the solvent usable include, for example, water, methanol, ethanol, benzyl alcohol, benzene, dimethylformamide, tetrahydrofurane or acetonitrile. The temperature of this reaction is about 20° C. to 200° C., while the reaction time ranges from about 30 minutes to 50 hours. This reaction, by changing the reaction conditions, such as a molar ratio of the compound (III) to the alkylating agent, permits selective production of a secondary amine, tertiary amine or quaternary amine compound. It is also possible to introduce different substituent groups into the nitrogen, by conducting the reaction in stepwise The reaction of introducing a group bonded through carbon other than alkyl groups can be carried out by procedures comparable to the above one.

Alternatively, the said alkylation can also be conducted by combining the compound (III) with a carbonyl compound in the presence of a reducing agent. Examples of the reducing agent which is useful in this reaction include lithium aluminum hydride, sodium cyanoborohydride, sodium borohydride, sodium, sodium amalgam and combinations of zinc with acids. Also, the reaction can be carried out through catalytic reduction using for example palladium, platinum and rhodium as a catalyst. The reaction of converting the amino group into a group represented by $R^{21}$—NH— (imino-substituted alkylamino, alkylimino-substituted alkylamino or substituted guanidino group):

The reaction of converting the amino group into an imino-substituted alkylamino or alkylimino-substituted alkylamino group is carried out by reacting the starting compound for example with imidoesters in a solvent such as dioxane, tetrahydrofurane, dimethylformamide, chloroform, acetone, acetonitrile and water. As the suitable imidoesters, there are used, for example, methyl formimidate, ethyl formimidate, benzyl formimidate, methyl acetoimidate, ethyl acetoimidate, methylphenyl acetoimidate, ethyl N-methylformimidate, methyl N-ethylformimidate or methyl N-isopropylformimidate. The reaction temperature is in the neighborhood of 0° C. to 25° C., while the reaction time ranges normally from 1 to 6 hours. The reaction of converting the amino group into guanidino group is conducted by reacting the starting compound, for example, with O-alkyl- or O-aryl pseudourea or S-alkyl- or S-aryl pseudothioureas in a solvent, such as water, dimethylformamide and hexamethylphosphoramide. As the above pseudoureas, there are used, for example, O-methyl pseudourea, O-2,4-dichlorophenyl pseudourea or O-N,N-trimethyl pseudourea, while as the above pseudothioureas, there are employed, for example, S-p-nitrophenyl pseudothiourea. The reaction temperature is in the neighborhood of 0° to 40° C., while the reaction time is normally in the range of 1 to 24 hours.

Alkenylation (imination):

Alkenylation (imination) of the compound (III) can be carried out by dehydration condensation of the compound (III) with a carbonyl compound. This reaction proceeds in the absence of solvent, but can also be carried out in a solvent. Acid or base is in some instances used as a catalyst. The objective compound can also be prepared by heating under reflux the compound (III) and a carbonyl compound in the presence of a dehydrating agent or with use of a dehydration apparatus such as Dean-Stark. The solvent, which is usable in this reaction, includes, for example, benzene, toluene, dichloromethane or ethanol. The reaction temperature ranges from about 0° C. to 200° C., while the reaction time ranges from about 1 hour to 20 hours. The acid, which is used as a catalyst, includes, for example, benzenesulfonic acid, methanesulfonic acid, sulfuric acid, boron trifluoride and zinc chloride, while the base includes, for example, potassium hydroxide, and sodium carbonate. The dehydrating agent, which is useful in this reaction, includes, for example, molecular sieves, silica gel, anhydrous magnesium sulfate and anhydrous sodium sulfate.

Thionation:

The thionation reaction for the compound (III) is normally carried out by reacting the compound (III) with a halogenated thio compound (e.g., halogenated sulfonyl, halogenated sulfinyl, halogenated sulfenyl, etc.) containing a group represented by the formula $R^{29}$—SOn— (wherein $R^{29}$ and n are as defined hereinbefore) in a solvent in the presence of a base. The solvent, which is used in this reaction, includes, for example, water, acetone, dioxane, dimethylformamide, benzene, tetrahydrofurane, dichloromethane, or solvent mixtures thereof. As the base, there are used, for example, organic bases, such as pyridine, picoline, triethylamine, isopropylamine and N-methylmorpholine, and inorganic bases, such as sodium hydroxide, potassium hydroxide, sodium carbonate, sodium hydrogencarbonate, and potassium carbonate. This reaction normally requires about equivalent of the halogenated thio compound and about 1 to 10 equivalents of the base to be used against the compound (III), whereby the reaction temperature is about $-20°$ C. to 80° C. and the reaction time ranges from 15 minutes to 10 hours.

This reaction is also conducted using a thioacid anhydride (e.g., toluenesulfonic anhydride, trifluoromethanesulfonic anhydride, etc.) in place of the halogenated thio compound. Also, this reaction can be carried out by reacting the starting compound with a thionating reagent such as N-sulfonyl-N-methylpyrrolidinium, N-sulfonylimidazolide or N-sulfonyl-1H-1,2,4-triazolide.

Silylation:

The silylation reaction for the compound (III) can be carried out normally by reacting the compound (III) with a halogenated silyl compound (e.g., silyl chloride compounds, silyl bromide compounds, etc.) containing a group represented by the formula

or $R^{33}$ (wherein $R^{30\text{-}33}$ are as defined hereinbefore) in the presence of a base. The said base includes for example, organic bases such as pyridine, picoline, triethylamine, diisopropylamine and N-methylmorpholine. The reaction is preferably carried out in a solvent, whereby the said solvent includes, for example, acetone, dioxane, dimethylformamide, benzene, tetrahydrofurane and dichloromethane. The reaction temperature is about $-20°$ C. to the boiling point of the solvent used, or about $-20°$ C. to 80° C., while the reaction time ranges from about 15 minutes to 20 hours.

Phosphorylation

The phosphorylation reaction for the compound (III) is normally carried out by reacting the compound (III) with an approximately equimolar amount of a phosphoryl chloride (e.g., dimethylphosphoryl chloride, diethylphosphoryl chloride, diphenylphosphoryl chloride, dibenzylphosphoryl chloride, etc.) containing a group represented by the formula

(wherein $R^{34}$ and $R^{35}$ are as defined hereinbefore) in a solvent in the presence of an approximately equimolar or excessive amount of a base. As the base, there are used, for example, organic bases such as pyridine, picoline, triethylamine and N-methylmorpholine, and inorganic bases, such as sodium hydroxide, potassium hydroxide, sodium hydrogencarbonate and sodium carbonate. As the solvent, there are employed, for example, either alone or as a solvent mixture, water, acetone, acetonitrile, dioxane, dimethylformamide, tetrahydrofurane and dichloromethane. The reaction temperature is about $-20°$ C. to 80° C., while the reaction time ranges from 15 minutes to 15 hours.

The methoxylation reaction and formylamination reaction for the compound (IV) are described in the following.

Methoxylation

With reference to the methoxylation of the compound (IV), there can be applied the methoxylation methods for the 6-position or 7-position conventionally adopted in the fields of penicillin or cephalosporin. The methoxylation of penicillin or cephalosporin is described in detail, for example, by E. M. Gordon, R. B. Sykes, et. al. in "Chemistry and Biology of β-Lactam Antibiotics", vol. 1, p. 199 (1982), published by Academic Press, where the description is given on the methods of methoxylation through (1) a diazo intermediate, (2) alkylimine intermediate, (3) keteneimine or related imine intermediate, (4) quinoidoimine intermediate, (5) sulfeneimine intermediate, (6) eneimine intermediate, etc. Any of these methods can permit the production of the objective compound, and as their representative example, the detailed description is to be given to the method of methoxylation through an acylimine intermediate.

The methoxylation reaction for the compound (IV) is carried out by acting an alkali metal salt of methanol and a halogenating agent on the compound (IV) in the presence of methanol. As the alkali metal salt of methanol, there are used, for example, lithium methoxide, sodium methoxide and potassium methoxide, while as the halogenating agent, there are employed, for example, t-butyl hypochloride, N-chlorosuccinimide, N-bromosuccinimide, N-chloroacetamide, N-bromoacetamide, N-chlorobenzenesulfonamide, chlorine and bromine. This reaction is carried out in a solvent, and as the solvent, there are used, for example, tetrahydrofurane, dioxane, dichloromethane, chloroform, acetonitrile, methanol and dimethylformamide. This reaction is desirably carried out by dissolving or suspending the compound (IV) in the above-mentioned solvent and adding an alkali metal salt of methanol, methanol and an halogenating agent to the solution or suspension to allow the reaction to proceed. In this case, it is preferable to add not less than 1 mole of methanol, about 1 to 3.5 moles of an alkali metal salt of methanol and about 1 to 2 moles of a halogenating agent per mole of the compound (IV) to allow the reaction to proceed. The reaction proceeds at about $-80°$ C. to 30° C., and is suspended by making the reaction system acidic.

As the acid to be used for the suspension of the reaction, there are used, for example, formic acid, acetic acid or trichloroacetic acid. After the termination of the reaction, the excess of halogenating agent is removed for example by treatment with a reducing agent, such as sodium thiosulfate and trialkyl esters of phosphorous acid.

Formylamination

The formylamination is carried out by converting the compound (IV) into an imine derivative of the formula:

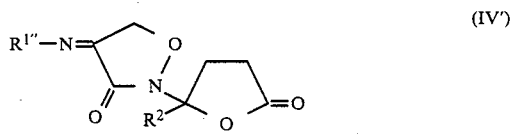

(IV')

[wherein $R^{1'''}$ is the moiety other than nitrogen in the organic residue ($R^1$) bonded through nitrogen; $R^2$ is as defined hereinbefore] and acting a nucleophilic derivative of formamide on it. The nucleophilic derivative of formamide includes, for example, N-silyl, N-stannyl and N-phosphorylformamide derivatives, and among others, the suitable one is N,N-bis(trimethylsilyl)formamide. The said formylamidation reaction is normally carried out in a solvent under an inert atmosphere of nitrogen, argon, etc., whereby the reaction temperature is about $-100°$ C. to $-20°$ C., preferably about $-80°$ C. to $-50°$ C., and the reaction time is about 10 minutes to 8 hours, preferably about 15 minutes to 2 hours. The solvent to be used may suitably be any aprotic solvent, and includes, for example, tetrahydrofurane, dimethylformamide, hexamethylphosphoramide or dioxane. Subsequent to the reaction, hydrolysis, with acid or base or treatment with metal ions such as ions of mercury, silver, thallium or copper, can be carried out to produce the formylamide group. It is added that the imine derivative (IV') can be produced by a procedure similar to the procedure as mentioned above (for the methoxylation) in the literature by E. M. Gordon, et. al.

The above-mentioned reaction, which involves reacting the compound (I; $R^2$ is carboxy) with a compound capable of introducing a group forming a group bonded to the carbon or oxygen atom of carboxy which is derivable from carboxy, yields a compound of the formula:

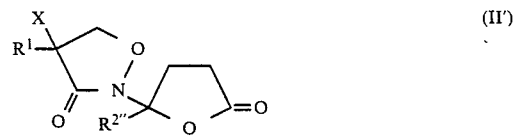

(II')

wherein $R^1$ is amino or an organic residue bonded through nitrogen; $R^{2''}$ is a group derivable from carboxy; X is hydrogen, methoxy or formylamino.

The reaction of the compound (I; $R^2$ is carboxy) with a compound capable of introducing a group bonded to the carbon or oxygen atom of carboxy which is derivable from carboxy is carried out, for example, by subjecting both compounds to an esterification or amidation reaction.

Synthesis of isocyano compound

Dehydration reaction of 4-formamido derivative of (I) is conducted by, for example, allowing trichloromethyl chloroformate to act on the 4-formamido derivative in an anhydrous non-polar solvent in the presence of a tertiary amine. As the solvent, use is made of dichloromethane, chloroform, dichloroethane, dioxane, tetrahydrofurane, acetonitrile, etc., singly or in a suitable combination thereof. As the tertiary amine, use is made of trimethylamine, triethylamine, tri-n-butylamine, N,N-dimethylcyclohexylamine, N,N-dimethylaniline, pyridine, quinoline, etc. This reaction is conducted by dissolving or suspending the starting compound in a solvent as mentioned above, to which are added tertiary amine then trichloromethyl chloroformate to thereby allow the reaction to undergo. Use of 2.1 mol. of tertiary amine and 0.5 mol. of trichloromethyl chloroformate relative to 1 mol. of the 4-formamido derivative is preferable. The reaction proceeds at a temperature range of from $-60°$ C. to $0°$ C. For preventing hydrolysis of the reaction product, the resulting reaction solution is preferably neutralized with a cold saturated aqueous solution of sodium hydrogen carbonate after completion of the reaction.

Synthesis of (I) by electrophilic substitution reaction

Electrophilic substitution reaction on the 4-isonitrile compound is conducted by first processing the isonitrile compound with a base in an organic solvent to cause formation of carbanion at $\alpha$-position of the isonitrile group, on which various electrophilic reagents are allowed to act. As the solvent, use is made of tetrahydrofurane, dimethyl sulfoxide, dichloromethane, benzene, dimethylformamide, methanol, ethanol, etc. As the base, use is made of n-butyl lithium, sodium hydroxide, sodium cyanide, lithium diisopropylamide, potassium carbonate, triethylamine, tri-n-butylamine, 1,8-diazabicyclo[5,4,0]undec-7-ene (DBU), etc. As the electrophilic reagent, use is made of relatively highly reactive-substituted lower alkyl halide such as benzyl bromide, phenacyl bromide, bromoacetic acid ester, etc., acrylic acid ester, methyl methanethiosulfonate. methoxycarbonyl disulfide, and lower oxoalkane such as acetone, aldehyde, etc. This reaction is preferably conducted by dissolving or suspending the 4-isonitrile compound in a solvent mentioned as above, then by adding thereto 0.5–2 mol. of a base and 1.0–1.5 mol. of an electrophilic reagent to allow the reaction to proceed. The reaction temperature is in the range from $-60°$ C. to $30°$ C., and the reaction time is within the range of from 0.5–3 hours. The substituent R of thus obtained compound can be further converted to another substituent. For example, methylthio group can be converted to a functional group such as methoxy, formamido, azido, etc. by processes similar to per se known ones, respectively. And, when R is hydroxymethyl, a number of derivatives through oxygen by the reaction with a variety of nucleophilic reagents. Among them, an active ester such as a sulfonic acid derivative can be converted to a variety of substituted methyl derivatives by the reaction of a nucleophilic reagent. As such substituted methyl derivatives are mentioned acyloxymethyl, carbomoyloxymethyl, methanesulfonyloxymethyl, permethyl of bromine, chlorine, iodine, etc., cyanomethyl, azidomethyl, aminomethyl, acylaminomethyl, etc.

Elimination reaction of isocyano group:

This elimination reaction of the isonitrile group can be conducted in the presence of reducing agent such as di(or tri)alkyltin hydride e.g. tri(normal or tert. butyl)-tin hydride, triaryl hydride e.g. triphenyltin hydride. The reaction is conducted in a nonprotonic solvent such as tetrahydrofurane, dimethylformamide, dioxane, benzene, toluene, etc. in the presence of a catalytic amount of azobisisobutyronitrile. The reaction temperature is not specifically limitative, but the reaction is conducted under cooling or under heating, and the reaction time ranges from 30 minutes to 3 hours. When the X of compound (I') obtained by this reaction is a hydroxymethyl derivative, it can be converted to an exomethylene derivative by further subjecting to dehydration.

Hydrolysis of isonitrile group:

The hydrolysis of the isonitrile group may be applied to the method utilized in the field of penicillin. This reaction is conducted usually in an organic solvent by allowing p-toluenesulfonic acid monohydrate to act on the reaction system. As the organic solvent, use is often made of acetone, dichloromethane, tetrahydrofurane, dimethylformamide, etc. The reaction temperature is not specifically limitative, but preferably ranges from $0°$ C. to $50°$ C., and the reaction time is within the range of from 15 minutes to 60 minutes. The compound (III) is obtained as p-toluenesulfonic acid sometimes in crystalline form, but usually, without isolation, further subjected in situ to a reaction for forming an organic residue through nitrogen.

Esterification of carboxylic acid

The esterification is carried out, for example, by the following procedures:

(1) The compound (v; $R^2$ in compound (I) is carboxy) is reacted with a diazoalkane, such as diazomethane, phenyldiazomethane and diphenyldiazomethane, in a solvent, such as tetrahydrofuran, dioxane, ethyl acetate and acetonitrile, at about $0°$ C. to its refluxing temperature for about 2 minutes to 2 hours.

(2) An alkali metal salt of the compound (V) is reacted with an activated alkyl halide such as methyl iodide, benzyl bromide, p-nitro-benzyl bromide, m-phenoxybenzyl bromide, t-butylbenzyl bromide and pivaloyloxymethyl chloride. With reference to the suitable reaction conditions, the reaction is allowed to proceed in a solvent, such as dimethylformamide, dimethylsulfoxide or hexamethylphosphoramide, at about $0°$ C. to $60°$ C. for about 2 minutes to 4 hours. Coexistence of triethylamine, etc. in this reaction solution does not affect adversely the reaction.

(3) The compound (V) is reacted with an alcohol such as methanol, ethanol and benzyl alcohol. This reaction is carried out in the presence of a carbodiimide coupling agent such as dicyclohexylcarbodiimide, at about $0°$ C. to the refluxing temperature of the used solvent for about 15 minutes to 18 hours. As the solvent, there are used, for example, chloroform, dichloromethane and dichloroethane.

(4) An acid anhydride of the compound (V) formed by reacting the compound (V) with an acid chloride, such as ethyl chloroformate and benzyl chloroformate is reacted with an alcohol, such as those as mentioned in the above item (3) under the reaction conditions as described in the above item (3). The acid anhydride is obtainable by reacting the compound (V) with the acid chloride in a solvent, such as tetrahydrofurane and dichloromethane, at $25°$ C. to the refluxing temperature for about 15 minutes to 10 hours.

(5) The compound (V) is reacted with a silylating agent, such as trimethylsilyl chloride and t-butyl-dimethylsilyl chloride, in the presence of, for example, triethylamine at about 0° C. to the refluxing temperature for about 15 minutes to 16 hours.

Amidation of carboxylic acid

The amidation of carboxylic acid is carried out by synthesizing an acid anhydride of the compound (V) from the compound (V) and an acid chloride, such as trimethylacetyl chloride, ethyl chloroformate and benzyl chloroformate, or an acid anhydride, such as acetic anhydride and trifluoroacetic anhydride, followed by reaction with, for example, the above-mentioned alkyl-, dialkyl-, aralkyl- or heterocyclic-ring amine reagent.

The above reaction is carried out in a solvent, such as dichloromethane, tetrahydrofurane and dimethylformamide, at about 0° C. to the refluxing temperature for 15 minutes to 16 hours.

The above-described reaction can produce the objective compound (I) of the formula:

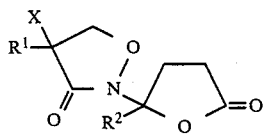

wherein $R^1$ is amino or an organic bonded through nitrogen; $R^2$ is a group derivable from carboxy; X is as defined hereinbefore.

Deprotection reaction

In cases in which the objective compound (I) thus obtained has a protective group, it is possible to remove the protective group, if necessary. As the method of removal of the said protective group, there can be suitably selected and carried out the conventional procedures, such as the procedure with acid, procedure with base, procedure with hydrazine or procedure by means of reduction, according to the type of such protective groups. In the case of the procedure with acid, as the acid, there are used inorganic acids such as hydrochloric acid, sulfuric acid and phosphoric acid, or organic acids such as formic acid, acetic acid, trifluoroacetic acid and propionic acid, as well as acidic ion exchange resins, etc., varying with the type of such protective groups and other conditions. In the case of the procedure with base, as the base, there are employed inorganic bases such as hydroxides and carbonates of alkali metals (e.g., sodium and potassium), and alkaline earth metals (e.g., calcium and magnesium), and organic bases such as metal alkoxides, organic amines and quaternary ammonium salts, as well as basic ion exchange resins, varying depending upon the type of such protective groups and other conditions. When a solvent is used in the case of the above-described procedure with acid or base, hydrophilic organic solvents, water or solvent mixtures are in many cases employed.

In the case of the procedure by means of reduction, there are adopted the procedure of using metals, such as tin and zinc, or metal compounds, such as chromium dichloride and chromium acetate, and acids, such as organic and inorganic acids being exemplified by acetic acid, propionic acid and hydrochloric acid, and the procedure of reducing in the presence of a metal catalyst for catalytic reduction, varying with the type of such protective groups and other conditions, whereby the catalyst to be used in the procedure by means of catalytic reduction includes, for example, platinum catalysts such as platinum lead, platinum sponge, platinum black, platinum oxide and colloidal platinum, palladium catalysts such as palladium sponge, palladium black, palladium oxide, palladium barium sulfate, palladium barium carbonate, palladium carbon, palladium silica gel and colloidal palladium, reduced nickel, nickel oxide, Raney nickel, Urushibara nickel, etc. In the case of the procedure through reduction with metal and acid, there are used metals, such as iron and chromium, and inorganic acids such as hydrochloric acid, or organic acids such as formic acid, acetic acid and propionic acid. The procedure by means of reduction is normally carried out in a solvent, and in the case of the procedure by means of catalytic reduction, for example, there are frequently used alcohols such as methanol, ethanol, propyl alcohol and isopropyl alcohol, ethyl acetate, and the like. In the case of the procedure with metal and acid, there are frequently used, water, acetone, etc., but when the acid presents form of liquid, the acid itself can also be used as a solvent.

In the cases of the procedure with acid, procedure with base and procedure by means of reduction, the reaction is normally carried out at a reaction temperature under cooling to under warming.

The compound (III) of the above formula (I) wherein $R^1$ is amino can be produced by allowing a compound of the formula (I ) wherein $R^1$ is an organic residue bonded through nitrogen other than amino to undergo a reaction similar to the above-mentioned deprotection reaction, or the above-mentioned hydrolysis of isonitrile group in compound (I; R' is isonitrile).

The compound (III) is useful as a starting material, i.e. intermediate, for the production of the compound of the formula (I') wherein $R^{1'}$ is an organic residue bonded through nitrogen other than amino.

The compound (V) of the above formula (I) wherein $R^2$ is carboxyl group can be produced by allowing a compound of the formula (II) wherein $R^{2'}$ is a group derivable from carboxyl group to undergo a reaction similar to the above-mentioned deprotection reaction.

In the process of the present invention, the antibiotic TAN-588, i.e. 2-[(4S)-4-acetamido-3-oxo-2-isoxazolidinyl]-5-oxo-2-tetrahydrofurancarboxylic acid, its salts, its p-nitrobenzyl ester, its benzhydryl ester, or their N-deacetyl derivative can be employed as starting materials.

The antibiotic TAN-588, which is useful as a starting compound in the processes of this invention, can be produced by cultivating an antibiotic TAN-588 producing microorganism belonging to the genus Empedobacter or Lysobacter in a culture medium to have the antibiotic TAN-588 elaborated and accumulated in the culture broth, followed by harvesting. The said producing microorganism includes, for example, the strains *Empedobacter lactamgenus* YK-258 and *Lysobacter albus* sp. nov. YK-422. The said microorganisms have been deposited at Institute for Fermentation, Osaka (IFO, 17-85, Juso-honmachi 2-chome, Yodogawa-ku, Osaka, Japan) as described below.

| Microorganism | IFO Accession Number Date of Deposition |
|---|---|
| YK-258 | IFO 14322 |
|  | 20th February, 1984 |
| YK-422 | IFO 14384 |

|  | IFO Accession Number |
|---|---|
| Microorganism | Date of Deposition |
|  | 5th October, 1984 |

Also the said microorganisms have been deposited at Fermentation Research Institute, Agency of Industrial Science and Technology, Ministry of International Trade and Industry, Japan, (FRI, 1-3, Yatabe-cho higashi 1-chome, Tsukuba-gun, Ibaragi Prefecture, Japan) under the accession number of FERM P-number as described below, and the deposits were converted to deposits under the Budapest Treaty and have been stored at FRI under the accetion numbers of FERM BP given.

| Microorganism | FRI Accession Number Date of Deposition | Accession Number under the Budapest Treaty |
|---|---|---|
| YK-258 | FERM P-7558 26th March, 1984 | FERM BP-699 |
| YK-422 | FERM P-7938 14th November, 1984 | FERM BP-698 |

As concretly shown in the below mentioned Reference Examples, N-deacetyl derivatives of TAN-588 can be produced by introducing a p-nitrobenzyl or benzhydryl group into TAN-588 or its salt to prepare the p-nitrobenzyl ester or benzhydryl ester derivative, deacetylating the said ester derivative to prepare the p-nitrobenzyl ester or benzhydryl ester derivative of N-deacetyl TAN-588, and eliminating such ester groups.

The objective compound (I) thus obtained can be isolated and purified by the per se known means, such as concentration, solvent extraction, lyophilization, crystallization, recrystallization, fractional distillation and chromatography.

The presence of two asymmetric carbons in the basic skeleton allows theoretically the objective compound (I) to exist in four kinds of stereoisomers, and their individual stereoisomers and mixtures thereof fall into the scope of this invention. Similarly, the occurrence of any asymmetric carbon in the groups represented by $R^1$ and $R^2$ results in existence of stereoisomers, and their individual stereoisomers and mixtures thereof are also included in the scope of this invention. In cases in which the above-described reaction produces these stereoisomers as a mixture, their individual stereoisomers can be isolated by the conventional methods, such as various chromatographic procedures and recrystallization, if necessary.

The compound (I) of this invention can in some instances action bases to form salts. The said base includes, for example, inorganic bases, such as sodium, potassium, lithium, calcium, magnesium and ammonia, and organic bases, such as pyridine, collidine, triethylamine and triethanolamine.

The compound (I), when produced in the free form, may be allowed to form salts by use of the conventional means, and the compound (I) obtained in the form of salt may be converted into the free form by use of the conventional means.

Also, the compound (I) in some instances forms the intramolecular salt, and such salt falls within the scope of this invention, as well.

The stereoisomers of the compound (I), either alone or as a mixture, can be used as a drug.

The compound (I) thus obtained is useful as a drug, having antimicrobial activity against some species of gram-positive and gram-negative bacteria.

Biological properties of the compound (I) are described in the following. Typical compounds of the compound (I) demonstate antimicrobial spectra against different microorganisms as shown in Table 1 and Table 2.

TABLE 1:

| Test microorganism | Minimum growth inhibitory concentration ($\mu$g/ml) Compound** | | | | | |
|---|---|---|---|---|---|---|
|  | 21b | 6b | 1c | 1b | 28c | R-4 |
| Staphylococcus aureus FDA 209P | 6.25 | 1.56 | 12.5 | 12.5 | 3.18 | 100 |
| Escherichia coli NIHJ JC-2 | 25 | 25 | 1.56 | 3.13 | >100 | >100 |
| Klebsiella pneumonae DT | 50 | 50 | 0.78 | 1.56 | 100 | >100 |
| Pseudomonas aeruginosa IFO 3455 | >100 | >100 | 50 | >100 | >100 | >100 |

*Medium, Trypticase soy agar
**Amount of a bacterium inoculated, $10^8$ CFU/ml The compound number designates a number as referred to in the examples in Part A. The compound (R-4) means the compound as obtained in Reference Example 4.

TABLE 2:

| Test microorganisms | Compound** | | | | | Control |
|---|---|---|---|---|---|---|
|  | 1b | 6b | 9b | 10b | 15 |  |
| Staphylococcus aureus FDA 209P | 0.2 | <0.1 | <0.1 | 0.78 | 0.78 | 100 |
| Escherichia coli NIHJ JC-2 | 3.13 | 1.56 | 6.25 | 6.25 | 6.25 | >100 |
| Klebsiella pneumoniae DT | 3.13 | 3.13 | 3.13 | 6.25 | 6.25 | >100 |
| Pseudomonas aeruginosa IFO 3455 | >100 | >100 | >100 | >100 | >100 | >100 |

*Medium : Trypticase soy agar Amount of a bacterium inoculated : $10^8$ CFU/ml
**The compound number corresponds to that referred to in working examples in Part B. As the control, a deacetyl compound of the known antibiotic TAN-588 (cf. Reference Example 4) was employed.

The compound of the compound (I) of this invention wherein $R^1$=—NHCOH, $R^2$=—COONa and X=H, as obtained in Example 21 (b) in Part A, when administered subcutaneously to mice in the amount 400 mg/kg, was observed to cause no lethal case. Therefore, the compound (I) or its salts are considered to be of low toxicity.

As described above, the compound (I) of this invention and its salts have antimicrobial activity against some species of gram-positive and gram-negative bacteria, and in addition, are of low toxicity. Consequently, they can be used, as an antimicrobial agent or as a therapeutic agent for bacterial infections, for the treatment of bacterial infections (e.g., respiratory tract infections, urinary tract infections, suppurative diseases, bile duct infections, intratestinal infections, gynecological infections, surgical infections, etc.) in mammals (e.g., mouse, rat, dog, cattle, pig, human) being caused by infections with bacteria.

The daily dosage of the compound (I) or its salt is in the amount of about 2 to 100 mg/kg as the compound (I), more preferably about 5 to 40 mg/kg.

For administration of the compound (I), the compound (I') or its pharmacologically acceptable salt can be formulated by the conventional means with suitable, pharmacologically acceptable carrier, excipient and diluent into such dosage forms as tablet, granule, capsule or elixir to administer orally, and also can be processed into injectable solution by the conventional means, followed by incorporation into a sterile carrier prepared by the conventional means to administer parenterally.

In producing the above-described oral pharmaceutical preparations, such as tablets, there can suitably be formulated binding agents (e.g., hydroxylpropylcellulose, hydroxypropylmethyl cellulose, macrogol, etc.), disintegrating agents (e.g., starch, carboxymethylcellulose calcium, etc.), excipients (e.g., lactose, starch, etc.), lubricants (e.g., magnesium stearate, talc, etc.) and the like.

In manufacturing non-oral or parenteral pharmaceutical preparations, such as injectable solutions, there can suitably be formulated isotonizing agents (e.g., glucose, D-sorbitol, D-mannitol, sodium chloride, etc.), preservatives (e.g., benzyl alcohol, chlorobutanol, methyl p-oxybenzoate, propyl p-oxybenzoate, etc.), buffering agents (e.g., phosphate buffers, sodium acetate buffer, etc.) and the like.

The Reference Example and Examples are described in the following to illustrate this invention in more detail, but this invention is understood not to be limited to these. The term "percent" means "weight/volume %", unless specified otherwise.

In the resins to be used, the ones designated by the abbreviations are defined as follows.
CHP-20: Diaion CHP-20 (produced by Mitsubishi Chemical Industries, Ltd., Japan)
HP-20: Diaion HP-20 (produced by Mitsubishi Chemical Industries, Ltd., Japan)
LH-20: Sephadex LH-20 (produced by Pharmacia Co., Sweden)
XAD-2: Amberlite XAD-2 (produced by Rohm & Haas Co., U.S.A.)
SP-207: Diaion SP-207 (produced by Mitsubishi Chemical Industries, Ltd., Japan)

The abbreviations used in the examples are as defined as follows.
rt: Room temperature
h: Hour
Me: Methyl
Ac: Acetyl
DMA: Dimethylacetamide

REFERENCE EXAMPLE 1

(1) The strain *Empedobacter lactamgenus* YK-258 (IFO 14322, FERM BP-699) grown on a slant of nutrient agar was inoculated into a 2-l Sakaguchi flask containing 500 ml of a medium comprising an aqueous solution (pH 7.0) containing 2% of glucose, 3% of soluble starch, 1% of raw soybean flour, 0.5% of Polypepton (produced by Daigo Nutritive Chemicals, Japan) and 0.3% of sodium chloride being admixed with 0.5% precipitating calcium carbonate, and shake culture was carried out on a reciprocating shaker at 24° C. for 48 hours. The whole volume of the resulting culture broth was inoculated into 50-l capacity tank containing 30 l of the medium comprising the above medium admixed with 0.05% of Actcol (produced by Takeda Chemical Industries, Ltd., Japan), and culture was conducted at 24° C. under the conditions of aeration of 50 l/min and agitation of 200 r.p.m. for 48 hours. 6 l of this culture broth was inoculated into a 200-l capacity tank containing 120 l of a medium comprising an aqueous solution (pH 6.5) containing 3% of dextrin, 1.5% of raw soybean flour, 1.5% of corn gluten meal, 0.2% of Polypepton and 0.1% of sodium thiosulfate being admixed with 0.05% of Actcol, and culture was carried out at 17° C. under the conditions of aeration of 200 l/min and agitation of 150 r.p.m. for 66 hours.

This cultivation was repeated twice, and the culture broth (230 l) was adjusted to pH 8 and filtered with use of 9 kg of Hyflo Supercel (produced by Johns Manville Co. of U.S.A.). The filtrate (200 l) was adjusted to pH 6 and chromatographed on a column of Amberlite IRA-402 (Cl type, 10 l, produced by Rohm & Haas Co. of U.S.A.). The antibiotic was eluted with 2% aqueous sodium chloride solution, and the eluate (53 l) was adjusted to pH 6 and chromatographed on activated carbon (5 l produced by Takeda Chemical Industries, Ltd. of Japan). The antibiotic was eluted with 8% aqueous isobutanol, and the 15 eluate (14 l) was concentrated under reduced pressure to 5 l of the total volume. The concentrate was adjusted to pH 6, followed by extraction with 2% tri-n-octylammonium chloride/dichloromethane solution (2.5 l×2). The extract was treated with 1.6% aqueous sodium iodide solution (2.5 l), and the antibiotic was transferred into the aqueous phase. The aqueous layer was concentrated, and the concentrate was chromatographed on activated carbon (500 ml), followed by elution with 8% aqueous isobutanol. The eluate was concentrated and lyophilized, to give 1.41 g of a crude powder. The crude powder (1.4 g) was dissolved in water (100 ml), and the solution was chromatographed on a column of 200 ml of QAE-Sephadex A-25 (Cl type, produced by Pharmacia Co. of Sweden), followed by elution and fractionation with 0.03M aqueous sodium chloride solution. The fractions were collected (600 ml), adjusted to pH 5.1 and desalted through chromatography on activated carbon, and the eluate was concentrated and lyophilized to give a powder (384 mg). The powder was dissolved in water, and the solution was subjected to preparative HPLC using YMC-Pack SH-343 (produced by Yamamura Chemical Laboratory of Japan), followed by elution with 0.01M phosphate buffer. The eluates containing the antibiotic were collected and desalted through chromatography on activated carbon, and the eluate was concentrated and lyophilized to give a white powder (141 mg) of TAN-588 sodium salt.

The TAN-588 sodium salt (an equilibrium mixture of isomers A and B) as obtained above shows physicochemical properties as illustrated below.

(1) Appearance: White powder
(2) Specific rotation: $[\alpha]_D^{23} -19.0° \pm 10°$ (c=0.5, in water)
(3) Elemental analysis (%) for the compound consisting of the elements, C, H, N, O and Na: for a sample dried over phosphorus pentoxide at 40° C. for 6 hours.

| Found | | Calculated* | |
| --- | --- | --- | --- |
| C, | 38.5 ± 2.0 | C, | 39.61 |
| H, | 4.5 ± 1.0 | H, | 3.99 |
| N, | 9.1 ± 1.5 | N, | 9.24 |

-continued

| | Found | | Calculated* |
|---|---|---|---|
| | | O, | 39.58 |
| Na, | 6.9 ± 1.5 | Na, | 7.58 |

(*calculated assuming that 0.5 mole of adhesive water is contained)

(4) Content of adhesive water: 3.0±1.5% (by the thermoglavimetric method)

(5) Molecular ion peaks obtained by means of the SIMS method: m/z 611 (2M+Na)+, 317 (M+Na)+, 295 (M+H)+

(6) Molecular formula: $C_{10}H_{11}N_2O_7Na$ (7) Ultraviolet absorption (UV) spectrum (in water): $\lambda_{max}$ 216 nm ($E_{1\ cm}^{1\%}$ = 130, shoulder)

(8) Infrared absorption (IR) spectrum (by the KBr tablet method): The major absorptions (wave number) as measured in KBr tablets are as follows: 3450, 1780, 1730, 1660, 1550, 1385, 1320, 1290, 1260, 1200, 1120, 1040, 980, 910, 810, 770, 690, 600, 540 cm$^{-1}$ (9) $^{13}$C-nuclear magnetic resonance (NMR) spectrum (100 MHz, in heavy water): The following signals are observed: 182.02(s), 177.30(s), 173.79(s), 173.30(s), 173.25(s), 172.58(s), 96.97(s), 96.92(s), 74.27(t), 72.63(t), 55.57(d) 55.34(d), 31.92(t), 31.08(t),30.98(t), 24.58(q) ppm where the abbreviations denote the following: s; singlet, d; doublet, t; triplet, q; quartet).

(10) Circular dichroism (CD) spectrum (in water): The negative Cotton effect is exhibited at 232±3 nm.

(11) Solubility: Soluble in: water, dimethylsulfoxide. Sparingly soluble in: ethyl acetate, chloroform, diethyl ether.

(12) Color reactions: Positive to: ninhydrin reaction. Negative to: Greig-Leaback reaction, Sakaguchi reaction, Ehrlich reaction, Barton reaction and Dragendorff reaction.

(13) Amino acid analysis: Hydrolysis in 6N hydrochloric acid at 105° C. for 20 hours produces serine detected as the known amino acid.

(14) Stability: Stable in an aqueous solution at pH 5; slightly stable at pH 3 and pH 7; unstable at pH 9.

(15) Thin-layer chromatography (TLC) (cellulose f, produced by Tokyo Kasei Co. of Japan).

| Solvent system | Rf |
|---|---|
| Acetonitrile: water (4:1) | 0.33 |
| Butanol: acetic acid: water (1:1:1) | 0.77 |
| Acetonitrile: 3% ammonium sulfate (4:1) | 0.28 |

(16) Distinction between acidity, neutrality and basicity: Neutral substance.

(17) High-performance liquid chromatography (HPLC) (carrier: YMC A-312, produced by Yamamura Chemical Laboratories, Japan; Mobile phase: 4% methanol/0.01M phosphate buffer (pH 6.3), 2 ml/min.): Rt=4.3 and 4.8 (min).

(2) Using *Lysobacter albus* sp. nov. YK-422 (IFO 14383, FERM BP-698), cultivation and purification by a procedure similar to the above mentioned procedure produced Antibiotic TAN-588 sodium salt (620 g) a mixture of two isomers A and B).

In the examples to be described in the following, the TAN-588 sodium salt (a mixture of two isomers A and B) as obtained in the above is in some instances referred to as "Compound (R-1)".

REFERENCE EXAMPLE 2

In 500 ml of dichloromethane were dissolved 58.8 g of benzophenone hydrazone, 42 ml of 1,1,3,3-tetramethylguanidine and 150 mg of iodine, and after the mixed solution was cooled to 0° C. to −5° C., 74 g of m-chloroperbenzoic acid (with a purity of 70%) was added, followed by stirring at 0° C. for 40 minutes. The reaction solution was washed with water and dried over sodium sulfate, and the solvent was distilled off to give diphenyldiazomethane.

31 g of TAN-588 sodium salt (a mixture of two isomers A and B) was suspended in tetrahydrofurane, and the whole amount of diphenyldiazomethane as obtained in the above was dissolved in 150 ml of tetrahydrofurane and added to the suspension. The mixed solution was cooled at 0° C., and 60 ml of 2N HCl was added dropwise, followed by stirring at room temperature for 1 hour. 10 ml of 2N HCl was added, followed by stirring for another 1 hour, and 3 l of dichloromethane was added. The resulting solution was washed with water and concentrated, and ether was added to the residue to give 28 g of a white crystalline powder of TAN-588 benzhydryl ester (a mixture of isomers A and B).

The above mixture (1.8 g) was chromatographed on a column of silica gel (180 ml), and elution was performed with the solvent system of chloroform:methanol (97:3), whereby the compound isomer B eluted firstly and then the compound of isomer A eluted. Each of the fractions was concentrated to give the isomer A (433 mg), isomer B (400 mg) and a mixture of the isomer A and B (476 mg) of TAN-588 benzhydryl ester in the form of colorless crystals.

In the examples to be described in the following, the TAN-588 benzhydryl ester (a mixture of isomers A and B) as obtained in the above is in some instances referred to as "Compound (R-2)".

The TAN-588 benzyhydryl ester (admixture of isomer A and B) as obtained in the above shows physicochemical properties as illustrated in the following.

(1) Appearance: Colorless crystals (2) Melting point: 153° to 155° C. (decomposition)

(3) Specific rotation: $[\alpha]_D^{23}$+9.2°±5° (c=0.52, in CHCl$_3$)

(4) Molecular weight: m/z, 438 (M+) (EI-MS method)

(5) Elemental analysis: Calcd: C, 63.01; H, 5.06; N, 6.39; O, 25.54. Found: C, 62.83; H, 5.32; N, 6.28.

(6) Molecular formula: $C_{23}H_{22}N_2O_7$ (7) UV spectrum: in methanol: $\lambda_{max}$ 220±2 nm ($E_{1\ cm}^{1\%}$=285±50, shoulder) and 250-260 nm ($E_{1\ cm}^{1\%}$=28±10, shoulder)

(8) IR spectrum: KBr method; 3380, 3080, 3050, 2960, 1800, 1780, 1750, 1705, 1690, 1600, 1590, 1540, 1500, 1460, 1380, 1310, 1280, 1190, 1110, 1060, 980, 920, 880, 750, 710, 700, 650, 630, 610, 570, 550, 470 cm$^{-1}$.

(9) $^1$H-NMR spectrum: 90 MHz, in CDCl$_3$. δppm J (Hz) 1.97(3H,s), 2.1–3.5(4H,m), 3.8–4.2(1H,m), 4.5–5.1(2H,m), 6.1–6.4(1H,b), 6.97(1H,s), 7.3–7.4(10H,m). (where the abbreviations denote the following: m; multiplet, b; broad, H; proton)

(10) TLC: the same conditions as those to be described below. Rf value, 0.58 and 0.65

(11) Distinction between acidity, neutrality and basicity: Neutral substance.

The TAN-588 benzhydryl ester (isomer A) and TAN-588 benzhydryl ester (isomer B) as obtained in the above show the properties as illustrated in the following.

Isomer A (1) Appearance: Colorless crystals (2) Melting point: 97°-135° C. (the compound undergoes gradual bubbling or foaming and decomposition).

(3) Specific rotation: $[\alpha]_D^{21} +44.2° \pm 10°$ (c=0.505, in $CHCl_3$)

(4) Molecular weight: Molecular ion peak by means of the EI-MS method. m/z 438(M+)

(5) Elemental analysis: Calcd.: C, 63.01; H, 5.06; N, 6.39; O, 25.54 Found : C, 62.62; H, 5.06; N, 6.32.

Molecular formula: $C_{23}H_{22}N_2O_7$ (7) UV spectrum (in methanol): $\lambda_{max}$ 220±2 nm ($E_1^{1\%}_{cm}$=290±50, shoulder) and 250-260 nm ($E_1^{1\%}_{cm}$=30±10, shoulder)

(8) IR spectrum: KBr method: 3380, 3080, 3050, 1800, 1780, 1760, 1685, 1540, 1500, 1450, 1380, 1310, 1280, 1190, 1110, 1050, 980, 920, 880, 750, 710, 650, 610, 550 $cm^{-1}$.

(9) Nuclear magnetic resonance ($^1$H-NMR) spectrum: 100 MHz, in $CDCl_3$-$d_6$-DMSO mixture, δppm J(Hz). 1.98(3H,s), 2.2-3.4(4H,m), 4.10(1H,dd,J=8.10), 4.4-5.0(2H,m), 6.93(1H,s), 7.3-7.5(10H,m), 8.27(1H,d,J=7)

(10) Thin-layer chromatography (TLC): Carrier, silica gel (produced by Merck & Co. of West Germany). Developing solvent, ethyl acetate. Rf value, 0.58

(11) Distinction between acidity, neutrality and basicity: Neutral substance.

Isomer B (1) Appearance: Colorless crystals (2) Melting point: 157°-160° C. (decomposition)

(3) Specific rotation: $[\alpha]_D^{21} -28.8° \pm 10°$ (c=0.5, in $CHCl_3$)

Molecular weight: m/z 438(M+) (EI-MS method)

(5) Elemental analysis: Calcd.: C, 63.01; H, 5.06; N, 6.39; O, 25.54. Found: C, 63.11; H, 5.13; N, 6.30

(6) Molecular weight: $C_{23}H_{22}N_2O_7$ (7) UV spectrum: in methanol: $\lambda_{max}$ 220±2 nm ($E_1^{1\%}_{cm}$=300±50, shoulder) and 250-260 nm ($E_1^{1\%}_{cm}$=26±10, shoulder).

(8) IR spectrum: KBr method: 3400, 3080, 3050, 1815, 1780, 1735, 1705, 1540, 1460, 1380, 1290, 1265, 1190, 1060, 980, 920, 880, 760, 715, 610, 550 $cm^{-1}$ (9) $^1$H-NMR spectrum: 100 MHz, in $CDCl_3$, δppm J(Hz) 1.98(3H,s), 2.2-2.3(4H,m), 4.03(1H,dd,J=8,10), 4.6-5.2(2H,m), 6.32(1H,d,J=5), 6.96(1H,s), 7.2-7.5(10H,m)

(10) TLC: (the same conditions as described for isomer A): Rf value, 0.65

(11) Distinction between acidity, neutrality and basicity: Neutral substance.

REFERENCE EXAMPLE 3

In 1.2 l of dichloromethane was suspended 26 g (59 mmole) of TAN-588 benzhydryl ester (a mixture of isomers A and B), and the suspension was cooled to −20° C. 49 ml of pyridine and 37.6 g of phosphorus chloride were added to it, followed by stirring at −10° to −15° C. for 50 minutes. The mixed solution was cooled to −30° C., and 180 ml of methanol was added, followed by stirring at −5° to −15° C. for 30 minutes and then at room temperature for 1 hour. 100 ml of 1N HCl was added to the mixture, followed by stirring at room temperature for 45 minutes, and 100 ml of 50% aqueous sodium phosphate and 2N sodium hydroxide (ca. 500 ml) were added to the reaction solution to adjust a pH of the aqueous layer to 8.0. The aqueous layer was separated from the dichloromethane layer and extracted with dichloroemthane (600 ml), and the organic layers were combined and concentrated, followed by addition of ether to the residue to give 17.9 g of a white powder of a benzhydryl ester of the N-deacetyl TAN-588 (a mixture of isomers A and B).

In the examples to be described below, the benzhydryl ester of the N-deacetyl TAN-588 (a mixture of isomers A and B) as obtained in the above is in some instances referred to as "Compound (R-3)".

The benzhydryl ester (a mixture of isomers A and B) of the N-deacetyl TAN-588 as obtained in the above shows physicochemical properties as illustrated below.

(1) Appearance: White powder (2) Specific rotation: $[\alpha]_D^{25} -15.2 \pm 5°$ (c=0.5, in $CHCl_3$)

(3) Molecular weight: m/z, 396(M+)(EI-MS method)

(4) Elemental analysis: Calcd.: C, 63.63; H, 5.09; N, 7.07; O, 24.22 Found: C, 63.63; H, 5.05; N, 7.02.

(5) Molecular weight: $C_{21}H_{20}N_2O_6$ (6) UV spectrum: in methanol: $\lambda_{max}$ 220±2 nm ($E_1^{1\%}_{cm}$=336±50, in shoulder) and 250-260 nm ($E_1^{1\%}_{cm}$=32±10, shoulder)

(7) IR spectrum: KBr method: 3400, 3050, 2970, 1800, 1780, 1740, 1600, 1500, 1460, 1305, 1270, 1190, 1110, 1060, 980, 920, 880, 850, 750, 710, 650, 620, 605 $cm^{-1}$.

(8) $^1$H-NMR spectrum: 90 MHz, in $CDCl_3$ δppm J(Hz) 2.2-3.5(4H,m), 3.7-4.0(2H,m), 4.4-4.6(1H,m), 6.97(1H,s), 7.2-7.4(10H,m).

(9) HPLC: Apparatus, Model 6000A/660/440 (Waters Assoc. of U.S.A.), Carrier, YMC-Pack A-312 (Produced by Yamamura Chemical Laboratories of Japan). Mobile phase, 65% methanol/0.01M phosphate buffer (pH 6.3). Rate of flow, 2 ml/min, Rt, 5.3 and 5.6 min.

(10) Color reactions: Positive to: Nynhydrin reaction. Negative to: Ferric chloride.

(11) Distinction between acidity, neutrality and basicity:
Basic substance.

REFERENCE EXAMPLE 4

In 10 ml of dichloromethane was suspended 396 mg of benzhydryl ester (a mixture of isomers A and B) of the N-deacetyl TAN-588, and the suspension was cooled to −20° C. 434 μl of anisole and 924 μl of trifluoroacetic acid were added to the suspension, followed by stirring at −20° to −10° C. for 40 minutes. 280 ml of dichloromethane was added to the reaction on with 0.1M H3P04-Na2HP04 solution, followed by extraction with 0.1M $H_3PO_4$-$Na_2HPO_4$ solution (pH 7.3) (420 ml). The extract was adjusted to pH 5.5 and concentrated, and the concentrate was passed through a column packed with Diaion HP-20 (50 to 100 mesh, 100 ml). The column was washed with water, and elution was effected with 40% aqueous methanol. The fractions exhibiting antimicrobial activity were collected, concentrated and lyophilized to give 143 mg of a white powder of the N-deacetyl TAN-588 (a mixture) of isomers A and B).

The N-deacetyl TAN-588 (a mixture of isomers A and B) as obtained in the above shows physico-chemical properties as illustrated in the following.

(1) Appearance:
White powder.

(2) Specific rotation: $[\alpha]_D^{25} -11°\pm 5°(c=0.1$, in water)

(3) Molecular weight: m/z, 231(M+H)+(FD-MS method)

(4) Elemental analysis:

| Found | Calcd.* |
|---|---|
| C, 40.42 | C, 40.17 |
| H, 4.36 | H, 4.64 |
| N, 11.65 | N, 11.71 |
|  | O, 43.48 |

(*calculated assuming that 0.5 mole of adhesive water is contained).

Molecular formula: $C_8H_{10}N_2O_6$ (0.5$H_2O$)

(6) UV spectrum: in water: $\lambda_{max}$ 221±2 nm ($E_{1cm}^{1\%}=154\pm 20$)

(7) IR spectrum: KBr method; Major peaks are as follows: 3450, 3220, 2960, 2900, 1800, 1760, 1740, 1670, 1580, 1420, 1390, 1370, 1310, 1250, 1200, 1120, 1050, 1030, 980, 950, 920, 810, 770, 720, 690, 610, 540 $cm^{-1}$.

(8) $^1$H-NMR spectrum: 400 MHz, in $D_2O$. The following signals are observed. δppm J (Hz) 2.52(1H,m), 2.27(1H,m), 2.91(1H,m), 3.08(1H,m), 4.35(1H,m), 4.56(1H,m), 4.80(1H,m).

(9) Circular dichroism (CD) spectrum: in water. The negative Cotton effect is exhibited at 233±3 nm.

(10) Solubility: Soluble in: water. Sparingly soluble in: dimethylsulfoxide, ethyl acetate, diethyl ether.

(11) HPLC: The apparatus, carrier and rate of flow are as described above for the benzhydryl ester (a mixture of isomers A and B) of the N-deacetyl TAN-588. Mobile phase, 0.01M phosphate buffer (pH 6.3). Rt: 3.1 and 3.3 min.

(12) Color reactions: Positive to: Nynhydrin, Iodine. Negative to: Ferric chloride

(13) Distinction between acidity, neutrality and basicity: Amphoteric substance.

In the examples to be described below, the N-deacetyl TAN-588 (a mixture of isomers A and B) is in some instances referred to as "Compound (R-4)".

REFERENCE EXAMPLE 5

In water was dissolved 100 mg of a white powder of the N-deacetyl TAN-588 (a 1:1 mixture of isomers A and B), and the solution was allowed to stand overnight at 7° C., whereby colorless crystals separated out. The crystals which separated out were recovered by filtration to give 40 mg of the N-deacetyl TAN-588 (isomer A) in the form of crystals.

The crystals of the N-deacetyl TAN-588 as obtained in the above show physico-chemical properties as illustrated in the following.

(1) Appearance: Colorless crystals.

(2) Melting point: 177–181° C. (decomposition)

(3) Specific rotation: $[\alpha]_d^{25} +124°\pm 20°$)c=0.1, in water)

(4) Molecular weight: m/z 231(M+H)+(FD-MS method)

(5) Elemental analysis:

| Found | Calcd. |
|---|---|
| C, 41.57 | C, 41.75 |
| H, 4.39 | H, 4.38 |
| N, 12.11 | N, 12.17 |
|  | O, 41.71 |

(6) Molecular formula: $C_8H_{10}N_2O_6$ (7) UV spectrum: in water: $\lambda_{max}$221±2 nm ($E_{1cm}^{1\%}=151\pm 20$)

(8) IR spectrum: KBr method: Major absorption peaks are as follows. 3450, 3220, 2950, 2900, 1800, 1735, 1660, 1580, 1440, 1420, 1400, 1360, 1340, 1310, 1280, 1200, 1160, 1110, 1050, 1025, 980, 940, 920, 810, 770, 710, 690, 600, 540 $cm^{-1}$.

(9) $^1$H-NMR spectrum: 400 MHz, in $D_2O$, the following signals are observed. δppm J(Hz) 2.52(1H,m), 2.72(1H,m), 2.91(1H,m), 3.08(1H,m), 4.34(1H,m), 4.55(1H,m), 4.78(1H,m).

(10) CD spectrum: in water: The negative Cotton effect is exhibited at 238±3 nm.

(11) Solubility: Soluble in: water Sparingly soluble in: dimethylsulfoxide, ethyl acetate, chloroform, diethyl ether.

(12) HPLC: The conditions are as described above for the mixture of isomers A and B. Rt, 3.3 min.

(13) Distinction between acidity, neutrality and basicity: Amphoteric substance.

REFERENCE EXAMPLE 6

By following the procedure of Reference Example 3, 657 mg of TAN-588 benzhydryl ester (isomer B) was reacted and treated to give 200 mg of a benzhydryl ester (isomer B) of the N-deacetyl TAN-588. 180 mg of the said compound was dissolved in 18 ml of aqueous tetrahydrofurane (1:1), and 90 mg of 10% palladium-carbon was added to the solution, followed by stirring under a stream of hydrogen. After the catalyst was filtered out, the filtrate was concentrated, and the aqueous layer was washed with diethyl ether, concentrated and lyophilized to give 77 mg of a powder of the N-deacetyl TAN-588 (isomer B).

The powder of the N-deacetyl TAN-588 as obtained in the above shows physico-chemical properties as illustrated in the following.

(1) Appearance: White powder (2) Molecular weight: m/z 231 (M+H)+(FD-MS method)

(3) Elemental analysis:

| Found | Calcd.* |
|---|---|
| C, 40.98 | C, 40.17 |
| H, 4.88 | H, 4.64 |
| N, 12.17 | N, 11.71 |
|  | O, 43.48 |

(*calculated assuming that 0.5 mole of adhesive water is contained).

(4) Molecular formula: $C_8H_{10}N_2O_6$ (5) UV spectrum: in water: $\lambda_{max}$ 221±2 nm ($E_{1cm}^{1\%}=133\pm 20$).

(6) IR spectrum: KBr method: Major peaks are as follows. 3440, 2980, 1800, 1760, 1670, 1570, 1520, 1390, 1290, 1250, 1190, 1090, 1050, 990, 920, 810, 760, 720, 690 $cm^{-1}$.

(7) $^1$H-NMR spectrum: 400 MHz, in $D_2O$, the following signals are observed. ppm J(Hz). 2.52(1H,m), 2.72(1H,m), 2.90(1H,m), 3.08(1H,m), 4.44(1H,m), 4.68(1H,m), 4.86(1H,m).

(8) CD spectrum: in water: The negative Cotton effect is exhibited at 224+2 nm.

(9) Solubility: Soluble in: water. Sparingly soluble in: dimethylsulfoxide, ethyl acetate, chloroform, diethyl ether.

(10) HPLC: The conditions are as described above for the mixture of isomers A and B. Rt, 3.1 min.

(11) Distinction between acidity, neutrality and basicity: Amphoteric substance.

REFERENCE EXAMPLE 7

In DMF (4 ml) was dissolved TAN-588 sodium salt (400 mg), and triethylamine (10 μl) and p-nitrobenzyl bromide (800 mg) were added to the solution, followed by stirring at room . temperature for 3 hours. 0.1M phosphate buffer (pH 6.3, 50 ml) was added to the reaction solution, and extraction was effected twice with ethyl acetate (50 ml). The extract was washed with water, and concentrated, and the resultant oily material was treated with ethyl acetate-petroleum benzin to convert into powder (507 mg), thereby giving a mixture of TAN-588 p-nitrobenzyl benzyl ester (isomer A) and TAN-588 p-nitrobenzyl ester (isomer B). The resultant powder was chromatographed on a column of Sephadex LH-20 using ethyl acetate:methanol=19:1 as a mobile phase to give TAN-588 p-nitrobenzyl ester (isomer A) (105 mg), TAN-588 p-nitrobenzyl ester (isomer B)(67 mg) and a mixture thereof (280 mg).

The p-nitrobenzyl ester of TAN-588 as obtained in the above (a mixture of isomers A and B) shows physico-chemical properties as illustrated in the following.

(1) Appearance: White powder.

(2) Specific rotation: $[\alpha]_D^{23} + 16.3° \pm 5°(c=0.485$, in $CHCl_3)$ (3) Molecular weight: 407 (by means of the SIMS method)

(4) Elemental analysis: Calcd.: C, 50.13; H, 4.21; N, 10.32; O, 35.35. Found : C, 50.26; H, 4.32; N, 10.31.

(5) Molecular formula: $C_{17}H_{17}N_3O_9$ (6) UV spectrum: $\lambda_{max}^{MeOH}$ nm $(E_{1\ cm}^{1\%})=262\pm2$ $(281\pm20), 214\pm2 (278\pm20$, shoulder)

(7) IR spectrum: KBr method: 3400, 3080, 2960, 1805, 1760, 1680, 1610, 1520, 1450, 1380, 1350, 1270, 1180, 1105, 1050, 1015, 970, 905, 850, 740, 690, 600, 540 $cm^{-1}$.

(8) $^1$H-NMR spectrum: 90 MHz, in $CDCl_3$. δppm J(Hz). 2.05(3H,s), 2.3–3.3(4H,m), 4.10(1H,m), 4.5–5.1(2H,m), 5.35 (2H,s), 6.25(1H,d,like), 7.55(2H,dd,like), 8.27(2H,d,like)

(9) TLC: Carrier: silica gel (produced by Merck & Co. of West Germany) Developping solvent: chloroform:methanol (19:1) Rf value, 0.25 and 0.32.

(10) Distinction between acidity, neutrality and basicity: Neutral substance.

The TAN-588 p-nitrobenzyl ester (isomer A) as obtained in the above shows physico-chemical properties as illustrated in the following.

(1) Appearance: White powder.

(2) Specific rotation: $[\alpha]_D^{20} \pm 97.3° \pm 15°$ (c=0.48, in $CHCl_3)$ (3) Molecular weight: 407 (by means of the SIMS method)

(4) Elemental analysis: Calcd.: C, 50.13; H, 4.21; N, 10.32; O, 35.35. Found : C, 50.20; H, 4.22; N, 10.13

(5) Molecular formula: $C_{17}H_{17}N_3O_9$ (6) UV spectrum: $\lambda_{max}^{MeOH}$ $(E_{1\ cm}^{1\%})=262\pm2$ nm $(280\pm30), 214\pm2 (276\pm30$, shoulder)

(7)$^{13}$C-NMR spectrum: (100 MHz, $CDCl_3$). 173.70(s), 171.53(s), 170.72(s), 165.09(s), 148.06(s), 141.38(s), 128.86(d), 123.91(d), 91.82(s), 71.60(t), 67.29(t), 53.00(d), 29.09(t), 27.49(t), 22.64(q) ppm.

(8) IR spectrum: KBr method 3400, 3080, 2950, 1805, 1775, 1760, 1680, 1610, 1530, 1450, 1380, 1350, 1300, 1275, 1190, 1105, 1060, 1020, 980, 910, 850, 740, 700, 600, 540 $cm^{-1}$.

(9) TLC: Carrier: silica gel (produced by Merck & Co. of West Germany) Developing solvent: chloroform:methanol (19:1) Rf value, 0.25

(10) Distinction between acidity, neutrality and basicity: Neutral substance.

The TAN-588 p-nitrobenzyl ester (isomer B) as obtained in the above shows physico-chemical properties as illustrated in the following.

(1) Appearance: White powder (2) Specific rotation: $[\alpha]_D^{20} - 64.5° \pm 15°(c=0.50$, in $CHCl_3)$ (3) Molecular weight: 407 (by means of the SIMS method)

(4) Elemental analysis: Calcd.: C, 50.13; H, 4.21; N, 10.32; O, 35.35. Found : C, 50.10; H, 4.21; N, 10.15.

(5) Molecular formula: $C_{17}H_{17}N_3O_9$ (6) UV spectrum: $\lambda_{max}^{MeOH}(E_{1\ cm}^{1\%})=262\pm2$ nm $(282\pm30), 214\pm2$ nm $(280\pm30$, shoulder)

(7) $^{13}$C-NMR spectrum: (100 MHz, $CDCl_3$) 173.59(s), 170.86(s), 170.61(s), 165.06(s), 148.12(s), 141.24(s), 128.96(d), 123.96(d), 91.69(s), 74.60(t), 67.39(t), 51.94(d), 29.11(t), 27.38(t), 22.67(q), ppm.

(8) IR spectrum: KBr method: 3400, 3090, 2950, 1805, 1760, 1680, 1610, 1530, 1450, 1380, 1355, 1270, 1180, 1105, 1055, 1015, 965, 910, 855, 740, 695, 600, 540 $cm^{-1}$.

(9) TLC: The conditions are as described above for the TAN-588 p-nitrobenzyl ester (Isomer A). Rf value, 0.32.

(10) Distinction between acidity, neutrality and basicity: Neutral substance.

EXAMPLES

The present invention will be illustrate detailedly hereinafter by the three Parts of Examples, i.e. Part A containing Examples 1 to 133 [Compounds (1) to (133)], Part B containing Examples 1 to 30 [Compounds (1) to (30)]and Part C containing Examples 1 to 18 [Compounds (1) to (16)], respectively.

Part A

EXAMPLE 1

Production of Sodium 2-{(4S)-4-[2-(2-amino-4-thiazolyl)-(Z)-2-(methoxyimino)acetamido]-3-oxo-2-isoxazolidinyl}-5-oxo-2-tetrahydrofurancarboxylate [Compound (lc)]:

(a) Production of diphenylmethyl 2-{(4S)-4-[2-(2-chloroacetamido-4-thiazolyl)-(Z)-2-(methoxyimino)acetamido]-3-oxo-2-isoxazolidinyl}-5-oxo-2-tetrahydrofurancarboxylate [Compound (la)]:

Diphenylmethyl 2-[(4S)-4-amino-3-oxo-2-isoxazolidinyl]-5-oxo-2-tetrahydro furancarboxylate Compound (R-3)] as obtained in Reference Example 3 was added to a solution in dimethylformamide (DMF) of 2-(2-chloroacetamido-4-thiazolyl)-(Z)-2-methoxyiminoacetic acid, 1-hydroxybenzotriazole (HOBT) and dicyclohexylcarbodiimide (DCC) under ice-cooling, followed by stirring for 1 hour. Ethyl acetate was added to the reaction solution, and the precipitate which separated out was filtered off, and the filtrate was washed with aqueous sodium hydrogencarbonate solution and water, successively, and dried over anhydrous sodium sulfate. Then, the solvent was distilled off, and the residue was chromatographed on silica gel,followed by elution with ethyl acetate-hexane (2:1) to give Compound (la) in the form of a colorless foamed substance.

(b) Production of diphenylmethyl 2-{(4S)-4-[2-(2-amino-4-thiazolyl)-(Z)-2-(methoxyimino)acetamido]-3-oxo-2-isoxazolidinyl}-5-oxo-2-tetrahydrofurancarboxylate [Compound (1b)]:

Compound (1a) as obtained in the above was dissolved in a mixed solution of tetrahydrofurane and water, and sodium N-methyldithiocarbamate was added little by little to the solution, followed by stirring at room temperature for 1 hour. THF was distilled off, and the residue was extracted with ethyl acetate. The extract was washed with saturated aqueous sodium chloride solution and dried over anhydrous sodium sulfate. The extract was freed of solvent, and the residue was chromatographed on silica gel, followed by elution with ethyl acetate to give Compound (1b) in the form of a colorless foamed substance.

(c) Production of the subject Compound (1c):

Anisole and trifluoroacetic acid were added to a dichloromethane solution of the Compound (1b) under an atmosphere of nitrogen at −10° C. to −15° C., followed by stirring for 5.5 hours. The reaction solution was poured into a phosphate buffer of pH 7.0 (8 ml) containing sodium hydrogencarbonate (220 mg) under, cooling, and the aqueous layer was separated, while the organic layer was extracted with a phosphate buffer of pH 7.0 (4 ml). The aqueous layers were combined, washed with dichloromethane and concentrated under reduced pressure. The concentrate was chromatographed on HP-20, and elution was performed with water, followed by lyophilization of the eluate to give the subject Compound (1c) in the form of a colorless powder.

EXAMPLE 2

Production of sodium 2-{(4S)-4-[D-2-(4-ethyl-2,3-dioxo-1-piperazinocarboxamido)-2-phenylacetamido]-3-oxo-2-isoxazolidinyl}-5-oxo-2-tetrahydrofurancarboxylate [Compound (2b)]:

(a) Production of Compound (2a), diphenylmethyl ester of the subject Compound (2b):

From Compound (R-3) and N-(4-ethyl-2,3-dioxo-1-piperizinylcarbonyl)-D-phenylglycine, there was obtained Compound (2a), diphenylmethyl ester of the subject Compound (2b), by the procedure of Example 1 (a). (b) Production of the subject Compound (2b):

Compound (2a) as obtained above was dissolved in THF (10 ml) and a buffer of pH 6.86 (5 ml), and 5% palladium-carbon (141 mg) was added to the solution followed by stirring under a hydrogen atmosphere and under ice-cooling for 20 minutes. The catalyst was filtered off, and the filtrate was freed of THF under reduced pressure. The residual solution was washed with ethyl acetate, and the aqueous layer was concentrated under reduced pressure and chromatographed on a column of XAD-2, followed by elution with 20% aqueous ethanol. The eluate was concentrated under reduced pressure, and the concentrate was lyophilized to give the subject Compound (2b) in the form of a colorless powder.

EXAMPLE 3

Production of sodium 2-{(4S)-4-[D-2-(3-methylsulfonyl-2-oxoimidazolidine-1-carboxamido)-2-phenylacetamido]-3-oxo-2-isoxazolidinyl}-5-oxo-2-tetrahydrofurancarboxylate [Compound (3b)]:

From Compound (R-3) and N-(3-methylsulfonyl-2-oxoisoxazolidinyl-1-carbonyl)-D-phenylglycine, there was obtained Compound (3a), diphenylmethyl ester of the subject Compound (3b) by the procedure of Example 1 (a), and by following the procedure of Example 2, there was obtained the subject Compound (3b).

EXAMPLE 4

Production of sodium 2-{(4S)-4-[D-2-(3-furfurylideneamino-2-oxoimidazolidine-1-carboxamido)-2-phenylacetamido]-3-oxo-2-isoxazolidinyl}-5-oxo-2-tetrahydrofurancarboxylate [Compound (4b)]:

By the procedure of Example 1 (a), Compound (R-3) was acylated to give Compound (4a), diphenylmethyl ester of the subject Compound (4b), and by the procedure of Example 2, there was obtained the subject Compound (4b).

EXAMPLE 5

Production of sodium 2-[(4S)-4-(2-thienylacetamido)-3-oxo-2-isoxazolidinyl]-5-oxo-2-tetrahydrofurancarboxylate [Compound (5b)]:

Dimethylformamide and 2-thiopheneacetyl chloride were added to a dichloromethane solution of Compound (R-3) under ice-cooling, followed by stirring for 10 minutes and then at room temperature for 20 minutes. Ethyl acetate was added to the reaction solution, and the organic layer was washed with aqueous sodium hydrogencarbonate solution and water, successively, and dried over anhydrous magnesium sulfate. The solvent was distilled off under reduced pressure, and ether was added to the residue to give Compound (5a), a diphenylmethyl ester of the subject Compound (5a) in the form of a colorless powder. Then, the Compound (5a) was treated by the procedure of Example 1 (c) to give the subject Compound (5b).

EXAMPLE 6

Production of sodium 2-[(4S)-4-(2-cyanoacetamido)-3-oxo-2-isoxazolidinyl]-5-oxo-2-tetrahydrofurancarboxylate [Compound (6b)]:

Using Compound (R-3) and cyanoacetic acid, there was obtained Compound (6a), a diphenylmethyl ester of the subject Compound (6b), by the procedure of Example 1 (a), and then, the procedure of Example 2 (b) was carried out to give the subject Compound (6b).

EXAMPLE 7

Production of sodium 2-{(4S)-4-[(1H)-tetrazolylacetamido]-3-oxo-2-isoxazolidinyl}-5-oxo-2-tetrahydrofurancarboxylate [Compound (7b)]:

Using Compound (R-3) and (1H)-tetrazolylacetic acid, there was obtained Compound (7a), a diphenylmethyl ester of the subject Compound (7b), by the procedure of Example 1 (a), and then the procedure of Example 2 (b) was carried out to give the subject Compound (7b).

EXAMPLE 8

Production of sodium 2-[(4S)-4-(2,6-dimethoxybenzamido)-3-oxo-2-isoxazolidinyl]-5-oxo-2-tetrahydrofurancarboxylate [Compound (8b)]:

Using Compound (R-3) and 2,6-dimethoxybenzoyl chloride, there was obtained Compound (8a), a diphenylmethyl ester of the subject Compound (8b), by the procedure of Example 5 and 2 (b), and then, the subject Compound (8b) was produced.

EXAMPLE 9

Production of sodium 2-[(4S)-4-(5-methyl-3-phenyl-2-isoxazoline-4-carboxamido)-3-oxo-2-isoxazolidinyl]-5-oxo-2-tetrahydrofurancarboxylate [Compound (9b)]:

Using Compound (R-3) and 5-methyl-3-phenyl-2-isoxazolyl-4-carbonyl chloride, there was obtained Compound (9a), a diphenylmethyl ester of the subject Compound (9b), by the procedure of Example 5, and then, the procedure of Example 2 (b) was conducted to give the subject Compound (9b)

EXAMPLE 10

Production of sodium 2-[(4S)-4-(2-ethoxynaphthalenyl-1-carboxamido)-3-oxo-2-isoxazolidinyl]-5-oxo-2-tetrahydrofurancarboxylate [Compound (10b)]:

Using Compound (R-3) and 2-ethoxynaphthalenyl-1-carbonyl chloride, there was obtained Compounds (10a), a diphenylmethyl ester of the subject Compound (10b), by the procedure of Example 5, and then, the procedure of Example 2 (b) was carried out to give the subject Compound (10b).

Below given are the reaction conditions of Examples 1 to 10 as well as the yields and typical physico-chemical properties of the compounds obtained.

| Product | Reaction conditions | Yield (mg) St. mat → Prod. | IR$\nu_{max}^{KBr}$cm$^{-1}$ | NMR(90 MHz)$\delta$ |
|---|---|---|---|---|
| 1a | 2-(2-chloroacetamido-4-thiazolyl)-(Z)-2-methoxyiminoacetic acid (155 mg), HOBT (75 mg), DCC (115 mg), DMF (0.5 ml) 0° C., 1 h reacted, extraction with ethyl acetate, silica gel chromatography (ethyl actate-hexane = 2:1):1) | 198 → 300 | 3250, 1800, 1760, 1680 | 2.2-3.3 (4H,m), 3.98 (3H,s), 4.0-5.3 (3H,m), 4.13 (2H,s), 6.95, 6.98 (each 0.5H,s), 7.20 (1H,s), 7.3-7.4 (10H, m), 7.7 (1H,b) (solvent: CDCl$_3$) |
| 2a | N—(4-ethyl-2,3-dioxo-1-piperazinylcarbonyl)-D-phenylglycine (81 mg), HOBT (10 mg), DCC (58 mg), DMF (2 ml) rt, 1 h reacted, extraction with ethyl acetate, silica gel chromatography (ethyl-acete) | 100 → 145 | 3300, 1805, 1760, 1720, 1685, 1500, 1180 | 1.09, 1.12 (each 1.5H,t,J=7Hz), 3.2-3.6 (2H,m), 3.8-4.1 (2H,m), 5.53, 5.75 (each 0.5H,d,J=7Hz), 6.87, 6.90 (each 0.5H,s), 7.1-7.6 (15 H,m), 7.86, 7.92 (each 0.5H, d,J=7Hz), 9.75, 9.81 (each 0.5H,d,J=7Hz) (solvent: CDCl$_3$) |
| 3a | N—(3-methylsulfonyl-2-oxoimidazolidinyl-1-carbonyl)-D-phenylglycine (116 mg), HOBT (15 mg), DCC (71 mg), DMF (3 ml) rt, 2 h reacted, extraction with ethyl acetate, silica gel chromatography (ethyl acetate) | 120 → 178 | 3325, 1800, 1735, 1680, 1525, 1390, 1355, 1255, 1170 | 1.5-3.1 (4H,m), 3.18, 3.20 (each 1.5H,s), 3.72, 3.76 (each 0.5H,b), 4.42, 4.53 (each 1H,t,J=9Hz), 4.4-5.2 (1H,m), 5.51, 5.67 (each 0.5H,d,J=7Hz), 6.90, 6.91 (each 0.5H,s), 7.1-7.5 (15H,m), 7.50 (0.5H,d,J=6Hz), 8.77, 8.90 (each 0.5H, d,J=7Hz) (solvent: CDCl$_3$) |
| 4a | N—(3-furfurylideneamino-2-oxo imidazolidinyl-1-carbonyl)-D-phenylglycine (178 mg), HOBT (30 mg), DCC (103 mg), DMF (5 ml), rt, 3 h reacted, extraction with ethyl acetate, silica gel chromatography (ethyl acetate) | 150 → 282 | 3310, 1805, 1765 (sh), 1735, 1675, 1530, 1480, 1410, 1390, 1270, 1230 | 1.9-3.4 (4H,m), 3.5-5.3 (3H, m), 3.68 (4H,s), 5.57, 5.74 (each 0.5H,d,J=7Hz), 6.87, 6.89 (each 0.5H,s), 6.3-7.5 (18H,m), 7.57 (1H, s), 7.78, 7.95 (each 0.5H,d, J=7Hz), 9.10, 9.23 (each 0.5H,d,J=7Hz) (solvent: CDCl$_3$) |
| 5a | 2-thiopheneacetyl chloride (60 mg), DMA (0.16 ml), CH$_2$Cl$_2$ (3 ml), 0° C., 10 min→ r.t. 20 min | 100 → 110 | 3400, 1780, 1760, 1680, 1510, 1180 | 2.2-3.3 (4H,m), 4.76 (2H,s), 3.5-4.2 (1H,m), 4.63-4.9 (2H,m), 6.2-6.5 (1H,m), 7.0-7.61 (13H,m) (solvent: CDCl$_3$) |

| Product | Reaction conditions | Yield (mg) St. mat → Prod. | IR$\nu_{max}^{KBr}$cm$^{-1}$ | NMR(90 MHz)δ |
|---|---|---|---|---|
| | extraction with ethyl acetate, crystallized from ether | | | |
| 6a | cyanoacetic acid (47 mg), HOBT (37 mg), DCC (128 mg), DMF (2 ml), rt, 60 min extraction with ethyl acetate, silica gel chromatography (ethyl acetate-hexane = 2:1) | 100 → 76 | 3320, 2250, 1790, 1760, 1720, 1685, 1620, 1530, 1180, 1050 | 3.66 (2H,s), 3.91–4.47 (1H, m), 4.55–5.09 (1H,m), 5.41–5.60 (1H,m), 6.91 (1H,s), 7.3–7.4 (10H,m) (solvent: d$_6$-DMSO) |
| 7a | (1H)—tetrazolyl-acetic acid (484 mg), HOBT (51 mg), DCC (78 mg), DMF (2 ml), rt. 40 min extraction with ethyl acetate, silica gel chromatography (ethyl acetate) | 100 → 88 | 3320, 2930, 2850, 1790, 1765, 1690, 1620, 1570, 1180, 1050 | 3.95–4.35 (1H,m), 4.51–5.09 (1H,m), 5.32 (2H,s), 5.43–5.61 (1H,m), 6.91 (1H,s), 7.3–7.4 (10H,m), 9.24 (1H,s) (solvent: d$_6$-DMSO) |
| 8a | 2,6-dimethoxy-benzoyl chloride (101 mg), DMA (0.2 ml), CH$_2$Cl$_2$ (3 ml), rt, 24 h extraction with ethyl acetate, silica gel chromatography (ethyl acetate) | 100 → 100 | 3350, 2990, 1800, 1740, 1660, 1600, 1480, 1180, 1050 | 2.25–3.32 (4H,m), 3.78(6H, s), 3.97–4.29 (1H,m), 3.75–4.99 (1H,m), 6.50 (2H,d,J=8Hz), 6.92 (1H,s), 7.13–7.40 (11H,m) (solvent: CDCl$_3$) |
| 9a | 5-methyl-3-phenyl-2-isoxazolyl-4-carbonyl chloride (112 mg), DMA (0.2 ml), CH$_2$Cl$_2$ (5 ml), 0° C., 5 min, rt, 30 min, extraction with ethyl acetate, silica gel chromatography (ethyl acetate-hexane = 1:1) | 100 → 124 | 3400, 3040, 1800, 1760, 1660, 1420, 1180, 1050 | 2.19–3.30 (4H,m), 2.67 (3H, s), 3.35–4.00 (1H,m), 4.41–4.78 (1H,m), 5.81–6.09 (1H, m), 6.87, 6.90 (1H,sX2), 7.20–7.60 (15H,m) (solvent: CDCl$_3$) |
| 10a | 2-ethoxynaphthalenyl-1-carbonyl chloride (177 mg), DMA (0.4 ml), CH$_2$Cl$_2$ (10 ml), 0° C., 10 min, rt. 120 min extraction with ethyl acetate, silica gel chromatography (ethyl acetate-hexane = 1:1) | 200 → 160 | 3400, 2900, 1800, 1750, 1660, 1595, 1510, 1250, 1180, 1050 | 1.42 (3H,t,J=7Hz), 2.31–3.46 (4H,m), 3.18 (2H,q), 3.02–3.61 (1H,m), 4.83–5.22 (1H,m), 6.70–6.84 (1H,m), 6.97, 7.01 (1H,sX2), 7.18–8.15 (16H,m), (solvent: CDCl$_3$) |
| 1b | CH$_3$NHCS$_2$Na.2H$_2$O (120 ml) THF (8 ml)-H$_2$O (17 ml) r.t. 1 h extraction with ethyl acetate, silica gel chromatography (ethyl acetate) | 300 → 250 | 3330, 1800, 1750, 1680, 1610 | 2.2–3.3 (4H,m), 3.90 (3H,s), 4.0–4.9 (3H,m), 5.7 (2H,b), 6.70, 6.77 (each 0.5H,s), 6.93 (1H,s), 7.2–7.4 (10H, m), 8.2 (1H,b) (solvent: CDCl$_3$) |
| 1c | CF$_3$COOH (0.2 ml) anisole (0.15 ml) CH$_2$Cl$_2$ (8 ml) −10° C.~−15° C., 5.5 h HP-20 column (water), | 120 → 45 | 3430, 1780, 1730, 1660, 1540 | 2.4–3.3 (4H,m), 4.03 (3H,s), 4.3–4.8 (3H,m), 7.03 (1H,s) (solvent: D$_2$O) |

-continued

| Product | Reaction conditions | Yield (mg) St. mat → Prod. | IR$\nu_{max}^{KBr}$cm$^{-1}$ | NMR(90 MHz)δ |
|---|---|---|---|---|
| | lyophilization | | | 1.14 (3H,t,J=7Hz), 3.3–3.6 |
| 2b | H$_2$/5% Pd-C (141 mg) | 141 | 1780, 1720, | (2H,m), 3.44 (2H,q,J=7Hz), |
| | THF-buffer (pH 6.86) | → | 1690–1650, | 3.8–4.1 (2H,m), 4.2–4.6 (2H, |
| | 0° C., 20 min | 89 | 1510, 1370, | m), 4.7–5.1 (1H,m), 5.55 (1H, |
| | XAD-2 column | | 1190 | d,J=7Hz), 7.2–7.6 (5H,m), |
| | (20% ethanol) | | | 9.26 (1H,b), 9.82 (1H,d,J= |
| | lyophilization | | | 7Hz) (solvent: D$_2$O) |
| 3b | H$_2$/5%Pd-C (98 mg) | 176 | 1785, 1740, | 3.35 (3H,s), 3.82 (4H,s), |
| | THF-buffer (pH 7.0) | → | 1670, 1535, | 4.32, 4.42 (each 1H,t,J= |
| | 0° C., 20 min | 89.5 | 1400, 1360, | 8Hz), 4.6–5.1 (1H,m), 5.48, |
| | XAD-2 column | | 1175 | 5.53 (each 0.5H,d,J=7Hz), |
| | (10% ethanol) | | | 7.1–7.6 (5H,m), 8.77 (1H,d, |
| | lyophilization | | | J=7Hz), 9.17, 9.26 (each |
| | | | | 0.5H,d,J=8Hz) |
| | | | | (solvent: D$_2$O) |
| 4b | H$_2$/5%Pd-C (120 mg) | 120 | 1780, 1725, | 3.7–4.7 (2H,m), 3.86 (4H,s), |
| | THF-buffer (pH 7.0) | → | 1660, 1530, | 4.7–5.7 (1H,m), 5.59 (1H,d, |
| | 0° C., 20 min | 64 | 1480, 1415, | J=7Hz), 6.4–7.8 (8H,m), |
| | XAD-2 column | | 1390, 1270, | 7.72 (1H,s), 8.9–9.3 (1H,b), |
| | (20% ethanol) | | 1235, 1190 | 9.10 (1H,d,J=7Hz) |
| | lyophilization | | | (solvent:D$_2$O) |
| 5b | CF$_3$COOH (0.18 ml) | 105 | 3420, 1780, | 2.41–3.42 (4H,m), 4.11 (2H, |
| | anisole (0.092 ml) | → | 1720, 1650, | s), 4.29–4.54 (1H,m), 4.79– |
| | CH$_2$Cl$_2$ 8 ml | 35 | 1540, 1380, | 5.05 (1H,m), 5.13–5.43 (1H, |
| | −10° C.∼−15° C., 3 h | | 1190 | m), 7.24–7.81 (3H,m) |
| | XAD-2 column | | | (solvent: D$_2$O) |
| | (10% ethanol) | | | |
| | lyophilization | | | |
| 6b | H$_2$/5% Pd-C (100 mg) | 100 | 3420, 2250, | 2.41–3.41 (4H,m), 4.00 (2H, |
| | THF-buffer (pH 7.0) | → | 1775, 1720, | s), 4.31–4.60 (1H,m), 4.81– |
| | 0° C., 20 min | 50 | 1660, 1540, | 5.09 (1H,m), 5.19–5.48 (1H,m) |
| | HP-20 column (water), | | 1380, 1190 | (solvent: D$_2$O) |
| | lyophilization | | | |
| 7b | H$_2$/5%Pd-C (133 mg) | 133 | 3420, 1780, | 2.42–3.42 (4H,m), 4.32–4.59 |
| | THF-buffer (pH 7.0) | → | 1720, 1650, | (1H,m), 4.81–5.09 (1H,m), |
| | 0° C., 20 min | 49 | 1550, 1380, | 5.21–5.49 (1H,m), 5.77 (1H, |
| | HP-20 column (water), | | 1190 | s), 9.58 (1H,s) |
| | lyophilization | | | (solvent: D$_2$O) |
| 8b | H$_2$/5% Pd-C (100 mg) | 100 | 3420, 1780, | 2.41–3.42 (4H,m), 4.05 (6H, |
| | THF-buffer (pH 7.0) | → | 1730, 1650, | s), 4.38–4.64 (1H,m), 4.85– |
| | 0° C., 25 min | 54 | 1595, 1530, | 5.16 (1H,m), 5.27–5.58 (1H, |
| | XAD-2 column | | 1375, 1250, | m), 7.04 (2H,d,J=8Hz), 7.70 |
| | (10% ethanol) | | 1105 | (1H,d,J=8Hz) |
| | lyophilization | | | (solvent: D$_2$O) |
| 9b | H$_2$/5% Pd-C (124 mg) | 124 | 3420, 1780, | 2.42–3.41 (4H,m), 3.87 (3H, |
| | THF-buffer (pH 7.0) | → | 1730, 1660, | s), 4.31–4.55 (1H,m), 4.81– |
| | 0° C., 40 min | 53 | 1380, 1190 | 5.07 (1H,m), 5.20–5.48 (1H, |
| | XAD-2 column | | | m), 7.82 (5H,s) |
| | (20% ethanol) | | | (solvent: D$_2$O) |
| | lyophilization | | | |
| 10b | H$_2$/5% Pd-C (134 mg) | 134 | 3420, 1780, | 1.53 (3H,t,J=7Hz), 2.43– |
| | THF-buffer (pH 7.0) | → | 1730, 1650, | 3.42 (4H,m), 4.34–4.72 (1H, |
| | 0° C., 1 h | 62 | 1590, 1520, | m), 4.48 (2H,q,J=7.15Hz), |
| | XAD-2 column | | 1380, 1250, | 4.85–5.17 (1H,m), 5.35– |
| | (20% ethanol) | | 1190 | 5.58 (1H,m), 7.58–8.31 (6H,s) |
| | lyophilization | | | (solvent: D$_2$O) |

EXAMPLE 11

Production of sodium 2-[(4S)-4-(2cyanomethylthioacetamido)-3-oxo-2-isoxazolidinyl]-5-oxo-2-tetrahydrofurancarboxylate [Compound (11b)]:

Using Compound (R-3) and cyanomethylthioacetyl chloride, there was obtained Compound (11a), a diphenylmethyl ester of the subject Compound (11b), by the procedure of Example 5, and then the procedure of Example 1 (c) was carried out to give the subject Compound (11b).

EXAMPLE 12

Production of sodium 2-[(4S)-4-(2-difluoromethylthioacetamido)-3-oxo-2-isoxazolidinyl]-5-oxo-2-tetrahydrofurancarboxylate [Compound (12b)]:

Using Compound (R-3) and difluoromethylthioacetyl chloride, there was ontained Compound (12a), a diphenylmethyl ester of the subject Compound (12b), by the procedure of Example 5, and then, the procedure of Example 1 (c) was carried out to give the subject Compound (12b).

EXAMPLE 13

Production of sodium 2-{(4S)-4-[(R)-2-(4-cyclohexyl-2,3-dioxo-1-piperazinocarboxamido-2-phenylacetamido]-3-oxo-2-isoxazolidinyl}-5-oxo-2-tetrahydrofurancarboxylate [Compound (13b)]:

Using Compound (R-3) and N-(4-cyclohexyl-2,3-dioxo-1-piperazinylcarbonyl)-D-phenylglycine, there was obtained Compound (13a) (chromatography on silica gel permitted isolation of the stereoisomers in relation to the 2-position, A and B), a diphenylmethyl ester of the subject Compound (13b), by the procedure of Example 2 (a). Then, using the isomers, A and B, of Compound (13a), there was obtained the subject Compound (13b) by the procedure of Example 2 (b).

EXAMPLE 14

Production of sodium 2-{(4S)-4-chloroacetamido-3-oxo-2-isoxazolidinyl}-5-oxo-2-tetrahydrofurancarboxylate [Compound (14b)]

Propylene oxide was added to a dichloromethane solution of Compound (R-3) under cooling at $-10°$ C. to $-20°$ C., and then, chloroacetyl chloride was added dropwise to the mixture, followed by stirring at the same temperature for 1 hour. The reaction solution was poured into aqueous sodium hydrogencarbonate solution (10 ml), and the organic layer was separated, washed with saturated aqueous sodium chloride solution and dried over anhydrous magnesium sulfate. The solvent was distilled off, and the residue was chromatographed on a column of silica gel, followed by eltuion with dichloromethanethyl acetate: hexane (1:1:1) to give Compound (14a), a diphenylmethyl ester of the subject Compound (14b), in the form of crystals.

Then, a deprotection reaction was carried out by the procedure of Example 1 (c) with Compound (14a) to give the subject Compound (14b).

EXAMPLE 15

Production of sodium 2-{(4S)-4-[2-(4-pyridylthio)acetamido]-3-oxo-2-isoxazolidinyl}-5-oxo-2-tetrahydrofurancarboxylate [Compound (15b)]:

Using Compound (14a) as obtained in Example 14, a reaction was carried out with 4-pyridinethiol to give Compound (15a), a diphenylmethyl ester of the subject Compound (15b), and the procedure of Example 1 (c) was carried out to give the subject Compound (15b). Below given are the reaction conditions of Examples 11 to 15 as well as the yields and typical physico-chemical properties of the compounds obtained.

| Product | Reaction conditions | Yield (mg) St. mat → Prod. | IR$\nu_{max}^{KBr}$cm$^{-1}$ | NMR (90MHz)δ (solvent) |
|---|---|---|---|---|
| 11a | cyanomethylthioacetyl chloride (176.4 mg), propyleneoxide (2 ml), CH$_2$Cl$_2$ (9 ml) $-20°$ C., 20 min extraction with ethyl acetate, silica gel chromatography (CH$_2$Cl$_2$:ethyl acetate-hexane = 1:1:1) | 230.9 → 163 | 3340, 2230, 1765, 1670, 1180, 1050, 735, 690 | (d$_6$-DMSO + D$_2$O) 3.40 (2H,s), 4.5–5.8 (3H,m), 6.85 (1H,s), 7.3–7.5 (10H,m) |
| 12a | difluoromethyl thioacetyl chloride (181 mg), propyleneoxide (2 ml), CH$_2$Cl$_2$ (9 ml) $-20°$ C., 30 min extraction with ethyl acetate, silica gel chromatography (CH$_2$Cl$_2$-ethyl acetate-hexane= 1:1:1) | 221.5 → 285 | 3350, 1790, 1765, 1735, 1510, 1180, 1050, 735, 695 | (d$_6$-DMSO + D$_2$O) 2.60–3.35 (4H,m), 3.65 (2H, s), 4.6–4.8 (1H,m), 6.92 (1H, s), 7.30 (1H,t,J=55Hz), 7.35–7.50 (10H,m) |
| 13a | N—(4-cyclohexyl-2,3-dioxo-1-piperazinylcarbonyl)-D—phenylglycine (233 mg), DCC (125 mg), HOBT (30 mg), DMF (5 ml), rt, 3 h extraction with ethyl acetate, silica gel chromatography (hexane-ethyl acetate = 1:3) | 200 → A, 64 B, 92 A + B 113* | isomer A 3310, 2940, 1810, 1765, 1720, 1680, 1520, 1175, 700 isomer B 3300, 2940, 1800, 1760, 1720, 1680, 1510, 1175, 700 | isomer A not measured because of insolubility in CDCl$_3$, (CD$_3$)$_2$CO isomer B 0.9–1.9 (10H,m), 2.0–3.3 (4H,m), 3.2–3.5 (2H,m), 3.7–4.0 (2H,m), 4.38 (1H, t,J=8Hz), 4.6–5.0 (1H, m), 5.48 (1H,d,J=6Hz), 6.88 (1H,s), 7.0–7.5 (15H, m), 7.74 (1H,d,J=7Hz), 9.70 (1H,d,J=6Hz) |
| 14a | chloroacetyl chloride (208 mg), propyleneoxide (5 ml), CH$_2$Cl$_2$ (40 ml), $-10°$ C.~ $-20°$ C., 1 h extraction with | 1000 → 750 | 3500, 3450, 1795, 1785, 1670, 1525, 1180, 1050, 740, 700 | (d$_6$-DMSO) 2.6–3.3 (4H,m), 4.12 (2H,s), 4.5–5.2 (3H,m), 6.90 (1H,s), 7.3–7.5 (10H,m), 8.91 (1H,d, J=7.5Hz) |

-continued

| Product | Reaction conditions | Yield (mg) St. mat → Prod. | IR$\nu_{max}^{KBr}$cm$^{-1}$ | NMR (90MHz)δ (solvent) |
|---|---|---|---|---|
| | ethyl acetate, silica gel chromatography (CH$_2$Cl$_2$-ethyl acetate-hexane = 1:1:1) | | | |
| 15a | 4-pyridine thiol (56.4 mg), NaH (19.2 mg), NaI (100 mg), DMF (1 ml), r.t. 30 min extraction with ethyl acetate, silica gel chromatography (ethyl acetate-acetone = 2:1) | 200 → 163 | 3350, 1770, 1740, 1680, 1570, 1520, 1180, 1050 | (CDCl$_3$) 2.12-3.22 (4H,m), 3.38-4.09 (1.5H,m), 4.69 (2H,s), 4.46-4.93 (1.5H,m), 6.91, 6.93 (each 0.5H,s), 7.02-7.40 (12H,m), 8.39 (2H,d,J=7Hz) |
| 11b | CF$_3$COOH (0.12 ml) anisole (1.0 ml) CH$_2$Cl$_2$ (0.8 ml) −20° C.~0° C., 6 h CHP-20 column (water) lyophilization | 130 → 46 | 2240, 1780, 1660, 1200, 1030, 905, 830, 690 | (d$_6$-DMSO) 2.55-3.10 (4H,m), 3.40 (2H, s), 3.72 (2H,s), 3.9-5.1 (3H, m), 8.85 (1H,d,J=7.5Hz) |
| 12b | CF$_3$COOH (0.5 ml) anisole (0.5 ml) CH$_2$Cl$_2$ (4 ml) −20° C.~−10° C., 7 h CHP-20 column (20% ethanol) lyophilization | 240 → 82 | 3350, 3250, 1800, 1740, 1670, 1540, 1320, 1190, 1060, 1050, 900, 750 | (d$_6$-DMSO) 2.85-3.20 (1H,m), 3.55 (2H, s), 3.9-4.2 (1H,m), 4.45-5.10 (3H,m), 7.32 (1H,t,J=55Hz), 8.90 (1H,d,J=6Hz) |
| 13b | H$_2$/5%Pd-C (120 mg) THF (8 ml)-pH 7.0 buffer (4 ml) 0° C., 20 min XAD-2 column (20% ethanol) lyophilization | 120 → 71 | 2940, 1790, 1720, 1670, 1515, 1190 | (d$_6$-DMSO + CDCl$_3$) 0.9-1.9 (10H,m), 2.2-3.2 (4H,m), 3.3-3.6 (2H,m), 3.7-4.0 (2H,m), 3.7-4.6 (2H,m), 4.7-5.1 (1H,m), 5.53, 5.55 (each 0.5H,d,J=7Hz), 7.2-7.6 (5H,m), 9.17, 9.26 (each 0.5H,d,J=8Hz), 9.82 (1H,d, J=7Hz) |
| 14b | CF$_3$COOH (0.3 ml) anisole (0.5 ml) CH$_2$Cl$_2$ (3 ml) −20° C.~0° C., 3.5 h CHP-20 column (water) lyophilization | 159 → 85 | 1780, 1660, 1540, 1380, 1200, 1120, 1030, 910, 765, 680 | (D$_2$O) 2.6-3.6 (4H,m), 4.44 (2H,s), 4.3-4.6 (1H,m), 4.8-5.1 (1H, m), 5.2-5.5 (1H,m) |
| 15b | CF$_3$COOH (0.228 ml) anisole (0.113 ml) CH$_2$Cl$_2$ (10 ml) −10° C.~−15° C., 3 h XAD-2 column (water) lyophilization | 135 → 21 | 3420, 1780, 1730, 1660, 1585, 1540, 1380, 1190 | (D$_2$O) 2.41-3.42 (4H,m), 4.22 (2H, s), 4.15-4.50 (1H,m), 4.73-5.02 (1H,m), 5.12-5.48 (1H, m), 7.59 (2H,m), 8.61 (2H,m) |

EXAMPLE 16

Production of methyl 2-[(4S)-4-acetamido-3-oxo-2-isoxazolidinyl]-5-oxo-2-tetrahydrofurancarboxylate [Compound (16)]:

Sodium 2-[(4S)-4-acetamido-3-oxo-2-isoxazolidinyl]-5-oxo-2-tetrahydrofurancarboxylate [Compound (R-1)] as obtained in Reference Example 1 was dissolved in DMF, and methyl iodide was added to the solution, followed by stirring under shield of sunlight at room temperature for 5 hours. The reaction solution was concentrated, and 50 ml of water was added to the concentrate, followed by extraction with 20 ml of dichloromethane. The extract was concentrated, and the residue was crystallized from ethyl acetate-ether to give crystals (1.36 g). The crystals (a mixture of isomers A and B, 1 g) was chromatoqraphed on silica gel (50 g), and elution for fractionation was performed with a solvent system of chloroform-methanol (30:1). The fractions which flowed out of the column first were concentrated and crystallized to give the subject Compound (isomer B of 16), while the fraction which flowed out of the column subsequently afforded the subject Compound (isomer A of 16) in the form of a crystalline powder.

EXAMPLE 17

Production of pivaloyloxymethyl 2-[(4S)-4-acetamido-3-oxo-2-isoxazolidinyl]-5-oxo-2-tetrahydrofurancarboxylate [Compound (17)]:

Compound (R-1) was dissolved in DMF, and chloromethyl pivalate was added to the solution, followed by stirring . Water was added to the reaction solution, and the mixture was extracted with 150 ml of ethyl acetate.

The extract was concentrated, and the resultant residue was powdered from petroleum ether. 140 mg of the resulting powder was chromatographed on Sephadex LH-20 (500 ml), and elution was performed with ethyl acetatemethanol (19:1). The corresponding fractions afforded the subject Compound (isomer B of 17) and Compound (isomer A of 17) in the form of crystals, respectively.

EXAMPLE 18

Production of 3,5-dinitrobenzyl 2-[(4S)-4-acetamido-3-oxo-2-isoxazolidinyl]-5-oxo-2-tetrahydrofurancarboxylate [Compound (18)]:

Compound (R-1) was dissolved in DMF, and 3,5-dinitrobenzyl chloride was added to the solution, followed by stirring. Water was added to the reaction system, and the mixture was extracted with ethyl acetate. The extract was concentrated, and the residue was powdered from petroleum ether. 624 mg of the resultant powder crystallized from acetone-hexane to give crystals of Compound (isomer A of 18). The mother liquor was also crystallized from the same solvent to give crystals of the subject Compound (isomer B of 18).

EXAMPLE 19

Production of p-bromophenacyl 2-[(4S)-4-acetamido-3-oxo-2-isoxazolidinyl]-5-oxo-2-tetrahydrofurancarboxylate [Compound (19)]:

Compound (R-1) was dissolved in DMF, and p-bromophenacyl bromide was added to the solution, followed by stirring. Water was added to the reaction solution, and the mixture was extracted with ethyl acetate. The extract was concentrated, and petroleum benzine was added to the residue to give 410 mg of a powder. The powder was chromatographed on Sephadex LH-20 (500 ml), and elution for fractionation was performed with a solvent system of ethyl acetate-methanol (19:1). The fraction which flowed out of the column first produced a powder of the subject Compound (isomer B of 19) and the fraction which flowed out of the column last afforded a powder of Compound (isomer A of 19), while the fraction which flowed out intermediate yielded a powder of Compound (a mixture of isomers A and B of 19).

EXAMPLE 20

Production of p-bromobenzyl 2-[(4S)-4-acetamido-3-oxo-2-isoxazolidinyl]-5-oxo-2-tetrahydrofurancarboxylate [Compound (20)]:

Compound (R-1) was dissolved in DMF, and triethylamine and p-bromobenzyl bromide were added to the solution, followed by stirring. 100 ml of 0.1M phosphate buffer (pH 6.3) was added to the reaction solution, and the mixture was extracted with ethyl acetate. The extract was concentrated, and chloroform and petroleum benzine were added to the residue to convert into powder, thereby giving 562 mg of a powder. The powder was chromatographed on a column of Sephadex LH-20, and elution was performed with ethyl acetate-methanol (19:1). The fraction which flowed out of the column first yielded crystals of the subject Compound (isomer B of 20), and the fraction which flowed out last afforded crystals of Compound (isomer A of 20), while the fraction which flowed out intermediate gave a powder of Compound (a mixture of isomers A and B of 20).

Below given are the reaction conditions of Examples 16 to 20 as well as the yields and typical physico-chemical properties of the compounds obtained.

| Product | Reaction conditions of esterification | Yield (mg) St. mat → Prod. | $IR\nu_{max}^{KBr}cm^{-1}$ | NMR (90 MHz)δ (solvent) |
|---|---|---|---|---|
| 16 | methyl iodide (0.8 ml) DMF(10 ml) rt,5h,ethyl acetate, extraction with CH₂Cl A,B were separated with silica gel chromatography (chloroform-methanol) | 2000 → 1360 | isomer A 1800, 1760, 1750, 1650, 1305, 1180, 900 | isomer A (CDCl₃) 2.03(3H,s), 2.3~3.4(4H,m), 3.88(3H,s), 3.9~4.3(1H,m), 4.6~5.2(2H,m), 6.40(1H,d, J = 6Hz) |
| | | | isomer B 1815, 1805, 1760, 1740, 1665, 1305 | isomer B (CDCl₃) 2.04(3H,s), 2.3~3.3(4H,m), 3.87(3H,s), 4.11(1H,dd,J = 8,10Hz), 4.7~5.3(2H,m), 6.39(1H,d,J = 6Hz) |
| 17 | Chloromethyl pivalate(360 μl) DMF(5 ml) rt, 14h extraction with ethyl acetate Sephadex LH-20 chromatography (ethyl acetate-methanol = 19:1) | 500 → A, 116 B,105 A + B 173 | isomer A 3400, 1810, 1760, 1675, 1540 | isomer A (CDCl₃) 1.22(9H,s), 2.03(3H,s), 2.2 −3.4(4H,m), 3.9–4.3(1H,m), 4.6–5.0(2H,m), 5.83(2H,s), 6.55(1H,d,J = 5Hz) |
| | | | isomer B 3320, 1800, 1750, 1660, 1535 | isomer B (CDCl₃) 1.22(9H,s), 2.05(3H,s), 2.2 −3.4(4H,m), 4.13(1H,dd,J = 8,10Hs), 4.6–5.3(2H,m), 5.85 (2H,m), 6.55(1H,d,J = 6Hz) |
| 18 | 3,5-dinitrobenzyl chloride (570 mg) DMF(5 ml) tr, 13h extraction with ethyl acetate, fractional recrystallization with acetone-hexane | 570 → A,330 B, 187 | isomer A 3370, 1805, 1775, 1755, 1670, 1550, 1350 | isomer A (CDCl₃ + d₈-DMSO) 1.93(3H,s), 2.4–3.3(4H,m), 4.0–4.4(1H,m), 4.4–5.0(2H, m), 5.6(2H,m), 8.37(1H,d,J = 7Hz), 8.7–8.8(2H,m), 8.9–9.0(1H,m) |
| | | | isomer B 3310, 1815, 1760, 1670, 1550, 1350 | isomer B (CDCl₃ + d₆-DMSO) 1.93(3H,s), 2.4–3.3(4H,m), 3.9–4.4(1H,m), 4.4–5.2(2H, m), 5.6(2H,m), 8.53(1H,d,J = 7Hz), 8.7–8.8(2H,m), 8.9–9.0(1H,m) |

-continued

| Product | Reaction conditions of esterification | Yield (mg) St. mat → Prod. | IR$\nu_{max}^{KBr}$cm$^{-1}$ | NMR (90 MHz)δ (solvent) |
|---|---|---|---|---|
| 19 | p-bromophenacyl bromide(280 mg) DMF(3 ml) rt, 2h extraction with ethyl acetate, Sephadex LH-20 chromatography (ethyl acetate-methanol = 19:1) | 312 → A, 176 B, 124 A + B, 76 | isomer A 3390, 1810, 1780, 1710, 1540<br><br>isomer B 3400, 1810, 1780, 1745, 1710, 1540 | isomer A (CDCl$_3$) 2.03(3H,s), 2.5–3.4(4H,m), 3.9–4.4(1H,m), 4.6–5.1(2H, m), 5.48(2H,s), 6.37(1H,d,J = 6Hz), 7.67(2H,d,J = 8Hz), 7.80(2H,d,J = 8Hz)<br><br>isomer B (CDCl$_3$) 2.03(3H,s), 2.5–3.5(4H,m), 4.0–4.3(1H,m), 4.7–5.3(2H, m), 5.5(2H,m), 6.57(1H,d,J = 6Hz), 7.67(2H,d,J = 8Hz), 7.80(2H,d,J = 8Hz) |
| 20 | p-bromobenzyl bromide(800 mg) Et$_3$N(250 μl) DMF(5 ml) rt,3h extraction with ethyl acetate powdered with chloroform-petroleum benzine | 500 → 562 | 3400, 1810, 1760, 1680, 1540 | (CDCl$_3$) 2.02(3H,s), 2.3–3.4(4H,m), 3.9–4.3(1H,m), 4.6–5.1(2H, m), 5.25(2H,s), 6.18(0.5H,d, J = 6Hz), 6.32(0.5H,d,J = 6 Hz), 7.23(1H,d,J = 8Hz), 7.27(1H,d,J = 8Hz), 7.53(2H, d,J = 8Hz) |

EXAMPLE 21

Production of sodium 2-[(4S)-4-formylamino-3-oxo-2-isoxazolidinyl]-5-oxo-2-tetrahydrofurancarboxylate [Compound (21b)]:

(a) Production of diphenylmethyl 2-[(4S)-4-formylamino-3-oxo-2-isoxazolidinyl]-5-oxo-2-tetrahydrofurancarboxylate [Compound (21a)]:

Compound (R-3) was dissolved in dichloromethane, and pyridine and a mixed solution of acetic anhydride formic acid were added to the solution, followed by stirring. The reaction solution was washed with N-hydrochloric acid and 2% aqueous sodium hydrogencarbonate solution, successively, and the organic layer was dried and concentrated, followed by adding ether to the residue to give a powder of Compound (21a).

(b) Production of the subject Compound (21b):

10% palladium-carbon was suspended in THF, and Compound (21a) was added to the suspension, followed by stirring under a stream of hydrogen. After the catalyst was filtered off, the filtrate was concentrated, and water was added to the concentrated residue, followed by adjustment to pH 6. The aqueous layer was washed with ether, and chromatographed on activated carbon. Elution for fractionation was performed with a solvent system of 8% isobutanol/0.02N aqueous ammonia, and the eluate fraction was concentrated. The residue was treated with acetone and converted into powder to give a powder of the subject Compound (21b).

EXAMPLE 22

Production of sodium 2-[(4S)-4-n-butyrylamino-3-oxo-2-isoxazolidinyl]-5-oxo-2 tetrahydrofurancarboxylate [Compound (22b)]:

(a) Production of diphenylmethyl 2-[(4S)-4-n-butyrylamino-3-oxo-2-isoxazolidinyl]-5-oxo-2-tetrahydrofurancarboxylate [Compound (22a)]:

Compound (R-3) was dissolved in dichloromethane, and N,N-dimethylacetamide (DMA) and n-butyryl chloride were added to the solution, followed by stirring. The reaction solution was treated by the procedure of Example 21 (a) to give a powder of Compound (22a).

(b) Production of the subject Compound (22b)

10% Palladium-carbon was suspended in THF and 0.1M phosphate buffer (pH 7.0), and Compound (22a) was added to the suspension, followed by stirring under a stream of hydrogen. After the catalyst was filtered off, the THF was distilled off, and the aqueous layer was washed with ether and chromatographed on a column of Diaion HP-20. Elution was performed with water, and the effective fraction was concentrated and lyophilized to give a powder of the subject Compound (22b).

EXAMPLE 23

Production of sodium 2-[(4S)-4-methoxycarbonylamino-3-oxo-2-isoxazolidinyl]-5-oxo-2-tetrahydrofurancarboxylate [Compound (23b)]:

(a) Production of diphenylmethyl 2-[(4S)-4-methoxycarbonylamino-3-oxo-2-isoxazolidinyl]-5-oxo-2-tetrahydrofurancarboxylate [Compound (23a)]:

Compound (R-3) was dissolved in THF, and triethylamine and methyl chlorocarbonate were added to the solution, followed by stirring. The reaction solution was treated by the procedure of Example 21 (a) to give a powder of Compound (23a).

(b) Production of the subject Compound (23b):

Compound (23a) was subjected to a reaction analogous to Example 22 (b), and the reaction solution was treated by the procedure of Example 21 (b) to give a powder of the subject Compound (23b).

EXAMPLE 24

Production of sodium 2-[(4S)-4-(N-benzyloxycarbonyl)glycylamino-3-oxo-2-isoxazolidinyl]-5-oxo-2-tetrahydrofurancarboxylate [Compound (24b)]:

(a) Production of diphenylmethyl 2-[(4S)-4-(N-benzyloxycarbonyl)glycylamino-3-oxo-2-isoxazolidinyl]-5-oxo-2-tetrahydrofurancarboxylate [Compound (24a)]:

Methyl chlorocarbonate, N-benzyloxycarbonylglycine (Z-glycine) and triethylamine were added to THF, and a suspension of Compound (R-3) in THF was added to the said solution, followed by stirring. The reaction solution was treated by the procedure of Example 21 (a) to give crystals of Compound (24a).

(b) Production of the subject Compound (24b):

Compound (24a) was subjected to a reaction analogous to Example 22 (b), followed by treatment to give a powder of the subject Compound (24b).

EXAMPLE 25

Production of sodium 2-[(4S)-4-benzoylamino-3-oxo-2-isoxazolidinyl]-5-oxo-2-tetrahydrofurancarboxylate [Compound (25b)]:

(a) Production of diphenylmethyl 2-[(4S)-4-benzoylamino-3 -oxo-2-isoxazolidinyl]-5-oxo-2-tetrahydrofurancarboxylate [Compound (25a)]:

Compound (R-3) was dissolved in dichloromethane, and DMA and benzoyl chloride were added to the solution, followed by stirring. The reaction solution was treated by the procedure of Example 21 (a) to give crystals of Compound (25a).

(b) Production of the subject Compound (25b):

Compound (25a) was subjected to a reaction analogous to Example 22 (b), and after treatment was conducted, the residue was chromatographed on a column of Diaion HP-20, followed by elution with 40% aqueous methanol to give a powder of the subject Compound (25b).

EXAMPLE 26

Production of sodium 2-[(4S)-4-phenylacetylamino-3-oxo-2-isoxazolidinyl]-5-oxo-2-tetrahydrofurancarboxylate [Compound (26b)]:

(a) Production of diphenylmethyl 2-[(4S)-4-phenylacetylamino-3-oxo-2-isoxazolidinyl]-5-oxo-2-tetrahydrofurancarboxylate [Compound (26b)]:

Compound (R-3) was dissolved in dichloromethane, and DMA and phenylacetyl chloride were added to the solution, followed by stirring. The reaction solution was treated by the procedure of Example 21 (a) to give crystals of Compound (26a).

(b) Production of the subject Compound (26b):

Compound (26a) was subjected to a reaction analogous to Example 25 (b), followed by treatment to give a powder of the subject Compound (26b).

EXAMPLE 27

Production of sodium 2-[(4S)-4-nicotinylamino-3-oxo-2-isoxazolidinyl]-5-oxo-2-tetrahydrofurancarboxylate [Compound (27b)]:

(a) Production of diphenylmethyl 2-[(4S)-4-nicotinylamino-3-oxo-2-isoxazolidinyl]-5-oxo-2-tetrahydrofurancarboxylate [Compound (27a)]:

Compound (R-3) was dissolved in dichloromethane, and DMA and nicotinyl chloride hydrochloride were added to the solution, followed by stirring. The reaction solution was treated by the procedure of Example 21 (a) to give crystals of Compound (27a).

(b) Production of the subject Compound (27b):

Compound (27a) was subjected to a reaction analogous to Example 22, followed by treatment to give the subject Compound (27b) in the form of powder.

EXAMPLE 28

Production of pivaloyloxymethyl 2-[(4S)-4-phenoxyacetylamino-3-oxo-2-isoxazolidinyl]-5-oxo-2-tetrahydrofurancarboxylate [Compound (28c)]:

(a) Production of diphenylmethyl 2-[(4S)-4-phenoxyacetylamino-3-oxo-2-isoxazolidinyl]-5-oxo-2-tetrahydrofurancarboxylate [Compound (28a)]:

Compound (R-3) was dissolved in dichloromethane, and DMA and phenoxyacetyl chloride were added to the solution, followed by stirring. The reaction solution was treated by the procedure of Example 21 (a) to give crystals of Compound (28a).

(b) Production of sodium 2-[(4S)-4-phenoxyacetylamino-3-oxo- 2-isoxazolidinyl]-5-oxo-2-tetrahydrofurancarboxylate [Compound (28b)]:

Compound (28a) was subjected to a reaction analogous to Example 25 (b), followed by work up to give a powder of the subject Compound (28b).

(c) Production of the subject Compound (28c):

Compound (28b) was dissolved in DMF, and chloromethyl pivalate was added to the solution, followed by stirring. Water was added to the reaction solution, and the mixture was extracted with ethyl acetate. The extract was concentrated, and hexane was added to the residue. The mixture was subjected to decantation twice and to further decantation (twice) with petroleum benzine. The residue was dried through a vacuum pump to give the subject Compound (28c).

EXAMPLE 29

Production of sodium 2-[(4S)-4-(p-toluenesulfonyl)amino-3-oxo-2-isoxazolidinyl]-5-oxo-2-tetrahydrofurancarboxylate [Compound (29b)]:

(a) Production of diphenylmethyl 2-[(4S)-4-p-toluenesulfonyl-amino-3-oxo-2-isoxazolidinyl]-5-oxo-2-tetrahydrofurancarboxylate [Compound (29a)]:

Compound (R-3) was dissolved in pyridine, and p-toluenesulfonyl chloride was added to the solution, followed by stirring. Dichloromethane and water were added to the reaction solution, and the organic layer was washed with dilute hydrochloric acid and dilute aqueous sodium hydrogencarbonate solution, successively, and concentrated. Ether was added to the concentrate to give a powder of Compound (29a).

(b) Production of the subject Compound (29b):

Compound (29a) was subjected to the reaction similar to Example 25 (b), followed by work up to give a powder of the subject Compound (29b).

EXAMPLE 30

Production of diphenylmethyl 2-[(4S)-4-(p-bromobenzoyl)amino-3-oxo-2-isoxazolidinyl]-5-oxo-2-tetrahydrofurancarboxylate [Compound (30a)]:

Compound (R-3) was dissolved in dichloromethane, and DMA and p-bromobenzoyl chloride were added to the solution, followed by stirring. The reaction solution was subjected to work up analogous to Example 25 (b) to give 528 mg of a crude substance of Compound (30a). This product was chromatographed on silica gel (50 g), and elution was performed with a solvent system of ethyl acetate-hexane (2:3). The eluate was concentrated to give crystals of the subject Compound (30a).

EXAMPLE 31

Production of diphenylmethyl 2-[(4S)-4-(N-benzyloxy- carbonyl-D-alanyl)amino-3-oxo-2-isoxazolidinyl]-5-oxo-2-tetrahydrofurancarboxylate [Compound (31a)]:

N-Benzyloxycarbonyl-D-alanine and triethylamine were added to a THF solution of methyl chlorocarbonate, and a solution of Compound (R-3) in THF was added gradually to the solution, followed by stirring. The work up was carried out according to the procedure to Example 21 (a) to give a powder of the subject Compound (31a).

Below given are the reaction conditions of Examples 21 to 31 as well as the yields and typical physico-chemical properties of the compounds obtained.

| Product | Reaction conditions | Yield (mg) St. mat → Prod. | IR$\nu_{max}^{KBr}$cm$^{-1}$ | NMR $\delta$ (solvent)(MHz) |
|---|---|---|---|---|
| 21a | HCOOH—Ac$_2$O(1.0 ml) Py(1.6 ml) CH$_2$Cl$_2$(40 ml) 0° C. 1.5h extraction with CH$_2$Cl$_2$, powdered with ether | 800 → 720 | 3400, 1800, 1775, 1745, 1735, 1700, 1530 | (d$_6$-DMSO)(90 MHz) 2.4–3.3(4H,m), 3.8–4.2(1H, m), 4.4–5.2(2H,m), 6.90(1H, s), 7.2–7.4(10H,m), 8.13(1H, s), 8.70(1H,d,J = 7Hz) |
| 22a | n-butyryl chloride(0.265 ml), DMA(1.0 ml) CH$_2$Cl$_2$(20 ml) rt, 30 min extraction with CH$_2$Cl$_2$, powdered with ether | 1000 → 860 | 3370, 2970, 1805, 1785, 1750, 1685, 1185, 1055 | (CDCl$_3$)(90MHz) 0.91(3H,t,J = 7Hz), 1.63(2H, sextet,J = 7Hz), 1.9–3.4(6H, m), 4.00(1H,m), 4.5–5.1(2H, m), 7.00(1H,s), 7.36(10H,m) |
| 23a | methyl chlorocarbonate(0.204 ml) Et$_3$N(0.368 ml) THF20 ml −10° C.~5° C., 3h extraction with ethyl acetate powdered by ether | 1000 → 1010 | 3430, 1805, 1775, 1740, 1260, 1190, 1060 | (CDCl$_3$)(90MHz) 2.1–3.5(4H,m), 3.69(3H,s), 3.8–4.3(1H,m), 4.4–5.0(2H, m), 5.29(1H,m), 6.99(1H,s), 7.38(10H,m) |
| 24a | methyl chlorocarbonate(0.196 ml) N—benzyloxycarbonyl glycine (531 mg) Et$_3$N(0.357 ml) THF(50 ml) −10° C.~−5° C., 2h extraction with ethyl acetate powdered by ether | 1000 → 1238 | 3360, 1800, 1780, 1740, 1700, 1530, 1190, 1060 | (CDCl$_3$)(90MHz) 2.1–3.4(4H,m), 3.6–4.3(3H, m), 4.4–5.2(2H,m), 5.11(2H, s), 5.61(1H,m), 6.93,7.10 (each 0.5H,d,J = 7Hz), 7.00(1 H,s), 7.36(15H,m) |
| 25a | benzoyl chloride (0.28 ml) DMA(0.8 ml) CH$_2$Cl$_2$(20 ml) rt, 30 min extraction with CH$_2$Cl$_2$, powered with ether | 800 → 557 | 3420, 1810, 1780, 1675, 1190, 1055 | (d$_6$-DMSO)(90MHz) 2.4–3.4(4H,m), 4.1–5.5(3H, m), 6.95(1H,s), 7.2–7.7(13H, m), 7.90(2H,m), 9.12(1H,d,J = 8Hz) |
| 26a | phenylacetyl chloride(0.26 ml) DMA(0.64 ml) CH$_2$Cl$_2$(20 ml) rt, 30 min extraction with CH$_2$Cl$_2$, powdered with ether | 800 → 694 | 3430, 1805, (sh), 1775, 1685, 1185, 1050 | (d$_6$-DMSO)(90MHz) 2.3–3.4(4H,m), 3.50(2H,s), 3.7–4.3(1H,m), 4.4–5.2(2H, m), 6.90(1H,s), 7.1–7.6(15H, m), 8.77(1H,d,J = 7Hz) |
| 27a | nicotinyl chloride hydrochloride(356 mg) DMA(0.8 ml) CH$_2$Cl$_2$(20 ml) rt, 30 min extraction with CH$_2$Cl$_2$,powdered with ether | 800 → 762 | 3400, 1810, 1780, 1750, 1680, 1190, 1060 | (d$_6$-DMSO)(90MHz) 2.3–3.5(4H,m), 4.0–5.5(3H, m), 6.95(1H,b), 7.2–7.7(11H, m), 8.28(1H,dt,J = 8,2Hz), 8.76(1H,d,J = 4Hz), 9.09(1H, b), 9.35(1H,d,J = 7Hz) |
| 28a | phenoxyacetyl chloride(0.62 DMA(1.0 ml) CH$_2$Cl$_2$(40 ml) rt,30 min | 1200 → 975 | 3400, 1815, 1775, 1700, 1500, 1190, 1055 | (d$_6$-DMSO)(90MHz) 2.3–3,3(4H,m), 3.9–5.3(3H, m), 4.56(2H,s), 6.92(1H,s), 6.99(3H,m), 7.37(12H,m), 8.78(1H,d,J = 8Hz) |
| 29a | p-toluensulfonyl chloride(457 mg) Pyridine(195μμ) CH$_2$Cl$_2$(30 ml) rt, 3h extraction with CH$_2$Cl$_2$, powdered with hexane-ether | 800 → 745 | 3270, 1805, 1775, 1750, 1340, 1300, 1275, 1185, 1170 | (d$_6$-DMSO + CDCl$_3$)(90MHz) 2.40(3H,s), 2.3–3.4(4H,m), 3.9–4.7(3H,m), 6.93(1H,s), 7.2–7.4(12H,m), 7.78(1H,d, J = 8Hz), 7.80(1H,d,J = 8Hz) |

-continued

| Product | Reaction conditions | Yield (mg) St. mat → Prod. | IR $\nu_{max}^{KBr}$ cm$^{-1}$ | NMR δ (solvent)(MHz) |
|---|---|---|---|---|
| 30a | p-bromobenzoyl chloride(530 mg) DMA(0.8 ml) CH$_2$Cl$_2$(20 ml) rt, 30 min silica gel chromatography(ethyl acetate-hexane) | 800 → 232 | 3400, 1810, 1775, 1675, 1490, 1190, 1060 | (d$_6$-DMSO)(90MHz) 2.3–3.3(4H,m), 4.0–5.5(3H, m), 6.93(1H,s), 7.38(10H,m), 7.77(4H,m), 9.17(1H,d,J = 7 Hz) |
| 31a | methyl chlorocarbonate(232 μl) N—benzyloxycarbonyl D-alanine (677 mg) Et$_3$N(417 μl) THF(30 ml) −10° C., 2.5h THF(30 ml) extraction with CH$_2$Cl$_2$,powdered with ethyl acetate-ether | 990 → 1170 | 3350, 1800, 1780, 1760, 1700, 1520, 1500 | (CDCl$_3$)(90MHz) 1.35(3H,d,J = 7Hz), 3.2–3.4 (4H,m), 3.8–5.0(4H,m), 5.10 (2H,s), 5.40(0.5H,d,J = 7 Hz), 5.48(0.5H,d,J = 7Hz), 7.00(1H,s), 6.9–7.1(1H,m), 7.3–7.5(15H,m) |
| 21b | H$_2$/10% Pd-C(650 mg ), THF-buffer(pH 7.0), rt, 1h column of carbon powder(8% isobutanol-0.02N aqueous ammonia) powdered with acetone | 650 → 306 | 1780, 1730, 1670, 1540 | (D$_2$O)(100MHz) 2.4–3.4(4H,m), 4.1–4.4(1H, m), 4.6–4.9(1H,m), 5.0–5.3(1 |
| 22b | H$_2$/10% Pd-C(760 mg ), THF-buffer(pH 7.0), rt, 50 min HP-20column(H$_2$O) lyophilization | 760 → 295 | 2980, 1790, 1730, 1660, 1540, 1385, 1200 | (D$_2$O)(100MHz) 0.94(3H,t,J = 7Hz), 1.64(2H, sextet, J = 7Hz), 2.32(2H,t,J = 7Hz), 2.4–3.4(2H,m), 4.22 (1H,m), 4.5–5.3(2H,m) |
| 23b | H$_2$/10% Pd-C(900 mg ), THF-buffer(pH 6.3), rt, 40 min column of carbon powder (8% isobutanol-0.02N ammonia), powdered with acetone | 900 → 343 | 1795, 1725, 1660, 1550, 1280, 1200 | (D$_2$O)(100MHz) 2.3–3.4(4H,m), 3.75(3H,s), 4.1–4.4(1H,m), 4.4–5.2(2H,m) |
| 24b | H$_2$/10% Pd-C(1000 mg), THF-buffer( pH7.0), rt, 45 min HP-20 column (40% methanol), lyophilization | 1000 → 270 | 1790, 1730 1670, 1540 1390, 1260, 1200 | (D$_2$O)(100MHz) 2.3–3.4(4H,m), 3.8–5.2(3H, m), 3.91(2H,s), 5.17(2H,s), 7.45(5H,s) |
| 25b | H$_2$/10% Pd-C(450 mg ), THF-buffer(pH 7.0), rt, 45 min HP-20 column (40% methanol), lyophilization | 690 → 163 | 1785, 1730, 1660, 1540, 1380, 1200 | (D$_2$O)(100 MHz) 2.4–3.3(4H,m), 4.1–5.6(3H, m), 7.4–7.9(5H,m) |
| 26b | H$_2$/10% Pd-C(650 mg ), THF-buffer(pH 7.0), rt, 40 min HP-20 column (40% methanol), lyophilization | 690 → 325 | 1790, 1730, 1660, 1540, 1385, 1195 | (D$_2$O)(100 MHz) 2.3–3.3(4H,m), 3.69(2H,s), 4.18(1H,m), 4.5–5.3(2H,m), 7.38(5H,m) |
| 27b | H$_2$/10% Pd-C(650 mg ), THF-buffer(pH 7.0), rt, 60 min HP-20 column (H$_2$O), lyophilization | 650 → 160 | 1790, 1630, 1665, 1380, 1200 | (D$_2$O)(100 MHz) 2.4–3.4(4H,m), 4.2–5.5(3H, m), 7.59(1H,dd,J = 8,5Hz), 8.24(1H,dt,J = 8,2Hz), 8.72(1H,b,J = 5Hz),8.92(1H ,b |
| 28b | H$_2$/10% Pd-C(900 mg ), THF-buffer(pH 7.0), rt, 40 min HP-20 column (40% methanol), lyophilization | 900 → 464 | 1790, 1730, 1665, 1540, 1495 | (d$_6$-DMSO)(100MHz) 2.1–3.2(4H,m), 3.7–5.2(3H, m), 4.54(2H,s), 7.00(3H,m), 7.31(2H,m), 8.67,8.85(each 0.5H,d,J = 8Hz) |
| 29b | H$_2$/10% Pd-C(650 mg ), THF-buffer(pH 7.0), rt, 30 min | 650 → 238 | 1785, 1740, 1660, 1390, 1340, 1160 | (D$_2$O)(100MHz) 2.46(3H,s), 2.4–3.2(4H,m), 3.98(1H,t,J = 9Hz), 4.3–4.8( |

-continued

| Product | Reaction conditions | Yield (mg) St. mat → Prod. | IR$\nu_{max}^{KBr}$cm$^{-1}$ | NMR δ (solvent)(MHz) |
|---|---|---|---|---|
| | HP-20 column (40% methanol), lyophilization | | | 2H,m), 7.46(2H,d,J = 8Hz), 7.80(2H,d,J = 8Hz) |
| 28c | chloromethyl pivalate(185 μl) DMF(1 ml) rt, 8.5 h extraction with ethyl acetate powdered with petroleum benzine | 260 → 182 | 3400, 1815, 1770, 1700, 1540 | (CDCl$_3$)(90MHz) 1.02(9H,s), 2.3–3.1(4H,m), 4.0–4.4(1H,m), 4.53(2H,s), 4.6–5.2(2H,m),5.87(2H,s), 6.8–7.5(6H,m) |

EXAMPLE 32

Production of 2-[(4S)-4-dimethylamino-3-oxo-2-isoxazolidinyl]-5-oxo-2-tetrahydrofurancarboxylic acid [Compound (32b)]:

(a) Production of diphenylmethyl 2-[(4S)-4-dimethylamino-3-oxo-2-isoxazolidinyl]-5-oxo-2-tetrahydrofurancarboxylate [Compound (32a)]:

Compound (R-3) was dissolved in acetonitrile, and formaldehyde, sodium cyanoborohydride and acetic acid were added to the solution, followed by stirring. Water was added to the reaction solution, and the acetonitrile was distilled off, followed by extraction of the aqueous layer with ethyl acetate. The extract was washed with 2% aqueous sodium hydogencarbonate solution and concentrated, and the concentrate was admixed with THF and then 2N hydrochloric acid, followed by stirring at room temperature overnight. The organic layer was concentrated, and water was added to the concentrate, followed by adjustment with aqueous dilute sodium hydroxide solution to pH 10. The water layer was extracted with ethyl acetate, and the extract was concentrated to give a powder of Compound (32a).

(b) Production of the subject Compound (32b):

Compound (32a) was subjected to a reaction analogous to Example 25 (b), followed by work up to give a powder of the subject Compound (32b).

Below given are the reaction conditions of Example 32 as well as the yield and typical physico-chemical properties of the compound obtained.

| Product | Reaction conditions | Yield (mg) St. mat → Prod. | IR:$\nu_{max}^{KBr}$cm$^{-1}$ | NMR(90MHz) δ (solvent) |
|---|---|---|---|---|
| 32a | (i) 37% CH$_2$O(2.05 ml), NaBH$_3$CN(480 mg),AcOH(0.30 ml) CH$_3$CN(20 ml) 0° C., 40 min extraction with ethyl acetate (ii) THF—2NHCl rt, one overnight, extraction with ethyl acetate | 1000 → 809 | 1800, 1775, 1750, 1730 | (CDCl$_3$) 2.1–3.5(4H,m), 2.40,2.41 (each 3H,s), 3.5–4.6(3H,m), 7.00(1H,s), 7.2–7.6(10H,m) |
| 32b | H$_2$,10% Pd—C THF—water rt, 40 min HP—20 column (water) lyophilization | 650 → 194 | 1790, 1720, 1665 | (D$_2$O) 2.3–3.4(4H,m), 2.90(6H,s) 4.2–5.4(3H,m) |

EXAMPLE 33

Production of sodium 2-{(4S)-4-[2-(2-amino-4-thiazolyl)acetamido]-3-oxo-2-isoxazolidinyl}-5-oxo-2-tetrahydrofurancarboxylate [Compound (33c)]:

(a) Production of diphenylmethyl 2-{(4S)-4-[2-(2-chloroacetamido-4-thiazolyl)acetamido]-3-oxo-2-isoxazolidinyl}-5-oxo-2-tetrahydrofurancarboxylate [Compound (33a)]:

Using Compound (R-3) and 2-(2-chloroacetamido-4-thiazolyl)acetyl chloride, there was obtained Compound (33a) by the procedure of Example 5.

(b) Production of diphenylmethyl 2-{(4S)-4-[2-(2-amino-4-thiazolyl)acetamido]-3-oxo-2-isoxazolidinyl}-5-oxo-2-tetrahydrofurancarboxylate [Compound (33b)]:

The Compound (33a) as obtained above was subjected to a reaction analogous to Example 1 (b) to give Compound (33b).

(c) Production of the subject Compound (33c):

The Compound (33b) as obtained above was subjected to a reaction analogous to Example 1 (c) to give the subject Compound (33c).

Below given are the reaction conditions of Example 33 as well as the yield and physico-chemical properties of the compound obtained.

| Product | Reaction conditions | Yield (mg) St. mat → Prod. | IR$\nu_{max}^{KBr}$cm$^{-1}$ | NMR (d$_6$-DMSO,90MHz) |
|---|---|---|---|---|
| 33a | 2-(2-chloroaceto amide-4-thiazolyl) acetyl chloride(380 mg) butylene oxide (0.8 ml) CH$_2$Cl$_2$(12 ml) 0° C. 1 h | 396 → 595 | 3350, 1770, 1670, 1540, 1185, 1190, 1060 | 2.40–3.55(4H,m), 3.56(2H, s), 3.70–5.10(3H,m), 6.90 (1H,s), 6.97(1H,s), 7.25– 7.50(10H,m), 8.71(1H,d,J = 7Hz) |
| 33b | CH$_3$NHCSSNa.2H$_2$O (129 mg) THF (4 ml)—H$_2$O(4 ml) rt, 1 h extraction with ethyl acetate, silica gel chromatography(ethyl acetate) | 400 → 225 | 3330, 1770, 1745, 1670, 1525, 1180, 1055 | 2.30–3.50(4H,m), 3.80–5.10 (3H,m), 6.26(1H,s),6.83 (2H,b), 6.90(1H,s), 7.20– 7.55(10H,m), 8.57(1H,d,J = 7Hz) |
| 33c | CF$_3$COOH(0.30 ml) anisole(0.15 ml) CH$_2$Cl$_2$(12 ml) −10°~−15°, 4h XAD-2 column (water), lyophilization | 160 → 71 1030 | 3430, 1780, 1720, 1660, 1520, 1380, 1200, 1120, 1030 | 2.10–3.50(4H,m), 3.60–5.05 (3H,m), 6.,23(1H,s), 6.83 (2H,b), 8.46,8.60(each 0.5 H,d,J = 7Hz) |

EXAMPLE 34

Production of sodium 2-[4-methoxy-4-(2-thienylacetamido)-3-oxo-2-isoxazolidinyl]-5-oxo-2-tetrahydrofurancarboxylate [Compound (34b)]:

The Compound (5a) as obtained in Example 5 was dissolved in THF, and a methanol solution of t-butyl hypochloride and lithium methoxide was added to the solution under cooling with dry ice-acetone, followed by stirring for 5 minutes. Then, after one drop of acetic acid was added, the reaction solution was diluted with ethyl acetate, and the organic layer was washed with aqueous sodium thiosulfate solution and saturated aqueous sodium chloride solution, successively, and dried over anhydrous magnesium sulfate. The solvent was distilled off, and the residue was chromatographed on a column of silica gel to give Compound (34a), a diphenylmethyl ester of the subject Compound (34b). Subsequently, the Compound (34a) was dissolved in THF, and a buffer of pH 7.0, palladium-black and palladium oxide were added to the solution, followed by stirring under a stream of hydrogen. After the catalyst was filtered off, the filtrate was concentrated under reduced pressure, and the aqueous layer was washed with ether and concentrated. The concentrate was chormatographed on a column of XAD-2, and elution was performed with 10% ethanol. The eluate was concentrated under reduced pressure, and lyophilized to give the subject Compound (34b) in the form of grey-white powder.

EXAMPLE 35

Production of disodium 2-{(4S)-4-(2-[2-amino-4-thiazolyl)-(Z)-2-(carboxymethyloxyimino)acetamido]-3-oxo-2-isoxazolidinyl}-5-oxo-2-tetrahydrofurancarboxylate [Compound (35d)]:

(a) Production of diphenylmethyl 2-{(4S)-4-[2-(2-chloroacetamido-4-thiazolyl)-(Z)-2-(4-nitrobenzyloxycarbonylmethyloxyimino)acetamido]-3-oxo-2-isoxazolidinyl}-5-oxo-2-tetrahydrofurancarboxylate [Compound (35a)]:

Compound (R-3) was suspended in dichloromethane, and butylene oxide and 2-(2-chloroacetamido-4-thiazolyl)-(Z)-2-(4-nitrobenzyloxycarbonylmethoxyimino)acetyl chloride hydrochloride were added to the suspension under ice-cooling to allow the reaction to proceed for 1 hour. Ethyl acetate was added, and the organic layer was washed with aqueous sodium hydrogencarbonate solution and aqueous sodium chloride solution, successively, and dried over anhydrous sodium sulfate. The solvent was distilled off under reduced pressure to give Compound (35a) in the form of a foamed substance.

(b) Production of diphenylmethyl 2-{(4S)-4-[2-(2-amino-4-thiazolyl)-(Z)-2-(4-nitrobenzyloxycarbonylmethoxyimino)acetamido]-3-oxo-2-isoxazolidinyl}-5-oxo-2-tetrahydrofurancarboxylate [Compound (35b)]:

The Compound (35a) as obtained above was subjected to a reaction and treatment similar to those of Example 1 (b) to give Compound (35b).

(c) Production of sodium 2-{(4S)-4-[2-(2-amino-4-thiazolyl)(Z)-2-(4-nitrobenzyloxycarbonylmethoxyimino)acetamido]-3-oxo2-isoxazolidinyl}-5-oxo-2-tetrahydrofurancarboxylate [Compound (35c)]:

The Compound (35b) as obtained above was subjected to a reaction and treatment analogous to Example 1 (c) to give Compound (35c).

(d) Production of the subject Compound (35d):

The Compound (35c) as obtained above was subjected to a reaction and treatment analogous to Example 2 (b) to give the subject Compound (35d).

Below given are the reaction conditions of Example 34 and 35 as well as the yields and typical physicochemical properties of the compounds obtained.

| Product | Reaction conditions | Yield (mg) St. mat → Prod. | IR$\nu_{max}^{KBr}$cm$^{-1}$ | NMR(90MHz)$\delta$ |
|---|---|---|---|---|
| 34a | THF(10 ml) t-BuOCl(30 μl) MeOLi in MeOH (0.22 μl of a solution of 1.368 mmol /ml), =78° C., 5 min, extraction with ethyl acetate, silica gel chromatography (hexane-ethyl acetate = 3:2) | 210→ 144 | 3350, 1800, 1795(sh), 1770, 1690, 1175, 1055 | 2.3–3.2(4H,m), 3.17,3.21 (each1.5H,s), 3.81(2H,s), 4.32,4.96(each0.5H,d,J = 10Hz), 4.41,4.92(each0.5H, d,J = 10Hz), 6.69,6.72(each 0.5H,s), 6.9–7.5(3H,m), 7.29 , 7.32(each5H,s) (solvent:CDCl$_3$) |
| 34b | THF(10 ml) pH7.0 buffer(10 ml) Pd-black(150 mg) PdO(74 mg), rt, 1 h XAD-2 column (10% ethanol), lyophilization | 144→ 75.5 | 1785, 1730, 1695(sh), 1660, 1520, 1380, 1250, 1195, 1105, 1040 | 2.7–3.8(4H,m), 3.79(3H,s), 4.36(2H,s), 5.08(2H,ABq, 10,34Hz), 7.4–7.9(3H,m) (solvent:D$_2$O) |
| 35a | CH$_2$Cl$_2$(12 ml) butylene oxide (0.8 ml) 2-(2-chloroacet amide-4-thiazolyl)- (Z)—2-(4-nitro benzyloxycarbonyl methoxyimino)- acetyl chloride hydrochloride(665 mg) 0° C., 1 h extraction with ethyl acetate | 396→ 835 | 1800, 1750, 1690, 1520, 1190, 1050 | 2.15–3.50(4H,m), 3.60–5.35 (3H,m), 4.26(2H,s), 4.90(2H, s), 5.27(2H,s), 6.98(2H,b), 7.30–7.36(10H,s), 7.40–8.30 (5H,m) (solvent:CDCl$_3$) |
| 35b | THF(8 ml)—H$_2$O(8 ml) CH$_3$NHCS$_2$Na(233 mg) rt, 2 h extraction with ethyl acetate, silica gel chromatography(ethyl acetate-hexane = 7:3) | 835→ 541 | 3330, 1800, 1750, 1680, 1605, 1520, 1195, 1050 | 1.66(2H,b), 2.10–3.50(4H, m), 3.60–5.50(3H,m), 4.87 (2H,s), 5.25(2H,s), 6.96(1H, s), 7.20(1H,s), 7.30, 7.33 (each5H,s), 7.40–8.30(4H, m), 7.80–8.00(1H,m) (solvent;d$_6$-DMSO) |
| 35c | CH$_2$Cl$_2$(24 ml) CF$_3$COOH(0.66 ml) anisole(0.33 ml) −15° C., 5h decantation after adding hexane XAD-2 column (20% ethanol), lyophilization | 500→ 275 | 3420, 2930, 1770, 1740, 1660, 1520, 1350, 1200, 1030 | 2.10–3.50(4H,m), 3.60–5.50 (3H,m), 4.76(2H,s), 5.33 (2H,s), 6.96,7.00(each0.5H, s), 7.20(2H,b), 7.56–8.27 (4H,m), 9.00–9.30(1H,m) (solvent:d$_6$-DMSO) |
| 35d | H$_2$O(10 ml) 10% Pd-C(100 mg) rt, 2h, XAD-2 column(H$_2$O), then CHP-20 column(H$_2$O) lyophilization | 200→ 85 | 3400, 1780, 1730, 1660, 1610, 1540, 1390, 1320, 1190, 1040 | 2.10–3.50(4H,m), 3.60–5.50 (3H,m), 4.30(2H,s), 6.85, 6.86(each0.5H,s), 7.20 (2H,b) (solvent:d$_6$-DMSO) |

EXAMPLE 36

Using the following ingredients, tablets are produced by the conventional means:

| | |
|---|---|
| Compound (1c) as obtained in Example 1 | 300 mg |
| Corn starch | 50 mg |
| Lactose | 28 mg |
| Hydroxypropylcellulose L | 20 mg |
| Magnesium stearate | 2 mg |
| | 400 mg per tablet |

4 to 8 tablets are to be administered to an adult daily after each meal (three times per day).

EXAMPLE 37

Using the following ingredients, tablets are produced by the conventional means:

| | |
|---|---|
| Compound (35d) as obtained in Example 35 | 300 mg |
| Corn starch | 50 mg |
| Lactose | 28 mg |
| Hydroxypropylcellulose L | 20 mg |
| Magnesium stearate | 2 mg |

| |
|---|
| 400 mg per tablet |

4 to 8 tablets are to be administered to an adult daily after each meal (three times per day).

EXAMPLE 38

Production of 2-{(4S)-4-[2-(2-aminomethyl)-phenylacetamido]-3-oxo-2-isoxazolidinyl}-5-oxo-2-tetrahydrofurancarboxylic acid [Compound (38b)]:

(a) Production of diphenylmethyl 2-{(4S)-4-[2-(2-benzyloxycarbonylaminomethyl)phenylacetamido]-3-oxo-2-isoxazolidinyl}-5-oxo-2-tetrahydrofurancarboxylate [Compound (38a)]:

Using Compound (R-3) and 2-benzyloxycarbonylaminomethylphenylacetic acid, there was obtained Compound (38a) by the procedure of Example 1 (a).

(b) Production of the subject Compound (38b):

Compound (38a) was subjected to a reaction and treatment analogous to Example 2 (b) to give the subject Compound (38b).

EXAMPLE 39

Production of sodium 2-[(4S)-4-(4-fluorobenzenesulfonylamino)-3-oxo-2-isoxazolidinyl]-5-oxo-2-tetrahydrofurancarboxylate [Compound (39b)]:

(a) Production of diphenylmethyl 2-[(4S)-4-(4-fluorobenzenesulfonylamino)-3-oxo-2-isoxazolidinyl]-5-oxo-2-tetrahydrofurancarboxylate [Compound (39a)]:

Compound (R-3), 4-fluorobenzenesulfonyl chloride and propylene oxide were stirred in DMA under ice-cooling for 1 hour, followed by a treatment analogous to Example 1 (a) to give Compound (39a).

(b) Production of the subject Compound (39b):

Compound (39a) was catalytically reduced with use of palladium black, followed by treatment by the procedure of Example 2 (b) to give the subject compound.

EXAMPLE 40

Production of sodium 2-{(4S)-4-{2-[1-dimethylaminoethyl)-1H-5-tetrazolylthio]acetamido}-3-oxo-2-isoxazolidinyl}-5-oxo-2-tetrahydrofurancarboxylate [Compound (40b)]:

Using Compound (14a) and 1-(2-dimethylaminoethyl)-5-mercapto -1H-tetrazole, there was obtained Compound (40a), a diphenylmethyl ester of the subject Compound (40b), by the procedure of Example 15, and then, the subject Compound (40b) was formed.

EXAMPLE 41

Production of sodium 2-{(4S)-4-[2-(4-methyl-4H-1,2,4-triazolyl-3-ylthio)acetamido]-3-oxo2-isoxazoliidiinyl]-5-oxo-2-tetrahydrofurancarboxylate [Compound (41b)]:

Using Compound (14a) and 3-mercapto-4-methyl-4H-1,2,4-triazole, there was obtained Compound (41a), a diphenylmethyl ester of the subject Compound (41b), by the procedure of Example 15, and then, the subject Compound (41b) was formed.

EXAMPLE 42

Production of sodium 2-{(4S)-4-[(2R,3S)-2-(4-ethyl-2,3-dioxo-1-piperazinecarboxamido)-3-formyloxybutylamido]-3-oxo- oxo-2-isoxazolidinyl}-5-oxo-2-tetrahydrofurancarboxylate [Compound (42b)]:

Using Compound (R-3) and (2R,3S)-2-(4-ethyl-2,3-dioxo-1-piperazinecarboxamido)-3-formyloxybutyric acid, there was obtained Compound (42a), a diphenylmethyl ester of the subject compound, by the procedure of Example 5, and then by following the procedure of Example 2(b), there was formed the subject Compound (42b).

EXAMPLE 43

Production of disodium 2-[(4S)-4-(2-phenyl-2-sulfoacetamido)-3-oxo-2-isoxazolidinyl]-5-oxo-2-tetrahydrofurancarboxylate [Compound (43)]:

Compound (R-4) as obtained in Reference Example 4 was dissolved in water, and sodium hydrogencarbonate and an ether solution of phenylsulfoacetyl chloride were added to the solution under ice-cooling with stirring. After the reaction was allowed to proceed for 1 hour, the aqueous layer was separated, washed with ethyl acetate and concentrated, and the concentrate was chromatographed on a column of XAD-2. The fraction eluted with water was lyophilized to give the subject Compound (43) in the form of a colorless powder.

EXAMPLE 44

Production of sodium 2-{(4S)-4-[2-(2-amino-4-thiazolyl)-(E)-2-methoxyiminoacetamido]-3-oxo-2-isoxazolidinyl}-5-oxo-2-tetrahydrofurancarboxylate [Compound (44c)]:

(a) Production of diphenylmethyl 2-{(4S)-4-[2-(2-chloroacetamido-4-thiazolyl)-(E)-2-methoxyiminoacetamido]-3-oxo-2-isoxazolidinyl}-5-oxo-2-tetrahydrofurancarboxylate [Compound (44a)]:

Compound (R-3) and 2-[2-chloroacetamido-4-thiazolyl)-(E)-2-methoxyiminoacetic acid, there was obtained Compound [44a] by conducting a reaction and treatment analogous to Example 1 (a).

(b) Production of diphenylmethyl 2-{(4S)-4-[2-(2-amino-4-thiazolyl)-(E)-2-methoxyiminoacetamido]-3-oxo-2-isoxazolidinyl}-5-oxo-2-tetrahydrofurancarboxylate [Compound (44b)]:

Using Compound (44a), there was obtained Compound [44b) by conducting a treatment by the procedure of Example 1 (b).

(c) Production of the subject Compound (44c):

Using Compound (44b), there was obtained the subject Compound (44c) by conducting a treatment by the procedure of Example 1 (c).

EXAMPLE 45

Production of sodium 2-[(4S)-4-(2-trimethylsilyl)ethoxycarbonylamino-3-oxo-2-isoxazolidinyl]-5-oxo-2-tetrahdyrofurancarboxylate [Compound (45b)]:

Butylene oxide and trimethylsilylethoxycarbonyl chloride were added to a dichloromethane suspension of Compound (R-3), followed by stirring for 2 hours. The solvent was distilled off, and a powder which separated out upon addition of hexane was collected by filtration to give Compound (45a), a diphenylmethyl ester of the subject compound. This product was treated by the procedure of Example 2 (b) to give the subject Compound (45b).

EXAMPLE 46

Production of 2-[(4S)-4-[1-aminocyclohexylcarbonylamino)-3-oxo-2-isoxazolidinyl]-5-oxo-2-tetrahydrofurancarboxylic acid [Compound (46b)]:

Using Compound (R-3) and 1-benzyloxycarbonylaminocyclohexanecarboxylic acid, a treatment was carried out by the procedure of Example 1 (a) to give diphenylmethyl 2-[(4S)-4-(1-benzyloxycarbonylaminocyclohexylcarbonylamino)-3-oxo-2-isoxazolidinyl]-5-oxo-2-tetrahydrofurancarboxylate [Compound (46a)]. This product was treated by the procedure of Example 2 (b) to give the subject Compound (46b).

EXAMPLE 47

Production of sodium 2- {(4S)-4-[3-(2,6-dichlorophenyl)-5-methyl-4-isoxazolylcarbonylamino]-3-oxo-2-isoxazolidinyl}-5-oxo-2-tetrahydrofurancarboxylate [Compound (47b)]:

Using Compound (R-3) and 3-(2,6-dichlorophenyl)-5-methyl-4-isoxazolylcarbonyl chloride, there was obtained Compound (47a), a diphenylmethyl ester of the subject Compound (47b), by the procedure of Example 5. This product was treated by the procedure of Example 1 (c) to give the subject Compound (47b).

EXAMPLE 48 Production of sodium 2-{(4S)-4-[2(2-pyridylthio)acetamido]3-oxo-2-isoxazolidinyl}-5-oxo-2-tetrahydrofurancarboxylate [Compound (48b)]:

Using Compound (14a) and 2-pyridinethiol, there was obtained Compound (48a), a diphenylmethyl ester of the subject Compound (48b), by the procedure of Example 15, and then, there was formed the subject Compound [48b].

EXAMPLE 49

Production of sodium -2-{(4S)-4-[2-(4-pyridylmethylthio)-2-tetrahydrofuranacetamido]-3-oxo-2-isoxazolidinyl}-5 -oxocarboxylate [Compound (49b)]:

Using Compound (14a) and 4-pyridylmethanethiol, there was obtained Compound [49a), a diphenylmethyl ester of the subject Compound (49b), by the procedure of Example 15, and then, there was formed the subject Compound (49b).

EXAMPLE 50

Production of sodium 2-{(4S)-4-[2-(2-pyrimidinylthio)acetamido]-3-oxo-2-isoxazolidinyl}-5-oxo-2-tetrahydrofurancarboxylate [Compound (50b)]:

Using Compound (14a) and 2-pyrimidinethiol, there was obtained Compound (50a), a diphenylmethyl ester of the subject Compound (50b), by the procedure of Example 15, and then, there was formed the subject Compound (50b).

Example 51

Production of sodium 2-{(4S)-4-{2-[(E)-2-(acetamidovinythiol acetamido}-3-oxo-2-isoxazolidinyl}-5-oxo-2-tetrahydrofurancarboxylate [Compound (51b)]:

Using Compound (14a) and (E)-2-acetamidovinylthiol silver salt, there was obtained Compound [51a], a diphenylmethyl ester of the subject Compound (51b), by the procedure of Example 15, and then, there was formed the subject Compound (51b)

EXAMPLE 52

Production of sodium 2-[(4S)-4- cyclopropylcarbonylamio3-oxo-2-isoxazolidinyl]-5-oxo-2-tetrahydrofurancarboxylate [Compound (52b)]:

Using Compound (R-3) and cyclopropanecarboxylic acid, there was obtained Compound (52a), a diphenylmethyl ester of the subject Compound (52b), by the procedure of Example 1 (a), and then, there was formed the subject Compound (52b) by the procedure of Example 2 (b).

EXAMPLE 53

Production of sodium 2-[(4S)-4- methoxalylamino-3-oxo-2-isoxazolidinyl]-5-oxo-2-tetrahydrofurancarboxylate [Compound (53b)]:

Using Compound (R-3) and methyl oxalyl chloride, there was obtained Compound (53a), a diphenylmethyl ester of the subject Compound (53b), by the procedure of Example 2(b), and then, there was formed the subject Compound (53b) by the procedure of Example 2 (b).

EXAMPLE 54

Production of sodium 2-[(4S)-4-acrylamido-3-oxo-2-isoxazolidinyl]-5-oxo-2-tetrahydrofurancarboxylate [Compound (54)]:

Compound (R-3) was suspended in tetrahydrofuran, and water and 5% palladium-carbon were added to the suspension, followed by stirring under ice-cooling and under a stream of hydrogen. After the catalyst was filtered off, the filtrate was washed with water, and the filtrate and washings were combined and concentrated under reduced pressure. The concentrate was washed with ethyl acetate, and the aqueous layer was separated out and admixed, under ice-cooling with stirring, with sodium hydrogencarbonate and a tetrahydrofuran solution of acryloyl chloride. The reaction solution was washed with ethyl acetate, and the aqueous layer was concentrated. The concentrate was chromatographed on a column of HP-20, and the fraction eluted with water was lyophilized to give the subject Compound (54).

EXAMPLE 55

Production of sodium 2-{(4S)-4-[2-(2-chloro-4-pyridylthio)ccetamido]-3-oxo-2-isoxazolidinyl}-5-oxo-2-tetrahydrofurancarboxylate [Compound (55b)]:

Using Compound (14a) and 2-chloro-4-pyridinethiol, there was obtained Compound (55a), a diphenylmethyl ester of the subject Compound (55b), by the procedure of Example 15, and then, there was formed the subject Compound (55b).

EXAMPLE 56

Production of sodium 2-[(4S)-4-(2acetamido-5-oxo-2-tetrahydrofurancarbonylamino)-3-oxo-2-isoxazolidinyl]-5-oxo2-tetrahydrofurancarboxylate [Compound (56b)]:

Using Compound (R-3)and 2-acetamido-5-oxo-2-tetrahydrofurancarboxylate, there was obtained Compound (56a), a diphenylmethyl ester of the subject Compound (56b), by the procedure of Example 1 (a), and then, there was formed the subject Compound (56b) by the procedure of Example 2 (b).

EXAMPLE 57

Production of sodium 2-{(4S)-4-[2-(1-pyrazolyl)acetamido]-3-oxo-2-isoxazolidinyl}-5-oxo-2-tetrahydrofurancarboxylate [Compound (57b)]:

Using Compound (R-3) and 1-pyrazolylacetic was obtained Compound (57a), a diphenylmethyl ester of the subject Compound (57b), by the procedure of Example 1 (a), and then, there was formed the subject Compound (57b) by the procedure of Example 2 (b).

EXAMPLE 58

Production of sodium 2-{(4S)-4-[2-[5-amino-1,2,4-thiadiazole-3-yl)-(Z)-2-ethoxyiminoacetamido]-3-oxo-2-isoxazolidinyl}-5-oxo-2-tetrahydrofurancarboxylate [Compound (58b)]:

Using Compound (R-3) and 2-(5-amino-1,2,4-thidiazole-3-yl)-(Z)-2-ethoxyiminoacetic acid, there was obtained Compound (58a), a diphenylmethyl ester of the ubject Compound (58b), by the procedure of Example 1 (a), and then, there was formed the subject Compound (58b)by the procedure of Example 1 (c).

EXAMPLE 59

Production of sodium 2-{(4S)-4-[2-(3-pyridazinylthio)-acetamido]-3-oxo-2-isoxazolidinyl}-5-oxo-2-tetrahydrofurancarboxylate [Compound (59b)]:

Using Compound (14a) and3-pyridazinethiol lithium salt, there was obtained Compound (59a), a diphenylmethyl ester of the subject Compound (59b), by the procedure of Example 15, and then, there was formed the subject Compound (59b).

EXAMPLE 60

Production of sodium 2-[(4S)-4-dichloroacetamido-3-oxo-2-isoxazolidinyl]-5-oxo-2-tetrahydrofurancarboxylate [Compound (60b)]:

Using Compound (R-3) and dichloroacetyl chloride, there was obtained Compound (60a), a diphenylmethyl ester of the subject Compound [60b), by the procedure of Example 14, and then, there was formed the subject Compound (60b).

EXAMPLE 61

Production of sodium 2-{(4S)-4-[(2R,3S)-2-(4-ethyl-2,3-dioxo-1-piperazinecarboxamido)-3-hydroxybutyramido]-3-oxo-2-isoxazolidinyl}-5-oxo-2-tetrahydrofurancarboxylate [Compound (61b)]:

Using Compound (R-3) and (2R,3S)-2-(4-ethyl-2,3-dioxo-1-piperazinecarboxamido)-3-hydroxybutyric acid, there was obtained Compound (61a), a diphenylmethyl ester of the subject Compound (61b), through a reaction analogous to Example 1 (a), and there was formed the subject Compound (61b) through catalytic reduction with use of palladium black.

EXAMPLE 62

Production of sodium 2-{(4S)-4-[2-(5-trifluoromethyl1,3,4-thiadiazol 2-ylthio)acetamido]-3-oxo-2-isoxazolidinyl}-5-oxo-2-tetrahydrofurancarboxylate [Compound (62b)]:

Using Compound 14 (a) and 5-trifluoromethyl-1,3,4-thiadiazole-2-thiol, there was obtained Compound (62a), a diphenylmethyl ester of the subject Compound (62b), by the procedure of Example 15, and then, there was formed the subject Compound (62b).

EXAMPLE 63

Production of disodium 2-{(4S)-4-{2-[1-ethoxy(hydroxy)phosphinylmethyl-1H-5-tetrazolylthio]acetamido}-3-oxo-2-isoxazolidinyl}-5-oxo-2-tetrahydrofurancarboxylate [Compound (63b)]:

Using Compound (14a) and 1-[ethoxy(hydroxy)phosphinylmethyl]-1H-tetrazole-5-thiol O,S-disodium salt, there was obtained Compound (63a), a diphenylmethyl ester of the subject Compound (63b), by the procedure of Example 15, and then, there was formed the subject Compound (63b).

EXAMPLE 64

Production of sodium 2-{(4S)-4-{2-[5-(2-diethoxyphosphinylethylthio)-1,3,4-thiadiazolylthio]acetamido}-3-oxo-2-isoxazolidinyl}-5-oxo-2-tetrahydrofurancarboxylate [Compound (64b)]:

Using Compound (14a) and 5-(2-diethoxyphosphinylethylthio)-1,3,4-thiadiazole-2-thiol, there was obtained Compound (64a), a diphenylmethyl ester of the subject Compound (64b), by the procedure of Example 15, and then, there was formed the subject Compound (64b).

EXAMPLE 65

Production of sodium 2-{(4S)-4-[2-(1-dimethylamino-1H-5-tetrazolylthio)acetamido]-3-oxo-2-isoxazolidinyl}-5-oxo-2-tetrahydrofurancarboxylate [Compound (65b)]:

Using Compound (14a) and 1-dimethylamino-1H-tetrazole-5-thiol, there was obtained Compound (65a), a diphenylmethyl ester of the subject Compound (65b), by the procedure of Example 15, and then, there was formed the subject Compound (65b).

EXAMPLE 66

Production of sodium 2-{(4S)-4-[2-(4,5-dimethyl-2-thiazolylthio)acetamido]-3-oxo-2-ioxazolidinyl}-5-oxo-2-tetrahydrofurancarboxylate [Compound (66b)];

Using Compound 14 (a) and 4,5-dimethyl-2-thiazolethiol, there was obtained Compound (66a), a diphenylmethyl ester of the subject Compound (66b), by the procedure of Example 15, and then, there was formed the subject Compound (66b).

EXAMPLE 67

Production of sodium 2-{(4S)-4-[2-(4,5-dimethyl-2-oxazolylthio)acetamido]-3-oxo-2-isoxazolidinyl}-5-oxo-2-tetrahydrofurancarboxylate [Compound [67b)]:

Using Compound (14a) and 4,5-dimethyl-2-oxazolethiol, there was obtained Compound (67a), a diphenylmethyl ester of the subject Compound (67b), by the procedure of Example 15, and then, there was formed the subject Compound (67b)

EXAMPLE 68

Production of sodium 2-{(4S)-4-[2-[5-methoxymethyl-1,3,4-thiadiazol-2-ylthio)acetamido]-3-oxo-2-isoxazolydinyl}-5-oxo-2-tetrahydrofurancarboxylate [Compound (68b)[:

Using Compound (14a) and 5-methoxymethyl-1,3,4-thiadiazole-2-thiol, there was obtained Compound (68a), a diphenylmethyl ester of the subject Compound (68b), by the procedure of Example 15, and then, there was formed the subject Compound (68b).

EXAMPLE 69

Production of sodium 2-{(4S)-4-[2-(5-methylsulfonylmethyl-1,3,4-thiadiazol 2-ylthio)acetamido]-3-oxo-2-isoxazolidinyl}-5-oxo-2-tetrahydrofurancarboxylate [Compound (69b)]:

Using Compound (14a) and 5-methylsulfonylmethyl-1,3,4-thiadiazole-2-thiol, there was obtained Compound (69a), a diphenylmethyl ester of the subject Compound (69a), by the procedure of Example 15, and then, there was formed the subject Compound (69b).

EXAMPLE 70

Production of sodium 2-{(4S)-4-[2-(4-ethyl-4H-1,2,4triazol 3 ylthio)acetamido]-3-oxo-2-isoxazolidinyl}-5-oxo-2tetrahydrofurancarboxylate [Compound (70b)]:

Using Compound [14a] and 4-ethyl-4H-1,2,4-triazole-3-thiol, there was obtained Compound (70a), a diphenylmethyl ester of the subject Compound (70b), by the procedure of Example 15, and then, there was formed the subject Compound (70b).

EXAMPLE 71

Production of disodium 2-{(4S)-4-[2-(5-carboxymethyl-1,3,4-thiadiazol -2-ylthio)acetamido]-3-oxo-2-isoxazolidinyl}-5-oxo-2-tetrahydrofurancarboxylate [Compound (71b)]:

Using Compound (14a) and sodium 2-mercapto-1,3,4thiadiazol-5-ylacetate, there was obtained Compound (71a), a diphenylmethyl ester of the subject Compound (71b), by the procedure of Example 15, and then, there was formed the subject Compound (71b).

EXAMPLE 72

Production of sodium 2-{(4S)-4-{2-[1-(2-hydroxyethyl)-1H-5-tetrazolylthio)acetamido}-3-oxo-2-isoxazolidinyl-5-oxo-2-tetrahydrofurancarboxylate [Compound (72b)]:

Using Compound (14a) and 1-(2-hydroxyethyl)-1H-tetrazole-5-thiol, there was obtained Compound [72a), a diphenylmethyl ester of the subject Compound (72b), by the procedure of Example 15, and then, there was formed the subject Compound (72b).

EXAMPLE 73

Production of sodium 2-{(4S)-4-{2-[1-(3-dimethylaminopropyl)-1H-5-tetrazolylthio]acetamido}-3-oxo-2-isoxazolidinyl}-5-oxo-2-tetrahydrofurancarboxylate [Compound (73b)]:

Using Compound (14a) and 1-(3-dimethylaminopropyl)-1H-tetrazole-5-thiol, there was obtained Compound (73a), a diphenylmethyl ester of the subject Compound (73b), by the procedure of Example 15, and then, there was formed the subject Compound (73b).

EXAMPLE 74

Production of 2-[(4S)-4-(2-amino-3-sulfamoylpropionamido)-3-oxo-2-isoxazolidinyl]-5-oxo-2-tetrahydrofurancarboxylic acid [Compound (74b)]:

Using Compound (R-3) and 2-benzyloxycarbonylamino-3-sulfamoylpropionic acid, there was obtained Compound (74a), a diphenylmethyl ester of the subject Compound (74b), through a reaction analogous to Example 1 (a), and then, there was formed the subject Compound (74b) through catalytic reduction with use of palladium-black as a catalyst.

EXAMPLE 75

Production of sodium 2-{(4S)-4-[2-(4-cyano-3-hydroxy-5-isothiazolylthio)acetamido]-3-oxo-isoxazolidinyl}-5-oxo-2tetrahydrofurancarboxylate [Compound (75b)]:

Using Compound (R-3) and 4-cyano-3-hydroxy-5-isothiazolylacetic acid, there was obtained Compound (75a), a diphenylmethyl ester of the subject Compound (75b), through a reaction analogous to Example 1 (a), and then there was obtained the subject Compound (75b).

EXAMPLE 76

Production of sodium 2-{(4S)-4-[2-(2-amino-4-thiazolyl)-2-oxoacetamido]-3-oxo-2-isoxazolidinyl}-5-oxo-2-terahydrofurancarboxylate [Compound (76c)]:

Using Compound (R-3) and 2-(2-chloroacetamido-4-thiazolyl)-2-oxoacetic acid, there was obtained diphenylmethyl (4S)-2isoxazolidinyl}-5-oxo-2-tetrahydrofurancarboxylate [Compound (76a)]through a reaction analogous to Example 1, and after this product was converted into Compound (76b), a diphenyl methyl ester of the subject Compouhd (76c), there was formed the subject Compound (76c).

EXAMPLE 77

Production of sodium 2-{(4S)-4-[2-(2-amino-4-thiazolyl)-(Z)-2-isopropoxyiminoacetamido]-3-oxo-2-isoxazolidinyl}-5-oxo-2-tetrahydrofurancarboxylate [Compound (77c)]:

Using Compound (R-3) and 2-(2-chloroacetamido-4-thiazolyl-(Z)-2-isopropoxyiminoacetic acid, there was obtained diphenylmethyl 2-{(4S)-4-[2-(2-chloroacetamido-4-thiazolyl)-(Z)-2isopropoxyiminoacetamido]-3-oxo-2-isoxazolidinyl}-5-oxo-2tetrahydrofurancarboxylate [Compound (77a)]through a reaction analogous to Example 1, and after this product was converted into Compound (77b), a diphenylmethyl ester of the subject Compound (77c), there was obtained the subject Compound (77c).

EXAMPLE 78

Production of sodium 2-[(4S)-4-trifluoroacetamido-3-oxo-2-isoxazolidinyl]-5-oxo-2-tetrahydrofurancarboxylate [Compound (78b)]:

Compound (R-3) and trifluoroacetic anhydride were stirred in dichloromethane under ice cooling, and the reaction solution was poured into water, followed by extraction with ethyl acetate. The organic layer was washed with aqueous sodium hydrogencarbonate solution, water and saturated aqueous sodium chloride solution, successively, and dried (MgSO$_4$). The solvent was distilled off, and the residue was chromatographed on a column of silica gel to give Compound (78a), a diphenylmethyl ester of the subject Compound (78b) and then, a reaction and treatment analogous to Example 2 (b) yielded the subject Compound (78b).

EXAMPLE 79

Production of disodium 2-{(4S)-4-[2-(2-amino-4-thiazolyl)-(Z)-2-(1-carboxy-1-methylethoxyimino)acetamido]-3-oxo-2-isoxazolidinyl}-5-oxo-2-tetrahydrofurancarboxylate [Compound (79d)]:

(a) Production of diphenylmethyl 2-{(4S)-4-{2-(-2-chloroacetamido-4-thiazolyl)-(Z)-2-[1-methyl-1-(4-nitrobenzyloxycarbonyl)ethoxyimino]acetamido}-3-oxo-2-isoxazolidinyl}-5-oxo-2-tetrahydrofurancarboxylate [Compound (79a)]:

Using Compound (R-3) and 2-(2-chloroacetamido-4-thiazolyl)-(Z)-2-[1-methyl-1-(4-nitrobenzyloxycarbonyl)ethoxyimino]acetic acid, there was obtained Compound (79a) by the procedure of Example 1 (a).

(b) Production of diphenylmethyl 2-{(4S)-4-{2-(2-amino-4-thiazolyl)-(Z)-2-[1-methyl-1-(4-nitrobenzyloxycarbonyl)ethoxyimino]acetamido}-3-oxo-2-isoxazolidinyl}-5-oxo-2-tetrahydrofurancarboxylate [Compound (79b)]:

Compound (79a) was treated by the procedure of Example 1 (b), there was obtained Compound (79b).

(c) Production of sodium 2-{(4S)-4-{2-(2-amino-4-thiazolyl)-(Z)-2-[1-methyl-1-(4-nitrobenzyloxycarbonyl)ethoxyimino]acetamido}-3-oxo-2-isoxazolidinyl}-5-oxo-2-tetrahydrofurancarboxylate [Compound (79c)]:

Compound(79b) was treated in accordance with Example 1

(c) to give Compound (79c).

(d) Production of the subject Compound (79d):

Compound (79c) was treated the procedure of Example 2 (b) to give the subject Compound (79d).

EXAMPLE 80

Production of sodium 2-{(4S)-4-[2-(2-amino-4-thiazolyl)-(Z)-2-(hydroxyimino)acetamido]-3-oxo-2-isoxazolidinyl}-5-oxo-2-tetrahydrofurancarboxylate [Compound (80b)]

(a) Production of diphenylmethyl 2-{(4S)-4-{2-(2-tritylamino4-thiazolyl)-(Z)-2-(trityloxyimino)acetamido}-3-oxo-isoxazolidinyl}-5-oxo-2-tetrahydrofurancarboxylate [Compound (80a)]:

A solution of Compound (R-3) in N,N-dimethylformamide was added to a solution of 2-(2-tritylamino-4-thiazolyl)-)-(Z)-2-(trityloxyimino)acetic acid 2-benzothiazolylthio ester in tetrahydrofuran, followed by stirring at room temperature for 16 hours. The reaction soluion was diluted with ethyl acetate, washed with aqueous sodium hydrogencarbonate solution and water, successively, and dried ($Na_2SO_4$). Then, the solvent was distilled off, and the residue was chromatographed on a column of silica gel to give Compound (80a).

(b) Production of the subject Compound (80b):

Formic acid (>98%) was added to a dichloromethane solution of Compound (80a), followed by stirring at roomtemperature for 1 hour. After the solvent was distilled off under reduced pressure, the residue was dissolved in dichloromethane, and the solution was shaken after the addition of phosphate buffer of pH 7.0 (10 ml) containing sodium hydrogencarbonate (400 mg), followed by separating the aqueous layer. The organic layer was further extracted with a phosphate buffer of pH 7.0 (5 ml), and the aqueous layers were combined and concentrated under reduced pressure. The concentrate was chromatographed on a column of HP-20, followed by lyophilization to give the subject Compound (80b)

EXAMPLE 81

Production of sodium 2-[(4S)-4-isobutyloxycarbonylamino-3-oxo-2-isoxazolidinyl]-5-oxo-2-tetrahydrofurancarboxylate [Compound (81b)]:

(a) Production of sodium diphenylmethyl 2-[(4S)-4-isobutyloxycarbonylamino-3-oxo-2-isoxazolidinyl -5-oxo-2-tetrahydrofurancarboxylate [Compound (81a)];

Using Compound (R-3) and isobutyl chlorocarbonate, there was obtained Compound (81a) by the procedure of Example 23 (a).

(b) Production of the subject Compound (81b):

Compound (81a) was treated by the procedure of Example 23 (b) to give the subject Compound (81b).

EXAMPLE 82

Production of diphenylmethyl 2-{(4S)-4-[N-(4-nitrobenzyloxycarbonyl)glycylamino]-3-oxo-2-isoxazolidinyl}-5-oxo-2-tetrahydrofurancarboxylate [Compound (82)]:

Using Compound (R-3), methyl chlorocarbonate and N-(4-nitrobenzyloxycarbonyl)glycine, there was obtained the subject Compound (82) by the procedure of Example 24 (a).

EXAMPLE 83

Production of diphenylmethyl 2-{(4S)-4-[N-(2,2,2-trichloroethoxycarbonyl)phenylglycylamino]-3-oxo-2-isoxazolidinyl}-5-oxo-2-tetrahydrofurancarboxylate [Compound (83)]:

Using Compound (R-3), methyl chlorocarbonate and N-(2,2,2-trichloroethoxycarbonyl)phenylglycine, there was obtained the subject Compound (83) by the procedure of Example 24 (a).

EXAMPLE 84

Production of sodium 2-{(4S)-4-[N-(benzyloxycarbonyl)-D-phenylglycylamino]-3-oxo-2-isoxazolidinyl}-5-oxo-2-tetrahydrofurancarboxylate [Compound (84b)]:

(a) Production of diphenylmethyl 2-{(4S)-4-[N-(benzyloxycarbonyl)-D-phenylglycylamino]-3-oxo-2-isoxazolidinyl}-5-oxo-2-tetrahydrofurancarboxylate [Compound (84a)]:

Using Compound (R-3) and N-benzyloxycarbonyl-D-phenylglycine, there was obtained Compound (84a) by the procedure of Example 1 (a).

(b) Production of the subject Compound (84b):

Compound (84a) was treated by the procedure of Example 2 (b) to give the subject Compound (84b).

EXAMPLE 85

Production of 2-[(4S)-4-L-phenylglycylamino-3-oxo-2-isoxazolidinyl]-5-oxo-2-tetrahydrofurancarboxylic acid [Compound (85b)]:

(a) Production of diphenylmethyl 2-{(4S)-4-[N-(4-methoxybenzyloxycarbonyl)-L-phenylglycylamino]-3-oxo-2-isoxazolidinyl}-5-oxo-2-tetrahydrofurancarboxylate [Compound (85a)]:

Using Compound (R-3) and N-(4-methoxybenzyloxycarbonyl)-L-phenylglycine, there was obtained Compound (85a) by the procedure of Example 1 (a).

(b) Production of the subject Compound (85b):

Compound (85a) was treated by the procedure of Example 1 (c) to give the subject Compound (85b).

EXAMPLE 86

Production of 2-{(4S)-4-D-phenylglycylamino-3-oxo-2-isoxazolidinyl)-5-oxo-2-tetrahydrofurancarboxylic acid [Compound (86b)]:

(a) Production of diphenylmethyl 2-{(4S)-4-[N-(4-methoxybenzyl-oxycarbonyl)-D-phenylglycylamino]-3-oxo-2-isoxazolidinyl}-5-oxo-2-tetrahydrofurancarboxylate [Compound (86a)]:

Using Compound (R-3) and N-(4-methoxybenzyloxycarbonyl)-D-phenylglycine, there was obtained Compound (86a) by the procedure of Example 1 (a).

(b) Production of the subject Compound (86b)

Compound (86a) was treated by the procedure of Example 1 (c) to give the subject Compound (86b).

EXAMPLE 87

Production of sodium 2-{(4S)-4-[(2S)-(2-hydroxy-2-phenylacetamido]-3-oxo-2-isoxazolidinyl]-5-oxo-2-tetrahydrofurancarboxylate [Compound (87b)]:

(a) Production of diphenylmethyl 2-{(4S)-4-[(2S)-(2-hydroxy- 2-phenyl)acetamido]-3-oxo-2-isoxazolidinyl}-5oxo-2-tetrahydrofurancarboxylate [Compound (87a)]:

Using Compound (R-3) and S-mandelic acid, there was obtained Compound (87a) by the procedure of Example 1 (a).

(b) Production of the subject Compound (87b):
Compound (87a) was treated by the procedure of Example 2 (b) to give the subject Compound (87b).

EXAMPLE 88

Production of sodium 2-{(4S)-4-[(2R)-(2-hydroxy-2-phenyl)-acetamido]-3-oxo-2-isoxazolidinyl}-5-oxo-2-tetrahydrofurancarboxylate [Compound (88b)]:

Using Compound (R-3) and R-mandelic acid, there was obtained Compound (88a), a diphenylmethyl ester of the subject Compound (88b), by the procedure of Example 87, and then, there was formed the subject Compound (88b).

EXAMPLE 89

Production of sodium 2-{(4S)-4-[2-(4-chlorophenyl)-2-hydroxyacetamido]-3-oxo-2-isoxazolidinyl}-5-oxo-2-tetrahydrofurancarboxylate [Compound (89b)]:

Using Compound (R-3) and 4-chloro-DL-mandelic acid, there was obtained Compound (89a), a diphenylmethyl ester of the subject Compound (89b), by the procedure of Example 87, and then, there was formed the subject Compound (89b).

EXAMPLE 90

Production of sodium 2-{(4S)-4-[2-hydroxy-2-(4-hydroxyphenyl)-acetamido]-3-oxo-2-isoxazolidinyl}-5-oxo-2-tetrahydrofurancarboxylate [Compound (90b)]:

Using Compound (R-3) and 4-hydroxy-DL-mandelic acid, there was obtained Compound (90a), a diphenylmethyl ester of the subject Compound (90b), by the procedure of Example 87, and then, there was formed the subject Compound (90b).

EXAMPLE 91

Production of sodium 2-[(4S)-4-(2-hydroxypropionamido)-3-oxo-2-isoxazolidinyl]-5-oxo-2-tetrahydrofurancarboxylate [Compound (91b)]:

Using Compound (R-3) and DL-lactic acid, there was obtained Compound (91a), a diphenylmethyl ester of the subject Compound (91b), by the procedure of Example 87, and then, there was formed the subject Compound (91b).

EXAMPLE 92

Production of disodium 2-[(4S)-4-(2-carboxy-2-phenylacetamido)-3-oxo-2-isoxazolidinyl]-5-oxo-2-tetrahydrofurancarboxylate [Compound (92b)]:

Using Compound (R-3) and monodiphenylmethyl DL-phenylmalonate, there was obtained Compound (92a), a bis(diphenylmethyl ester) of the subject Compound (92b), by the procedure of Example 87, and then, there was formed the subject Compound (92b).

EXAMPLE 93

Production of sodium 2-[(4S)-4-benzyloxycarbonylamino-3-oxo-2-isoxazolidinyl]-5-oxo-2-tetrahydrofurancarboxylate [Compound (93b)]:

Using Compound (R-3) and benzyloxycarbonyl chloride, there was obtained Compound (93a), a diphenylmethyl ester of the subject Compound (93b), by the procedure of Example 5, and then, there was formed the subject Compound (93b).

EXAMPLE 94

Production of sodium 2-{(4S)-4-pyruvamido-3-oxo-2-isoxazolidinyl}-5-oxo-2-tetrahydrofurancarboxylate [Compound (94b)]:

Using Compound (R-3) and pyruvic acid, there was obtained Compound (94a), a diphenylmethyl ester of the subject Compound (94b), by the procedure of Example 87, and then, there was formed the subject Compound (94b).

EXAMPLE 95

Production of pivaloyloxymethyl 2-{(4S)-4-[(2R)-(2-hydroxy-2-phenyl)acetamido]-3-oxo-2-isoxazolidinyl}-5-oxo-2-tetrahydrofurancarboxylate [Compound (95)]:

Using Compound (88b) and chloromethyl pivalate, there was obtained the subject Compound (95) by the procedure of Example 28 (c).

EXAMPLE 96

Production of diphenylmethyl 2-[(4S)-4-(4-nitrobenzylidene)-amino-3-oxo-2-isoxazolidinyl]-5-oxo-2-tetrahydrofurancarboxylate [Compound (96)]:

Molecular sieves 4A was added to a dichloromethane solution of Compound (R-3) and 4-nitrobenzaldehyde, followed by stirring at room temperature for 8 hours. Molecular sieves were filtered off, and the filtrate was concentrated to dryness under reduced pressure. Ether was added to the residue, which was converted into powder to give the subject Compound (96).

EXAMPLE 97

Production of sodium 2-{(4S)-4-[2-(3-chloro-6-pyridazinylthio)acetamido]-3-oxo-2-isoxazolidinyl}-5-oxo-2-tetrahydrofurancarboxylate [Compound (97b)]:

Using Compound (14a) and 3-chloro-6-pyridazinethiol sodium salt, there was obtained Compound (97a), a diphenylmethyl ester of the subject Compound (97b), by the prodedure of Example 15, and then, there was formed the subject Compound (97b).

EXAMPLE 98

Production of sodium 2-[(4S)-4-(2-phenylthioacetamido)-3-oxo-2-isoxazolidinyl]-5-oxo-2-tetrahydrofurancarboxylate [Compound (98b)]:

Using Compound (R-3) and phenylthioacetic acid, there was obtained Compound (98a), a diphenylmethyl ester of the subject Compound (98b), by the procedure of Example 1 (a), and then, there was formed the subject Compound (98b) by the procedure of Example 1 (c).

EXAMPLE 99

Production of sodium 2-[(4S)-4-(2-ethoxydithiocarbonylacetamido)-3-oxo-2-isoxazolidinyl]-5-oxo-2-tetrahydrofurancarboxylate [Compound (99b)]:

Using Compound (14a) and potassium ethylxanthate, there was obtained Compound (99a), a diphenylmethyl ester of the subject Compound (99b), by the procedure of Example 15, and then, there was formed the subject Compound (99b).

Below given are the reaction conditions of Examples 38 to 99 as well as the yields and typical physico-chemical properties of the compounds obtained.

| Product | Reaction conditions | Yield (mg) St. mat → Prod. | KBr IRν cm⁻¹ max | NMR(90MHz)δ |
|---|---|---|---|---|
| 38a | 2-benzyloxycarbo-nylaminomethyl-phenylacetic acid(166 mg) HOBT(75 mg) DCC(128 mg) DMF(4 ml) rt,1 h extraction with ethyl acetate, silica gel chromatography (CH₂Cl₂—ethyl acetate=2:1) | 200 → 200 | 3320,2920, 2840,1770, 1760,1710, 1670,1610, 1530,1260, 1180,1060 | 2.22–3.30(4H,m),3.5–4.1 (1H,m),3.62(2H,s),4.36(2H, d,J=6Hz),4.48–4.90(1H,m), 5.10(2H,s),5.61–5.80(1H, m),6.67–6.80(1H,m),6.97 (1H,s),7.17–7.40(19H,m) (solvent:CDCl₃) |
| 38b | H₂/Pd—C(200 mg) THF(3 ml)—water (1 ml)0° C.,90 min XAD-2 column (20% ethanol) lyophilization | 200 → 53 | 3410,3240, 3040,1780, 1730,1640, 1540,1370, 1190 | 2.41–3.42(4H,m),4.08(2H, s),4.30–4.59(1H,m),4.48 (2H,s),4.73–5.01(1H,m), 5.05–5.45(1H,m),7.58– 7.78(4H,m) (solvent:D₂O) |
| 39a | 4-fluorobenzene-sulfonyl chloride(100 mg) propylene oxide (0.5 ml) DMA(1 ml) 0° C., 1 h extraction with ethyl acetate, silica gel chromatography (hexane-ethyl acetate=1:1) | 200 → 179 | 3260,1795, 1765,1750, 1590,1490, 1340,1170, 1150,1050 | 2.2–2.9(4H,m),3.9–4.3(2H, m),4.5–4.7(1H,m),5.1–5.3 (1H,m),6.94(1H,s),7.1–7.5 (12H,m),7.7–8.0(2H,m) (solvent:CDCl₃) |
| 39b | H₂/Pd—black(80 mg) THF(3 ml)—NaHCO₃ (23 mg) | 149 → 88 | 1780,1725, 1650,1395, 1490,1380, 1340,1155, 1090 | 2.6–3.4(4H,m),4.1–4.4(1H, m),4.6–5.1(2H,m),7.5–7.8 (2H,m),8.1–8.4(2H,m) (solvent:D₂O) |
| 39b | 0° C., 1 h HP-20 column (10% ethanol) lyophilization | | | |
| 40a | 1-(2-dimethyl-aminoethyl)-1H—tetrazole-5-thiol(77 mg) NaH(16 mg) DMF(0.5 ml) rt,3 h extraction with ethyl acetate, crystallized from hexane | 200 → 234 | 3340,1790, 1730,1680, 1530,1450, 1300,1260, 1180,1050 | 2.30(6H,s),2.2–3.4(5H,m), 2.78(2H,t,J=8Hz),3.95 (2H,d,J=2Hz),4.0–4.8(2H, m),4.35(2H,t,J=8Hz),6.99 (1H,s),7.2–7.4(10H,m), 7.8–7.9(1H,m) (solvent:D₂O) |
| 40b | CF₃COOH(0.3 ml) anisole(0.5 ml) −20°~0° C.,3 h CHP-20 column (5% ethanol) lyophilization | 200 → 93 | 1770,1730, 1655,1370, 1190,1110, 1020 | 2.6–3.4(4H,m),3.20(6H,s), 4.00(2H,t,J=6.6Hz),4.3–4.6(1H,m),4.40(2H,d,J=2 Hz),5.11(2H,t,J=6.6Hz), 4.8–5.3(2H,m) (solvent:D₂O) |
| 41a | 1-methyl-1H—1,3, 4-triazole-3-thiol(56 mg) NaH(18 mg) DMF(1 ml) rt,3 h extraction with ethyl acetate, silica gel chromatography (ethyl acetate-ethanol=5:1) | 209 → 140 | 3360,1770, 1745,1725, 1680,1525, 1260,1185, 1050 | 2.3–3.3(4H,m),3.59(3H,s), 3.85(2H,s),3.8–5.0(3H,m), 6.90(1H,s),7.2–7.5(10H,m), 8.50(1H,s),8.89(1H,d,J= 7Hz) (solvent:d₆-DMSO) |
| 41b | CF₃COOH(0.22 ml) anisole(0.37 ml) −20°~0° C.,3 h CHP-20 column (water) lyophilization | 140 → 72 | 1775,1720, 1660,1550, 1520,1375, 1195,1015, 1030 | 2.6–3.5(4H,m),3.93(3H,s), 4.10(2H,s),4.2–4.5(1H,m), 4.8–5.4(2H,m),7.80(1H,s) (solvent:D₂O) |
| 42a | (2R,3S)—2-(4-ethyl-2,3-dioxo- | 360 → | 2950,1805, 1720,1680, | 1.1–1.4(6H,m),2.2–3.0(4H, m),3.3–3.7(4H,m),3.9–4.3 |

-continued

| Product | Reaction conditions | Yield (mg) St. mat → Prod. | KBr IRν cm⁻¹ max | NMR(90MHz)δ |
|---|---|---|---|---|
| | 1-piperazino-carboxamide)-3-formyloxybutyric acid(315 mg) DCC(206.3 mg) DMF(3 ml) rt,3 h extraction with ethyl acetate, silica gel chromatography (ethyl acetate) | 239 | 1520,1365, 1260,1180, 1050 | (2H,m),4.4–4.8(2H,m),4.9–5.2(1H,m),5.5–5.9(1H,m), 6.93(1H,s),7.1–7.4(10H, m),7.7–8.0(1H,m),7.96(1H, s),9.4–9.6(1H,m) (solvent:CDCl$_3$) |
| 42b | H$_2$/10% Pd—C (200 mg) THF(2 ml) NaHCO$_3$(24 mg) rt,2 h CHP-20 column (5% ethanol) lyophilization | 198 → 88 | 2975,1775, 1710,1670, 1520,1365, 1190,1060, 1030,1005 | 1.46(3H,t,J=7Hz),1.61 (3H,d,J=6.6Hz),2.5–3.6 (4H,m),3.75(2H,q,J=7 Hz),3.9–4.1(2H,m),4.2–4.6 (3H,m),5.1–5.5(1H,m),5.7–6.0(1H,m),7.43(1H,s) (solvent:D$_2$O) |
| 43 | water(20 ml) NaHCO$_3$(148 mg) phenylsulfoacetyl chloride (119 mg) ether(10 ml) 0°C.,1 h XAD-2 column (water) lyophilization | 115 → 34 | 3450,1780, 1720,1660, 1540,1380, 1200,1120, 1050 | 2.55–3.42(4H,m),4.32–4.59 (1H,m),4.80–5.09(1H,m), 5.31(1H,s),5.21–5.46(1H, m),7.61–7.92(5H,m) (solvent:D$_2$O) |
| 44a | 2-(2-chloroaceto amide-4-thiazolyl)-(E)—2-methoxy iminoacetic acid (310 mg) HOBT(150 mg) DCC(230 mg) DMF(3 ml) 0° C.,1 h extraction with ethyl acetate, silica gel chromatography (hexane-ethyl acetate = 1:2) | 396 → 600 | 3240,1800, 1760,1690, 1660,1550, 1260,1180, 1040 | 2.20–3.43(4H,m),4.11(3H, s),4.18(2H,s),4.05–5.10 (3H,m),6.97(1H,s),7.24–7.44(10H,m),7.83(1H,s), 8.52(1H,b) (solvent:CDCl$_3$) |
| 44b | CH$_3$NHCS$_2$Na.2H$_2$O (290 mg) THF(16 ml)-water (14 ml) rt,1 h extraction with ethyl acetate, silica gel chromatography (ethyl acetate) | 600 → 440 | 3300,1800, 1755,1680, 1610,1530, 1180,1050, 1020 | 2.20–3.39(4H,m),4.00–5.12 (3H,m),4.14(3H,s),5.29 (2H,b),6.98(1H,s),7.22–7.39(10H,m),7.51(1H,s), 9.29,9.50(each 0.5H,b) (solvent:CDCl$_3$) |
| 44c | CF$_3$COOH(0.35 ml) anisole(0.26 ml) CH$_2$Cl$_2$(14 ml) −10°∼−15° C., 5.5 h HP-20 column (5% ethanol) lyophilization | 210 → 115 | 3430,1780, 1730,1660, 1530,1380, 1190,1010 | 2.60–3.49(4H,m),4.28(3H, s),4.41–4.67(1H,m),4.90–5.12(1H,m),5.31–5.59(1H, m),7.76(1H,s) (solvent:D$_2$O) |
| 45a | trimethylsilyl ethoxycarbonyl chloride(0.7 ml) butylene oxide (1.6 ml) CH$_2$Cl$_2$(40 ml) 0° C.,2 h powdered with hexane | 792 → 1000 | (Nujol) 3330,1760, 1710,1530, 1240,1180, 1050 | 0.80–1.33(2H,m),2.25–3.40 (4H,m),3.90–5.00(5H,m), 6.90(1H,s),7.20–7.60(10H, m),7.60–7.90(1H,m) (solvent:CDCl$_3$) |
| 45b | 10% Pd—C(500 mg) NaHCO$_3$(160 mg) THF(10 ml)-water (5 ml) rt,2 h | 1000 → 490 | (Nujol) 3300,1780, 1720,1645, 1520,1240, 1180,1050 | 0.80–1.10(2H,m),2.20–3.40 (4H,m),3.50–4.90(5H,m), 7.40–7.70(1H,m) (solvent:d$_6$-DMSO) |

-continued

| Product | Reaction conditions | Yield (mg) St. mat → Prod. | KBr IRν cm$^{-1}$ max | NMR(90MHz)δ |
|---|---|---|---|---|
| | CHP-20 column (20% ethanol) lyophilization | | | |
| 46a | 1-benzyloxy-carbonylamino cyclohexane carbonic acid (181 mg) HOBT(88 mg) DCC(135 mg) CH$_2$Cl$_2$(10 ml) rt,4days extraction with ethyl acetate, silica gel chromatography (hexane-ethyl acetate=1:1) | 199 → 240 | 3350,2940, 1800,1760, 1720,1680, 1520,1450, 1240,1180, 1050 | 1.08–2.07(10H,m),2.22–3.31(4H,m),3.79–4.78(3H,m),5.03(2H,s),6.97(1H,s), 7.08–7.39(15H,m) (solvent:CDCl$_3$) |
| 46b | H$_2$/5% Pd—C (240 mg) THF(3 ml)-water (1 ml) 0° C., 90min XAD-2 column (20% ethanol) lyophilization | 240 → 35 | 3450,1780, 1730,1650, 1520,1370, 1190,1030 | 1.48–2.34(10H,m),2.41–3.47(4H,m),4.32–4.65(1H, m),4.81–5.05(1H,m),5.21 5.49(1H,m) (solvent:D$_2$O) |
| 47a | 3-(2,6-dicloro phenyl)-5-methyl-4-isoxazolyl-carbonyl chloride (192 mg) DMA(0.4 ml) CH$_2$Cl$_2$(10 ml) 0° C., 5min→rt, 30min extraction with ethyl acetate, silica gel chromatography (hexane-ethyl acetate=1:1) | 200 → 230 | 3400,3040, 1820,1760, 1670,1420, 1180,1050 | 2.19–3.30(4H,m),2.79(3H, s),3.69–4.02(1H,m),4.63–4.89(1H,m),5.59–5.81(1H, m),6.94(1H,s),7.14–7.59 (13H,m) (solvent:CDCl$_3$) |
| 47b | CF$_3$COOH(0.32 ml) anisole(0.24 ml) CH$_2$Cl$_2$(13 ml) −10°∼−15° C., 4 h XAD-2 column (20% ethanol) lyophilization | 218 → 79 | 3450,1780, 1730,1650, 1520,1380, 1190,1030 | 2.41–3.40(4H,m),3.90(3H, s),4.21–4.55(1H,m),4.80–5.06(1H,m),5.21–5.48(1H, m),7.82(3H,s) (solvent:D$_2$O) |
| 48a | 2-pyridinethiol (56.4 mg) NaH(19.2 mg) NaI(100 mg) DMF(1 ml) rt,30min extraction with ethyl acetate, silica gel chromatography (hexane-ethyl acetate=2:3) | 200 → 157 | 3350,1770, 1730,1670, 1570,1510, 1180,1050 | 2.21–3.40(4H,m),3.68(2H, s),3.87–4.19(1.5H,m),4.46 –4.82(1.5H,m),6.92(1H,s), 6.93–8.81(14H,m) (solvent:CDCl$_3$) |
| 48b | CF$_3$COOH(0.28 ml) anisole(0.21 ml) CH$_2$Cl$_2$(11 ml) −10°∼−15° C., 5 h XAD-2 column (10% ethanol) lyophilization | 157 → 85 | 3450,1780, 1730,1650, 1380,1190, 1100,1030 | 2.48–3.47(4H,m),4.09–4.42 (1H,m),4.13(2H,m),4.63–4.93(1H,m),5.08–5.42(1H, m),7.35–8.80(4H,m) (solvent:D$_2$O) |
| 49a | 4-pyridinemetha-nethiol(99 mg) DMF(3 ml) rt,1 h extraction with ethyl acetate, silica gel chromatography | 300 → 75 | 3340,1770, 1730,1670, 1590,1510, 1180,1050 | 2.20–3.49(4H,m),3.10(2H, s),3.71(2H,s),3.79–4.11 (1.5H,m),4.51–4.97(1.5H, m),6.97(1H,s),7.13–8.62 (14H,m) (solvent:CDCl$_3$) |

-continued

| Product | Reaction conditions | Yield (mg) St. mat → Prod. | KBr IRν cm⁻¹ max | NMR(90MHz)δ |
|---|---|---|---|---|
| | (ethyl acetate-acetone=3:1) | | | |
| 49b | CF₃COOH(0.3 ml) anisole(0.23 ml) CH₂Cl₂(12 ml) −10°∼−15° C., 4 h XAD-2 column (10% ethanol) lyophilization | 175 → 86 | 3410,1780, 1720,1650, 1380,1190, 1030 | 2.60-3.46(4H,m),3.54(2H, s),4.17(2H,s),4.25-4.42 (1H,m),4.62-5.31(2H,m), 7.80-8.02(2H,m),8.68-9.00 (2H,m) (solvent:D₂O) |
| 50a | 2-pyridinethiol (55 mg) NaH(19.2 mg) NaI(100 mg) DMF(1 ml) rt,30min extraction with ethyl acetate, crystallized from ether | 124 → 128 | 3350,1770, 1720,1670, 1550,1510, 1380,1180, 1050 | 2.30-3.45(4H,m),3.79(2H, s),3.89-4.20(1.5H,m), 4.45-4.90(1.5H,m),6.99 (1H,s),7.02-8.64(13H,m) (solvent:CDCl₃) |
| 50b | CF₃COOH(0.4 ml) anisole(0.31 ml) CH₂Cl₂(16 ml) −10°∼−15° C., 3 h XAD-2 column (10% ethanol) lyophilization | 228 → 88 | 3430,1780, 1720,1650, 1550,1380, 1190,1030 | 2.61-3.49(4H,m),4.22(2H, s),4.28-4.56(1H,m),4.77- 5.03(1H,m),5.13-5.46(1H, m),7.53(1H,t,J=5Hz), (solvent:D₂O) |
| 51a | (E)—2-acetamide-vinylthiol silver salt(85 mg) NaI(89 mg) DMF(2 ml) rt,4 h extraction with ethyl acetate, silica gel chromatography (ethyl acetate) | 89 → 65 | 3340,1765, 1720,1670, 1610,1500, 1370,1180, 1050 | 1.91,2.00(each 1.5H,s), 2.30-3.45(4H,m),3.22(2H, s),3.89-4.29(1.5H,m), 4.41-4.95(1.5H,m),5.72 (1H,d,J=14Hz),6.82-7.49 (11H,m),6.91(1H,s),8.71 (1H,m) (solvent:d₆-DMSO) |
| 51b | CF₃COOH(0.247 ml) anisole(0.189 ml) CH₂Cl₂(10 ml) −10°∼−15° C., 3 h XAD-2 column (water) lyophilization | 142 → 27 | 3250∼ 3450,1780, 1720,1650, 1520,1380, 1190,1030 | 2.27,2.32(each 1.5H,s), 2.61-3.49(4H,m)3.59,3.70 (each 2H,s),4.29-4.60(1H, m),4.77-5.02(1H,m),5.13- 5.49(1H,m),5.69-6.20(1H, m),7.14-7.40(1H,m) (solvent:D₂O) |
| 52a | cyclopropanecar-boxylic acid(86 mg) HOBT(134 mg) DCC(206 mg) DMF(4 ml) rt,1 h extraction with ethyl acetate, silica gel chromatography (hexane-ethyl acetate=1:2) | 200 → 183 | 3350,1760, 1720,1680, 1540,1180, 1050 | 0.91-1.15(4H,m),1.42-1.80 (1H,m),2.21-3.40(4H,m), 3.87-4.21(1.5H,m),4.61- 4.90(1.5H,m),6.27-6.51 (1H,m),6.93(1H,s),7.25- 7.45(10H,m) (solvent:CDCl₃) |
| 52b | H₂/5% Pd—C (180 mg) THF-buffer (pH7.0) 0° C.,30min HP-20 column (water) lyophilization | 180 → 60 | 3450,1780, 1720,1650, 1540,1380, 1200,1030 | 1.02-1.15(4H,m),1.70-2.02 (1H,m),2.59-3.42(4H,m), 4.28-4.57(1H,m),4.81-5.05 (1H,m),5.13-5.42(1H,m) (solvent:D₂O) |
| 53a | methyl oxalyl chloride(0.65 ml) DMA(0.4 ml) CH₂Cl₂(10 ml) rt,30min extraction with ethyl acetate, crystallized from ether | 200 → 200 | 3350,1760, 1730,1700, 1530,1450, 1180,1050 | 2.31-3.40(4H,m),3.81(3H, s),3.91-4.46(1H,m),4.55- 5.09(1H,m),5.43-5.60(1H, m),6.92(1H,s),7.31-7.55 (10H,m) (solvent:d₆-DMSO) |
| 53b | H₂/5% Pd—C(150 mg) | 150 | 3400,1780, | 2.62-3.52(4H,m),4.18(3H, |

-continued

| Product | Reaction conditions | Yield (mg) St. mat → Prod. | KBr IR$\nu$ cm$^{-1}$ max | NMR(90MHz)$\delta$ |
|---|---|---|---|---|
| | THF-buffer(pH7.0)<br>0° C.,30min<br>HP-20 column<br>(water)<br>lyophilization | 91 | 1760–1740,<br>1700,1650,<br>1540,1380,<br>1190,1030 | s),4.40–4.68(1H,m),4.88–<br>5.10(1H,m),5.28–5.61(1H,<br>m)<br>(solvent:D$_2$O) |
| 54 | H$_2$/5% Pd—C(300 mg)<br>THF(20 ml)-<br>(water)(10 ml)<br>NaHCO$_3$(222 mg)<br>acryloyl<br>chloride(81 mg)<br>THF(6 ml)<br>HP-20 column<br>(water)<br>lyophilization | 300<br>→<br>19 | 3450,1780,<br>1730,1660,<br>1540,1380,<br>1200,1120,<br>1040 | 2.53–3.41(4H,m),4.35–4.63<br>(1H,m),4.81–5.09(1H,m),<br>5.21–5.51(1H,m),6.00–6.21<br>(1H,m),6.47–6.60(2H,m)<br>(solvent:D$_2$O) |
| 55a | 2-chloro-4-pyri-<br>dinethiol<br>(215 mg)<br>DMF(4 ml)<br>rt,1 h<br>extraction with<br>ethyl acetate,<br>silica gel chro-<br>matography<br>(hexane-ethyl<br>acetate=1:2) | 300<br>→<br>170 | 3350,1770,<br>1720,1680,<br>1570,1520,<br>1180,1050 | 2.20–3.51(4H,m),3.69(2H,<br>s),3.81–4.19(1.5H,m),<br>4.48–4.88(1.5H,m),6.98<br>(1H,s),7.02–8.23(13H,m)<br>(solvent:CDCl$_3$) |
| 55b | CF$_3$COOH(0.28 ml)<br>anisole(0.22 ml)<br>CH$_2$Cl$_2$(14 ml)<br>−10°∼−15° C.,<br>5 h<br>XAD-2 column<br>(10% ethanol<br>lyophilization | 170<br>→<br>82 | 3450,1780,<br>1720,1650,<br>1560,1380,<br>1190,1020,<br>1040 | 2.60–3.43(4H,m),4.12–4.53<br>(1H,m),4.20(2H,s),4.75–<br>5.02(1H,m),5.13–5.40(1H,<br>m),7.42–7.61(2H,m),8.40<br>(1H,d,J=5Hz)<br>(solvent:D$_2$O) |
| 56a | 2-acetamide-5-<br>oxo-2-tetrahydro-<br>furancarboxylic<br>acid(187 mg)<br>HOBT(134 mg)<br>DCC(206 mg)<br>DMF(6 ml)<br>rt,1 h<br>extraction with<br>ethyl acetate,<br>silica gel chro-<br>matography<br>(ethyl acetate-<br>acetone=20:1) | 300<br>→<br>370 | 3350,1800,<br>1780,1720,<br>1670,1530,<br>1180,1050 | 1.91(3H,s),2.21–3.29(8H,<br>m),3.82–4.20(1.5H,m),4.50<br>–4.87(1.5H,m),6.97(1H,s),<br>7.28–7.49(10H,m)<br>(solvent:d$_6$-DMSO) |
| 56b | H$_2$/5% Pd—C<br>(250 mg)<br>THF-buffer<br>(pH7.0)<br>0° C.,25min<br>HP-20 column<br>(water)<br>lyophilization | 250<br>→<br>123 | 3450,1780,<br>1730,<br>1680–1640,<br>1540,1380,<br>1190,1040 | 2.26(3H,s),2.59–3.48(8H,<br>m),4.32–4.62(1H,m),4.80–<br>5.06(1H,m),5.13–5.50(1H,<br>m)<br>(solvent:D$_2$O) |
| 57a | 1-pyrazolylace-<br>tic acid(126 mg)<br>HOBT(134 mg)<br>DCC(206 mg)<br>DMF(4 ml)<br>rt,10min<br>extraction with<br>ethyl acetate,<br>silica gel chro-<br>matography<br>(ethyl acetate) | 200<br>→<br>230 | 3350,1770,<br>1730,1680,<br>1580,1520,<br>1180,1050 | 2.22–3.51(4H,m),3.87–4.21<br>(1.5H,m),4.48–4.88(1.5H,<br>m),4.83(2H,s),6.34(1H,m),<br>6.98(1H,s),7.05–7.68(12H,<br>m)<br>(solvent:CDCl$_3$) |
| 57b | H$_2$/5% Pd—C<br>(230 mg)<br>THF-buffer<br>(pH7.0)<br>0° C., 40min<br>XAD-2 column<br>(water)<br>lyophilization | 230<br>→<br>96 | 3400,1780,<br>1720,1650,<br>1400,1190,<br>1040 | 2.59–3.43(4H,m),4.30–4.59<br>(1H,m),4.81–5.08(1H,m),<br>5.21–5.51(1H,m),5.31(2H,<br>s),6.65–6.74(1H,m),7.91–<br>8.07(2H,m)<br>(solvent:D$_2$O) |
| 58a | 2-(5-amino-1,2,<br>4-thiadiazol-3- | 280<br>→ | 3320,1800,<br>1760,1660, | 1.23(3H,t,J=7Hz),2.23–<br>3.28(4H,m),3.93–4.32 |

-continued

| Product | Reaction conditions | Yield (mg) St. mat → Prod. | KBr IR$\nu$ cm$^{-1}$ max | NMR(90MHz)$\delta$ |
|---|---|---|---|---|
| | yl)-(Z)—2-etho-xyiminoacetic acid(235 mg) HOBT(145 mg) DCC(222 mg) rt,1 h extraction with ethyl acetate, silica gel chromatography (ethyl acetate-CHCl$_3$=2:1) | 299 | 1520,1180, 1050 | (3.5H,m),4.58–4.96(1.5H, m),6.63(2H,bs),6.91(1H, s),7.19–7.34(10H,m) (solvent:CDCl$_3$) |
| 58b | CF$_3$COOH(0.48 ml) anisole(0.36 ml) CH$_2$Cl$_2$(20 ml) −10°~−15° C., 4 h XAD-2 column (water) lyophilization | 299 → 62 | 3400,1780, 1720,1650, 1520,1390, 1190,1050 | 1.53(3H,t,J=7Hz),2.59–3.53(4H,m),4.39–4.71(3H, m),4.98–5.17(1H,m),5.32–5.61(1 h,m) (solvent:D$_2$O) |
| 59a | lithium 3-pyridazinethiol (90 mg) NaI(100 mg) DMF(60 ml) rt,1 h extraction with ethyl acetate, silica gel chromatography (ethyl acetate-acetone=9:1) | 300 → 263 | 3340,1770, 1740,1680, 1420,1180, 1050 | 2.21–3.32(4H,m),3.98(2H, s),3.83–4.27(1.5H,m), 4.58–4.91(1.5H,m),6.98 (1H,s),7.19–7.52(11H,m), 7.91–8.10(1H,m),8.89–9.00 (1H,m) (solvent:CDCl$_3$) |
| 59b | CF$_3$COOH(0.45 ml) anisole(0.35 ml) CH$_2$Cl$_2$(20 ml) −10°~−15° C., 4 h HP-20 column (water) lyophilization | 263 → 93 | 3450,1780, 1720,1650, 1410,1380, 1190,1040 | 2.58–3.51(4H,m),4.21–4.52 (1H,m),4.32(2H,s),4.74–5.00(1H,m),5.12–5.43(1H, m),7.77–8.08(2H,m),9.17–9.30(1H,m) (solvent:D$_2$O) |
| 60a | dichloroacetic chloride(111 mg) propyleneoxide (5 ml) CH$_2$Cl$_2$(15 ml) −20° C., 5min extraction with ethyl acetate, silica gel chromatography (hexane-CH$_2$Cl$_2$-ethyl acetate=1:2:1) | 300 → 301 | 3480,1780, 1765,1720, 1690,1520, 1490,1450, 1300,1260, 1180,1050 | 2.4–3.6(4H,m),3.9–5.3(3H, m),6.51(1H,d,J=3.3Hz), 6.91(1H,s),7.2–7.5(10H, m),9.30(1H,d,J=8.3Hz) (solvent:d$_6$-DMSO) |
| 60b | CF$_3$COOH(0.44 ml) anisole(0.74 ml) CH$_2$Cl$_2$(4 ml) 0° C.,2 h CHP-20 column (water) lyophilization | 274 → 167 | 3400,1780, 1690,1650, 1525,1380, 1190,1115, 1030 | 2.6–3.5(4H,m),4.4–4.7(1H, m),4.8–5.1(1H,m),5.2–5.5 (1H,m),6.64(1H,s) (solvent:D$_2$O) |
| 61a | (2R,3S)—2-(4-ethyl-2,3-dioxo-1-piperazine-carboxamide)-3-hydroxybutyric acid(238 mg) DCC(156.5 mg) DMF(3 ml) rt,5 h extraction with ethyl acetate, silica gel chromatography (ethyl acetate-methanol=5:1) | 300 → 350 | 3320,1810, 1715,1680, 1520,1370, 1250,1195, 1050 | 1.0–1.4(6H,m),2.1–3.1(4H, m),3.1–4.8(11H,m),4.9–5.4 (1H,m),6.88(1H,d,J=3Hz), 7.1–7.5(10H,m),7.8–8.2 (1H,m),9.4–9.6(1H,m) (solvent:CDCl$_3$) |
| 61b | H$_2$/10% Pd-black (150 mg) | 349 → | 3310,1780, 1720,1670, | 1.44(3H,t,J=8Hz),1.49 (3H,d,J=8.3Hz),2.5–3.5 |

-continued

| Product | Reaction conditions | Yield (mg) St. mat → Prod. | KBr IRν cm⁻¹ max | NMR(90MHz)δ |
|---|---|---|---|---|
| | NaHCO₃(44 mg) THF(5 ml)-water (1 ml) 0° C., 5 h CHP-20 column 10% ethanol) lyophilization | 102 | 1520,1370, 1195,1105, 1005 | (4H,m),3.6-4.1(4H,m),4.2-5.1(7H,m),5.2-5.6(1H,m) (solvent:D₂O) |
| 62a | 5-trifluoromethyl-1,3,4-thiadiazole-2-tiol (137.8 mg) NaH(29.6 mg) DMF(3 ml) 0° C., 4 h extraction with ethyl acetate, silica gel chromatography (hexane-CH₂Cl₂-ethyl acetate(1:1:1) | 350 → 391 | 3400,3350, 1800,1770, 1730,1680, 1520,1325, 1300,1180, 1050 | 2.5-3.4(4H,m),3.8-5.2(3H,m),4.26(2H,s),6.90(1H,s), 7.2-7.6(10H,m),9.09(1H,d,J=8.3Hz) (solvent:d₆-DMSO) |
| 62b | CF₃COOH(0.48 ml) anisole(0.8 ml) CH₂Cl₂(4 ml) 0° C., 4 h CHP-20 column (10% ethanol) lyophilization | 350 → 190 | 3380,1780, 1720,1650, 1540,1480, 1380,1325, 1190,1150, 1225 | 2.6-3.6(4H,m),4.49(2H,s), 4.3-4.6(1H,m),4.8-5.5(2H,m) (solvent:D₂O) |
| 63a | 1-[ethoxy(hydroxy)phosphinyl methyl]-5-mercapto-1H—tetrazole O,S-disodium salt (208 mg) DMF(3 ml) rt,4 h CHP-20 column (50% ethanol) lyophilization | 350 → 460 | 3350,1765, 1730,1675, 1540,1450, 1390,1300, 1250,1180, 1050 | 0.9-1.2(3H,m),2.3-3.3(4H,m),3.4-4.2(4H,m),3.98(2H,s),4.2-4.8(3H,m),6.91(1H,s),7.2-7.6(10H,m),9.3-9.7(1H,m) (solvent:d₆-DMSO) |
| 63b | CF₃COOH(0.35 ml) anisole(0.6 ml) CH₂Cl₂(4 ml) 0° C.,2 h CHP-20 column (water) lyophilization | 296 → 210 | 3420,1780, 1650,1540, 1440,1380, 1220,1190, 1040 | 1.48(3H,t,J=8.6Hz),2.4-3.5(4H,m),4.0-4.6(3H,m),4.35(2H,s),5.2-5.5(1H,m) (solvent:D₂O) |
| 64a | 5-(2-diethoxy phosphinylethyl thio)-1,3,4-thiadiazole-2-thiol (219.4 mg) NaH(27.8 mg) DMF(3 ml) rt,3 h→40° C.,2 h extraction with silica gel chromatography (ethyl acetate) | 300 → 375 | 3360,1770, 1740,1680, 1550,1390, 1300,1240, 1180,1050 | 1.32(6H,t,J=8.3Hz),2.3-3.7(8H,m),3.9-4.4(6H,m), 3.95(2H,s),4.6-4.8(1H,m), 6.97(1H,s),7.2-7.5(10H,m),7.5-7.8(1H,m) (solvent:CDCl₃) |
| 64b | CF₃COOH(0.37 ml) anisole(0.62 ml) CH₂Cl₂(2 ml) 0° C.,4 h CHP-20 column (20% ethanol) lyophilization | 340 → 110 | 3440,1780, 1720,1650, 1540,1380, 1230,1190, 1030 | 1.54(3H,t,J=7Hz),2.4-3.9 (8H,m),4.2-4.6(6H,m),4.31 (2H,s),5.2-5.4(1H,m) (solvent:D₂O) |
| 65a | 1-dimethylamino-1H—tetrazole-5-thiol (110.5 mg) NaH(30 mg) DMF(3 ml) rt,2 h→40° C.,1 h extraction with ethyl acetate, silica gel chromatography | 300 → 352 | 3360,1800, 1760,1685, 1530,1450, 1250,1180, 1050 | 2.5-3.4(4H,m),2.90(6H,s), 3.8-5.2(3H,m),4.15(2H,s), 6.91(1H,s),7.2-7.6(10H,m),9.05(1H,d,J=8.3Hz) (solvent:d₆-DMSO) |

|Product|Reaction conditions|Yield (mg) St. mat → Prod.|KBr IRν cm$^{-1}$ max|NMR(90MHz)δ|
|---|---|---|---|---|
| | (hexane-CH$_2$Cl$_2$-ethyl acetate=2:1:2) | | | |
|65b|CF$_3$COOH(0.42 ml) anisole(0.7 ml) CH$_2$Cl$_2$(2 ml) 0° C.,3 h CHP-20 column (10% ethanol) lyophilization|289 → 125|3430,1790, 1730,1660, 1530,1450, 1390,1195, 1115,1030|2.6-3.5(4H,m),3.23(6H,s), 4.3-4.6(1H,m),4.40(2H,s), 4.8-5.5(2H,m) (solvent:D$_2$O)|
|66a|4,5-dimethyl-2-thiazolethiol (79 mg) NaH(25.4 mg) DMF(3 ml) 0° C.,1 h→rt,1 h extraction with ethyl acetate, silica gel chromatography (hexane-CH$_2$Cl$_2$-ethyl acetate=2:1:2)|300 → 291|3340,1770, 1680,1510, 1300,1260, 1180,1050|2.2-3.5(4H,m),2.29(6H,s), 3.73(2H,s),3.9-4.2(1H,m), 4.6-5.0(2H,m),6.97(1H,s), 7.2-7.5(10H,m),8.9-9.2 (1H,m) (solvent:CDCl$_3$)|
|66b|CF$_3$COOH(0.36 ml) anisole(0.6 ml) CH$_2$Cl$_2$(3 ml) 0° C.,4 h CHP-20 column (10% ethanol) lyophilization|240 → 173|3350,1780, 1720,1650, 1500,1380, 1190,1115, 1035|2.26(3H,s),2.45(2H,s), 2.6-3.5(4H,m),4.14(2H,s), 4.25-4.55(1H,m),4.8-5.4 (2H,m) (solvent:D$_2$O)|
|67a|4,5-dimethyl-2-oxazolethiol (90.1 mg) NaH(25.4 mg) DMF(3 ml) rt,1.5 h extraction with ethyl acetate, silica gel chromatography (hexane-CH$_2$Cl$_2$-ethyl acetate=2:1:2)|300 → 285|3340,1765, 1680,1500, 1450,1300, 1180,1050|2.04(3H,d,J=2Hz),2.20 (3H,s),2.2-3.4(4H,m), 3.69(2H,s),3.9-4.2(1H,m), 4.5-5.0(2H,m),6.99(1H, s),7.2-7.5(10H,m),8.6-8.9(1H,m) (solvent:CDCl$_3$)|
|67b|CF$_3$COOH(0.36 ml) anisole(0.6 ml) CH$_2$Cl$_2$(3 ml) 0° C.,4 h CHP-20 column (10% ethanol) lyophilization|240 → 173|3350,1780, 1720,1650, 1500,1380, 1190,1115, 1035|2.26(3H,s),2.45(2H,s), 2.6-3.5(4H,m),4.14(2H,s), 4.3-4.6(1H,m),4.8-5.4 (2H,m) (solvent:D$_2$O)|
|68a|5-methoxymethyl-1,3,4-thiadiazole-2-thiol (113.2 mg) NaH(25.4 mg) NaI(10 mg) DMF(4 ml) rt,2 h extraction with ethyl acetate, silica gel chromatography (CH$_2$Cl$_2$-ethyl acetate=3:1)|300 → 276|3325,1810, 1770,1765, 1680,1530, 1180,1070, 1055|2.4-3.5(4H,m),3.21(3H,s), 4.14(2H,s),3.9-4.9(3H,m), 4.78(2H,s),6.94(1H,s), 7.2-7.5(10H,m),8.9-9.1 (1H,m) (solvent:CDCl$_3$ + d$_6$-DMSO)|
|68b|CF$_3$COOH(0.33 ml) anisole(0.56 ml) CH$_2$Cl$_2$(3 ml) 0° C.,5 h CHP-20 column (10% ethanol) lyophilization|222 → 81|3400,1780, 1720,1650, 1530,1370, 1190,1110, 1070,1030|2.6-3.5(4H,m),3.70(3H,s), 4.36(2H,s),4.3-4.6(1H,m), 4.8-5.5(2H,m),5.13(2H,s) (solvent:D$_2$O)|
|69a|5-methylsulfonyl-methyl-1,3,4-thiadiazole-2-thiol(146.7 mg) NaH(25.4 mg) NaI(10 mg)|300 → 330|3360,1770, 1735,1685, 1540,1310, 1190,1060|2.4-3.3(4H,m),2.09(3H,s), 3.9-4.3(1H,m),4.19(2H,s), 4.4-5.3(2H,m),5.18(2H,s), 6.91(1H,s),7.2-7.6(10H, m),9.05(1H,d,J=8.3Hz) (solvent:d$_6$-DMSO)|

-continued

| Product | Reaction conditions | Yield (mg) St. mat → Prod. | KBr IRν cm⁻¹ max | NMR(90MHz)δ |
|---|---|---|---|---|
| | DMF(4 ml) rt,2 h extraction with ethyl acetate, silica gel chromatography (CH₂Cl₂-ethyl acetate=3:1) | | | |
| 69b | CF₃COOH(0.36 ml) anisole(0.6 ml) CH₂Cl₂(3 ml) 0° C.,4 h CHP-20 column (10% ethanol) lyophilization | 274 → 115 | 3400,1780, 1720,1650, 1530,1370, 1300,1190, 1140,1040 | 2.6–3.6(4H,m),3.46(3H,s), 4.3–4.6(1H,m),4.40(2H,s), 4.3–4.6(1H,m),4.8–5.5 (2H,m),5.39(2H,s) (solvent:D₂O) |
| 70a | 4-ethyl-4H—1,2, 4-triazole-3- thiol(90.1 mg) NaH(25.4 mg) NaI(10 mg) DMF(1 ml) rt,1 h extraction with ethyl acetate, silica gel chromatography (CH₂Cl₂-ethyl acetate=1:1) | 300 → 304 | 3380,3320, 1765,1720, 1670,1510, 1450,1360, 1260,1180, 1050 | 1.34(3H,t,J=7Hz),2.3-3.4 (4H,m),3.88(2H,s),3.8-4.3 (3H,m),4.4-5.2(2H,m),6.92 (1H,s),7.2-7.6(10H,m), 8.47(1H,s),8.86(1H,d,J= 8.3Hz) (solvent:d₆-DMSO) |
| 70b | CF₃COOH(0.37 ml) anisole(0.63 ml) CH₂Cl₂(3 ml) 0° C.,3 h CHP-20 column (10 % ethanol) lyophilization | 250 → 142 | 3440,1790, 1730,1660, 1520,1380, 1270,1190, 1120,1030 | 1.67(3H,t,J=7Hz),2.6–3.6 (4H,m),4.10(2H,s),4.2–4.6 (3H,m),4.7–5.4(2H,m) (solvent:D₂O) |
| 71a | 2-mercapto-1,3, 4-thiadiazol-5- ylacetic acid sodium salt (123 mg) NaH(50.8 mg) DMF(1 ml) rt,1 h CHP-20 column (50% ethanol) lyophilization | 300 → 265 | 3380,1765, 1720,1670, 1600,1370, 1185,1055 | 2.3–3.2(4H,m),3.59(2H,s), 4.10(2H,s),4.4–5.2(2H,m), 6.89(1H,s),7.2–7.5(10H, m),9.0–9.2(1H,m) (solvent:d₆-DMSO) |
| 71b | CF₃COOH(0.3 ml) anisole(0.5 ml) CH₂Cl₂(3 ml) 0°C.,5 h CHP-20 column (water) lyophilization | 230 → 117 | 3420,1780, 1660,1600, 1370,1195, 1120,1025 | 2.6–3.6(4H,m),4.23(2H,s), 4.34(2H,s),4.2–4.6(1H,m), 4.8–5.5(2H,m) (solvent:D₂O) |
| 72a | 1-(2-hydroxyethyl- 1H—tetrazole- 5-thiol (92.7 mg) NaH(25.4 mg) DMF(1 ml) rt,3 h extraction with ethyl acetate, crystallization | 300 → 263 | 3340,1795, 1765,1725, 1670,1520, 1450,1295, 1260,1180, 1050 | 2.5–3.4(4H,m),3.7–4.9(6H, m),4.9–5.2(1H,m),6.91(1H, s),7.2–7.5(10H,m),8.99 (1H,d,J=7Hz) (solvent:d₆-DMSO) |
| 72b | CF₃COOH(0.31 ml) anisole(0.52 ml) CH₂Cl₂(2 ml) 0°C.,2.5 h CHP-20 column (5% ethanol) lyophilization | 215 → 104 | 3410,1780, 1720,1660, 1540,1380, 1195,1120, 1030 | 2.6–3.5(4H,m),4.2–4.6(3H, m),3.37(2H,s),4.7–5.4(4H, m) (solvent:D₂O) |
| 73a | 1-(3-dimethyl aminopropyl)-1H— tetrazole-5- thiol(118.8 mg) NaH(25.4 mg) DMF(1 ml) rt,2 h | 300 → 350 | 3340,1800, 1765,1730, 1680,1520, 1450,1300, 1260,1180, 1100,1050 | 1.8–3.7(9H,m),2.14(6H,s), 3.8–5.2(5H,m),6.90(1H,s), 7.2–7.5(10H,m),9.01(1H,d, J=7Hz) (solvent:d₆-DMSO) |

-continued

| Pro-duct | Reaction conditions | Yield (mg) St. mat → Prod. | KBr IRν cm⁻¹ max | NMR(90MHz)δ |
|---|---|---|---|---|
| | extraction with ethyl acetate, crystallization | | | |
| 73b | CF₃COOH(0.38 ml) anisole(0.63 ml) CH₂Cl₂(2 ml) 0°C.,4 h CHP-20 column (20% ethanol) lyophilization | 279 → 147 | 3420,1780, 1730,1640, 1540,1465, 1370,1195, 1110,1030 | 2.4–3.7(8H,m),3.14(6H,s), 4.37(2H,s),4.3–4.6(1H,m), 4.7–5.4(4H,m) (solvent:D₂O) |
| 74a | 2-benzyloxycar- bonylamino-3- sulfamoylpropi- onic acid (270.2 mg) DCC(206.3 mg) DMF(3 ml) rt,3 h extraction with ethyl acetate, silica gel chro- matography (hexane-ethyl acetate=1:3) | 396.4 → 645 | 3370,3070, 3050,2950, 1805,1760, 1730,1690, 1520,1450, 1340,1260, 1180,1050 | 2.2–3.2(4H,m),3.4–3.7(2H, m),3.9–5.0(4H,m),5.3–5.7 (2H,m),6.2–6.5(1H,m),6.94 (1H,s),7.1–7.5(10H,m), 7.5–7.8(1H,m) (solvent:CDCl₃) |
| 74b | H₂/10% Pd-black (300 mg) THF(3 ml)-water (1 ml) 0°C.,3 h CHP-20 column (water) lyophilization | 200 → 34 | 3240,1780, 1695,1645, 1560,1380, 1330,1195, 1155,1030 | 2.6–3.4(4H,m),4.16(2H,s), 3.9–4.2(2H,m),4.4–5.5 (4H,m) (solvent:D₂O) |
| 75a | 4-cyano-3-hydroxy- 5-isothiazolyl- acetic acid (163 mg) DCC(155.9 mg) DMF(2 ml) rt,5 h extraction with thyl acetate, silica gel chro- matography (ethyl acetate) | 300 → 270 | 3330,2120, 1800,1765, 1740,1650, 1520,1495, 1390,1300, 1260,1180, 1050 | 2.5–3.3(4H,m),4.04(2H,s), 3.9–4.3(1H,m),4.5–5.2(2H, m),6.91(1H,s),7.2–7.7 (10H,m),9.09(1H,d,J= 8.3Hz) (solvent:d₆-DMSO) |
| 75b | CF₃COOH(0.32 ml) anisole(0.54 ml) CH₂Cl₂(3 ml) CHP-20 column (water) lyophilization | 235 → 105 | 2120,1780, 1720,1665, 1645,1520, 1460,1380, 1190,1120, 1030 | 2.6–3.5(4H,m),4.18(2H,s), 4.3–4.6(1H,m),5.2–5.5 (1H,m) (solvent:D₂O) |
| 76a | 2-(2-chlorace- toamide-4-thia- zolyl)-2-oxoace- tic acid(273 mg) DCC(206.3 mg) DMF(2 ml) rt,1 h extraction with ethyl acetate, silica gel chro- matography (hexane-ethyl acetate=1:2) | 396.4 → 372 | 3340,1810, 1760,1630, 1550,1270, 1180,1050 | 2.3–3.5(4H,m),4.1–5.2(3H, m),4.36(2H,s),6.96(1H,s), 7.2–7.5(10H,m),8.78(1H, s),8.90(1H,d,J=8.3Hz) (solvent:CDCl₃+d₆-DMSO) |
| 76b | CH₃NHCS₂Na (64.9 mg) DMF(2 ml)-water (1 ml) rt,5 h extraction with ethyl acetate, silica gel chro- matography (ethyl acetate) | 314.9 → 180 | 3420,3325, 3140,1800, 1750,1660, 1520,1480, 1380,1260, 1175,1045 | 2.2–3.5(4H,m),4.0–5.2(3H, m),5.8–6.3(2H,m),6.99 (1H,s),7.2–7.5(10H,m), 8.01(1H,s),8.1–8.5(1H,m), (solvent:CDCl₃) |
| 76c | CF₃COOH(0.23 ml) anisole(0.39 ml) CH₂Cl₂(4 ml) 0°C.,3 h | 155 → 71 | 3270,1780, 1720,1650, 1520,1480, 1370,1190, | 2.6–3.5(4H,m),4.3–4.7(1H, m),4.8–5.1(1H,m),5.3–5.6 (1H,m),8.55(1H,s) (solvent:D₂O) |

-continued

| Product | Reaction conditions | Yield (mg) St. mat → Prod. | KBr IR$\nu$ cm$^{-1}$ max | NMR(90MHz)$\delta$ |
|---------|---------------------|---------------------------|--------------------------|---------------------|
|  | CHP-20 column (water) lyophilization |  | 1110,1020 |  |
| 77a | 2-(2-chloroacet-amide-4-thiazolyl-(Z)—2-isopropoxy-iminoacetic acid (305.74 mg) DCC(206.3 mg) DMF(2 ml) rt,1 h extraction with ethyl acetate, silica gel chromatography (hexane-ethyl acetate=1:1) | 396.4 → 462 | 3280,1800, 1750,1675, 1540,1450, 1365,1260, 1175,1045 | 1.28(6H,d,J=6.6Hz),2.2-3.4(4H,m),4.20(2H,s),4.0-5.0(4H,m),6.96(1H,d,J=3Hz),7.1-7.5(10H,m),7.40 (1H,d,J=2Hz) (solvent:CDCl$_3$) |
| 77b | CH$_3$NHCS$_2$Na (72.5 mg) DMF(2 ml)-water (1 ml) rt,9 h extraction with ethyl acetate silica gel chromatography (hexane-ethyl acetate=1:2) | 355 → 342 | 3400,1810, 1740,1670, 1630,1530, 1295,1180, 1120,1050 | 1.30(6H,d,J=6.7Hz),2.2-3.5(4H,m),4.0-5.0(4H,m), 5.2-5.4(2H,m),6.94(1H,s), 6.98(1H,d,J=3Hz),7.2-7.5 (10H,m) (solvent:CDCl$_3$) |
| 77c | CF$_3$COOH(0.42 ml) anisole(0.71 ml) CH$_2$Cl$_2$(2 ml) 0°C.,5 h CHP-20 column (10% ethanol) lyophilization | 314 → 75 | 3430,1780, 1730,1660, 1530,1380, 1200,1105 | 1.46(6H,d,J=6.6Hz), 2.6-3.4(4H,m),4.4-5.2 (3H,m),5.3-5.6(1H,m), 7.24(1H,s) (solvent:d$_2$O) |
| 78a | trifluoroacetic anhydride (159 mg) CH$_2$Cl$_2$(15 ml) 0°C.,15 min extraction with ethyl acetate, silica gel chromatography (CH$_2$Cl$_2$-ethyl acetate=1:1) | 300 → 220 | 3440,1765, 1715,1540, 1445,1295, 1170,1050 | 2.4-3.3(4H,m),4.0-5.3(3H, m),6.90(1H,s),7.2-7.6 (10H,m) (solvent:d$_6$-DMSO) |
| 78b | H$_2$/10% Pd-C (200 mg) NaHCO$_3$(32 mg) THF(3 ml)-water (1 ml) rt,20min CHP-20 column (water) lyophilization | 189 → 130 | 3420,1780, 1720,1650, 1560,1380, 1190,1160, 1120,1030 | 2.6-3.6(4H,m),4.4-4.6(1H, m),4.9-5.1(1H,m),5.3-5.6 (1H,m) (solvent:d$_2$O) |
| 79a | 2-(2-chloroaceta-mide-4-thiazolyl-(Z)—2-[1-methyl-1-(4-nitrobenzyl-oxycarbonyl)-ethoxyimino]-acetic acid (533 mg) HOBT(150 mg) DCC(230 mg) DMF(3 ml) rt,1 h extraction with ethyl acetate, silica gel chromatography (hexane-ethyl acetate=3:4) | 396 → 683 | 3320,1800, 1760,1690, 1520,1350, 1180,1050 | 1.61(6H,s),2.20-3.33(4H, m),3.91-4.18(1.5H,m),4.21 (2H,s),4.59-4.92(1.5H,m), 5.20(2H,s),6.97(1H,s), 7.19(1H,s),7.20-7.59(12H, m),7.92-8.11(2H,m) (solvent:CDCl$_3$) |
| 79b | CH$_3$NHCS$_2$Na (206 mg) THF(18 ml)-water (1 6 ml) | 683 → 474 | 3420,3350, 1800,1760, 1690,1520, 1350,1180, | 1.61(6H,s),2.28-3.32(4H, m),3.97-4.36(1.5H,m),4.71 -4.98(1.5H,m),5.26(2H,s), 6.41(2H,bs),6.77(1H,s), |

| Product | Reaction conditions | Yield (mg) St. mat → Prod. | KBr IR$\nu$ cm$^{-1}$ max | NMR(90MHz)$\delta$ |
|---|---|---|---|---|
| | rt,90min extraction with ethyl acetate, silica gel chromatography (hexane-ethyl acetate=2:1 →ethyl acetate) | | 1050 | 7.01(1H,s),7.21–7.51(12H, m),7.90–8.07(2H,m) (solvent:CDCl$_3$) |
| 79c | CF$_3$COOH(0.64 ml) anisole(0.48 ml) CH$_2$Cl$_2$(28 ml) −10° ~ −15°C., 5 h XAD-2 column (30% ethanol) lyophilization | 474 → 213 | 3420,1780, 1740,1660, 1530,1350, 1180,1150, 1050,980, 910 | 1.81(6H,s),2.57–3.42(4H, m),4.38–4.70(1H,m),4.81– 5.11(1H,m),5.29–5.51(1H, m),5.52(2H,s),7.19(1H,s), 7.73(2H,d,J=8Hz),8.28 (2H,d,J=8Hz) (solvent:D$_2$O) |
| 79d | H$_2$/10% Pd-C (183 mg) NaHCO$_3$(26 mg) ethyl acetate(8 ml)— water(8 ml) 0°C.,90min HP-20 column (water) lyophilization | 183 → 111 | 3400,1780, 1730,1650, 1580,1190, 1040,980, 910 | 1.71(6H,s),2.57–3.51(4H, m),4.32–4.71(1H,m),4.91– 5.17(1H,m),5.31–5.59(1H, m),7.27(1H,s) (solvent:D$_2$O) |
| 80a | 2-(2-tritylamino-4-thiazolyl)-(Z)—2-(trityl oxyimino)acetic acid 2-benzothiazolylthiol ester(497 mg) THF(4 ml) DMF(2 ml) rt,16 h extraction with ethyl acetate, silica gel chromatography (hexane-ethyl acetate=2:1 →3:2) | 200 → 488 | 3890,1800, 1740,1680, 1520,1490, 1440,1190, 1050 | 2.31–3.35(4H,m),3.93–4.26 (1.5H,m),4.67–4.95(1.5H, m),6.52(1H,s),6.89(1H,s), 6.98(1H,s),7.11–7.42(40H, m) (solvent:CDCl$_3$) |
| 80b | HCOOH(3 ml) CH$_2$Cl$_2$(1 ml) 0°C.→rt,1 h HP-20 column (water) lyophilization | 488 → 48 | 3400,1780, 1720,1650, 1530,1390, 1190,1030 | 2.61–3.53(4H,m),4.31–4.68 (1H,m),4.83–5.12(1H,m), 5.31–5.62(1H,m),7.20(1H, s) (solvent:D$_2$O) |
| 81a | isobutyl chlorocarbonate(82 mg) Et$_3$N(60.6 mg) THF(6 ml) DMF(2 ml) −10°C.,60min→ rt,30min extraction with ethyl acetate, silica gel chromatography (hexane-ethyl acetate=3:2) | 200 → 150 | 3350,1770, 1730,1530, 1180,1050 | 0.91(6H,d,J=6Hz),1.81– 2.13(1H,m),2.34–3.39(4H, m),3.87(2H,d,J=6Hz), 3.86–4.13(1.5H,m),4.43– 4.85(1.5H,m),6.98(1H,s), 7.21–7.43(10H,m) (solvent:CDCl$_3$) |
| 81b | H$_2$/5% Pd-C (150 mg) THF-water NaHCO$_3$(25 mg) 0°C.,60min XAD-2 column (water) lyophilization | 150 → 17 | 3400,1780, 1720,1650, 1390,1190, 1030 | 1.11(6H,d,J=6Hz),1.91– 2.37(1H,m)2.61–3.49(4H, m),4.13(2H,d,J=6Hz), 4.31–4.59(1H,m),4.80–5.02 (1H,m),5.11–5.42(1H,m) (solvent:D$_2$O) |
| 82 | methyl chlorocarbonate(196μl) Et$_3$N(357μl) N—(4-nitrobenzyl-oxycarbonyl)-glycine (645 mg) THF(50 ml) | 1000 → 1470 | 1805,1775, 1740,1700, 1610 | 2.1–3.3(4H,m),3.6–4.2(3H, m),4.3–5.3(2H,m),5.17 (2H,s),5.73(1H,m),6.93 (1H,s),6.87,7.11(each 0.5 H,d,J=7Hz),7.2–7.5(10H, m),7.45(2H,d,J=9Hz), 8.16(2H,d,J=9Hz), (solvent:CDCl$_3$) |

-continued

| Product | Reaction conditions | Yield (mg) St. mat → Prod. | KBr IRν cm$^{-1}$ max | NMR(90MHz)δ |
|---|---|---|---|---|
| | $-10° \sim -5°C.$, 60min extraction with ethyl acetate, after concentration, the product was powdered with ethyl acetate | | | |
| 83 | methyl chlorocarbonate(98μl) Et₃N(179μl) N—(2,2,2-trichloroethoxycarbonyl)-phenylglycine (414 mg) THF(25 ml) $-10°C \sim -5°C.$, 60min silica gel chromatography (hexane-ethyl acetate=1:1) | 500 → 250 | 1810,1750, 1700,1500 | 2.1–3.4(4H,m),3.6–5.2(3H, m),4.68(2H,s),5.24,5.31 (each 0.5H,s),6.25(1H,m), 6.50(0.5H,m),6.73(0.5H, d,J=5Hz),6.97(1H,s), 7.2–7.5(10H,m) (solvent:CDCl₃) |
| 84a | N—benzyloxycarbonyl-D-phenyl glycine (723 mg) HOBT(350 mg) DCC(530 mg) DMF(10 ml) 0°C.,40min extraction with ethyl acetate, silica gel chromatography (hexane-ethyl acetate=1:1) | 1000 → 1170 | 3350,1810, 1775,1735, 1700,1500 | 2.1–3.4(4H,m),3.7–4.0(1H, m),4.4–5.0(2H,m),5.04 (2H,s),5.25(1H,d,J=7Hz), 5.90(1H,d,J=7Hz),6.4– 6.8(1H,m),6.95(1H,s),7.2– 7.5(20H,m) (solvent:CDCl₃) |
| 84b | H₂10% Pd—C (500 mg) THF(30 ml)-pH7.0 buffer(20 ml) 0°C., 40min HP-20 column (50% methanol) lyophilization | 1000 → 250 | 3400,1795, 1730,1670, 1500,1390 | 2.3–3.4(4H,m),3.9–5.3(3H, m),5.15(2H,s),5.29(1H,s), 7.46(10H,m) (solvent:D₂O) |
| 85a | N—(4-methoxybenzyloxycarbonyl)-L-phenylglycine (800 mg) HOBT(350 mg) DCC(528 mg) DMF(10 ml) 0°C.,30min extraction with ethyl acetate, silica gel chromatography (hexane-ethyl acetate=1:1) | 1000 → 1100 | 3400,1815, 1760,1735, 1700,1520 | 2.2–3.3(4H,m),3.77(3H,s), 3.8–4.2(1H,m),4.4–4.9(2H, m),4.99(2H,s),5.21(1H,d, J=7Hz),5.87(1H,d,J=7 Hz),6.54(1H,m),6.84(2H,d, J=8Hz),6.94(1H,s),7.1– 7.4(17H,m) (solvent:CDCl₃) |
| 85b | CF₃COOH(1.6 ml) anisole(752 μl) CH₂Cl₂(40 ml) $-10°C.$, 6.5 h HP-20 column (30% methanol) lyophilization | 800 → 315 | 3400,1790, 1740,1670 | 2.3–3.3(4H,m),4.0–5.2 (3H,m),5.25(1H,s),7.4–7.7 (5H,m) (solvent:D₂O) |
| 86a | N—(4-methoxybenzyloxycarbonyl)-D-phenylglycine (1200 mg) HOBT(525 mg) DCC(792 mg) DMF(15 ml) 0°C., 30min extraction with ethyl acetate, silica gel chro- | 1500 → 1770 | 1815,1765, 1740,1705 | 2.1–3.4(4H,m),3.78(3H,s), 3.85(1H,m),4.4–5.1(2H,m), 4.98(2H,s),5.25(1H,d,J= 7Hz),5.88(1H,d,J=7Hz), 6.5–6.9(3H,m),6.94(1H,s), 7.1–7.5(17H,m) (solvent:CDCl₃) |

-continued

| Product | Reaction conditions | Yield (mg) St. mat → Prod. | KBr IRν cm⁻¹ max | NMR(90MHz)δ |
|---|---|---|---|---|
| | matography (hexane-ethyl acetate=1:1) | | | |
| 86b | CF₃COOH(2 ml) anisole(940 μl) CH₂Cl₂(50 ml) −10°C., 6.5 h HP-20 column (20% methanol→ 50% methanol) lyophilization | 1000 → 410 | 1790,1730, 1700,1665 | 2.3–3.3(4H,m),3.9–5.3(3H, m),5.25(1H,s),7.4–7.7(5H, m) (solvent:D₂O) |
| 87a | S—mandelic acid (387 mg) HOBT(350 mg) DCC(530 mg) DMF(10 ml) 0°C., 1 h extraction with ethyl acetate, silica gel chromatography (hexane-ethyl acetate=1:2) | 1000 → 628 | 3400,1805, 1775,1690 | 2.1–3.5(4H,m),3.5–5.2(4H, m),5.10(1H,s),6.95(1H,s), 7.2–7.6(16H,m) (solvent:CDCl₃) |
| 87b | H₂10% Pd—C (450 mg) THF(12 ml)- pH7.0 buffer(3 ml) rt,30min HP-20 column (20% methanol) lyophilization | 450 → 230 | 3400,1785, 1730,1670 | 2.3–3.3(4H,m),4.28(1H,t, J=9Hz),4.5–5.3(2H,m), 5.29(1H,s),7.50(5H,s) (solvent:D₂O) |
| 88a | R—mandelic acid (387 mg) HOBT(350 mg) DCC(530 mg) DMF(10 ml) 0°C.,1 h extraction with ethyl acetate, silica gel chromatography (hexane-ethyl acetate=2:3) | 1000 → 485 | 3400,1810, 1770,1680 | 2.1–3.5(4H,m),3.50(1H, br),4.03(1H,m),4.60(2H, m),5.07(1H,s),6.96(1H,s), 7.05(1H,m),7.2–7.5(15H,m) (solvent:CDCl₃) |
| 88b | H₂/10% Pd—C (180 mg) THF(12 ml)- pH7.0 buffer(8 ml) rt,30min HP-20 column(water-20% methanol) lyophilization | 350 → 150 | 1785,1730, 1665 | 2.4–3.3(4H,m),4.23(1H,t, J=9Hz),4.5–5.3(2H,m), 5.25(1H,s),7.50(5H,s) (solvent:D₂O) |
| 89a | 4-chloro-DL-mandelic acid(711 mg) HOBT(525 mg) DCC(792 mg) DMF(15 ml) 0°C.,30min extraction with ethyl acetate, silica gel chromatography (hexane-ethyl acetate=1:1) | 1500 → 1410 | 3400,1810, 1775,1690 | 2.1–3.3(4H,m),3.8–4.3(2H, m),4.4–5.2(3H,m),6.96(1H, s),7.2–7.7(15H,m) (solvent:CDCl₃) |
| 89b | H₂/10% Pd—C (500 mg) THF(30 ml)-pH7.0 buffer(20 ml) rt,50min HP-20 column (20% methanol→ 50% methanol) lyophilization | 100 → 330 | 3420,1780, 1730,1660 | 2.3–3.3(4H,m),4.1–5.3(3H, m),5.25,5.28(each 0.5H, s),7.49(4H,s) (solvent:D₂O) |
| 90a | 4-hydroxy-DL-mandelic acid (711 mg) HOBT(525 mg) DCC(795 mg) | 1500 → 898 | 3380,1805, 1775,1750, 1665 | 2.2–3.5(4H,m),3.9–5.2(4H, m),6.10(1H,m),6.70(2H,d, J=8Hz),6.92(1H,s),7.1– 7.6(12H,m),8.60(1H,d,J=8 Hz),9.33(1H,s) |

-continued

| Product | Reaction conditions | Yield (mg) St. mat → Prod. | KBr IRν cm⁻¹ max | NMR(90MHz)δ |
|---|---|---|---|---|
| | DMF(15 ml) 0°C.,1 h extraction with ethyl acetate, silica gel chromatography (hexane-ethyl acetate=1:2) | | | (solvent:d₆-DMSO) |
| 90b | H₂/10% Pd—C (350 mg) THF(21 ml)-pH7.0 buffer(14 ml) rt,40min SP-207 column (water→20% methanol) lyophilization | 700 → 354 | 3430,1790, 1730,1660 | 2.3-3.4(4H,m),4.1-4.5(1H, m),4.4-5.3(2H,m),5.20, 5.22(each 0.5H,s),6.97 (2H,d,J=8Hz),7.38,7.40 (each 1H,d,J=8Hz) (solvent:D₂O) |
| 91a | DL-lactic acid (222 μl) HOBT(350 mg) DCC(636 mg) 0°C.,1.5 h extraction with ethyl acetate, silica gel chromatography (hexane-ethyl) acetate=1:2) | 1000 → 597 | 3420,1800, 1700,1680 | 1.1-1.5(3H,m),2.3-3.3 (4H,m),3.9-5.2(4H,m),5.39 (0.25H,d,J=5Hz),5.63 (0.75H,m),6.91(1H,s),7.2- 7.5(10H,m),8.37(0.75H,d, J=7Hz),8.67(0.25H,d,J= 6Hz) (solvent:d₆-DMSO) |
| 91b | H₂/10% Pd—C (300 mg) THF(21 ml) pH7.0 buffer (14 ml) rt,40min SP-207 column (water) lyophilization | 700 → 292 | 3430,1795, 1730,1660 | 1.40(3H,d,J=7Hz),2.3-3.4 (4H,m),4.2-4.5(2H,m), 4.6-5.3(2H,m) (solvent:D₂O) |
| 92a | DL-phenylmalonic acid monodiphenylmethyl ester(880 mg) HOBT(350 mg) DCC(530 mg) DMF(13 ml) 0°C.,30min extraction with ethyl acetate, silica gel chromatography (hexane-ethyl acetate=1:1) | 1000 → 570 | 3370,1810, 1760,1700, 1530,1500, 1455,1270, 1185 | 2.1-3.0(3H,m),3.0-3.5 (1H,m),3.7-4.2(1H,m),4.5- 4.9(2H,m),4.64(1H,s),6.87 (1H,s),6.97(1H,s),6.9-7.8 (26H,m) (solvent:CDCl₃) |
| 92b | H₂/10% Pd—C (400 mg) THF(12 ml) pH7.0 buffer(8 ml) rt,30min HP-20 column (water) lyophilization | 400 → 153 | 1790,1730, 1670,1615 | 2.4-3.4(4H,m),4.1-5.3 (3H,m),4.60(1H,s),7.41 (5H,s) (solvent:D₂O) |
| 93a | benzyloxycarbonyl chloride (360 μl) DMA(1.0 ml) CH₂Cl₂(40 ml) rt,30min washed with 2% NaHCO₃aqueoeus solution silica gel chromatography (hexane-ethyl acetate=1:4) | 1000 → 740 | 3360,1805, 1780,1730 | 2.1-3.5(4H,m),4.05(1H,m), 4.3-5.0(2H,m),5.10(2H,s), 5.28(1H,m),6.97(1H,s), 7.2-7.5(15H,m) (solvent:CDCl₃) |
| 93b | CF₃COOH(462 μl) anisole(217 μl) CH₂Cl₂(10 ml) −10°C.,1 h HP-20 column | 265 → 127 | 1790,1730, 1670 | 2.3-3.4(4H,m),4.0-5.2(3H, m),5.18(2H,s),7.48(5H,s) (solvent:D₂O) |

| Product | Reaction conditions | Yield (mg) St. mat → Prod. | KBr IR$\nu$ cm$^{-1}$ max | NMR(90MHz)$\delta$ |
|---|---|---|---|---|
| 93b | (20% methanol) lyophilization | | | |
| 94a | pyruvic acid (177 μl) HOBT(350 mg) DCC(530 mg) DMF(10 ml) 0°C.,30min extraction with ethyl acetate, silica gel chromatography (hexane-ethyl acetate=1:1) | 1000 → 495 | 3350,1810, 1775,1700 | 2.37(3H,s),2.3–3.3(4H,m), 4.0–5.1(3H,m),6.92(1H,s), 7.2–7.5(10H,m),9.22(1H, d,J=8Hz) (solvent:d$_6$-DMSO) |
| 94b | H$_2$/10% Pd—C (350 mg) THF(12 ml)-pH7.0 buffer(8 ml) rt,20min SP-207 column (water→20% methanol) lyophilization | 700 → 300 | 1780,1730, 1660 | 1.59,2.49(total 3H,s), 2.4–3.3(4H,m),4.30(1H,m), 4.76(1H,m),5.11(1H,m) (solvent:D$_2$O) |
| 95 | chloromethyl pivalate(182 μl) DMF(1.0 ml) 50°C.,4 h extraction with ethyl acetate, after concentrated, the product was powdered with petroleum benzine | (88b) 250 → 219 | 3400,1810, 1760,1680 | 1.18(9H,s),2.2–3.3(4H,m), 4.10(1H,m),4.5–5.2(2H,m), 5.09(1H,m),5.83(2H,s), 7.1–7.6(6H,m) (solvent:CDCl$_3$) |
| 96 | 4-nitrobenz-aldehyde(30 mg) Molecular Sieves 4A CH$_2$Cl$_2$(5 ml) rt,8 h filtration concentration, drying powdered with ether | 80 → 46 | 3420,1800, 1765,1730, 1640,1600, 1520,1350 | 2.2–3.3(4H,m),4.4–4.8(3H, m),7.00(1H,s),7.3–7.4 (10H,m),7.92(2H,d,J= 8Hz),8.28(2H,d,J=8Hz), 8.47(0.5H,s),8.50(0.5H,s) (solvent:CDCl$_3$) |
| 97a | 3-chloro-6-pyri-dazinethiol sodium salt(143 mg) NaI(100 mg) DMF(4 ml) rt,30min extraction with ethyl acetate, silica gel chromatography (hexane-ethyl acetate=3:7) | 200 → 180 | 3350,1770, 1740,1680, 1390,1180, 1140,1050 | 2.20–3.38(4H,m),3.94(2H, s),3.83–4.25(1.5H,m),4.56 –4.94(1.5H,m),6.96(1H,s), 7.20–7.71(12H,m) (solvent:CDCl$_3$) |
| 97b | CF$_3$COOH(0.3 ml) anisole (0.24 ml) CH$_2$Cl$_2$(15 ml) −10°~−15°C., 4 h XAD-2 column (10% ethanol) lyophilization | 180 → 86 | 3400,1780, 1720,1650, 1390,1150, 1030 | (100MHz) 2.41–3.39(4H,m),4.03–4.30 (1H,m),4.11(2H,s),4.49– 4.78(1H,m),4.90–5.20(1H, m),7.65–7.72(2H,m) (solvent:D$_2$O) |
| 98a | phenylthioacetic acid(118 mg) HOBT(94 mg) DCC(144 mg) DMF(3 ml) rt,1 h extraction with ethyl acetate, silica gel chromatography (hexane-ethyl acetate=1:3) | 200 → 106 | 3350,1770, 1730,1670, 1510,1180, 1050 | 2.21–3.37(4H,m),3.61(2H, s),3.72–4.09(1.5H,m), 4.48–5.03(1.5H,m),6.91 (1H,s),7.17–7.71(15H,m) (solvent:CDCl$_3$) |
| 98b | CF$_3$COOH(0.2 ml) | 105 | 3400,1780, | (100MHz) |

-continued

| Product | Reaction conditions | Yield (mg) St. mat → Prod. | KBr IRν cm⁻¹ max | NMR(90MHz)δ |
|---|---|---|---|---|
| | anisole (0.16 ml) CH$_2$Cl$_2$(10 ml) −10°∼−15°C., 4 h XAD-2 column (10% ethanol) lyophilization | → 41 | 1720,1650, 1390,1190, 1030 | 2.41–3.29(4H,m),3.73(2H, s),3.84–4.05(1H,m),4.40– 4.73(1H,m),4.87–5.13(1H, m),7.32–7.58(5H,m) (solvent:D$_2$O) |
| 99a | potassiu methyl xanthate (156 mg) DMF(2 ml) rt,1 h extraction with ethyl acetate, silica gel chromatography (hexane-ethyl acetate=1:1) | 250 → 174 | 3350,1770, 1740,1680, 1180,1050 | 1.25(3H,t,J=7Hz),2.21– 3.59(4H,m),3.88(2H,s), 3.92–4.32(3.5H,m),4.51– 5.02(1.5H,m),7.01(1H,s), 7.29–7.58(10H,m) (solvent:CDCl$_3$) |
| 99b | CF$_3$COOH(0.3 ml) anisole (0.24 ml) CH$_2$Cl$_2$(10 ml) −10°∼−15°C., 4 h XAD-2 column (10% ethanol) lyophilization | 174 → 72 | 3400,1780, 1720,1650, 1390,1240, 1190,1050 | (100MHz) 1.39(3H,t,J=7Hz),2.40– 3.29(4H,m),3.98(2H,s), 4.12–4.34(1H,m),4.49–4.78 (1H,m),4.90–5.21(1H,m) (solvent:D$_2$O) |

EXAMPLE 100

Production of sodium 2-{(4S)-4-[2-(2-amino-4-thiazolyl)-(Z)-2-(ethoxyimino)acetamido]-3-oxo-2-isoxazolidinyl}-5-oxo-2-tetrahydrofurancarboxylate [Compound (100)]:

(a) Compound (R-3) was dissolved in a mix solvent of ethyl acetate and phosphate buffer (pH 7.0), with 10% palladium-carbon added. The resulting solution was stirred in hydrogen stream under ice-cooling for 1.5 hours. After catalyst removal by filtration and water rinsing, the filtrate and the rinsing liquid were combined and the aqueous layer separated. Tetrahydrofuran was added to the aqueous layer, with sodium bicarbonate and 2-(2-chloroacetamido-4-thiazolyl)-(Z)-2-ethoxyiminoacetyl chloride hydrochloride added; the resulting solution was stirred under ice-cooling for 30 minutes. Tetrahydrofuran was vaporized under reduced pressure and the resulting aqueous layer rinsed with ethyl acetate.

(b) Tetrahydrofuran and sodium N-methyldithiocarbamate were next added to the aqueous layer; the resulting solution was stirred at room temperature for 30 minutes. Tetrahydrofuran was vaporized under reduced pressure. After rinsing with ethyl acetate, the resulting concentrate was subjected to column chromatography using HP-20. The fraction eluted with 10% ethanol, after concentration, was subjected to freeze-drying, yielding Compound(100).

EXAMPLE 101

Production of sodium 2-{(4S)-4-[2-(2-amino-5-chloro-4-thiazolyl)-(Z)-2-(methoxyimino)acetamido]-3-oxo-2-isoxazolidinyl}-5-oxo-2-tetrahydrofurancarboxylate [Compound (101)]:

Compound (101) was obtained via reaction by a method analogous to Example 100, using Compound (R-3) and 2-(5-chloro-2-chloroacetamido-4-thiazolyl)-(Z)-2-methoxyiminoacetyl chloride hydrochloride.

EXAMPLE 102

Production of sodium 2-{(4S)-4-[2-4-ethyl-2,3-dioxo-1-piperazinocarboxamido)-2-thienylacetamido]-3-oxo-2-isoxazolidinyl}-5-oxo-2-tetrahydrofurancarboxylate [Compound (102b)]:

(a) Production of diphenylmethyl ester of Compound (102b) [Compound (102a)]:

Compound (102a) was obtained via reaction by a method analogous to Example 1 (a), using Compound (R-3) and 2-(4-ethyl-2,3-dioxo-1-piperazinylcarboxamido)-2-thienylacetic acid.

(b) Production of Compound (102b):

Compound (102b) was obtained via reaction on Compound (102a) by a method analogous to Example 1 (c).

EXAMPLE 103

Production of sodium 2-((4S)-4-ureido-3-oxo-2-isoxazolidinyl)-5-oxo-2-tetrahydrofurancarboxylate [Compound (103b)]:

(a) Production of diphenylmethyl ester of Compound (103b) [Compound (103a)]:

Aqueous solution of potassium isocyanate was added to acetic solution of Compound (R-3), the obtained solution being stirred at room temperature for 2 hours. The reaction solution obtained was added to water and eluted with ethyl acetate. The organic layer, after rinsing with water, aqueous solution of sodium bicarbonate and saturated saline solution, was in turn dried (Na$_2$SO$_4$). After the solvent was vaporized off, the residue was refined by column chromatography using silica gel, yielding Compound (103a).

(b) Production of Compound (103b):

Compound (103b) was obtained via reaction with Compound (103a) by a method analogous to Example 2 (b).

EXAMPLE 104

Production of sodium 2-{(4S)-4-phenylureylene-3-oxo-2-isoxazolidinyl}-5-oxo-2-tetrahydrofurancarboxylate [Compound (104b)]:

(a) Production of diphenylmethyl ester of Compound (104b) [Compound (104a)]:

Phenylisocyanate was added to dichloromethane solution of Compound (R-3), and stirred at room temperature for 10 minutes. The solvent was then vaporized off. The residue was refined by column chromatography using silica gel, yielding Compound (104a).

(b) Production of Compound (104b):

Compound (104b) was obtained via reaction with Compound (104a) by a method analogous to Example 2 (b).

EXAMPLE 105

Production of sodium 2-{(4S)-4-[2-(pyridyl)acetamido]-3-oxo-2-isoxazolidinyl}-5-oxo-2-tetrahydrofurancarboxylate [Compound (105)]:

Compound (105) was obtained by a method analogous to Example 100 (a), using Compound (R-3) and 2-pyridylacetyl chloride hydrochloride.

EXAMPLE 106

Production of sodium 2-{(4S)-4-[2-(4-chlorophenyl)acetamido]-3-oxo-2-isxazolidinyl}-5-oxo-2-tetrahydrofurancarboxylate [Compound (106)]:

Compound (106) was obtained by a method analogous to Example 100 (a), using Compound (R-3) and 4-chlorophenyl acetyl chloride.

EXAMPLE 107

Production of sodium 2- {(4S)-4-[(2-chloro-2-phenyl)acetamido]-3-oxo-2-isoxazolidinyl}-5-oxo-2-tetrahydrofurancarboxylate [Compound (107)]:

Compound (107) was obtained by a method analogous to Example 100 (a), using Compound (R-3) and 2-chloro-2-phenylacetyl chloride.

EXAMPLE 108

Production of sodium 2- {(4S)-4-[2-(3-pyridylthio)acetamido]-3-oxo-2-isoxazolidinyl}-5-oxo-2-tetrahydrofurancarboxylate [Compound (108b)]:

Diphenylmethyl ester of Compound (108b) [Compound (108a)] was first obtained by a method analogous to Example 15, using Compound (14a) and sodium 3-pyridinethiol, and then by a method analogous to Example 1 (c).

EXAMPLE 109

Production of sodium 2- {(4S)-4-[2-(4-chlorophenylthio)acetamido]-3-oxo-2-isoxazolidinyl}-5-oxo-2-tetrahydrofurancarboxylate [Compound (109b)]:

Diphenylmethyl ester of Compound (109b) [Compound (109a)] was obtained by a method analogous to Example 15, using Compound (14a) and sodium 4-chlorophenylthiol, Compound (109b) was then obtained.

EXAMPLE 110

Production of sodium 2-[(4S)-4-(2-isopropylphenoxycarbonylamino)-3-oxo-2-isoxazolidinyl]-5-oxo-2-tetrahydrofurancarboxylate [Compound (110b)]:

Compound (110a), diphenylmethyl ester of Compound (110b), was obtained by a method analogous to Example 5, using Compound (R-3) and 2-isopropylphenoxycarbonyl chloride; Compound (110b) was then obtained by a method analogous to Example 2 (b).

EXAMPLE 111

Production of sodium 2-((4S)-4-difluoroacetamido-3-oxo-2-isoxazolidinyl)-5-oxo-2-tetrahydrofurancarboxylate [Compound (111b)]:

Diphenylmethyl ester of Compound (111b) [Compound (111a)] was obtained by a method analogous to Example 1 (a), using Compound (R-3) and difluoroacetic acid; Compound (111b) was then obtained by a method analogous to Example 2 (b).

EXAMPLE 112

Production of sodium 2-[(4S)-4-(3-chloro)propionamido-3-oxo-2-isoxazolidinyl]-5-oxo-2-tetrahydrofurancarboxylate [Compound (112)]:

Compound (112) was obtained by a method analogous to Example 100 (a), using Compound (R-3) and 3-chloropropionyl chloride.

EXAMPLE 113

Production of pivaloyloxymethyl 2-{(4S)-4-chloroacetamido-3-oxo-2-isoxazolidinyl}-5-oxo-2-tetrahydofurancarboxylate [Compound (113)]:

Compound (113) was obtained by a method analogous to Example 17, using Compound (14b) and chloromethyl pivalate.

EXAMPLE 114

Production of pivaloyloxymethyl 2-[(4S)-4-(2-phenylthioacetamido)-3-oxo-2-isoxazolidinyl]-5-oxo-2-tetrahydrofurancarboxylate [Compound (114)]:

Compound (114) was obtained by a method analogous to Example 17, using Compound (98b) and chloromethyl pivalate.

EXAMPLE 115

Production of sodium 2-((4S)-4-propionamido-3-oxo-2-isoxazolidinyl)-5-oxo-2-tetrahydrofurancarboxylate [Compound (115b)]:

Diphenylmethyl ester of Compound (115b) [Compound (115a)] was obtained by a method similar to that shown in Example 5, using Compound (R-3) and propyonyl chloride Compound (115b) was then obtained by a method analogous to Example 2 (b).

EXAMPLE 116

Production of pivaloyloxymethyl 2-{(4S)-4-benzyloxycarbonylamino-3-oxo-2-isoxazolidinyl}-5-oxo-2-tetrahydrofurancarboxylate [Compound (116)]:

Compound (116) was obtained by a method analogous to Example 17, using Compound (93b) and chloromethyl pivalate.

EXAMPLE 117

Production of pivaloyloxymethyl 2- {(4S)-4-bromoacetamido-3-oxo-2-isoxazolidinyl}-5-oxo-2-tetrahydrofurancarboxylate [Compound (117)]:

Compound (116) was dissolved in ethyl acetate with 5% palladium-carbon added. The solution obtained was stirred in hydrogen stream under ice-cooling for 1 hour. After the catalyst was removed by filtration, DMA and bromoacetyl bromide were added and the solution stirred under ice-cooling for 0.5 hour. The organic layer , after rinsing with water, was dried ($Na_2SO_4$) to vaporize off the solvent. The residue was refined by column chromatography using silica gel, yielding Compound (117).

EXAMPLE 118

Production of pivaloyloxymethyl 2-[(4S)-4-(2,4-hexadiene)amido-3-oxo-2-isoxazolidinyl]-5-oxo-2-tetrahydrofurancarboxylate [Compound (118)]:

Compound (116) was subjected to catalytic reduction by a method analagous to Example 117. After the catalyst was removed by filtration, the filtrate was concentrated to dryness. The residue obtained was dissolved in DMF; sorbic acid, DCC and HOBT were then added and the solution stirred at room temperature for 1 hour. Ethyl acetate was added to the reaction mixture obtained, the crystals separated being removed by filtration. The organic layer, after rinsing with water, was dried ($Na_2SO_4$). The solvent was vaporized off. The residue was refined by column chromatography using silica gel, yielding Compound (118).

EXAMPLE 119

Production of pivaloyloxymethyl 2-[(4S)-4-(2-thienyl)acetamido-3-oxo-2-isoxazolidinyl]-5-oxo-2-tetrahydrofurancarboxylate [Compound (119)]:

Compound (119) was obtained by a method analogous to Example 117, using Compound (116) and thienylacetyl chloride.

Hereinafter are listed the reaction conditions, yields and physico-chemical properties of the compounds produced in Examples 100 to 119.

| Product | Reaction conditions | Yield (mg) St. mat. → Prod. | $IR\nu_{max}^{KBr}$ cm$^{-1}$ | NMR (90 MHz) δ |
|---|---|---|---|---|
| 100 | (1) $H_2$/10% Pd—C (290 mg) ethyl acetate (7 ml)- pH 7.0 phosphate buffer (10 ml) 0° C., 1.5 h (2) 2-(2-chloroacetamide-4-thiazolyl)- (Z)-2-ethoxyiminoacetyl chloride hydrochloride (233 mg), THF (7 ml) $NaHCO_3$ (145 mg) 0° C., 30 min (3) sodium N—methyl-dithiocarbamic acid (132 mg) rt, 30 min (4) HP-20 column (10% ethanol) lyophilization | 290 → 107 | 1780, 1720, 1650 | 1.48 (3H,t,J=7Hz), 2.5–3.6 (4H,m), 4.45 (2H,q,J=7Hz), 4.3–5.6 (3H,m), 7.20 (1H,s) (solvent: $D_2O$) |
| 101 | (1) $H_2$/10% Pd—C (225 mg) ethyl acetate (7 ml) pH 7.0 phosphate buffer (7.5 ml) 0° C., 1 h (2) 2-(5-chloro-2-chloroacetamide-4-thiazolyl-(Z)-2-methoxyimino acetyl chloride · hydrochloride (197 mg) THF (5 ml) $NaHCO_3$ (110 mg) 0° C., 30 min (3) sodium N—methyl-dithiocarbamic acid (103 mg) rt, 50 min (4) XAD-2 column (water) lyophilization | 225 → 97.6 | 3400, 1780, 1770, 1710, 1660, 1530, 1200, 1130 | 2.3–3.4 (4H,m), 4.1 (3H,s), 4.2–4.6 (1H,m), 5.0–5.4 (2H,m) (solvent: $D_2O$) |
| 102a | 2-(4-ethyl-2,3-dioxo-1-piperazinyl carboxamide-2-thienylacetic acid (390 mg) DCC (248 mg) HOBT (184 mg) DMF (5 ml) rt, 3.5 h extraction with ethyl acetate, silica gel chromatography ($CH_2Cl_2$— ethyl acetate = 1:2) | 396 → 299 | 3300, 1800, 1720, 1680, 1510, 1180 | 1.16 (3H,t,J=7Hz), 1.77–2.82(4H,m), 3.33–3.65 (4H,m), 3.89–4.24 (3H,m), 4.38–4.85 (2H,m), 5.73–5.88 (1H,m), 6.88–7.03 (3H,m), 7.14–7.58 (11H,m), 7.68–7.90 (1H,m) (solvent: $CDCl_3$) |

-continued

| Product | Reaction conditions | Yield (mg) St. mat. → Prod. | IR$\nu_{max}^{KBr}$ cm$^{-1}$ | NMR (90 MHz) δ |
|---|---|---|---|---|
| 102b | CF$_3$COOH (0.26 ml) anisole (0.20 ml) −15° ~ −10° C., 3.5 h XAD-2 column (10% ethanol) lyophilization | 191 → 48 | 3450, 1780, 1710, 1670, 1510, 1370, 1190 | 1.27 (3H,t,J=7Hz), 2.43–3.27 (4H,m), 3.44–3.90 (4H,m), 4.02–4.35 (3H,m), 4.55–5.24 (2H,m), 5.91 (1H,s), 7.14–7.42 (2H,m), 7.55–7.70 (1H,m) (solvent: D$_2$O) |
| 103a | KNCO (160 mg) acetic acid (4 ml) water (1 ml) rt, 2 h extraction with ethyl acetate, silica gel chromatography (CHCl$_3$-ethyl acetate-methanol = 85:5:10) | 400 → 220 | 3300, 1765, 1720, 1680, 1650, 1180, 1050 | 2.20–5.00 (7H,m), 5.73 (2H,bs), 6.60 (1H,d,J=6 Hz), 6.86 (1H,s), 7.20–7.52 (10H,m) (solvent: d$_6$-DMSO) |
| 103b | H$_2$/5% Pd—C (220 mg) THF (5 ml) water (5 ml) NaHCO$_3$ (43 mg) rt, 1 h CHP-20 column (water) lyophilization | 220 → 100 | 1770, 1718, 1580, 1400 | 2.00–3.20 (4H,m), 3.60–4.50 (3H,m) (solvent: D$_2$O) |
| 104a | phenylisocyanate (0.1 ml) CH$_2$Cl$_2$ (10 ml) rt, 10 min silica gel chromatography (CH$_2$Cl$_2$—ethyl acetate-methanol = 85:5:10) | 198 → 138 | 3300, 1760, 1720, 1670, 1180, 1055 | 2.20–5.20 (7H,m), 6.73–7.50 (16H,m), 8.73 (1H,d,J=7Hz) (solvent: d$_6$-DMSO) |
| 104b | H$_2$/5% Pd—C (140 mg) THF (4 ml) water (4 ml) NaHCO$_3$ (42 mg) rt, 1 h CHP-20 column (water) lyophilization | 138 → 70 | 3400, 1770, 1720, 1590, 1500, 1420 | 2.10–2.95 (4H,m), 4.35–4.90 (3H,m), 7.25–7.80 (5H,m) (solvent: D$_2$O) |
| 105 | (1) H$_2$/5% Pd—C (380 mg) ethyl acetate (10 ml) water (10 ml) 0° C., 1 h (2) 2-pyridylacetyl chloride · hydrochloride (292 mg) NaHCO$_3$ aqueous layer (mentioned above)-THF (10 ml) 0° C., 20 min → rt, 40 min (3) XAD-2 column (10% ethanol) lyophilization | 380 → 30 | 3400, 1770, 1710, 1675, 1645, 1190, 1105 | 2.3–3.3 (4H,m), 4.1–4.4 (1H,m), 4.50–5.25 (4H,m), 7.30–7.55 (2H,m), 7.80–8.05 (1H,m), 8.4–8.6 (1H,m) |
| 106 | (1) H$_2$/5% Pd—C (1.8 g) ethyl acetate (20 ml) pH 7.0 phosphate buffer (20 ml) rt, 1 h (2) 4-chlorophenyl acetyl chloride (1.05 g) NaHCO$_3$ (940 ml) phosphate buffer mentioned above, THF (30 ml) 0° C., 30 min (3) lyophilization | 1900 → 471 | 1780, 1720, 1660 | 2.40–3.25 (4H,m), 3.60 (2H,s), 4.04–4.78 (2H,m), 4.84–5.14 (1H,m), 7.15–7.36 (4H,m) (solvent: D$_2$O) |
| 107 | (1) H$_2$/5% Pd—C | 350 | 3430, | 2.2–3.3 (4H,m), |

-continued

| Product | Reaction conditions | Yield (mg) St. mat. → Prod. | IR $\nu_{max}^{KBr}$ cm$^{-1}$ | NMR (90 MHz) δ |
|---|---|---|---|---|
| | (350 mg) ethyl acetate (10 ml) pH 7.0 phosphate buffer (5 ml) rt, 1.5 h (2) 2-chloro-2-pheny-acetyl chloride (199 mg) NaHCO$_3$ aqueous solution the above phosphate buffer THF (10 ml) 0° C., 20 min → rt, 40 min (3) XAD-2 column (10% ethanol) lyophilization | → 25 | 1775, 1725, 1650, 1540, 1380, 1200 | 4.05–4.50 (2H,m), 4.8–5.3 (2H,m), 5.70 (1H,s), 7.4–7.7 (4H,m), 7.74–7.90 (1H,m) (solvent: D$_2$O) |
| 108a | sodium 3-phridine-thiol (113 mg) NaI (100 mg) DMF (4 ml) rt, 30 min extraction with ethyl acetate silica gel chromatography (hexane-ethyl acetate = 1:4) | 200 → 128 | 3350, 1770, 1740, 1680, 1510, 1180, 1050 | 2.21–3.40 (4H,m), 3.62 (2H,s), 3.84–4.09 (1.5H,m), 4.54–5.07 (1.5H,m), 6.97 (1H,s), 7.11–8.71 (14H,m) (solvent: CDCl$_3$) |
| 108b | CF$_3$COOH (0.25 ml) anisole (0.2 ml) CH$_2$Cl$_2$ (10 ml) −10° ~ −15° C., 5 h XAD-2 column (10% ethanol) lyophilization | 128 → 53 | 3440, 1780, 1720, 1650, 1380, 1190, 1120, 1040 | 2.41–3.28 (4H,m), 3.78 (2H,s), 3.92–4.13 (1H,m), 4.46–4.71 (1H,m), 4.86–5.10 (1H,m), 7.42–8.10 (4H,m) (solvent: D$_2$O) |
| 109a | sodium 4-chloro-phenylthiol (211 mg) NaI (150 mg) DMF (4 ml) rt, 1 h extraction with ethyl acetate silica gel chromatography (hexane-ethyl acetate = 3:4) | 300 → 160 | 3350, 1770, 1740, 1670, 1510, 1480, 1180, 1050 | 2.19–3.38 (4H,m), 3.60 (2H,s), 3.73–4.11 (1.5H,m), 4.50–5.02 (1.5H,m), 6.93 (1H,s), 7.01–7.70 (14H,m) (solvent: CDCl$_3$) |
| 109b | CF$_3$COOH (0.31 ml) anisole (0.25 ml) CH$_2$Cl$_2$ (15 ml) −10° ~ −15° C., 4 h XAD-2 column (30% ethanol) lyophilization | 160 → 76 | 3350, 1780, 1720, 1650, 1380, 1190, 1100, 1030 | 2.40–3.91 (4H,m), 3.71 (2H,s), 3.87–4.19 (1H,m), 4.42–4.73 (1H,m), 4.81–5.14 (1H,m), 7.43 (4H,s) (solvent: D$_2$O) |
| 110a | 2-isopropylpheno-xycarbonyl chloride (149 mg) DMA (0.4 ml) CH$_2$Cl$_2$ (10 ml) rt, 30 min extraction with ethyl acetate, crystallization with hexane-ether (1:1) | 200 → 202 | 3350, 2940, 1770, 1740, 1720, 1490, 1180, 1050 | 1.20 (3H,s), 1.31 (3H,s), 2.21–3.50 (5H,m), 4.01–4.39 (1H,m), 4.53–5.07 (1H,m), 5.58–5.82 (1H,m), 7.0 (1H,s), 7.07–7.51 (14 H,m) (solvent: CDCl$_3$) |
| 110b | H$_2$/5% Pd—C (202 mg) THF-buffer (pH 7.0) 0° C., 30 min XAD-2 column (30% ethanol) lyophilization | 202 → 83 | 3400, 1780, 1730, 1650, 1380, 1210, 1190, 1050 | 1.18 (3H,s), 1.27 (3H,s), 2.42–3.27 (5H,m), 4.18–4.39 (1H,m), 4.54–5.09 (2H,m), 7.07–7.53 (4H,m) (solvent: D$_2$O) |
| 111a | difluoroacetic acid (96 mg) DCC (206 mg) HOBT (134 mg) | 250 → 175 | 3350, 2930, 1770, 1740, | 2.22–3.48 (4H,m), 3.73–4.30 (1.5H,m), 4.55–5.01 (1.5H,m), 5.91 (1H,t,J=54Hz), |

-continued

| Product | Reaction conditions | Yield (mg) St. mat. → Prod. | IR $\nu_{max}^{KBr}$ cm$^{-1}$ | NMR (90 MHz) δ |
|---|---|---|---|---|
| | DMF (4 ml) rt, 1 h extraction with ethyl acetate, silica gel chromatography (hexan-ethyl acetate = 1:1) | | 1700, 1540, 1180, 1050 | 7.01 (1H,s), 7.25–7.40 (10H,m) (solvent: CDCl$_3$) |
| 111b | H$_2$/5% Pd—C (175 mg) THF-water NaHCO$_3$ (34 mg) 0° C., 25 min HP-20 column (water) lyophilization | 175 → 59 | 3400, 1780, 1720, 1650, 1540, 1380, 1190, 1105, | 2.35–3.32 (4H,m), 4.20–4.41 (1H,m), 4.55–4.87 (1H,m), 5.07–5.21 (1H,m), 6.25 (1H,t,J=48Hz) (solvent: D$_2$O) |
| 112 | (1) H$_2$/5% Pd—C (300 mg) THF (20 ml)-water (10 ml) 0° C., 40 min (2) 3-chloropropionyl chloride (0.08 ml) aqueous layer (mentioned above)-THF (6 ml) NaHCO$_3$ (222 mg) 0° C., 60 min (3) XAD-2 column (water) lyophilization | 300 → 21 | 3450, 1780, 1720, 1650, 1380, 1190, 1030 | 2.22–3.31 (4H,m), 2.83 (2H,t,J,=7Hz), 3.86 (2H,t,J=7Hz), 4.10–4.35 (1H,m), 4.51–4.82 (1H,m), 4.98–5.23 (1H,m) (solvent: D$_2$O) |
| 113 | chloromethyl pivalate (0.1 ml) DMF (3 ml) rt, 24 h extraction with ethyl acetate, silica gel chromatography (hexane-ethyl acetate = 1:2) | 160 → 111 | 3350, 1800, 1750, 1675, 1535 | 1.22 (9H,s), 2.29–3.40 (4H,m), 3.9–4.3 (1H,m), 4.11 (2H,s), 4.62–5.13 (2H,m), 5.87 (2H,s), 7.30 (1H,m) (solvent: D$_2$O) |
| 114 | chloromethyl pivalate (0.11 ml) DMF (4 ml) rt, 24 h extraction with ethyl acetate, silica gel chromatography (hexane-ethyl acetate = 2:3) | 200 → 172 | 3300, 1800, 1750, 1660, 1520 | 1.21 (9H,s), 2.29–3.32 (4H,m), 3.61 (2H,s), 3.81–4.10 (1H,m), 4.49–5.12 (2H,m), 5.81 (2H,s), 7.11–7.50 (5H,m) (solvent: CDCl$_3$) |
| 115a | propionyl chloride (0.13 ml) DMA (1 ml) CH$_2$Cl$_2$ (20 ml) 0° C., 1 h extraction with ethyl acetate, silica gel chromatography (hexane-ethyl acetate = 1:2) | 500 → 396 | 3350, 1770, 1740, 1680, 1530, 1190, 1050 | 1.10 (3H,t,J=8Hz), 1.98–3.59 (6H,m), 3.85–4.16 (1H,m), 4.57–5.09 (2H,m), 6.95 (1H,s), 7.21–7.52 (10H,m) (solvent: CDCl$_3$) |
| 115b | H$_2$/5% Pd—C (396 mg) THF-water NaHCO$_3$ (73 mg) 0° C., 30 min HP-20 column (water) lyophilization | 396 → 140 | 3450, 1790, 1730, 1650, 1380, 1190, 1050 | 1.23 (3H,t,J=8Hz), 2.23–3.31 (6H,m), 4.11–4.31 (1H,m), 4.59–4.82 (1H,m), 4.93–5.18 (1H,m) (solvent: D$_2$O) |
| 116 | chloromethyl pivalate (0.1 ml) DMF (4 ml) rt, 24 h extraction with ethyl acetate, silica gel chromatography (CH$_2$Cl$_2$—ethyl acetate = 5:1) | 900 → 620 | 3330, 1800, 1750, 1720, 1520, 1230, 1180, 1120, 1050, 1020 | 1.20 (9H,s), 2.30–3.35 (4H,m), 3.90–4.40 (1H,m), 4.50–4.90 (2H,m), 5.14 (2H,s), 5.68 (1H,bs), 5.86 (2H,s), 7.35 (5H,s) (solvent: CDCl$_3$) |
| 117 | (1) H$_2$/5% Pd—C | 215 | 3340, | 1.20 (9H,s), |

-continued

| Product | Reaction conditions | Yield (mg) St. mat. → Prod. | IR$\nu_{max}^{KBr}$ cm$^{-1}$ | NMR (90 MHz) δ |
|---|---|---|---|---|
| | (215 mg) ethyl acetate (6 ml) 0° C., 1 h (2) bromoacetyl bromide (90 mg) ethyl acetate (mentioned above) DMA (0.35 ml) 0° C., 0.5 h silica gel chromatography (CH$_2$Cl$_2$—ethyl acetate = 5:1) | → 103 | 1800, 1740, 1670, 1520 | 2.30–3.49 (4H,m), 3.83 (2H,s), 4.02–4.30 (1H,m), 4.59–5.21 (2H,m), 5.79 (2H,m), 7.32 (1H,m) (solvent: CDCl$_3$) |
| 118 | (1) H$_2$/5% Pd—C (146 mg) ethyl aetate (5 ml) 0° C., 1 h (2) sorbic acid (45 mg) DCC (83 mg) HOBT (54 mg) DMF (2 ml) rt, 1 h silica gel chromatography (CH$_2$Cl$_2$—ethyl acetate = 4:1) | 146 → 60 | 3320, 1800, 1740, 1660, 1520 | 1.20 (9H,s), 1.82 (3H,d,J=3Hz), 2.30–3.57 (4H,m), 4.00–4.31 (1H,m), 4.69–5.19 (2H,m), 5.80 (2H,s), 5.71–6.50 (3H,m), 7.04–7.38 (1H,m) (solvent: CDCl$_3$) |
| 119 | (1) H$_2$/5% Pd—C (185 mg) 0° C., 90 min ethyl acetate (6 ml) (2) thienylacetyl chloride (62 mg) ethyl acetate (mentioned above) DMA (0.3 ml) 0° C., 1 h silica gel chromatography (CH$_2$Cl$_2$—ethyl acetate = 5:1) | 185 → 88 | 3340, 1800, 1740, 1660, 1520 | 1.20 (9H,s), 2.29–3.30 (4H,m), 3.78 (2H,s), 3.93–4.20 (1H,m), 4.58–5.28 (2H,m), 5.81 (2H,m), 6.60–7.29 (3H,m) (solvent: CDCl$_3$) |

EXAMPLE 120

Production of pivaloyloxymethyl 2-[(4S)-4-(hexahydro-1H-azepin-1-yl)methyleneamino-3-oxo-2-isoxazolidinyl]-5-oxo-2-tetrahydrofurancarboxylate [Compound (120)]:

Compound (116) was subjected to catalytic reduction by a method analogous to Example 117. After removing the catalyst by filtration, to the filtrate were added 1-hexamethyleneiminecarboxyaldehyde dimethylacetal and a catalytic amount of boron trifluoride under ice-cooling and the mixture was stirred at room temperature for 20 hours. The solvent was removed by evaporation under reduced pressure, and then the residue was subjected to purification by column chromatography using Florisil to give the subject Compound (120).

EXAMPLE 121

Production of diphenylmethyl 2-[(4S)-4-(tert-butyldimethylsilyl)amino-3-oxo-2-isoxazolidinyl]-5-oxo-2-tetrahydrofurancarboxylate [Compound (121)]:

To a dimethylformamide solution of Compound (R-3) was added tert-butyldimethylsilyl chloride and triethylamine, and then the mixture was stirred at room temperature for one hour. The reaction solution was added to water-ethyl acetate and the mixture was shaken. The organic layer was recovered, washed with water and dried (Na$_2$SO$_4$). The solvent was removed by evaporation under reduced pressure to give the subject Compound (121).

EXAMPLE 122

Production of diphenylmethyl 2-[(4S)-4-tert-butyldiphenylsilyl)amino-3-oxo-2-isoxazolidinyl]-5-oxo-2-tetrahydrofurancarboxylate [Compound (122)]:

Using Compound (R-3) and tert-butyl-diphenylsilyl chloride, there was obtained the subject Compound (122) by the procedure of Example 121.

EXAMPLE 123

Production of sodium 2-[(4S)-3-diphenylphosphorylamino-3-oxo-2-isoxazolidinyl]-5-oxo-2-tetrahydrofurancarboxylate [Compound (123b)]:

To a dimethylformamide solution of Compound (R-3) was added diphenyl phosphorochloridate under ice-cooling, and the mixture was stirred for one hour. The reaction solution was added to water, and the mixture was subjected to extraction with ethyl acetate. The ethyl acetate layer was washed with water and then dried (Na$_2$SO$_4$). The solvent was removed by evaporation under reduced pressure, and then the residue was subjected to purification by silica gel column chromatography to give Compound (123a), a diphenylmethyl ester of the subject Compound (123b). Then thus obtained Compound (123a) was treated by the procedure of Example 2(b) to give the subject Compound (123b).

EXAMPLE 124

Production of diphenylmethyl 2-[(4S)-4-dimethylphosphorylamino-3-oxo-2-isoxazolidinyl]-5-oxo-2-tetrahydrofurancarboxylate [Compound (124)]:

Using Compound (R-3) and dimethyl phosphorochloridate, there was obtained the subject Compound (124) by the procedure of Example 123.

EXAMPLE 125

Production of sodium 2-[(4S)-4-ethylsulfonylamno-3-oxo-2-isoxazolidinyl]-5-oxo-2-tetrahydrofurancarboxylate [Compound (125b)]:

To a dichloromethane solution of Compound (R-3) were added ethanesulfonylchloride and triethylamine under icecooling. The mixture was stirred at 0° C. for 30 minutes, and then at room temperature for 90 minutes. The reaction mixture was washed with water and then dried (Na$_2$SO$_4$). The solvent was removed by evaporation under reduced pressure, and then the residue was subjected to purification of silica gel chromatography to give Compound (125a), diphenyl ester of the subject Compound (125b). Then, thus obtained Compound (125a) was treated by the procedure of Example 2(b) to give the subject Compound (125b).

EXAMPLE 126

Production of sodium 2-[(4S)-4-vinylsulfonylamino-3-oxo-2-isoxazolidinyl]-5-oxo-2-tetrahydrofurancarboxylate [Compound (126)]:

Using Compound (R-3) and 2-chloroethanesulfonyl chloride, there was obtained the subject Compound (126) by the procedure of Example 125 and then by the procedure of Example 1(c).

EXAMPLE 127

Production of 2-[(4S)-4-thienylacetamido-3-oxo-2-isoxazolidinyl]-5-oxo-2-tetrahydrofurancarbonylanilide [Compound (127)]:

To the suspension of Compound (5b) in dichloromethane was added trimethylacetyl chloride at 0° C., and then the mixture was stirred at 0° C. for one hour. To the resultant was added aniline, and then the mixture was stirred at room temperature for one hour. The reaction mixture was washed with water and dried (Na$_2$SO$_4$). The solvent was removed by evaporation under reduced pressure, and the residue was subjected to purification by column chromatography using Florisil to give Compound (127) as colorless oily product.

EXAMPLE 128

Production of 2-[(4S)-4-benzyloxycarbonylamino-3-oxo-2-isoxazolidinyl]-5-oxo-2-tetrahydrofurancarbonylanilide [Compound (128)]:

Using Compound (93b) and aniline, there was obtained the subject Compound (128) as colorless crystals by the procedure of Example 127.

EXAMPLE 129

Production of 2-[(4S)-4-benzyloxycarbonylamino-3-oxo-2-isoxazolidinyl]-5-oxo-2-tetrahydrofurancarbonylpyrrolidinamide [Compound (129)]:

Using Compound (93b) and pyrrolidine, thus was obtained the subject Compound (129) as colorless oily product by the procedure of Example 127.

EXAMPLE 130

Production of 2-[(4S)-4-thienylacetamido-3-oxo-2isoxazolidinyl]-5-oxo-2-tetrahydrofurancarbonylpyrrolidinamide [Compound (130)]:

Using Compound (5b) and pyrrolidine, there was obtained the subject Compound (130) as colorless oily product by the procedure of Example 127.

EXAMPLE 131

Production of 2-[(4S)-4-thienylacetamido-3-oxo-2isoxazolidinyl]-5-oxo-2-tetrahydrofurancarbonylpropylamide [Compound (131)]:

Using Compound (5b) and propylamine, there was obtained the subject Compound (131) as colorless oily product by the procedure of Example 127.

EXAMPLE 132

Production of sodium 2-[(4S)-4-γ-D-glutamylamino-3oxo-2-isoxazolidinyl]-5-oxo-2-tetrahydrofurancarboxylate [Compound (132)]:

Using Compound (R-3) and α-benzyl N-carbobenzoxy-D-glutamate, there was obtained the subject Compound (132) by the procedure of Example 1(a) and then by the procedure of Example 2(b).

EXAMPLE 133

Production of sodium 2-[(4S)-4-(2-hydroxy)isobutyrylamino-3-oxo-2-isoxazolidinyl]-5-oxo-2-tetrahydrofurancarboxylate [Compound (133)]:

Using Compound (R-3) and 2-hydroxyisobutyric acid, there was obtained the subject Compound (133) by the procedure of Example 1 (a) and then by the procedure of Example 2 (b).

Below given are the reaction conditions of Examples 120 to 133 as well as the yields and typical physicochemical properties of the compounds obtained.

| Product | Reaction conditions | Yield (mg) St. mat. → Prod. | IR$\nu_{max}^{KBr}$ cm$^{-1}$ | NMR (90 MHz) δ |
|---|---|---|---|---|
| 120 | (1) H$_2$/5% Pd—C (274 mg) ethyl acetate (10 ml l) (2) 1-hexamethyleneiminecarboxyaldehyde dimethylacetal (119 mg) BF$_3$·Et$_2$O (4 drops) | 274 → 180 | 1800, 1740, 1630, 1520, 1240, 1040 | 1.19 (9H,s), 1.40–1.81 (8H,m), 2.29–3.29 (4H,m), 3.30–3.47 (4H,m), 3.92–4.20 (1H,m), 4.42–4.89 (2H,m), 5.82 (2H,m), 8.03 (1H,s) (solvent: CDCl$_3$) |

-continued

| Product | Reaction conditions | Yield (mg) St. mat. → Prod. | IR$\nu_{max}^{KBr}$ cm$^{-1}$ | NMR (90 MHz) δ |
|---|---|---|---|---|
| | rt, 20 h Florisil chromatography (ethyl acetate) | | | |
| 121 | tert-butyldimethylsilyl chloride (115 mg), triethylamine (78 mg), DMF (4 ml), rt, 1 h extraction with ethyl acetate | 202 → 255 | 1800, 1730, 1250, 1180, 1090 | 0.89 (9H,s), 2.21-3.32 (4H,m), 3.57-3.90 (1H,m), 3.98-4.39 (2H,m), 6.96 (1H,s), 7.21-7.40 (10H,m) (solvent: CDCl$_3$) |
| 122 | tert-butyldiphenylsilyl chloride (211 mg) triethylamine (78 mg) DMF (4 ml) rt, 1 h extraction with ethyl acetate | 202 → 317 | 1800, 1730, 1240, 1180, 1100 | 1.09 (9H,s), 2.21-3.31 (4H,m), 3.57-3.90 (1H,m), 3.96-4.42 (2H,m), 7.01 (1H,s), 7.20-7.96 (20H,m) (solvent: CDCl$_3$) |
| 123a | diphenyl phosphorochloridate (134 mg) pyridine (0.04 ml) DMF (4 ml) 0° C., 1 h extraction with ethyl acetate silica gel chromatography (CH$_2$Cl$_2$—ethyl acetate = 1:1) | 198 → 83 | 3350, 1800, 1750, 1590, 1490, 1180, 940 | 2.20-3.35 (4H,m), 3.71-4.14 (1.5H,m), 4.31-4.70 (1.5H,m), 6.96 (1H,s), 7.03-7.49 (20H,m), (solvent: CDCl$_3$) |
| 123b | H$_2$/10% Pd—C (74 mg) THF (7 ml) - pH 7.0 phosphate buffer (3.5 ml) 0° C., 25 min XAD-2 column (20% ethanol) lyophilization | 74 → 28 | 3450, 1780, 1730, 1640, 1490, 1380, 1190 | 2.21-3.27 (4H,m), 3.83-4.08 (1H,m), 4.31-4.90 (2H,m), 7.18-7.57 (10H,m), (solvent: D$_2$O) |
| 124 | dimethyl phosphorochloridate (71 mg) pyridine (0.04 ml) DMF (4 ml) 0° C., 1 h extraction with ethyl acetate silica gel chromatography (ethyl acetate) | 198 → 30 | 3320, 1800, 1760, 1490, 1250, 1180, 1050, 1020 | 2.20-3.25 (4H,m), 3.65 (3H,s), 3.77 (3H,s), 3.75-4.10 (1.5H,m), 4.29-4.66 (1.5H,m), 6.98 (1H,s), 7.22-7.45 (10H,m) (solvent: CDCl$_3$) |
| 125a | ethanesulfonyl chloride (56 μl) thriethylamine (84 μl) CH$_2$Cl$_2$ (10 ml) 0° C., 30 min → rt, 90 min silica gel chromatogrpahy (hexane-ethyl acetate = 1:1) | 198 → 150 | 3300, 1800, 1770, 1550, 1330, 1180, 1160, 1050 | 1.39 (3H,t,J=8Hz), 2.31-3.59 (6H,m), 3.89-4.20 (1H,m), 4.51-4.69 (2H,m), 6.98 (1H,s), 7.31-7.50 (10H,m), (solvent: CDCl$_3$) |
| 125b | H$_2$/10% Pd—C (115 mg) NaHCO$_3$ (19.7 mg) THF (6 ml) - water (3 ml) 0° C., 30 min XAD-2 column (water) lyophilization | 115 → 54 | 3450, 1780, 1720, 1640, 1380, 1320, 1200, 1140 | 1.40 (3H,t,J=8Hz), 2.26-3.44 (6H,m), 4.07-4.41 (1H,m), 4.63-4.94 (2H,m) (solvent: D$_2$O) |
| 126 | (1) 2-chloroethanesulfonyl chloride (196 mg) | 396 → 64 | 3400, 1780, 1720, 1380, 1330, 1200, | 2.43-3.22 (4H,m), 4.08-4.32 (1H,m), 4.57-5.20 (2H,m), |

| Product | Reaction conditions | Yield (mg) St. mat. → Prod. | IR ν$_{max}^{KBr}$ cm$^{-1}$ | NMR (90 MHz) δ |
|---|---|---|---|---|
|  | triethylamine (0.169 ml) CH$_2$Cl$_2$ (20 ml) 0° C., 60 min silica gel chromatography (CH$_2$Cl$_2$—ethyl acetate = 5:1) (2) CF$_3$COOH (0.63 ml), anisole (0.24 ml) CH$_2$Cl$_2$ (24 ml) −10~−15° C., 4 h XAD-2 column (water) lyophilization |  | 1140, 1020 | 6.10–6.42 (2H,m), 6.60–6.98 (1H,m) (solvent: D$_2$O) |
| 127 | trimethylacetyl chloride (32 ml) CH$_2$Cl$_2$ (4 ml) 0° C., 1 h aniline (24 μl) rt, 1 h Florisil column (hexane-ethyl acetate = 2:3) | 100 → 11 | 3300, 1800, 1730, 1690, 1540, 1180, 1040 | 2.37–3.46 (4H,m), 3.80 (2H,s), 3.81–4.08 (1H,m), 4.57–5.01 (2H,m), 6.58–6.83 (1H,m), 6.83–7.61 (8H,m), 8.41–8.62 (1H,m), (solvent: CDCl$_3$) |
| 128 | trimethylacetyl chloride (32 μl) CH$_2$Cl$_2$ (4 ml) 0° C., 1 h aniline (24 μl) rt, 1 h silica gel chromatography (hexane-ethyl acetate = 1:1) | 103 → 31 | 3320, 1800, 1730, 1690, 1530, 1250, 1180, 1050 | 2.37–3.54 (4H,m), 4.01–4.29 (1H,m), 4.52–4.79 (2H,m), 5.10 (2H,s), 5.51–5.70 (1H,m), 7.09–7.60 (10H,m), 8.31–8.44 (1H,m), (solvent: CDCl$_3$) |
| 129 | trimethylacetyl chloride (32 μl) CH$_2$Cl$_2$ (4 ml) 0° C., 1 h pyrrolidine (22 μl) rt, 1 h silica gel chromatography (hexane-ethyl acetate = 50:80:1) | 103 → 18 | 3320, 1800, 1730, 1640, 1530, 1250, 1180, 1020 | 1.62–2.01 (4H,m), 2.39–3.26 (4H,m), 3.38–3.70 (4H,m), 4.02–4.29 (1H,m), 4.51–4.80 (2H,m), 5.10 (2H,s), 5.79–6.02 (1H,m), 7.15–7.42 (5H,m), (solvent: CDCl$_3$) |
| 130 | trimethylacetyl chloride (32 μl) CH$_2$Cl$_2$ (4 ml) 0° C., 1 h pyrrolidine (22 μl) rt, 1 h silica gel chromatography (hexane-ethyl acetate = 3:6:0.1 → 0:10:0.1) | 100 → 21 | 3270, 1790, 1720, 1680, 1540, 1180, 1040 | 1.73–2.01 (4H,m), 2.41–3.11 (4H,m), 3.40–3.71 (4H,m), 3.76, 3.78 (2H, each s), 4:01–4.29 (1H, m), 4.53–4.99 (2H, m), 6.88–7.28 (3H, m) (solvent: CDCl$_3$) |
| 131 | trimethylacetyl chloride (32 μl) CH$_2$Cl$_2$ (4 ml) 0° C., 1 h propylamine (22 μl) rt, 1 h silica gel chromatography (hexane-ethyl acetate = 25:75:1) | 100 → 18 | 3270, 1800, 1720, 1680, 1540, 1180, 1040 | 0.81–1.00 (3H,each t,J=6Hz), 1.38–1.68 (2H,m), 2.25–3.42 (6H,m), 3.70–4.09 (1H,m), 3.77 (2H,s), 4.59–4.98 (2H,m), 6.87–7.29 (3H,m), (solvent: CDCl$_3$) |
| 132 | (1) α-benzyl N—carbobenzoxy-D-glutamate (373 mg) DCC (206 mg) | 317 → 41 | 1780, 1720, 1650, 1520, 1380, 1200 | 1.23 (6H,s), 2.00–2.70 (3H,m), 2.70–3.20 (1H,m), 3.80–4.10 (1H,m), 4.20–4.50 (1H,m), |

-continued

| Product | Reaction conditions | Yield (mg) St. mat. → Prod. | IR$\nu_{max}^{KBr}$ cm$^{-1}$ | NMR (90 MHz) δ |
|---|---|---|---|---|
|  | HOBT (68 mg) DMF (5 ml) 20° C., 1.5 h silica gel chromatography (hexane-ethyl acetate =1:1) (2) H$_2$/10% Pd—C (150 mg) THF (10 ml) - water (3 ml) NaHCO$_3$ (17 mg) 20° C., 1.5 h CHP-20 chromatography (water) lyophilization |  |  | 4.60–4.80 (1H,m), 8.40 (1H,d,J=7Hz) (solvent: d$_6$-DMSO) |
| 133 | (1) 2-hydroxyisobutyric acid (53 mg) DCC (103 mg) HOBT (34 mg) DMF (3 ml) 20° C., 1.5 h silica gel chromatography (hexane-ethyl acetate = 1:3) (2) H$_2$/10% Pd—C (70 mg) THF (6 ml) - water (2 ml) NaHCO$_3$ (12 mg) 20° C., 0.5 h CHP-20 column (water) lyophilization | 200 → 30 | 1780, 1720, 1660, 1640, 1540, 1400 1380, 1200, | 1.70–3.20 (8H,m), 3.70–4.10 (1H,m), 4.20–4.60 (1H,m) 4.60–5.00 (2H,m), 8.40 (1H,d,J=7Hz) (solvent: d$_6$-DMSO) |

Part B

EXAMPLE 1

Production of diphenylmethyl 2-[(4S)-4-isocyano-3-oxo-2ioxazolidinyl]-5-oxo-2-tetrahydrofuran carboxylate:

In 400 ml of dry methylene chloride was dissolved 5.2 g of diphenyl methyl 2-[(4S)-4-formamido-3-oxo-2-isoxazolidinyl]-5-oxo-2-tetrahydrofuran carboxylate. To the solution were added, under cooling with acetone- ry ice, 4 g of pyridine and 0.8 ml of trichloromethyl chloroformate (diphosgene), and the mixture was stirred for one hour at the same temperature. The reaction solution was shaken with a saturated aqueous solution of sodium hdyrogen carbonate. Then, the methylene chloride layer was dried over anhydrous magnesium sulfate, which was concentrated under reduced pressure. The concentrate was subjected to a silica-gel column chromatography, eluting with ethyl acetate-n-hexane (1:1) to give 3.5 g of the above-titled compound as orange-colored powder.

I R$\lambda_{max}^{KBr}$ cm$^{-1}$: 2150,1800,1765,1740,1490, 1450,1295,1260,1170,1060,740,700

NMR (CDCl$_3$, pp.): 2.10~3.50(4H,m),4.00~4.90(3H,m),7.00(1H,s),7.35(10-H,s)

EXAMPLE 2

Production of diphenylmethyl 2-[(4RS)-4-isocyano-4-methylthio-3-oxo-2-isoxazolidinyl]-5-oxo-2-tetrahydrofuran carboxylate:

In 5 ml of anhydrous dimethylformamide was dissolved 1.0 g of diphenylmethyl 2-[(4S )-4-isocyano-3-oxo-2-isoxazolidinyl]-5-oxo-2-tetrahydrofuran carboxylate. To the solution was added 0.4 g of methyl methanethiosulfonate. The mixture was cooled, to which was added 0.37 g of anhydrous potassium carbonate. The mixture was stirred at the same temperature for one hour. The reaction solution was poured into water, which was subjected to extraction with ethyl acetate. The extract was washed with water and dried over anhydrous magnesium sulfate. The resultant was concentrated under reduced pressure, and the concentrate was subjected to a silica-gel column chromatography, eluting with ethyl acetate-n-hexane (1:2) to give 0.6 g of the above-titled compound.

I R $\lambda_{max}^{KBr}$ cm$^{-1}$:2120,1800,1765,1730,1490, 1450,1170,1060,695

NMR (CDCl$_2$, ppm):2.10~3.50(4H,m), 2.33 (3H,s),4.10~4.75(2H,m), 7.00(1H,s), 7.20~7.50(10H,br.s)

EXAMPLE 3

Production of diphenylmethyl 2-[(4RS)-4-isocyano-4-hydroxymethyl-3-oxo-2-isoxazolidinyl]-5-oxo-2-tetrahydrofuran carboxylate:

In 3 ml of anhydrous dimethylformamide was dissolved 203 mg of diphenylmethyl 2-[(4S)-4-isocyano-3-oxo-2-isoxazolidinyl]-5-oxo-2-tetrahydrofuran carboxylate. To the solution were added, under cooling, 0.5 m( of a 37% aqueous solution of formalin and 70 mg of pulverized potassium carbonate, and the mixture was stirred for 40 minutes at the same temperature. The reaction solution was poured into water, which was subjected to extraction with ethyl acetate. The extract was washed with water, dried over anhydrous magnesium sulfate and concentrated under reduced pressure. The concentrate was subjected to a silica-gel column chromatogrpahy, eluting ethyl acetate -n-hexane (1:1) to give 142 mg of the above-titled compound.

IR$\nu_{max}^{KBr}$ cm$^{-1}$: 2140,1800,1765,1740,1180,1060,695
NMR(CDCl$_3$,ppm):
2.10~3.60(5H,m),3.80~4.05(2H,m),4.10~4.80(2H,m),-7.00(1H,s),7.20~7.50(10H,br,s)

EXAMPLE 4

Production of diphenylmethyl 2-[(4RS)-4-isocyano-4-(2- hydroxy-2-propyl)-3-oxo-2-isoxazolidinyl]-5-oxo-2-tetrahydrofuran carboxylate :

In 8 ml of acetone was suspended 812 mg of diphenylmethyl 2-[(4S)-4-isocyano-3-oxo-2-isoxazolidinyl]-5-oxo-2-tetrahydrofuran carboxylate. To the suspension was added 276 mg of pulverized potassium carbonate, and the mixture was stirred for 2.5 hours under cooling with cold water. The reaction solution was concentrated under reduced pressure. The concentrate was subjected to extraction with ethyl acetate. The extract was washed with water, dried over anhydrous magnesium sulfate and concentrated under reduced pressure. The concentrate was subjected to a silica-gel column chromatography, eluting with ethyl acetate - n-hexane (1:1) to give 510 mg of the above-titled compound.

I R$\nu_{max}^{Nujol}$ cm$^{-1}$: 2130,1795,1760,1725, 1175,1060,725,700
NMR (CDCl$_3$, ppm): 1.40(6H,s),2.20~3.45 (5H,m) 4.00~4.80(2H,m),7.00(1H,s), 7.20~7.50(10H,br.s)

EXAMPLE 5

Production of diphenylmethyl 2-[(4RS)-4-isocyano-(diphenylmethyloxycarbonylmethyl)-3-oxo-2-isoxazolidinyl]- -oxo-2-tetrahydrofuran carboxylate :

In 3 ml of anhydrous dimethylformamide was dissolved 800 mg of diphenylmethyl 2-[(4S)-4-isocyano-3-oxo-2-isoxazolidinyl] -5-oxo-2-tetrahydrofuran carboxylate. To the solution were added, under cooling, 660 mg of diphenylmethyl bromoacetate and 272 mg of pulverized potassium carbonate. The mixture was stirred for 3 hours at the same temperature. The reaction solution was poured into water, which was subjected to extraction with ethyl acetate. The ethyl acetate layer was washed with water dried over anhydrous magnesium sulfate and concentrated under reduced pressure. The concentrate was subjected to a silica-gel column chromatography, eluting with ethyl acetate - n-hexane (1:2), to give 750 mg of the above-titled compound.

I R$\nu_{max}^{KBr}$ cm$^{-1}$: 2130,1805,1765,1730,1495,1450,1375,1060,740,690
NMR(CDCl$_3$, ppm): 2.20≧3.50(6H,m), 4.50(2H,s), 6.93 (1H,s), 7.00(1H,s), 7.20~7.50(20H,br.s)

EXAMPLE 6

Production of diphenylmethyl 2-[(4RS)-4-acetoxymethyl-4-isocyano-3-oxo-2-isoxazolidinyl]-5-oxo-2-tetrahydrofuran carboxylate:

In8 ml of methylene chloride was dissolved diphenylmethyl 2-[(4RS)-4-isocyano-4-hydroxymethyl-3-oxo-2-isoxazolidinyl]-oxo-2-tetrahydrofuran carboxylate. To the solution were added, under cooling, 118 mg of pyridine and 153 mg of acetic anhydride. The mixture was then stirred for 3 hours at room temperatures. The reaction solution was washed with water, dried over anhydrous sodium sulfate and concentrated under reduced pressure. The concentrate was eluted with ethyl acetate - n-hexane (1:2) to give 382 mg of the above-titled compound.

I R$_{max}^{KBr}$ cm$^{-1}$: 2140,1805,1760,1730(s), 1495,1450,1220,1180,1060,700
NMR (CDCl$_3$, ppm): 2.03(3H,s),2.20~3.45 (4H,m)4.10~4.60(2H,m), 4.40(2H,s), 6.93 (1H,s), 7.15~7.45(10H,br.s)

EXAMPLE 7

Production of diphenylmethyl 2-[(4RS)-4-chlorcarbamoyloxymethyl-4-isocyano-3-oxo-2-isoxazolidinyl]-5-oxo-tetrahydrofuran carboxylate :

In 20 ml of dry methylene chloride was suspended 970 mg of diphenylmethyl 2-[(4RS)-4-hydroxymethyl-4-isocyano-3-oxo-2-isoxasolidinyl]-5-oxo-2-tetrahydrofuran carboxylate. To the suspension was added, under ice-cooling, 400 mg of chloroacetyl isocyanate. The mixture was stirred for one hour at the same temperature, followed by concentration under reduced pressure. The concentrate was subjected to a silica-gel chromatography, eluting with ethyl acetate - n-hexane (1:1), to give 520 mg of the above-titled compound.

I R $\nu_{max}^{KBr}$ cm$^{-1}$: 2130,1800,1765,1490,1190,1050,750,690
NMR (CDCl$_3$, ppm): 2.10~3.60(4H,m),4.25~4.80(6H,m),7.00(1H,s),7.20~7.50(10H,m), 840~8.60 (1H,br,s)

EXAMPLE 8

Production of sodium 2-{(4RS)-4-[2-(2-amino-4-thiazolyl) -(Z)-2-(methoxyimino)acetamido]-4-methylthio-3-oxo-2-isoxazolidinyl}-5-oxo-2-tetrahydrofuran carboxylate [Compound (8c)]:

(a) Production of diphenylmethyl 2-{(4RS)-4-[2-(2-chloro- acetamido-4-thiazolyl)-(Z)-2-(methoxyimino)acetamido]-4- methylthio-3-oxo-2-isoxazolidinyl}-5-oxo-2-tetrahydrofuran carboxylate [Compound (8a)]:

In 20 ml of methylene chloride was dissolved 1.52 g of diphenylmethyl 2-[(4RS)-4-isocyano-4-methylthio-3-oxo-2isoxazolidinyl]-5-oxo-2-tetrahydrofuran carboxylate. To the solution was added, under ice-cooling, 0.8 g of p-toluenesulfonic acid monohydrate. The mixture was stirred at the same temperature for 2.5 hours, to which was then added an aqueous solution of sodium hydrogen carbonate to render the reaction mixture alkaline. The methylene chloride layer was dried over anhydrous magnesium sulfate, followed by concentration under reduced pressure. To the concentrate were added 10 ml of dimethylacetamide and 0.9 g of pyridine. To the mixture was added, under ice-cooling, 1.3 g of 2-(2-chloroacetamido-4-thiazolyl)-(Z)-2-methoxyiminoacetic acid chloride hydrochloride, followed by stirring at the same temperature for 40 minutes. The reaction mixture was poured into water, which was subjected to extraction with ethyl acetate. The organic layer was washed with water, dried over anhydrous magnesium sulfate and concentrated under reduced pressure. The concentrate was subjected to a silica-gel column chromatography, eluting with ethyl acetate : n-hexane (2:1) to give 0.7 g of the Compound (8a) as a pale yellow foamy product.

I R $\nu_{max}^{KBr}$ cm$^{-1}$: 1810,1770,1690,1545,1270,1180, 1050,740,700

NMR (CDCl₃, ppm): 2.10(3H,s),2.20~3.40(4H,m), 4.05(3H,s),4.20(2H,s),4.40~5.0(2H,m),7.00(1H,s),7.20-~7.50(10H,m)

(b) Production of diphenylmethyl 2-{(4RS)-4-[2-(2-amino-4-thiazolyl)-(Z)-2-(methoxyimino)acetamido-4-methylthio-3oxo-2-isoxazolidinyl}-5-oxo-2-tetrahydrofuran carboxylate [Compound (8b)]:

In 4 ml of dimethylformamide was dissolved the Compound (8a) obtained as above. To the solution was added, under ice-cooling, 106 mg of sodium N-methyldithiocarbamate. The mixture was stirred at the same temperature for 2.5 hours, which was poured into water, followed by extraciton with ethyl acetate. The extract solution was washed with water, dried over anhydrous magnesium sulfate, then concentrated under reduced pressure The concentrate was subjected to a silica-gel column chromatography, eluting with ethyl acetate n-hexane (2:1), to give 233 mg of the Compound (8b).

IR $v_{max}^{KBr}$ cm⁻¹:1805,1760,1730(s),1675, 1610,1530,1180,1050,750,695

NMR(DMSO-d₆, ppm): 2.20(3H,s),2.20~3.40(4H,m),4.00(3H,s),4.40~4.90(2H,m), 6.05~6.25(2H,br,s).7.00(1H,s), 7.10~7.50 (10H,br.s)8.75, 8.85(1H,br.s)

(c) Production of the above-titled Compound (8c):

To 185 mg of the Compound (8b) was added 2 ml of 99% formic acid, and the mixture was stirred at room temperature for 1.5 hour. Formic acid was distilled off under reduced pressure. The residue was neutralized by the addition of an aqueous solution of sodium hydrogen carbonate, which was subjected to a CHP-20 column chromatography. The portion eluted with a 10% aqueous solution of ethanol was freeze-dried to give 109 mg of the above-titled Compound (8c) as colorless powder.

IR $v_{max}^{KBr}$ cm⁻¹:1770,1715,1655,1525,1370,1190,1030,

NMR (DMSO-d₆, ppm): 2.15(3H,s), 2.10~3.20(4H,m),3.80(3H,s),4.35~4.70(2H,m), 6.70(1H,s),7.00~7.30(2H,br.s), 9.45~9.55 (1H,br.s)

EXAMPLE 9

Production of sodium 2-{(4RS)-4-[2-(2-amino-4-thiazolyl)- (Z)-2-(methoxyimino)acetamido]-4-hydroxymethyl-3-oxo-2isoxazolidinyl}-5-oxo-2-tetrahydrofuran carboxylate - 15 [Compound (9c)]:

(a) Production of diphenylmethyl 2-{(4RS)-4-[2-(2-chloroacetamido-4-thiazolyl)-(Z)-2-(methoxyimino)acetamido]-4- hydroxymethyl-3-oxo-2-isoxazolidinyl}-5-oxo-2-tetrahydrofuran carboxylate [Compound (9a)]:

In 3 ml of chloroform was suspended 436 mg of diphenylmethyl 2-[(4RS)-4-hydroxymethyl-4-isocyano-3-oxo-2-isoxazolidinyl]-5-oxo-2-tetrahydrofuran carboxylate. To the suspension was added, under ice-cooling, 209 mg of p-toluenesulfonic acid monohydrate, and the mixture was stirred at the same temperature for one hour. The reaction solution was made alkaline with an aqueous solution of sodium hydrogen carbonate. The chloroform layer was dried over anhydrous magnesium sulfate, followed by concentration under reduced pressure. The concentrate was dissolved in 3 ml of dimethylacetamide. To the solution was added, under ice-cooling, 174 mg of pyridine and subsequently 366 mg of 2-(2-chloroacetamido-4-thiazolyl)-(Z)-2-methoxyiminoacetic acid chloride hydrochloride. The reaction was then allowed to proceed at the same temperature for two hours. The reaction solution was poured into water, which was subjected to extraction with ethyl acetate. The ethyl acetate layer was washed with water, dried over anhydrous magnesium sulfate and concentrated under reduced pressure. The concentrate was subjected to a silica-gel column chromatography, eluting with ethyl acetate : n-hexane (3:1) to give 170 mg of the above-titled Compound (9a).

IR $v_{max}^{KBr}$ cm⁻¹:1810,1770,1740,1670,1540,1180,1050, 700

NMR(CDCl₃,ppm):2.10~3.50(4H,m),4.03(3H,s), 4.23(2H,s),4.50~5.00(4H,M), 7.00(1H,m),7.00(1H,s),7.20~7.50 (10H,m)

(b) Production of diphenylmethyl 2-{(4RS)-4-[2-(2-amino-4-thiazolyl)-(Z)-2-(methoxyimino)acetamido]-4-hydroxymethyl -3-oxo-2-isoxazolidinyl}-5-oxo-tetrahydrofuran carboxylate [Compound (9b)]:

In 3 ml of dimethylformamide was dissolved 170 mg of the Compound (9a) obtained as above. To the solution was added, under ice-cooling, 48 mg of sodium N-methyldithiocarbamate, and the mixture was stirred at room temperature for one hour. The reaction solution was poured into water, which was subjected to extraction with ethyl acetate. The ethyl acetate layer was washed with water, dried over anhydrous magnesium sulfate, then concentrated under reduced pressure. The concentrate was subjected to a silica-gel column chromatography, eluting with ethyl acetate - n-hexane (2:1) to give 115 mg of the above-titled Compound (9b).

IR $v_{max}^{KBr}$ cm⁻¹:1805,1760,1735,1670,1535,1180,1050,700

NMR(CDCl₃,ppm): 2.10~3.50(4H,m),4.00(3H,S), 4.50~5.00(4H,m),5.10~5.30 (2H,br.s),6.86(1H,s), 7.00(1H,s), 7.20~7.50(10H,br.s)

(c) Production of the above-titled Compound (9c).

In 4 ml of formic acid was dissolved, under ice-cooling, 115 mg of the Compound (9b) obtained as above. The solution was allowed to undergo reaction at room temperature for one hour, from which was distilled off formic acid. The residue was adjusted to pH 7 with an aqueous soltuion of sodium hydrogen carbonate, which was then subjected to a CHP-20 column chromatography, eluting with a 10% aqueous solution of ethanol. The eluate was freeze-dried to give 47 mg of the above-titled Compound (9c).

IR $v_{max}^{KBr}$ cm⁻¹:1780,1730,1655,1530,1375,1180,1040

EXAMPLE 10

Production of sodium 2-{(4RS)-4-[2-(2-amino-4-thiazolyl) -(Z)-2-(methoxyimino)acetamido]-4-acetoxymethyl-3-oxo-2isoxazolidinyl}-5-oxo-2-tetrahydrofuran carboxylate [Compound (10c)]:

(a) Production of diphenylmethyl 2-{(4RS)-4-[2-(2-chloroacetamido-4-thiazolyl)-(Z)-2-(methoxyimino)acetamido]-4-acetoxymethyl-3-oxo-2-isoxazolidinyl}-5-oxo-2-tetrahydrofuran carboxylate [Compound (10a)]:

In 3 ml of chloroform was dissolved 400 mg of diphenylmethyl 2-[(4RS)-4-acetoxymethyl-4-isocyano-3-oxo-2-isoxazolidinyl]-5-oxo-2-tetrahydrofuran carboxylate. To the solution wad added, under ice-cooling, 175 mg of p-toluenesulfonic acid monohydrate. The mixture was stirred at the same temperature for one hour. The reaction solution was made alkaline with sodium hydrogen carbonate. The chloroform layer was dried over anhydrous magnesium sulfate, which was concentrated under reduced pressure. The concentrate was dissolved in 2 ml of dimethylacetamide. To the solution were added, under ice-cooling, 146 mg of pyridine then 305 mg of 2-(2-chloroacetamido-4-thiazolyl)-(Z)-2-methoxyiminoacetic acid chloride.hydrochloride. The mixture was stirred at the same temperature for one hour. To the reaction solution was added water, which was subjected to extraction with ethyl acetate. The ethyl acetate layer was washed with water, then dried over anhydrous magnesium sulfate, followed by concentration under reduced pressure. The concentrate was subjected to a silica-gel column chromatography, eluting with ethyl acetate - n-hexane (2:1) to give 510 mg of the above titled Compound (10a).

IR $\nu_{max}^{KBr}$ cm$^{-1}$: 1805,1755,1680,1545,1260,1230, 1180,1050,780,755,695

NMR(CDCl$_3$, ppm): 2.06(3H,s),2.10~3.50 (4H,m), 4.03(3H,s),4.20(2H,s), 4.30~4.80(4H,m),7.00(1H,s), 7.15~7.45(10H,m)

(b) Production of diphenylmlethyl 2-{(4RS)-4-[2-(2-amino-4-thiazolyl)-Z-2-(methoxyimino)acetamido]-4-acetoxymethyl-3-oxo-2-isoxazolidinyl}-5-oxo-2-tetrahydrofuran carboxylate [Compound (110b)]:

In 2 ml of dimethylfOrmamide was dissolved 470 mg of the Compound (10a) obtained as above. To the solution was added, under ice-cooling, 108 mg of sodium N-methyldithiocarbamate. The mixture was stirred at room temperature for one hour. To the reaction solution was added ethyl acetate, and the mixture was washed with water, dried over anhydrous sodium sulfate, followed by concentration under reduced pressure. The concentrate was subjected to a silica-gel colum chromatography, eluting with ethyl acetate - n-hexane (3:1) to give 251 mg of the above titled Compound (10b).

IR $\nu_{max}^{KBr}$ cm$^{-1}$:1805,1750,1675,1525,1045,750, 690

NMR (CDCl$_3$, ppm): 2.03 (3H,s),2.10~3.50(4H,m), 4.00(3H,s),4.40~4.90 (4,H,m), 5.10~5.35(2H,br.s), 7.00(1H,s), 7.20~7.50(20H,M )

(c) Production of the above-titled Compound (10c):

To 200 mg of the Compound (10b) obtained as above was added, under ice-cooling, 2 ml of 99% formic acid. The reaction was allowed to proceed at room temperature for one hour. The reaction solution was concentrated under reduced pressure, and the pH of the concentrate was adjusted to 7 with an aqueous solution of sodium hydrogen carbonate, which was subjected to a CHP-20 column chromatography, eluting with a 10% aqueous solution of ethanol. The eluate was freeze-dried to give 107 mg of the above-titled Compound (10c) as colorless powder.

IR $\nu_{max}^{KBr}$ cm$^{-1}$:1680,1740,1660,1530,1375,1240, 1200,1040

NMR (D$_2$O, ppm external standard): 2.39(3H,s),2.40~3.60(4H,m),4.23(3H,s),7.26(1H,s)

EXAMPLE 11

Production of sodium 2-{(4RS)-4-[2-(2-amino-4-thiazolyl) -(Z)-2-(methoxyimino)acetamido]-4-carbamoyloxymethyl-3-oxo-2-isoxazolidinyl}-5-oxo-2-tetrahydrofuran carboxylate [Compound (11c)]:

(a) Production of diphenylmethyl 2-{(4RS)-4-[2-(2-chloroacetamido-4-thiazolyl)-(Z)-2-(methoxyimino)acetamido]-4chloroacetylcarbamoyloxymethyl-3-oxo-2-isoxazolidinyl}-5-oxo-2-tetrahydrofuran carboxylate [Compound (11a)]:

In 4 ml of chloroform was dissolved 480 mg of diphenylmethyl 2-[(4RS)-4-chloroacetylcarbamoyloxymethyl-4-isocyano-3-oxo-2-isoxazolidinyl]-5-oxo-2-tetrahydrofuran carboxylate. To the solution was added, under ice-cooling, 181 mg of p-toluenesulfonic acid. The mixture was stirred at the same temperature for one hour. The reaction solution was made alkaline with an aqueous solution of sodium hydrogen carbonate. The chloroform layer was then dried over anhydrous magnesium sulfate, followed by concentration under reduced pressure. The concentrate was dissolved in 2 ml of dimethylacetamide. To the solution was added 164 mg of pyridine. To the mixture was added, under ice-cooling, 345 mg of 2-(2-chloroacetamido-4-thiazolyl)-(Z)-2-methoxyiminoacetic acid chloride hydrochloride. The mixture was stirred at the same temperature for one hour. To the reaction solution was added water, which was subjected to extraction with ethyl acetate. The ethyl acetate layer was washed with water, dried over anhydrous magnesium sulfate, then concentrated under reduced pressure. The concentrate was subjected to a silica-gel column chromatography, eluting with ethyl acetate to give 540 mg of the above-titled Compound (11a).

IR$\nu_{max}^{KBr}$ cm$^{-1}$:1800,1760,1730,1685,1540, 1495,1260,1190,1055,780,755,690

NMR(CDCl$_3$,ppm): 2,20~3.60(4H,m),4.03(3H,s), 4.29(2H,s),4.39(2H,s),4.30~4.80(4H,m),7.03(1H,s), 7.20~7.50(10H,br,s)

(b) Production of diphenylmethyl 2{(4RS)-4-[2-(2-amino-4-thiazolyl)-(Z)-2-(methoxyimino)acetamido]-4-carbamoyloxy- methyl-3-oxo-2-isoxazolidinyl}-5-oxo-2-tetrahydrofuran carboxylate [Compound (11b)]:

In 2 ml of dimethylformamide was dissolved 520 mg of the Compound (lla) obtained as above. To the solution was added, under ice-cooling, 217 mg of sodium N-methyldithiocarbamate. The mixture was stirred at the same temperature for 5 hours, to which was added water, followed by extraction with ethyl acetate. The ethyl acetate layer was washed with water, dried over anhydrous magnesium sulfate and concentrated under reduced pressure. The concentrate was subjected to a silica-gel column chromatography, eluting with ethyl acetate, to give 540 mg of the Compound (11a) titled above.

IR $\nu_{max}^{KBr}$ cm$^{-1}$:1800,1730,1675,1610,1515,1725, 1260,1175,1040,690

NMR (CDCl$_3$,ppm): 2.10~3.40(4H,m), 4.00(3H,s), 4.30~4.80(4H,m), 5.20~5.40(2H,br.s), 7.00(1H,s), 7.20~7.50(10H,br.s) (c) Prouction of the above-titled Compound (11c):

In 4 ml of ml of formic acid was dissolved under ice-cooling 150 mg of the Compound (llb) obtained above, which was allowed to undergo reaction at room temperature for 1.5 hour, followed by distilling off formic acid under reduced pressure. To the residue was added an aqueous solution of sodium hydrogen carbonate to adjust its pH at 7, which was subjected to a CHP-20 column chromatography, eluting with a 5% aqueous solution of ethanol. The eluate was freeze-dried to give 76 mg of the above-titled Compound (11c).

IR $\nu_{max}^{KBr}$ cm$^{-1}$:1780,1730,1660,1530,1380, 1335,1200,1085,1040

NMR (D$_2$O, ppm external standard):2.50~3.50(4H,m), 4.20(3H,s),4.66~4.86(2H,m), 7.26(1H,s)

EXAMPLE 12

Production of sodium 2-{(4RS)-4-[2-(2-amino-4-thiazolyl -2-(methoxyimino)acetamido]-4-diphenylmethyloxycarbonylmethyl-3-oxo-2-isoxazolidinyl}-5-oxo-2-tetrahydrofuran carboxylate [Compound (12c)]:

(a) Production of diphenylmethyl 2-{(4RS)-4-[2-(2-chloroacetamido-4-thiazolyl)-(Z)-2-(methoxyimino)acetamido]-4-diphenylmethyloxycarbonylmethyl-3-oxo-2-isoxazolidinyl}5-oxo-2-tetrahydrofuran carboxylate [Compound (12a)]:

In 8 ml of chloroform was dissolved 700 mg of diphenylmethyl 2-[(4RS)-4-diphenylmethyloxycarbonylmethyl-4-isocyano-3-oxo-2-isoxazolidinyl]-5-oxo-2-tetrahydrofuran carboxylate. To the solution was added, under ice-cooling, 232 mg of p-toluenesulfonic acid monohydrate. The mixture was stirred at the same temperature for one hour. The reaction solution was made alkaline with sodium hydrogen carbonate. The chloroform layer was then dried over anhydrous magnesium sulfate, followed by concentration under reduced pressure. The concentrate was dissolved in 3 ml of dimethylacetamide. To the solution were added, under ice-cooling, 211 mg of pyridine and, subsequently, 443 mg of 2-(2-chloroacetamido-4-thiazolyl)-(Z)-2-methoxyiminoacetic acid chloride hydrochloride. The mixture was stirred at the same temperature for one hour. To the reaction solution was added water, which was subjected to extraciton with ethyl acetate. The ethyl acetate layer was washed with water, dried over anhydrous magnesium sulfate and concentrated under reduced pressure. The concentrate was subjected to a silica-gel column chromatography, eluting with ethyl acetate - n-hexane (1:2), to give 458 mg of the above-titled Compound (12a).

IR $\nu_{max}^{KBr}$ cm$^{-1}$:1805,1760(s)1735,1680, 1540,1175,1040,750,690

NMR (CDCl$_3$, ppm): 2.10~3.40 (6H,m), 3.96 (3H,s), 4.23 (2H,s),4.53(2H,s), 6.86(1H,s),7.00(1H,s), 7.20~7.50(20H,m)

(b) Production of diphenylmethyl 2-{(4RS)-4-[2-(2-amino-4 -thiazolyl)-(Z)-2-(methoxyimino)acetamido]-4-diphenylmethyl- oxycarbonylmethyl-3-oxo-2-isoxazolidinyl}-5-oxo-2-tetrahydrofuran carboxylate [Compound (12b)]:

In 2 ml of dimethylformamide was dissolved 445 mg of the Compound (12a) obtained as above. To the solution was added, under ice-cooling, 85 mg of sodium N-methyldithiocarbamate. The mixture was stirred at room temperature for two hours. To the reaction solution was added water, which was subjected to extraction with ethyl acetate. The extract was washed with water and dried over anhydrous magnesium sulfate, which was concentrated under reduced pressure. The concentrate was subjected to a silica-gel column chromatography, eluting with ethyl acetate - n-hexane (2:1) to give 389 mg of the above-titled Compound (12a).

IR $\nu_{max}^{KBr}$ cm$^{-1}$:1805,1760(s),1730, 1675, 1605,1525,1170,1040,745,690

NMR (CDCl$_3$, ppm): 2.10~3.50(6H,m),3.93(3H,s), 4.50(2H,s),5.05~5.15(2H,br.s),6.90(1H,s), 7.00(1H,s), 7.20~7.50(20H,m) (c) Production of the above-titled Compound (12c):

In 4 ml of formic acid was dissolved, under ice-cooling, 310 mg of the Compound (12b) obtained as above. The solution was stirred at room temperature for 1.5 hour, from which was distilled off formic acid under reduced pressure. The pH of the residue was adjusted to 7 with an aqueous solution of sodium hydrogen carbonate. The resultant was subjected to a CHP-20 column chromatography, eluting with a 50% aqueous solution of ethanol. The eluate was freeze-dried to give 85 mg of the above-titled Compound (12c).

IR $\nu_{max}^{KBr}$ cm$^{-1}$:1775,1730,1660,1525,1370,1190,1035,690

NMR(D$_2$O, ppm):6.90(1H,s), 7.20~7.50(10H,m), 2.50~3.50(4H,m)4.10 (3H,s)

EXAMPLE 13

Production of diphenylmethyl 2-{(4RS)-4-azido-4-[2-(2-chloroacetamido-4-thiazolyl)-(Z)-2-(methoxyimino)actamido]-3-oxo-2-isoxazolidinyl}-5-oxo-2-tetrahydrofuran carboxylate :

In 5 ml of chloroform was dissolved 616 mg of diphenylmethyl 2-[(4RS)-4-isocyano-4-methylthio-3-oxo-2-isoxazolidinyl]-5-oxo-2-tetrahydrofuran carboxylate. To the solution was added, under ice-cooling, 250 mg of p-toluenesulfonic acid monohydrate, and the mixture was stirred at the same temperature for one hour. The reaction solution was made alkaline with sodium hydrogen carbonate. The chloroform layer was dried over anhydrous magnesium sulfate, which was concentrated under reduced pressure. The concentrate was dissolved in 2 ml of dimethylacetamide. To the solution were added, under ice-cooling, 0.2 ml of pyridine and 5 ml of a pyridinium azide - methylene chloride solution of 1.3 m mole concentration. The mixture was then cooled to $-20°$ C., to which was added 271 mg of mercuric chloride, followed by stirring for 30 minutes. The resultant was subjected to filtration. The filtrate was was washed with water and dried over anhydrous magnesium sulfate, which was concentrated under reduced pressure. The oily concentrate was dissolved in 2 ml of dimethylacetamide. To the solution were added, under ice-cooling, 200 mg of pyridine and, subsequently, 500 mg of 2-(2-chloroacetamido-4-thiazolyl)- (Z)-2-methoxyiminoaceticacid chloride hydrochloride, followed by stirring at room temperature for 40 minutes. The reaction solution was poured into water, which was subjected to extraction with ethyl acetate. The extract was washed with water, dried over anhydrous magnesium sulfate and concentrated under reduced pressure. The concentrate was subjected to a silica-gel column chromatography, eluting with ethyl acetate - n-hexane (1:1) to give 40 mg of the above-titled compound.

IR $\nu_{max}^{KBr}$ cm$^{-1}$:2120,1810,1770,1735,1690, 1540,1260,1180,1060,1040,690

NMR (CDCl$_3$, ppm): 2.10~3.40(4H,m),4.00(3H,s), 4.20(2H,s), 4.46, 4.86(2H,d,d,J=9Hz), 7.00(1H,s), 7.10~7.40(10H,m), 7.76~7.96(10H,br.s)

EXAMPLE 14

Production of diphenylmethyl 2-(4RS)-4-hydroxymethyl-3- oxo-2-isoxazolidinyl]-5-oxo-2-tetrahydrofuran carboxylate :

In 20 ml of dry benzene was suspended 878 mg of diphenylmethyl 2-[(4RS)-4-hydroxymethyl-4-isocyano-3-oxo-2-isoxazolidinyl]-5-oxo-2-tetrahydrofuran carboxylate. To the suspension were added 0.6 ml of tri-n-butyltin hydride and azobisisobutyronitrile of a catalytic amount. The mixture was subjected to heating under reflux in argon stream for 30 minutes. The solvent was distilled off under reduced pressure. The residue was washed several times with n-hexane by decantation. The remaining insoluble oily substance was then subjected to a silica-gel column chromatography, eluting with ethyl acetate - n-hexane (1:1) to give 560 mg of the above-titled compound.

IR $\nu_{max}^{Nujol}$ cm$^{-1}$: 1785,1760,1720,1615,1260, 1180,1050

NMR (CDCl$_3$, ppm): 2.15~3.50(5H,m), 3.70~4.60 (4H,m), 6.96(1H,s), 7.20~7.50 (10H,m)

EXAMPLE 15

Production of diphenylmethyl 2-[(4RS)-4-methanesulfonyl- oxymethyl-3-oxo-2-isoxazolidinyl]-5-oxo-2-tetrahydrofuran carboxylate:

In 2.4 m( of pyridine was dissolved 1.2 g of diphenylmethyl 2-[(4RS)-4-hydroxymethyl-3-oxo-2-isoxazolidinyl]-5-oxo-2-tetrahydrofuran carboxylate. To the solution was added, under ice-cooling, 0.24 ml of methanesulfonyl chloride. The mixture was stirred at the same temperature for 30 minutes, which was then poured into ice-water, followed by extraction with ethyl acetate. The organic layer was washed with dilute hydrochloric acid and a saturated aqueous saline solution in sequence, followed by drying over anhydrous sodium sulfate. The solvent was distilled off under reduced pressure to give 1.4 g of the above-titled compound.

IR $\nu_{max}^{Nujol}$ cm$^{-1}$:1785,1760,1720,1175,1060, 700

NMR (CDCl$_3$, ppm): 2.10~3.50(5H,m), 3.63 (3H,s), 4.10~4.70(4H,m), 6.96 (1H,s), 7.20~7.50(210H,m)

EXAMPLE 16

Production of diphenylmethyl 2-[(4RS)-4-azidomethyl-3-oxo-2-isoxazolidinyl]-5-oxo-2-tetrahydrofuran carboxylate :

In 10 ml of dimethylsulfoxide was dissolved 1.4 g of diphenylmethyl 2-[(4RS)-4-methanesulfonyloxymethyl-3-oxo-2-isoxazolidinyl]-5-oxo-2-tetrahydrofuran carboxylate. To the solution were added, under ice-cooling, 0.45 g of sodium iodide and 0.39 g of sodium azide. The mixture was stirred at room temperature for 30 minutes. The reaction solution was poured into ice-water, which was subjected to extraction with ethyl acetate. The organic layer was washed with water, which was then dried over anhydrous sodium sulfate, followed by distilling off the solvent under reduced pressure. The residue was subjected to a silica-gel column chromatography, eluting with ethyl acetate - n-hexane (1:2) to give 0.49 g of the above-titled compound.

IR $\nu_{max}^{Nujol}$ cm$^{-1}$:2100,1790,1760,1720,1170,1060

NMR (CDCl$_3$, ppm):2.10~3.45(5H,m), 3.45~4.70 (4H,m), 6.98(1H,s), 7.20≠7.50(10H,m)

EXAMPLE 17

Production of sodium 2-{(4RS)-4-[2-(2-amino-4-thiazolyl)-(Z)-2-(methoxyimino)acetamidomethyl]-3-oxo-2-isoxazolidinyl}-5-oxo-2-tetrahydrofuran carboxylate [Compound (17b)]:

(a) Production of sodium 2-{(4RS)-4-[2-(2-chloroacetamido4-thiazolyl)-(Z)-2-(methoxyimino)acetamidomethyl]-3-oxo-2-isoxyzolidinyl}-5-oxo-2-tetrahydrofuran carboxylate Compound (17a)]:

In 4 ml of a 50% tetrahydrofuran - water was dissolved 218 mg of diphenylmethyl 2-[(4RS)-4-azidomethyl-3-oxo-2isoxazolidinyl]-5-oxo-2-tetrahydrofuran carboxylate. To the solution was added 220 mg of 5% palladium carbon. The mixture was stirred under ice-cooling for 30 minutes in hydrogen stream The catalyst was then filtered off. To the filtrate was added 2 ml of tetrahydrofuran. To the mixture were added, under ice-cooling, 168 mg of sodium hydrogen carbonate and 150 mg of 2-(2-chloroacetamido-4-thiazolyl)-(Z)-2-methoxyiminoacetic acid chloride hydrochloride. The mixture was stirred at the same temperature for one hour. The reaction solution was shaken with ethyl acetate. The aqueous layer was separated and subjected to a CHP-20 column chromatography, eluting with 30% ethanol water. The eluate was freeze-dried to give 105 mg of the above-titled compound (17a) as colorless powder.

IR $\nu_{max}^{KBr}$ cm$^{-1}$:1770,1700(s), 1650,1540, 1370,1190

NMR (D$_2$O, ppm extarnal standard):2.35~5.00(9H,m), 4.03(3H,s), 4.445(2H,s), 7.50 (1H,s)

(b) Production of the above-titled Compound (17b) :

In 2 ml of 50% tetrahydrofuran - water was dissolved 105 mg of the Compound (17a) obtained as above. To the solution was added, under ice-cooling, 65 mg of sodium N-methyldithiocarbamate, followed by stirring at room temperature for one hour. The reaction solution was shaken with ethyl acetate, and the aqueous layer was separated, which was subjected to a CHP-20 column chromatography, eluting with water. The eluate was freeze-dried to give 40 mg of the above-titled Compound (17b) as pale yellow powder.

IR $\nu_{max}^{KBr}$ cm$^{-1}$:1780,1710,1660,1530,1380, 1190,1040

NMR (D$_2$O, ppm external standard):2.35~5.00(9H,m), 4.00 (3H,s), 6.97(1H,s)

EXAMPLE 18

Production of diphenylmethyl 2-[(4RS)-4-methylthio-3-oxo-2-isoxazolidinyl]-5-oxo-2-tetrahydrofuran carboxylate :

In 10 ml of dry benzene was dissolved 452 mg of diphenylmethyl 2-[(4RS)-4-isocyano-4-methylthio-3-oxo-2-isoxazolidinyl]-5-oxo-2-tetrahydrofuran carboxylate. To the solution were added 0.3 ml of tri-n-butyltin hydride and a catalytic amount of azobisisobutyronitrile. The mixture was heated under reflux for one hour under argon stream. The solvent was distilled off under reduced pressure. The residue was subjected to a silica-gel column chromatography, eluting with acetonitrile - methylene chloride (0.5 : 9.5) to give 235 mg of the above-titled compound.

IR $\nu_{max}^{Nujol}$ cm$^{-1}$:1790,1760,1705,1270,1180,1060

NMR (CDCl$_3$, ppm):2.20(3H,s), 2.20~3.50 (4H,m), 3.50~3.90 (1H,m), 3.95~4.80(2H,m), 7.00(1H,s),7.25~7.50(10H,m)

EXAMPLE 19

Production of sodium 2-[(4RS)-4-methylthio-3-oxo-2isoxazolidinyl]-5-oxo-2-tetrahydrofuran carboxylate :

To 3 ml of 99% formic acid was added 550 mg of diphenylmethyl 2-[(4RS)-4-methylthio-3-oxo-2-isoxazolidinyl]-5-oxo-2-tetrahydrofuran carboxylate, and the mixture was stirred at room temperature for one hour, which was concentrated under reduced pressure. The concentrate was washed with n-hexane. To insolubles were added 2 ml of water and 80 mg of sodium hydrogen carbonate to neutralize, followed by shaking with ethyl acetate. The aqueous layer was subjected to a CHP-20 column chromatogrpahy, eluting with 5% ethanol - water. The eluate was freeze-dried to give 65 mg of the above-titled compound.

IR $\nu_{max}^{KBr}$ cm$^{-1}$:1775,1710,1645,1380,1200,1115

NMR(D$_2$O,ppm external standard):2.25(3H,s), 2.20~3.30(4H,m),3.90~4.95 (3H,m)

EXAMPLE 20

Production of diphenylmethyl 2-[(4RS)-4-methylsulfonyl-3-oxo-2-isoxazolidinyl]-5-oxo-2-tetrahydrofuran carboxylate :

In 5 ml of methylene chloride was dissolved 180 mg of diphenylmethyl 2-[(4RS)-4-methylthio-3-oxo-2-isoxazolidinyl]5-oxo-2-tetrahydrofuran carboxylate. To the solution was added 245 mg of m-chloroperbenzoic acid. The mixture was allowed to undergo reaction at room temperature for 2 hours. The reaction solution was washed with an aqueous solution of sodium hydrogen carbonate and then with an aqueous solution of sodium thiosulfate, followed by drying over anhydrous sodium sulfate. The solvent was distilled off, and the residue was subjected to a silica-gel column chromatography, eluting with ethyl acetate - n-hexane (1:1) to give 164 mg of the above-titled compound.

IR $\nu_{max}^{Nujol}$ cm$^{-1}$:1780,1760,1700,1325,1180,1150

NMR (DMSO-d$_6$, ppm):2.30~4.00(4H,m), 3.20(3H,s), 4.10~4.90(3H,m)

EXAMPLE 21

Production of sodium 2-[(4RS)-4-methylsulfonyl-3-oxo-2isoxazolidinyl]-5-oxo-2-tetrahydrofuran carboxylate :

To 150 mg of diphenylmethyl 2-[(4RS)-4-methylsulfonyl-3- oxo-2-isoxazolidinyl]-5-oxo-2-tetrahydrofuran carboxylate was added 2 ml of 99% formic acid. The mixture was stirred at room temperature for one hour, followed by concentration under reduced pressure. The concentrate was washed with n-hexane, which was then neutralized by the addition of 2 ml of water and 70 mg of sodium hydrogen carbonate. The resultant was shaken with ethyl acetate, then the aqueous layer was subjected to a CHP-20 column chromatography, eluting with only water. The eluate was freeze-dried to give 65 mg of the above-titled compound as colorless powder.

IR $\nu_{max}^{KBr}$ cm$^{-1}$:1770,1710,1630,1370,1300,1190,1140

NMR (D$_2$O, ppm external standard):2.35~3.50(4H,m), 3.30(3H,s),4.10~5.00 (3H,m)

EXAMPLE 22

Production of diphenylmethyl 2-[(4RS)-4-(2-hydroxy-2- propyl)-3-oxo-2-isoxazolidinyl]-5-oxo-2-tetrahydrofuran carboxylate :

In 70 ml of dry benzene was suspended 600 mg of diphenylmethyl 2-[(4RS)-4-(2-hydroxy-2-propyl)-4-isocyano-3-oxo-2isoxazolidinyl]-5-oxo-2-tetrahydrofuran carboxylate. To the suspension were added 0.75 ml of tri-n-butyltin hydride and a catalytic amount of azobisisobutyronitrile. The mixture was heated under reflux for 30 minutes under argon stream. The solvent was distilled off under reduced pressure. The residue was subjected to a silica-gel column chromatography, eluting with methylene chloride - acetonitrile (9:1) to give 320 mg of the above-titled compound.

IR $\nu_{max}^{Nujol}$ cm$^{-1}$:1785,1765,1710,1175, 1050,750,705

NMR(CDCl$_3$, ppm):1.30(6H,s), 2.10~3.40(5H,m), 4.10~4.60(2H,m),7.00(1H,s),7.20~7.50(10H,s)

EXAMPLE 23

Production of sodium 2-[(4RS)-4-(2-hydroxy-2-propyl)-3-oxo-2-isoxazolidinyl]-5-oxo-2-tetrahydrofuran carboxylate :

In 0.5 m( of 99% formic acid was suspended 110 mg of diphenylmethyl 2-[(4RS)-4-(2-hydroxy-2-propyl)-3-oxo-2isoxazolidinyl]-5-oxo-2-tetrahydrofuran carboxylate. The suspension was stirred at room temperature for 3 hours, followed by distilling off formic acid under reduced pressure. The residue was adjusted to pH 7.2 with an aqueous solution of sodium hydrogen carbonate, which was shaken with ethyl acetate. The aqueous layer was subjected to a CHP-20 column chromatography, eluting with water. The eluate was freeze-dried to give 45 mg of the above-titled compound.

IR$\nu_{max}^{KBr}$ cm$^{-1}$:1775,1720(s),1710(s), 1650,1380, 1195

NMR (D$_2$O, ppm external standard):1.39(6H,s), 2.20~3.30(4H,m), 4.30~4.70(2H,m)

EXAMPLE 24

Production of diphenylmethyl 2-(4-isopropyliden-3-oxo-2-isoxazolidinyl)-5-oxo-2-tetrahydrofuran carboxylate :

In 3 ml of methylene chloride was dissolved 236 mg of diphenylmethyl 2-[(4RS)-4-(2-hydroxy-2-propyl)-3-oxo-2isoxazolidinyl]-5-oxo-2-tetrahydrofuran carboxylate. To the solution were added, under ice-cooling, 86 mg of pyridine and 95 mg of thionyl chloride. The mixture was stirred at the same temperature for 10 minutes. To the reaction solution was added ethyl acetate, which was washed with water, followed by drying over anhydrous sodium sulfate. The resultant was concentrated under reduced pressure, and the concentrate was subjected to a silica-gel column chromatography, eluting with ethyl acetate - n-hexane (1:1) to give 160 mg of the above-titled compound.

IR$\nu_{max}^{Neat}$ cm$^{-1}$:790,1760,1710,1665,1175, 1060,700

NMR (CDCl$_3$, ppm):1.73(3H,s), 2.20(3H,m), 2.30~3.40(4H,m),4.70~5.10(2H,m), 7.00(1H,s), 7.20~7.50(10H,m)

EXAMPLE 25

In 5 ml of tetrahydrofuran was dissolved 160 mg of diphenylmethyl 2-(4-isopropyliden-3-oxo-2-isoxazolidinyl)5-oxo-2-tetrahydrofuran carboxylate. To the solution were added 2.5 ml of water containing 31 mg of sodium hydrogen carbonate and 160 mg of 5% palladium carbon. The mixture was stirred for one hour in hydrogen stream. The catalyst was filtered off, and the filtrate was shaken with ethyl acetate. The aqueous layer was freeze-dried to give 62 mg of the above-titled compound as colorless powder.

IR$\nu_{max}^{KBR}$ cm$^{-1}$:1770,1710(s),1650,1380,1190,910

NMR (D$_2$O, ppm extarnal standard: 1.86(3H,s), 2.23(3H,s), 2.20~3.30(4H,m)

EXAMPLE 26

Production of diphenylmethyl 2-(3-oxo-2-isoxazolidinyl)- -oxo-2-tetrahydrofuran carboxylate :

In 20 ml of dry benzene was dissolved 203 mg of diphenylmethyl 2-[(4S)-4-isocyano-3-oxo-2-isoxazolidinyl]-5-oxo-2tetrahydrofuran carboxylate. To the solution were added 0.25 ml of tri-n-butyltin hydride and a catalytic amount of azobisisobutyronitrile. The mixture was heated under reflux for 30 minutes in argon stream. The solvent was distilled off under reduced pressure. The residue was subjected to a silica-gel column chromatography, eluting with ethyl acetate - n-hexane (1:1) to give 180 mg of the above-titled compound.

IR$\nu_{max}^{Nujol}$ cm$^{-1}$:1785,1760,1720,1180,1060

NMR (DMSO-d$_6$, ppm):2.10~3.30(6H,m), 4.33(2H,t,J=9Hz),6.90(1H,s), 7.20~7.50(10H,m)

EXAMPLE 27

Production of sodium 2-(3-oxo-2-isoxazolidinyl)-5-oxo-2-tetrahydrofuran carboxylate :

In 12 ml of tetrahydrofuran was dissolved 180 mg of diphenylmethyl 2-(3-oxo-2-isoxazolidinyl)-5-oxo-2-tetrahydrofuran carboxylate. To the solution were added 40 mg of sodium hydrogen carbonate, 180 mg of 5% palladium carbon and 6 ml of water. The mixture was stirred for one hour in hydrogen stream. The catalyst was filtered off, and the filtrate was concentrated under reduced pressure. The concentrate was subjected to a CHP-20 column chromatography, eluting with water. The eluate was freeze-dried to give 60 mg of the above-titled compound.

IR$\nu_{max}^{KBr}$ cm$^{-1}$:1780,1710,1650,1390,1195,

NMR (D$_2$O, ppm external standard): 2.30~3.30(6H,m), 4.46(2H,J=9Hz)

EXAMPLE 28

Production of diphenylmethyl 2-[(4RS)-4-(2-hydroxyethyl) -4-isocyano)-3-oxo-2-isoxazolidinyl]-5-oxo-2-tetrahydrofuran carboxylate :

In 4 ml of dimethylformamide was dissolved 406 mg of diphenylmethyl 2-[(4S)-4-isocyano-3-oxo-2-isoxazolidinyl]-5-oxo-2-tetrahydrofuran carboxylate. To the solution were added, under ice-cooling, 0.1 ml of 80% acetaldehyde and 138 mg of pulverized anhydrous potassium carbonate. The mixture was stirred at the same temperature for 30 minutes. To the resultant were added ethyl acetate and water, and the ethyl acetate layer was washed with water, dried over anhydrous sodium sulfate ad concentrated under reduced pressure. The concentrate was subjected to a silica-gel column chromatography, eluting with ethyl acetate : n-hexane (1:1) to give 280 mg of the above-titled compound.

IR$\nu_{max}^{Nujol}$ cm$^{-1}$:2120,1790,1760,1720,1380,1060

NMR (CDCl$_3$, ppm): 1.36(3H,d,J=7Hz), 1.60(1H, br.s), 2.20~3.50(4H,m), 4.00~4.80(3H,m),7.00(1H,s), 7.20~7.50(10H,br.s)

EXAMPLE 29

Production of diphenylmethyl 2-[(4RS)-4-(2-hydroxyethyl) -]-3-oxo-2-isoxazolidinyl]-5-oxo-2-tetrahydrofuran carboxylate:

In 5 ml of dry benzene was dissolved 200 mg of diphenylmethyl 2-[(4RS)-4-(2-hydroxyethyl)-4-isocyano-3-oxo-2-isoxazolidinyl]-5-oxo-2-tetrahydrofuran carboxylate. To the solution were added 0.15 ml of tri-n-butyltin hydride and a catalytic amount of azobisisobutyronitrile. The mixture was heated under reflux for 30 minutes in argon stream, which was concentrated under reduced pressure The concentrate was washed with n-hexane. The residual insolubles were subjected to a silica-gel column chromatography, eluting with ethyl acetate - n-hexane (1:1) to give 170 mg of the above-titled compound.

IR$\nu_{max}^{Nujol}$ cm$^{-1}$: 1790,1760,1720,1180,1060,750,705

NMR (CDCl$_3$,ppm): 1.23(3H,d,J=7Hz), 1.66(1H,br.s), 2.10~3.50(4H,m), 3.80≠4.90(3H,m), 6.96(1H,s), 7.20~7.50(10H,m)

EXAMPLE 30

Production of sodium 2-{4-[2-(2-amino-4-thiazolyl) (Z)-2-(methoxyimino)-acetamido]-3-oxo-2-isoxazolidinyl}-5-oxo-2-tetrahydrofuran carboxylate [Compound (30c)]:

(a) Production of diphenylmethyl 2-{4-[2-(2-chloroacetamido-4-thiazolyl}-(Z)-2-(methoxyimino)acetamido]-3-oxo-2-isoxazolidinyl}-5-oxo-2-tetrahydrofuran carboxylate [Compound (30a)]:

In 4 ml of dry methylene chloride was dissolved 210 mg of 2-{(4RS)-4-[2-(2-chloroacetamido-4-thiazolyl)-(Z)-2(methoxyimino)acetamido]-4-methylthio-3-oxo-2-isoxazolidinyl}-5-oxo-2-tetrahydrofuran carboxylate. To the solution was added 145 mg of m-chloroperbenzoic acid, and the reaction was allowed to proceed at room temperature for 20 hours. The reaction solution was concentrated under reduced pressure, and the concentrate was dissolved in ethyl acetate. The solution was washed with an aqueous solution of sodium hydrogen carbonate, dried over anhydrous magnesium sulfate and concentrated under reduced pressure. The concentrate was subjected to a silica-gel column chromatography, eluting with ethyl acetate - n-hexane (1:1) to give 162 mg of the above-titled Compound (30a).

IR$\nu_{max}^{KBr}$ cm$^{-1}$:1815,1765,1710(s),1675, 1640,1540,1260,1170,1040,785,755,695

NMR (CDCl$_3$, ppm): 2.20~3.00(3H,m), 3.36~3.80 (1H,m), 4.00(3H,s),4.16(2H,s), 7.00(1H,s),7.20~7.50 (11H,m), 8.60(1H,s),9.30(1H,br.s).

(b) Production of diphenylmethyl 2-{4-[2-(2-amino-4-thiazolyl-(Z)-2-(methoxyimino)acetamido]-3-oxo-2-isoxazolidinyl}-5-oxo-2-furan carboxylate [Compound (30b)]:

In 2 m( of dimethylformamide was dissolved 160 mg of the Compound (30a) obtained as above. To the solution was added, under ice-cooling, 41 mg of sodium N-methyldithiocarbamate. The reaction was allowed to proceed at the same temperature for 2.5 hours. The reaction solution was poured into water, which was subjected to extraction with ethyl acetate. The extract was washed with water, dried over anhydrous magnesium sulfate and concentrated under reduced pressure. The concentrate was subjected to a silica-gel column chromatography, eluting with ethyl acetate - n-hexane (1:1) to give 79 mg of the above-titled Compound (30b).

IR$\nu_{max}^{KBr}$ cm$^{-1}$:1820,1770,1710,1680,1645,1535, 1250,1180,1050,700

NMR (CDCl$_3$, ppm): 2.20∞3.10(3H,m),3.30~3.80(1H,m)3.93(3H,s), 5.63(2H,br.s), 6.73(1H,s), 6.96(1H,s), 7.20~7.50(10H,m), 8.70(1H,s)9.43(1H,br.s)

(c) Production of sodium 2- 4-[2-(2-amino-4-thiazolyl)}-(Z)-2-(methoxyimino)acetamido]-3-oxo-2-isoxazolidinyl -5-oxo-2-furan carboxylate [Compound (30c)]:

In 1 ml of formic acid was dissolved, under ice-cooling, 79 mg of the Compound (30b) obtained as above. The solution was stirred at room temperature for one hour. Formic acid was distilled off under reduced pressure. The residue was adjusted to pH 7 by the addition of an aqueous solution of sodium hydrogen carbonate, which was subjected to a CHP-20 column chromatography, eluting with 10% ethanol-water. The eluate was freeze-dried to give 43 mg of the above-titled Compound (30c).

IR$\nu_{max}^{KBr}$ cm$^{-1}$:1780,1700(s)1680(s), 1660,1635,1525,1380,1030

NMR (D$_2$O, ppm, external standard):2.10~3.20(3H,m), 3.20~3.70(1H,m),3.70(1H,m),3.80(3H,s), 7.20(1H,s),8.60(1H,s)

PART C

Example 1

Production of sodium 2-{(4S)-4-[(Z)-2-chlorovinyl-thioacetamido]-3-oxo-2-isoxazolidinyl}-5-oxo-2-tetrahydrofurancarboxylate [Compound (1b)]:

(a) To a solution of 152 mg of (Z)-2-chlorovinylthioacetic acid in 6 m( of N,N-dimethylformamide (DMF) were added 230 mg of N,N'-dicyclohexylcarbodiimide (DCC) and 150 mg of 1hydroxybenzotriazole (HOBT). The mixture was stirred at room temperature for 10 minutes, to which was added 300 mg of benzhydrylester of a deacetyl compound of TAN-588 (benzhydryl 2-[(4S)-4-amino-3-oxo-2-isoxazolidinyl]-5-oxo-2-tetrahydrofurancarboxylate), followed by stirring for one hour. The reaction solution was diluted with ethyl acetate, and precipitates then formed were filtered off. The filtrate was washed with water and dried ($Na_2SO_4$), then the solvent was distilled off. The residue was subjected t a silica gel column chromatography, followed by elution with ethyl acetate - n-hexane (4:3) to give 342 mg of benzhydryl 2-{(4S)4-[(Z)-2-chlorovinylthioacetamido]-3-oxo-2-isoxazolidinyl}5-oxo-2-tetrahydrofurancarboxylate [Compound (1a)].

$IR\nu_{max}^{KBr}$ $cm^{-1}$:3340,1780,1720,1680,1520,1180,1050

NMR (90MHz,$CDCl_3$)δ:2.32~3.40(4H,m), 4.52~5.01(2H,m), 6.12(1H,dJ=6Hz), 6.33(1H,d,J=6Hz,), 6.82(1H,s), 7.22~7.43(10H,m) (b) A solution of 200 mg of Compound (1a) as obtained above in 15 ml of dichlormethane was cooled at $-10°$ to $-15°$ C., to which were added 0.35 ml of trifluoroacetic acid and 0.29 ml of anisole, followed by stirring for 5 hours. The mixture was concentrated to dryness under reduced pressure, which was washed with n-hexane, followed by dissolving in ethyl acetate. To the solution was added 3 ml of water containing 40 mg of sodium hydrogencarbonate. The aqueous layer was separated and subjected to a column chromatography using XAD-2 (produced by Rohm & Haas Co., U.S.A.). Fractions eluted with 10% ethanol were combined and concentrated, followed by lyophilizing to give 85 mg of the subject Compound (1b).

$IR\nu_{max}^{KBr}$ $cm^{-1}$:3450,1780,1720,1650, 1380,1190,1110,1030

NMR (100MHz, $D_2O$)δ: 2.45~3.30(4H,m), 3.64(2H,s), 4.02~4.33(1H,m), 4.61–4.82 (1H,m), 4.97–5.24(1H,m), 6.33(1H,d,J=6Hz), 6.58(1D,J=6Hz)

EXAMPLE 2

Production of pivaloyloxymethyl 2-{(4S)-[(Z)-2-chlorovinylthioacetamido]-3-oxo-2-isoxazolidinyl}-5-oxo-2-tetrahydrofurancarboxylate [Compound (2)]:

To a solution of 237 mg of Compound (1b) obtained in Example 1 in 5 ml of DMF was added 0.18 ml of pivaloyoxymethylchloride, and the mixture was stirred at room temperature for 24 hours. The reaction solution was poured into water, followed by extraction with ethyl acetate. The organic layer was washed with water, which was then dried ($Na_2SO_4$), followed by distilling off the solvent. The residue was subjected to a silica gel column chromatography, eluting with ethyl acetate - n-hexane (2:1) to give 168 mg of the subject Compound (2).

$IR\nu_{max}^{KBr}$ $cm^{-1}$:3300,1800,1750,1660,1530,1180,1120,1030

NMR (90MHz,$CDCl_3$)δ:1.23(9H,s),2.31–3.39(4H,m), 3.48(2H,s), 4.01–4.55(1H,m), 4.65–5.07(2H,m), 5.83(2H,s), 6.19(1H,d,J=6Hz,), 6.41(1H,d,J=6Hz)

EXAMPLE 3

Production of 1-[(ethoxycarbonyl)oxy]ethyl-2-{(4S)-4-(Z)-2-chlorovinylthioacetamido]-3-oxo-2-isoxazolidinyl}- -oxo-2-tetrahydrofurancarboxylate [Compound (3)]:

To a solution of 115 mg of Compound (1b) obtained in Example 1 in 2 ml of DMF was added 0.2 ml of 1-[(ethoxycarbonyl)oxy]ethyl iodide. The mixture was stirred at room temperature for 2.5 hours, followed by workup in a manner similar to Example 2 to give 88 mg of the subject Compound (3).

$IR\nu_{max}^{KBr}$ $cm^{-1}$:3350,1800,1760,1680,1530,1180,1160,1050

NMR (90MHz,$CDCl_3$, )δ: 1.29(3H,t,J=7Hz), 2.53(3H,d,J=7Hz,), 2.38–3.48(4H,m), 3.42(2H,s), 3.98–4.31(3H,m), 4,62–5.12(2H,m), 6.16(1H,d,J=6Hz), 6.38 (1H,d,J=6Hz), 6.78(1H,q,J=7,12Hz)

Example 4

Production of 1-[(cyclohexyloxycarbonyl)oxy]ethyl 2-{(4S)-4-[(Z)-2-chlorovinylthioacetamido]-3-oxo-2-isoxazolidinyl}-oxo-2-tetrahydrofurancarboxylate [Compound (4)]

To a solution of 174 mg of Compound (1b) obtained in Example 1 in 4 ml of DMF was added 0.3 m( of 1-[(cyclohexyloxycarbonyl)oxy]ethyl iodide. The mixture was stirred at room temperature for 24 hours, followed by workup in a manner similar to Example 2 to give 118 mg of the subject Compound (4).

$IR\nu_{max}^{KBr}$ $cm^{-1}$:3350,1800, 1760, 1680, 1530, 1180, 1160, 1050

NMR (90MHz,$CdCl_3$)δ:1.12–1.99 (10H,m), 1.55(3H,d,J=6Hz), 2.32–3.53(4H,m), 3.41(2H,s), 3.92–4.20(1H,m), 4.41–4.90(3H,m), 6.11(1H,d,J=6Hz), 6.21 (1H,q,J=6.12Hz), 6.72 (1H,d,J=6Hz)

EXAMPLE 5

Production off 1,3-dihydro-3-oxo-1-isobenzofuranyl 2-{(4S)-4- (Z)-2-chlorovinylthioacetamido]-3-oxo-2-isoxazolidinyl}-5- oxo-2-tetrahydrofurancarboxylate [Compound (5)]:

To a solution of 100 mg of Compound (1b) obtained in Example 1 in 2 ml of DMF was added 81 mg of 3-bromophthalide. The mixture was stirred at room temperature for 24 hours, followed by workup in a manner similar to Example 2 to give 81 mg of the subject Compound (5).

$IR\nu_{max}^{KBr}$ $cm^{-1}$:3350, 1800–1750, 1670, 1530, 1180, 1050, 980

NMR (90MHz,$CDCl_3$)δ:2.40–3.41(4H,m), 3.48(2H,s), 40.5–4.31(1H,m), 4.62–5.17(2H,m), 6.19(1H,D,J=6Hz,) 6.41(1H,d,J=6Hz), 7.46 (1H,s), 7.63–8.01(4H,m)

Production of sodium 2-[(4S)-4-(2,2-dichlorovinylthio acetamido)-3-oxo-2-isoxazolidinyl]-5-oxo-2-tetrahydrofuran A procedure similar to Example 1 (a), using 187 mg of 2,2-dichlorovinylthioacetic acid and 320 mg of benzhydryl ester of a deacetyl compound of TAN-588, gave 330 mg of benzhydryl 2(4S)-4-(2,2-dichlorovinylthioacetamido)-3-oxo-2-isoxazolidinyl]rofurancarboxylate.

$IR\nu_{max}^{KBr}$ $cm^{-1}$:3350, 1770, 1720, 1680, 1180, 1050

NMR (90MHz, CDCl3)δ: 2.32–3.30(4H,m), 3.36,3.40(2H, each s), 3.97–4.22(1H,m), 4.53–5.08(2H,m), 6.40(1H,s), 6.93(1H,s), 7.19–7.55(10H,m)

A procedure similar to Example 1(b), using 200 mg of Compound (6a), gave 67 mg of the subject Compound (6b).

IR$\nu_{max}^{KBR}$ cm$^{-1}$:3400, 1780, 1730, 1650, 1380, 1190, 1110, 1030, 910

NMR (90HzD20)δ: 2.36–3.35(4H,m), 3.64(2H,s), 4.07–4.35(1H,m), 4.61–4.82(1H,m), 4.97–5.22(1H,m), 6.70(1H,s)

EXAMPLE 7

Production of sodium 2-[(4S)-4-(2,2-dichlorovinylsulfinyl- acetamido)-3-oxo-2-isoxazolidinyl]-5-oxo-2-tetrahydrofurancarboxylate [Compound (7b)]

(a) To a solution of 608 mg of Compound (6a) obtained in Example 6(a) in 36 ml of dichloromethane was added 265 mg of m-chloro perbenzoic acid (purity 70%). The mixture was stirred at 0° C. for 5 minutes and, then, at room temperature for 30 minutes, followed by extraction with ethyl acetate. The organic layer was washed with an aqueous solution of sodium hydrogencarbonate and dried (Na2SO4). The solvent was distilled off to give 540 mg of benzhydryl 2-[(4S)-4(2,2-dichlorovinylsulfinylacetamido)-3-oxo-2-isoxazolidinyl]-5-oxo-2-tetrahydrofurancarboxylate [Compound (7a)].

IR$\nu_{max}^{KBr}$ cm$^{-1}$: 3340, 1770, 1730, 1680, 1570, 1180, 1050

NMR(90MHz,CDCl3)δ: 2.25–3.60(4H,m), 3.34,3.53(2H,each s), 3.91–4.22(1H,m), 4.49–5.08(2H,m), 7.00(1H,s), 7.04,7.05(1H,each s), 7.29–7.50(10H,m)

(b) A procedure similar to Example 1 (b), using 200 mg of the above Compound (7a), gave 98 mg of the subject Compound (7b).

IR$\nu_{max}^{KBr}$ cm$^{-1}$: 3450, 1780, 1720, 1650, 1380, 1190, 104, 910

NMR(100MHz,D2O)δ: 2.42–3.20(4H,m), 4.10–4.39(1H,m)4.51–4.80(1H,m), 4.11,4.27(2H,each s), 4.92–5.28(1H,m), 7.24(1H,s)

EXAMPLE 8

Production of sodium 2-[(4S)-4-(2,2-dichlorovinylsulfon- ylacetamido)-3-oxo-2-isoxazolidinyl]-5-oxo-2-tetrahydrofuran) carboxylate [Compound (8b)]:

(a) To a solution of 340 mg of Compound (7a) obtained in Example 7(a) in 15 ml of dichloromethane was added 173 mg of m-chloro perbenzoic acid (purity 70%). The mixture was stirred at 0° C. for 5 minutes and, then, at room temperature for 5 hours. The resultant was subjected to workup in a manner similar to Example 7(a) to give 100 mg of benzhydryl 2-[(4S)-4-(2,2-dichlorovinylsulfonylacetamido)-3-oxo-2-isoxazolidinyl]-5-oxo-2-tetrahydrofurancarboxylate [Compound (8a)].

(b) A procedure similar to Example 1 (b), using 100 mg of Compound (8a), gave 45 mg of the subject Compound (8b).

IR$\nu_{max}^{KBr}$ cm$^{-1}$: 3400, 1780, 1720, 1650, 1380, 1330, 1190, 1140, 1030, 920

NMR(90MHz,D2O)δ:2.40–3.30(4H,m), 4.10–4.48(1H,m), 4.59–4.88(2H,s, 1H,m), 4.92–5.27(1H,m), 7.28(1H,s)

EXAMPLE 9

Production of sodium 2-{(4S)-4-[(Z)-1,2-dichlorovinylthioacetamido]-3-oxo-2-isoxazolidinyl}-5-oxo-2-tetrahydrofurancarboxylate [Compound (9b)]:

(a) A procedure similar to Example 1 (a), using 187 mg of (Z)-1,2-dichlorovinylthioacetic acid and 320 mg of benzhydryl ester of a deacetyl compound of TAN-588, gave 358 mg of benzhydryl 2-{(4S)-4-[(Z)-1,2-dichlorovinylthioacetamido]3-oxo-2-isoxazolidinyl}-5-oxo-2-tetrahydrofurancarboxylate [Compound (9a)].

IR$\nu_{max}^{KBr}$ cm$^{-1}$: 3340, 1770, 1720, 1680, 1520, 1180 1050

NMR (90MHz,CDCl3)δ: 2.15–3.52(4M,m), 3.67(2H,s), 3.91 4.20(1H,m), 4.53–4.98(2H,m), 6.50(1H,s),6.99(1H,s), 7.21–7.45(10H,m)

(b) procedure similar to Example 1 (b), using 200 mg of Compound (9a), gave 67 mg of the subject Compound (9b).

IR$\nu$max KBr cm-1: 3400, 1780, 1730, 1650, 1380, 1190, 1110, 1030, 910

NMR (90MHzD20)δ: 2.42–3.32(4H,m), 3.82(2H,s), 4.00–4.34(1H,m), 4.61–4.82(1H,m), 4.85–5.48(1H,m), 6.83(1H,s)

Production of sodium 2-{(4S)-4-[(Z)-1,2-dichlorovinyl sulfinylacetamido]-3-oxo-2-isoxazolindinyl)-5-oxo-2-tetrahydro furancarboxylate:

(a) A procedure similar to Example 7 (a), using 328 mg of Compound (9a) obtained in Example 9(a), gave 240 mg of benzhydryl 2-((4S)-4-[(Z)-2-dichlorovinylsulfinylacetamido]-3-oxo-2-isoxazolidinyl}-5-oxo-2-tetrahydrofurancarboxylate.

IR$\nu_{max}^{KBr}$ cm$^{-1}$: 3340, 1770, 1730, 1680, 1540, 1180, 1050

NMR (90MHz,CDCl3)δ: 2.18–3.60(4H,m), 3.73,3.79(2H,each s), 3.94–4.20(1H,m) 4.49–5.18(2H,m), 6.75,6.77(1H, each s), 7.0(1H,s), 7.22–7.53(1H,m)

(b) A procedure similar to Example 1 (b), using 240 mg of Compound (10a), gave 118 mg of the subject Compound (10b).

IR$\nu_{max}^{KBR}$ cm$^{-1}$: 3450, 1780, 1730, 1650, 380, 1190, 1110, 1040, 910

NMR (90MHz,D20)δ2.42–3.24(4H,m), 4.09–4.35(1H,m), 4.18(2H,s), 4.51–4.80(1H,m), 4.92–5.28(1H,m), 7.25(1H,s)

EXAMPLE 11

Production of sodium 2-((4S)-4-[(Z)-2-carbamoyl-2-fluoro vinylthioacetamido]-3-oxo-2-isoxazolidinyl]-5-oxo-2-tetra hydrofurancarboxylate:

(a) A procedure similar to Example 1 (a), using 179 mg of (Z)-2-carbamoyl-2-fluorovinylthioacetic acid and 356 mg of benzhydryl ester of a deacetyl compound of TAN-588, gave 358 mg of benzhydryl 2-{(4S)-4-[(Z)-2-carbamoyl-2-fluorovinylthioacetamido]-3-oxo-2-isoxazolidinyl}-5-oxo-2-tetrahydrofurancarboxylate.

IR$\nu_{max}^{KBr}$ cm$^{-1}$: 3320, 1770, 1720, 1670, 1620, 1400, 1180, 1050

NMR (90MHz,CDCl3+d6-DMSO)δ: 2.28–3.42(4H,m), 3.52(2H,s), 3.98–4 25(1H,m), 4.48–5.02(2H,m), 6.99(1H,s), 6.98–7.50(11H,m)

(b) A procedure similar to Example 1 (b), using 200 mg of the above Compound (11a), gave 90 mg of the subject Compound (11b).

IR$\nu_{max}^{KBr}$ cm$^{-1}$: 3400, 1780, 1720, 1680, 1650, 1400, 1190, 1030

NMR (100MHz,D₂O)δ: 2.43–3.36(4H,m), 3.80(2H,s), 4.13–4.35(1H,m), 4.64–4.83(1H,m), 4.93–5.23(1H,m). 6.94(1H,d,J=32Hz)

EXAMPLE 12

Production of pivaloyloxymethyl 2-{(4S)-4-[(Z)-2-carbamoyl-2-fluorovinylthioacetamido]-3-oxo-2-isoxazolidinyl}-5-oxo-2-tetrahydrofurancarboxylate [Compound (12)]:

A procedure similar to Example 2, using 214 mg of Compound (11b) obtained in Example 11 (b), gave 157 mg of the subject Compound (12).

IR$\nu_{max}^{KBr}$ cm⁻¹: 3350, 1800, 1740, 1680, 1650, 1400, 1180, 1030

NMR(90MHz, CDCl₃)δ:1.25(9H,s), 2.34–3.52(4H,m), 3.58(2H,s), 4.05–4.27(1H,m), 4.63–5.17(2H,m), 5.87(2H,s), 6.26(2H,bs), 7.06(1H,d,J=33Hz), 7.74(1H,m)

EXAMPLE 13

Production of 1-[(ethoxycarbonyl)oxy]ethyl 2-{(4S)-4[(Z)-2-carbamoyl-2-fluorovinylthioacetamido]-3-oxo-2-isoxazolidinyl}-5-oxo-2-tetrahydrofurancarboxylate [Compound (13)]:

A procedure similar to Example 11, using 243 mg of 35 Compound (11b) obtained in Example 11(b), gave 134 mg of the subject Compound (13).

IR$\nu_{max}^{KBr}$ cm⁻¹: 3350, 1800, 1760, 1680, 1660, 1400, 1250, 1180, 1030

NMR (90MHz,CDC13)δ: 1.29(3H,t,J=7 Hz), 2.56(3H,d,J=7Hz), 2.34–3.52(4H,m), 3.59(2H,s), 4.06–4.37(3H,m), 4.71–5.12(2H,m), 6.47(2H,bs), 6.76–6.88(1H,m), 7.06(1H,d,J=33Hz), 7.85(1H,m)

EXAMPLE 14

Production of sodium 2-((4S)-4-[(E)-2-cyanovinylthioacetamido]-3-oxo-2-isoxazolidinyl}-5-oxo-2-tetrahydrfurancarboxylate:

(a) A procedure similar to Example 1 (a), using 143 mg of (E)-2-cyanovinylthioacetic acid and 300 mg of benzhydryl ester of a deacetyl compound of TAN-588, gave 284 mg of benzhydryl 2-((4S)-4-[(E)-2-cyanovinyl-thioacetamido]-3-oxo-2-isoxazolidinyl]-5-oxo-2-tetrahydrofurancarboxylate.

IR$\nu_{max}^{KBr}$ cm⁻¹: 3340, 2220, 1770, 1720, 1680, 1570, 1180, 1050

NMR (90MHz,CDC13)δ: 2.39–3.32(4H,m), 3.71(2H,s), 3.95–4.27(1H,m), 4.42–5.09(2H,m), 5.39(1H,d,J=16Hz). 6.98(1H,s), 6.38–6.98( 10H,m), 6.50(1H,d,J=16Hz)

(b) A procedure similar to Example 1 (a), using 284 mg of Compound (14a) obtained as above, gave 127 mg of the subject Compound (14b).

IR$\nu_{max}^{KBr}$ cm⁻¹: 3350, 2220, 1770, 1720, 1650, 1550, 1380, 1190, 1110, 1040

NMR (100MHz,D20)δ: 2.46–3.30(4H,m), 3.84(2H,s), 4.12–4.34(1H,m), 4.58–4.86(1H,m), 4.96–5.22(1H,m), 5.54(1H,d,J=16Hz), 7.70(1H,d,J=16Hz)

EXAMPLE 15

Production of sodium 2-((4S)-4-[(Z)-2-cyanovinylthioacetamido]-3-oxo-2-isoxazolidinyl)-5-oxo-2-tetrahydrofurancarboxylate:

A procedure similar to Example 14, using 143 mg of (Z)2-cyanovinylthioacetic acid and 300 mg of benzhydryl ester of a deacetyl compound of TAN-588, gave 105 mg of the subject Compound (15).

IR$\nu_{mnax}^{KBr}$ cm⁻¹: 3350, 2220, 1780, 1720, 1650, 1540, 1380, 1190, 1110; 1040

NMR (100MHz,D20)δ: 2.45–3.30(4H,m), 3.84(2H,s), 4.12–4.36(1H,m), 4.56–4.84(1H,m), b 4.98–5.22(1H,m), 5.64(1H,d,J=10Hz), 7.52(1H,d,J=10Hz)

EXAMPLE 16

Production of 1-[(ethoxycarbonyl)oxy]ethyl 2-{(4S)-4[(Z)-2-cyanovinylthioacetamido]-3-oxo-2-isoxazolidinyl}5-oxo-2-tetrahydrofurancarboxylate:

A procedure similar to Example 3, using 220 mg of Compound (15) obtained in Example 15, gave 127 mg of the subject Compound (16).

IR$\nu_{max}^{KBr}$ cm⁻¹: 3340, 2220, 1800, 1760, 1680, 1540, 1260, 1180, 1050

NMR (90MHz,CDCl₃)δ1. 29(3H,t,J=7Hz), 1.57(3H,d,J+7Hz), 2.38–3.30(4H,m), 3.63(2H,s), 4.08–4.38(3H,m}, 4.59–5.17(2H,m), 5.39(1H, J=10 Hz). 6.70-6.96(1H,m), 7.35(1H,d,J=10Hz)

EXAMPLE 17

Using the following ingredients, tablets are produced by the conventional means:

| | |
|---|---|
| Compound (3) as obtained in Example 3 | 300 mg |
| Corn.starch | 50 mg |
| Lactose | 28 mg |
| Hydroxypropylcellulose L | 20 mg |
| Magnesium stearate | 2 mg |
| | 400 mg |
| | (per tablet) |

Dosage: 4 to 8 tablets/adult/day after each meal (three time per day)

EXAMPLE 18

Sterilized vials, 12 ml each capacity, are filled with 3 mg equivalent each of Compound (6b) as obtained in Example 6, which are sealed under 50 mmHg. Dissolution with 3 ml of distilled water gives an injectable solution.

What we claim is:

1. A compound of the formula

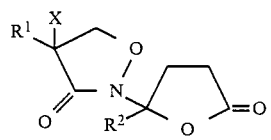

wherein R1 is hydrogen, amino, isonitrile or an acylamino group selected from the group consisting of
(1) a group of the formula:

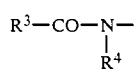

wherein $R^3$ is $C_{1-6}$ alkyl which is substituted with phenyl, thi(e)nyl or triazoyl each of which is unsubstituted or may be substituted with halogen, $R^4$ is hydrogen;
(2) a group of the formula:

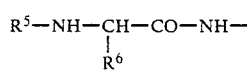

wherein $R^5$ is a group represented by the formula $R^7\text{-}(CH_2)n\text{-}C(=Z)\text{-}$ wherein $R^7$ is piperadinyl which is unsubstituted or may be substituted with at least one of oxo and $C_{1-6}$ alkyl; n is 0; Z is O; $R^6$ is phenyl;

(3) a group of the formula:

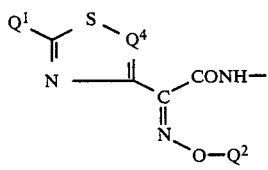

wherein Q1 is amino; Q2 is hydrogen, $C_{1-6}$ alkyl, a group $-CH_2COOQ3$ or a group

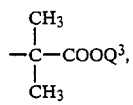

wherein Q3 is hydrogen or $C_{1-6}$ alkyl, Q4 is $-CH=$ or $-N=$;

(4) a group of the formula:

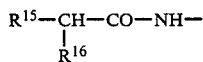

wherein $R_{15}$ is phenyl, $R_{16}$ is hydroxy, sulfamoyl, sulfo or sulfoxy, and (5) a group of the formula:
$R_{17}\text{-}R_{18}\text{-}CH_2\text{-}CO\text{-}NH-$ wherein $R_{17}$ is $C_{2-6}$ alkenylene which is unsubstituted or may be substituted with halogen, cyano or carbamoyl, $R_{18}$ is -S-; X is (a) hydrogen, (b) methoxy, (c) formylamino, (d) $C_{1-6}$ alkyl which is unsubstituted or may be substituted with hydroxyl, $C_{1-4}$ alkylsulfonyloxy or azido, (e) $C_{1-6}$ alkyl thio in which the sulfur atom is unoxidized or may be oxidized or (f) azido, or X forms a double bond together with the adjacent carbon atom;

and $R_2$ is carboxyl; or a physiological acceptable salt thereof.

2. A compound as claimed in claim 1, wherein $R_1$ is hydrogen or isonitrile and X is hydrogen, $C_{1-6}$ alkyl which is unsubstituted or may be substituted, $C_{1-6}$ alkyl thio in which the sulfur atom is unoxidized or may be oxidized or qzido, or X forms a double bond together with the adjacent carbon atom.

3. A compound as claimed in claim 1, wherein $R_1$ is amino.

4. A compound as claimed in claim 1, wherein $R_1$ is isonitrile.

5. A compound as claimed in claim 1, wherein the group of the formula : $R^{17}\text{-}R^{18}\text{-}CH2\text{-}CO\text{-}NH\text{-}$ is a group of the formula:

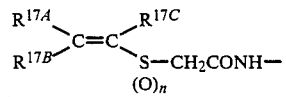

wherein $R^{17A}$, $R^{17B}$ and $R^{17C}$ are independ halogen, cyano or carbamoyl, and n is an integer of 0,1 or 2.

6. A compound as claimed in claim 5, wherein one or two of $R^{17A}$, $R^{17B}$ and $R^{17C}$ have substituents and the others are hydrogens.

7. A compound as claimed in claim 6, wherein the substituents are a combination of one or two halogens, one halogen and one carbamoyl, or one cyano.

8. A compound as claimed in claim 7, wherein halogen is chlorine or fluorine.

9. A compound as claimed in claim 5, wherein $R^{17A}$ is hydrogen, chlorine, carbamoyl or cyano.

10. A compound as claimed in claim 5, wherein $R^{17B}$ is chlorine, fluorine or cyano.

11. A compound as claimed in claim 5, wherein $R^{17C}$ is hydrogen or chlorine.

12. A compound as claimed in claim 5, wherein $R^{17A}$ is hydrogen or chlorine, $R^{17B}$ is chlorine or cyano and $R^{17C}$ is hydrogen or chlorine.

13. A compound as claimed in claim 1, wherein X is hydrogen.

14. A compound as claimed in claim 1, wherein the compound is sodium 2-{(4S)-4-[2-(2-amino-4-thiazolyl)-(Z)-2-(carboxymethyloxyimino)acetamido]-3-oxo-2-isoxazolidinyl}-5-oxo-2-tetrahydrofurancarboxylate.

15. A compound as claimed in claim 1, wherein the compound is sodium 2-{(4S)-4-[2-(5-amino-1,2,4-thiadiazole-3-yl)-(Z)-2-ethoxyiminoacetamido]-3-oxo-2 isoxazolidinyl}-5-oxo-2-tetrahydrofurancarboxylate.

16. A compound as claimed in claim 1, wherein the compound is sodium 2-{(4S)-4-[2-(2-amino-4-thiazolyl)-(Z)-2-(1-carboxy-1-methylethoxyimino)-acetamido]-3-oxo-2isoxazolidinyl}-5-oxo-2-tetrahydrofurancarboxylate.

17. A compound as claimed in claim 1, wherein the compound is sodium 2-{(4RS)-4-[2-(2-amino-4-thiazoly-1)-(Z)-2(methoxyimino)acetamido]-4-hydroxymethyl-3-oxo-2isoxazolidinyl}-5-oxo-2-tetrahydrofurancarboxylate.

18. A compound as claimed in claim, 1, wherein the compound is sodium 2-{(4RS)-4-[2-(2-amino-4-thiazolyl)-(Z)-2- (methoxyimino)acetamido]-4-acetoxymethyl-3-oxo-2isoxazolidinyl}-5-oxo-2-tetrahydrofurancarboxylate.

19. A compound as claimed in claim 1, wherein the compound is sodium 2-{(4RS)-4-[2-(2-amino-4-thiazolyl1)-(Z)-2(methoxyimino)acetamido]-4-carbamoylmethyl-3-oxo-2isoxazolidinyl}-5-oxo-2-tetrahydrofurancarboxylate.

20. A compound as claimed in claim 1, wherein the compound is sodium 2-{(4S)-4-[(Z)-2-chlorovinylthioacetamido]-3-oxo-2-isoxazolidinyl-}-5 oxo-2-tetrahydrofurancarboxylate.

21. A compound as claimed in claim 1, wherein the compound is sodium 2-{(4S)-4-(2,2-dichlonovinylthioacetamido]-3-oxo-2-isoxazolidinyl}-5-oxo-2-tetrahydrofurancarboxylate.

22. A compound as claimed in claim 1, wherein the compound is sodium 2-{(4S)-4-[(Z)-1,2-dichlorovinyl-thioacetamido]-3-oxo-2-isoxazolidinyl}-5-oxo-2-tetrahydrofurancarboxylate. 2-fluorovinylthioacetamido]-3-oxo-2-isoxazolidinyl}-5-oxo- 2-tetrahydrofurancarboxylate.

23. A compound as claimed in claim 1, wherein the compound is 1-[(ethoxycarbonyl)oxy]ethyl 2-{(4S)-4-[(Z)-2-carbamoyl-2-fluorovinylthioacetamido]-3-oxo-2-isoxazolidinyl}-5-oxo-2-tetrahydrofurancarboxylate.

24. A compound as claimed in claim 1, wherein the compound bis sodium 2-((4S)-4-[(Z)-2-cyanovinylthioacetamido]-3-oxo-2-isoxazolidinyl]-5-oxo-2-tetrahydrofurancarboxylate.

* * * * *